(12) United States Patent
Jones et al.

(10) Patent No.: US 10,538,530 B2
(45) Date of Patent: Jan. 21, 2020

(54) VASOPRESSIN RECEPTOR ANTAGONISTS AND PRODUCTS AND METHODS RELATED THERETO

(71) Applicant: BlackThorn Therapeutics, Inc., San Francisco, CA (US)

(72) Inventors: Robert M. Jones, San Mateo, CA (US); Mariangela Urbano, Del Mar, CA (US); Gary Brandt, Alameda, CA (US); Mark Chambers, Saffron Walden (GB); David Hardick, Saffron Walden (GB); Chris Knight, Saffron Walden (GB); Jason Tierney, Saffron Walden (GB); Chris Lock, Saffron Walden (GB)

(73) Assignee: BlackThorn Therapeutics, Inc., San Francisco, CA (US)

( * ) Notice: Subject to any disclaimer, the term of this patent is extended or adjusted under 35 U.S.C. 154(b) by 0 days.

(21) Appl. No.: 16/122,780

(22) Filed: Sep. 5, 2018

(65) Prior Publication Data
US 2019/0169202 A1 Jun. 6, 2019

Related U.S. Application Data

(60) Provisional application No. 62/554,452, filed on Sep. 5, 2017.

(51) Int. Cl.
| | | |
|---|---|---|
| *C07D 487/10* | (2006.01) | |
| *A61P 25/20* | (2006.01) | |
| *A61P 25/22* | (2006.01) | |
| *A61P 25/18* | (2006.01) | |
| *A61P 25/24* | (2006.01) | |

(52) U.S. Cl.
CPC ............ *C07D 487/10* (2013.01); *A61P 25/18* (2018.01); *A61P 25/20* (2018.01); *A61P 25/22* (2018.01); *A61P 25/24* (2018.01); *C07B 2200/07* (2013.01)

(58) Field of Classification Search
CPC .................................................. C07D 487/10
See application file for complete search history.

(56) References Cited

U.S. PATENT DOCUMENTS

| | | | | |
|---|---|---|---|---|
| 5,091,387 A * | 2/1992 | Evans | ................... | C07D 209/96 514/278 |
| 2004/0087800 A1* | 5/2004 | Claesson | .............. | C07D 471/10 548/147 |
| 2006/0063791 A1* | 3/2006 | Li | ........................ | C07D 409/14 514/278 |
| 2015/0329551 A1* | 11/2015 | Geneste | ............... | C07D 471/10 514/210.21 |
| 2015/0344489 A1* | 12/2015 | Braje | .................... | C07D 401/14 514/210.18 |
| 2019/0048013 A1* | 2/2019 | Jones | .................... | C07D 498/04 |

FOREIGN PATENT DOCUMENTS

| | | | | |
|---|---|---|---|---|
| CA | 2025005 A1 * | 3/1991 | .......... | C07D 487/10 |
| WO | 2008/068185 A1 | 6/2008 | | |
| WO | 2015/173392 A1 | 11/2015 | | |

OTHER PUBLICATIONS

T. Koshimizu et al., 92 Physiological Reviews, 1813-1864 (2012) (Year: 2012).*
R. Naik et al., 139 European Journal of Medicinal Chemistry, 644-656 (2017) (Year: 2017).*
G. Decaux et al., 371, The Lancet 1624-1632 (2008) (Year: 2008).*
CAS Abstract CA 2,025,005 (1991) (Year: 2007).*
Battle et al., "Vasopressin V1a Receptor Signaling in a Rat Choroid Plexus Cell Line," *Biochemical and Biophysical Research Communications* 275(2):322-327, 2000.
Bleickardt et al., "Characterization of the V1a antagonist, JNJ-17308616, in rodent models of anxiety-like behavior," *Psychopharmacology* 202:711-718, 2009.
Chen et al., "Vasopressin protects hippocampal neurones in culture against nutrient deprivation or glutamate-induced apoptosis," *J. Neuroendocrinol.* 22(10):1072-1081, 2010. (17 pages).
Decaux et al., "Non-peptide arginine-vasopressin antagonists: the vaptans," *The Lancet* 371:1624-1632, 2008.
Gould, "Salt selection for basic drugs," *International Journal of Pharmaceutics* 33:201-217, 1986.
International Search Report and Written Opinion of the International Searching Authority, dated Dec. 17, 2018, for International Application No. PCT/US2018/049607, 14 pages.
Meisenberg, "Vasopressin-induced Grooming and Scratching Behavior in Mice," *Annals of the New York Academy of Sciences* 525:257-269, 1988.
Szczepanska-Sadowska et al., "Vasopressin and Related Peptides; Potential Value in Diagnosis, Prognosis and Treatment of Clinical Disorders," *Current Drug Metabolism* 18:306-345, 2017.

* cited by examiner

*Primary Examiner* — Alexander R Pagano
(74) *Attorney, Agent, or Firm* — Seed IP Law Group LLP

(57) ABSTRACT

Compounds are provided that antagonize vasopressin receptors, particularly the V1a receptor products containing such compounds, as well as to methods of their use and synthesis. Such compounds have the structure of Formula (I), or a pharmaceutically acceptable isomer, racemate, hydrate, solvate, isotope, or salt thereof:

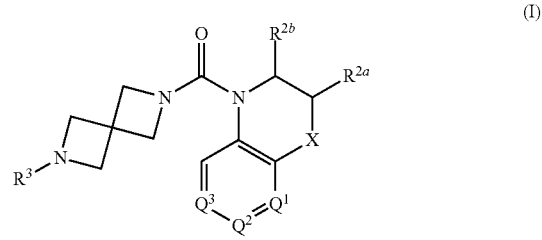

(I)

wherein $Q^1$, $Q^2$, $Q^3$, $R^{2a}$, $R^{2b}$, $R^3$ and X are as defined herein.

104 Claims, No Drawings

VASOPRESSIN RECEPTOR ANTAGONISTS AND PRODUCTS AND METHODS RELATED THERETO

FIELD OF THE INVENTION

The invention relates to vasopressin receptor antagonists and to products containing the same, as well as to methods of their use and preparation.

BACKGROUND

Arginine vasopressin (AVP) is a naturally occurring neurohormone released in the brain and the blood stream. AVP is important in regulating water conservation, blood pressure and pituitary adrenocorticotropic hormone (ACTH) secretion, and exerts its effects on physiology and behavior by binding to specific G protein-coupled receptors in the central nervous system and certain peripheral sites or tissues. Within the brain, AVP regulates circadian rhythms, facilitates hippocampal learning and memory and plays an important role in mediating social behaviors by acting in limbic circuits that are dysregulated in neurobehavioral disorders.

Three distinct AVP receptor subtypes have been identified on pharmacological and functional bases: V1a, V1b and V2. These receptors are located in the liver, vessels (coronary, renal, cerebral), platelets, kidney, uterus, adrenal glands, pancreas, central nervous system or pituitary gland. AVP is involved in the regulation of several functions, such as cardiovascular, hepatic, pancreatic, antidiuretic, and platelet-aggregating effects, and effects on the central and peripheral nervous system and on the uterine sphere. The effects of the AVP receptors depends on where they are located. The V1a receptor is found throughout the limbic system and cortex of the brain, and in the smooth muscle of blood vessels, uterus, and heart muscle. The V1b receptor is also located in limbic system and the pituitary gland. V2 receptors are located on the collecting ducts of nephrons in the kidney and have been a target for therapeutic approaches to the treatment of cardiovascular conditions.

Vasopressin functions as a neurochemical signal in the brain to affect social behavior. The V1a receptor is extensively expressed in the brain and particularly in limbic areas like the amygdala, lateral septum and hippocampus which are known to have an important role in the regulation of majority of the known effects of AVP, including anxiety, memory and learning, social cognition, aggressive behavior, affiliation, depression and the like. The V1a receptor is implicated in other neuropsychological disorders such as autistic spectrum disorders, schizophrenia, aggression, aggressive behavior and obsessive-compulsive disorders. The V1a receptor also mediates the cardiovascular effects of vasopressin in the brain by centrally regulating blood pressure and heart rate in the solitary tract nucleus and peripherally by inducing the contraction of vascular smooth muscles.

Use of vasopressin receptor antagonists, particularly V1a receptor antagonists, provides significant promise for the treatment of a variety of disorders which may benefit from antagonism of the V1a receptor. As a result, a number of V1a antagonists have been taken forward for clinical use and/or development. However, despite the advances made in this field, there remains a significant need for new and/or improved V1a receptor antagonists, as well as for pharmaceutical products containing the same, and for methods related to their use and manufacture.

SUMMARY OF THE INVENTION

The present invention is directed to compounds that antagonize vasopressin receptors, particularly the V1a receptor, to compositions containing the same, and to methods of their preparation and use for treatment of a malcondition wherein antagonism of the V1a receptor is medically indicated or beneficial.

In an embodiment, compounds are provided having the structure of Formula (I), or a pharmaceutically acceptable isomer, racemate, hydrate, solvate, isotope, or salt thereof:

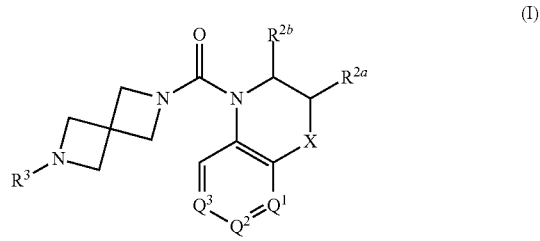

(I)

wherein $Q^1$, $Q^2$, $Q^3$, $R^{2a}$, $R^{2b}$, $R^3$, and X are as defined herein.

In an embodiment, a pharmaceutical composition is provided comprising a compound having the structure of Formula (I), or a pharmaceutically acceptable isomer, racemate, hydrate, solvate, isotope, or salt thereof, in combination with a pharmaceutically acceptable carrier, diluent, or excipient.

In an embodiment, use of a compound having the structure of Formula (I), or a pharmaceutically acceptable isomer, racemate, hydrate, solvate, isotope, or salt thereof, for the manufacture of a medicament is provided.

In an embodiment, a method is provided for antagonizing the V1a receptor, the method comprising contacting the receptor with an effective amount of a compound having the structure of Formula (I), or a pharmaceutically acceptable isomer, racemate, hydrate, solvate, isotope, or salt thereof, or a pharmaceutical composition comprising the same.

In an embodiment, a method is provided for treatment of a malcondition in a subject for which antagonism of the V1a receptor is medically indicated. Such method comprises administering to the subject an effective amount of a compound having the structure of Formula (I), or a pharmaceutically acceptable isomer, racemate, hydrate, solvate, isotope, or salt thereof, or a pharmaceutical composition comprising the same, at a frequency and for duration sufficient to provide a beneficial effect to the subject.

In an embodiment, a pharmaceutical composition is provided comprising a compound having the structure of Formula (I), or a pharmaceutically acceptable isomer, racemate, hydrate, solvate, isotope, or salt thereof, in combination with at least one pharmaceutically acceptable carrier, diluent, or excipient.

In an embodiment, a method of synthesis is provided for a compound having the structure of Formula (I), or a pharmaceutically acceptable isomer, racemate, hydrate, solvate, isotope, or salt thereof.

DETAILED DESCRIPTION OF THE INVENTION

As mentioned above, the invention relates to compounds that antagonize vasopressin receptors, particularly the V1a receptor, to products comprising the same, and to methods for their use and synthesis.

In one embodiment, compounds are provided having the structure of Formula (I), or a pharmaceutically acceptable isomer, racemate, hydrate, solvate, isotope, or salt thereof:

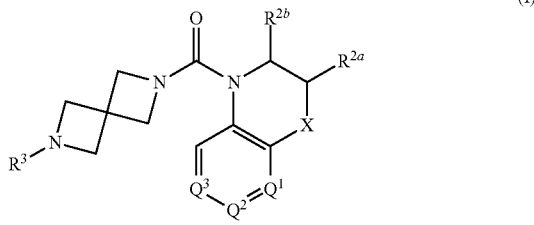

(I)

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—,

R$^x$ is, at each occurrence, independently H, lower alkyl, lower haloalkyl, halo, or R$^6$;

R$^y$ is, at each occurrence, independently H, —OH, lower alkyl, lower alkoxy, or halo;

Q$^1$ is N or CR$^{1a}$, Q$^2$ is N or CR$^{1b}$, and Q$^3$ is N or CR$^{1c}$, wherein at least one Q$^1$, Q$^2$, or Q$^3$ is not N;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^3$ is —(CHR$^z$)$_m$-Q-(R$^4$)$_p$, —S(═O)$_2$R$^5$, or —C(═O)R$^5$;

R$^z$ is H or CH$_3$

Q is aryl or heteroaryl;

R$^4$ is, at each occurrence, independently H, —OH, ═O, cycloalkyl, lower alkyl, lower haloalkyl, lower alkoxy, lower haloalkoxy, halo, or cyano;

R$^5$ is H, cycloalkyl, lower alkyl, lower haloalkyl, lower alkoxy, aryl, heteroaryl, cycloalkylalkyl, heterocyclyl, or —O-heterocyclyl;

R$^6$ is cycloalkyl, heterocyclyl, or —C(═O)R$^7$;

R$^7$ is H, lower alkyl, or lower haloalkyl;

n is 0, 1, or 2;

q is 0, 1, or 2;

t is 0, 1, or 2;

m is 0, 1, 2, 3, 4, 5, or 6; and p is 0, 1, or 2.

As used herein, "lower alkyl" means a straight chain or branched alkyl group having from 1 to 8 carbon atoms, in some embodiments from 1 to 6 carbon atoms, in some embodiments from 1 to 4 carbon atoms, and in some embodiments from 1 to 2 carbon atoms. Examples of straight chain lower alkyl groups include, but are not limited to, methyl, ethyl, n-propyl, n-butyl, npentyl-, n-hexyl, n-heptyl, and n-octyl groups. Examples of branched lower alkyl groups include, but are not limited to, isopropyl, iso-butyl, sec-butyl, t-butyl, neopentyl, isopentyl, and 2,2-dimethylpropyl groups.

"Halo" or "halogen" refers to fluorine, chlorine, bromine, and iodine.

"Hydroxy" refers to —OH.

"Cyano" refers to —CN.

"Lower haloalkyl" refers to a lower alkyl as defined above with one or more hydrogen atoms replaced with halogen. Examples of lower haloalkyl groups include, but are not limited to, —CF$_3$, —CH$_2$CF$_3$, and the like.

"Lower alkoxy" refers to a lower alkyl as defined above joined by way of an oxygen atom (i.e., —O-(lower alkyl). Examples of lower alkoxy groups include, but are not limited to, methoxy, ethoxy, n-propoxy, n-butoxy, iso-propoxy, sec-butoxy, tert-butoxy, and the like.

"Lower haloalkoxy" refers to a lower haloalkyl as defined above joined by way of an oxygen atom (i.e., —O-(lower haloalkyl). Examples of lower haloalkoxy groups include, but are not limited to, —OCF$_3$, —OCH$_2$CF$_3$, and the like.

"Cycloalkyl" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like "Cycloalkylalkyl" are alkyl groups as defined above in which a hydrogen or carbon bond of the alkyl group is replaced with a bond to a cycloalkyl group as defined above.

"Aryl" groups are cyclic aromatic hydrocarbons that do not contain heteroatoms. Thus, aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like). In one embodiment, aryl is phenyl or naphthyl, and in another embodiment aryl is phenyl.

"Heterocyclyl" or "heterocyclic" refers to aromatic and non-aromatic ring moieties containing 3 or more ring members, of which one or more is a heteroatom such as, but not limited to, N, O, S, or P. In some embodiments, heterocyclyl include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein.

Heterocyclyl groups also include fused ring species including those having fused aromatic and non-aromatic groups. A heterocyclyl group also includes polycyclic ring systems containing a heteroatom such as, but not limited to, quinuclidyl, and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups.

"Heteroaryl" refers to aromatic ring moieties containing 5 or more ring members, of which, one or more is a heteroatom such as, but not limited to, N, O, and S. Heteroaryl groups include, but are not limited to, groups such as pyrrolyl, pyrazolyl, pyridinyl, pyridazinyl, pyrimidyl, pyrazyl, pyrazinyl, pyrimidinyl, thienyl, triazolyl, tetrazolyl, triazinyl, thiazolyl, thiophenyl, oxazolyl, isoxazolyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups.

"Isomer" is used herein to encompass all chiral, diastereomeric or racemic forms of a structure, unless a particular stereochemistry or isomeric form is specifically indicated. Such compounds can be enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention. The isomers resulting from the presence of a chiral center comprise a pair of nonsuperimposable-isomers that are called "enantiomers." Single enantiomers of a pure compound are optically active (i.e., they are capable of rotating the plane of plane polarized light and designated R or S).

"Isolated optical isomer" means a compound which has been substantially purified from the corresponding optical isomer(s) of the same formula. For example, the isolated isomer may be at least about 80%, at least 80% or at least 85% pure. In other embodiments, the isolated isomer is at least 90% pure or at least 98% pure, or at least 99% pure by weight.

"Substantially enantiomerically or diastereomerically" pure means a level of enantiomeric or diastereomeric enrichment of one enantiomer with respect to the other enantiomer or diastereomer of at least about 80%, and more specifically in excess of 80%, 85%, 90%, 95%, 98%, 99%, 99.5% or 99.9%.

The terms "racemate" and "racemic mixture" refer to an equal mixture of two enantiomers. A racemate is labeled "(±)" because it is not optically active (i.e., will not rotate plane-polarized light in either direction since its constituent enantiomers cancel each other out). All compounds with an asterisk (*) adjacent to a tertiary or quarternary carbon are optically active isomers, which may be purified from the respective racemate and/or synthesized by appropriate chiral synthesis.

A "hydrate" is a compound that exists in combination with water molecules. The combination can include water in stoichiometric quantities, such as a monohydrate or a dihydrate, or can include water in random amounts. As the term is used herein a "hydrate" refers to a solid form; that is, a compound in a water solution, while it may be hydrated, is not a hydrate as the term is used herein.

A "solvate" is similar to a hydrate except that a solvent other that water is present. For example, methanol or ethanol can form an "alcoholate", which can again be stoichiometric or non-stoichiometric. As the term is used herein a "solvate" refers to a solid form; that is, a compound in a solvent solution, while it may be solvated, is not a solvate as the term is used herein.

"Isotope" refers to atoms with the same number of protons but a different number of neutrons, and an isotope of a compound of Formula (I) includes any such compound wherein one or more atoms are replaced by an isotope of that atom. For example, carbon 12, the most common form of carbon, has six protons and six neutrons, whereas carbon 13 has six protons and seven neutrons, and carbon 14 has six protons and eight neutrons. Hydrogen has two stable isotopes, deuterium (one proton and one neutron) and tritium (one proton and two neutrons). While fluorine has a number of isotopes, fluorine 19 is longest-lived. Thus, an isotope of a compound having the structure of Formula (I) includes, but not limited to, compounds of Formula (I) wherein one or more carbon 12 atoms are replaced by carbon-13 and/or carbon-14 atoms, wherein one or more hydrogen atoms are replaced with deuterium and/or tritium, and/or wherein one or more fluorine atoms are replaced by fluorine-19.

"Salt" generally refers to an organic compound, such as a carboxylic acid or an amine, in ionic form, in combination with a counter ion. For example, salts formed between acids in their anionic form and cations are referred to as "acid addition salts". Conversely, salts formed between bases in the cationic form and anions are referred to as "base addition salts."

Co-crystal forms of compounds having the structure of Formula (I) are also included within the scope of this invention; namely, solids that are crystalline single phase materials composed of two or more different molecular and/or ionic compounds generally in a stoichiometric ratio which are neither solvates nor simple salts.

The term "pharmaceutically acceptable" refers an agent that has been approved for human consumption and is generally non-toxic. For example, the term "pharmaceutically acceptable salt" refers to nontoxic inorganic or organic acid and/or base addition salts (see, e.g., Lit et al., Salt Selection for Basic Drugs, *Int. J. Pharm.*, 33, 201-217, 1986) (incorporated by reference herein).

Pharmaceutically acceptable base addition salts of compounds of the invention include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N'dibenzylethylenediamine, chloroprocaine, choline, diethanolamine-, ethylenediamine, meglumine (Nmethylglucamine-), and procaine.

Pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aromatic aliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, hippuric, malonic, oxalic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, βhydroxybutyric, salicylic, -galactaric, and galacturonic acid.

Although pharmaceutically unacceptable salts are not generally useful as medicaments, such salts may be useful, for example as intermediates in the synthesis of compounds having the structure of Formula I, for example in their purification by recrystallization.

In one embodiment, compounds are provided having the structure of Formula (II), or a pharmaceutically acceptable isomer, racemate, hydrate, solvate, isotope, or salt thereof:

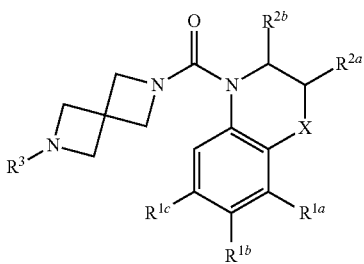

(II)

wherein:

X is —$(CR^xR^y)_nO(CR^xR^y)_q$—, —$(CR^xR^y)_nS(O)_t(CR^xR^y)_q$—, —$(CR^xR^y)_nN(R^x)(CR^xR^y)_q$—, or —$(CR^xR^y)_n$—, $R^x$ is, at each occurrence, independently H, lower alkyl, lower haloalkyl, halo, or $R^6$;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^3$ is —$(CHR^z)_m$-Q-$(R^4)_p$, —$S(=O)_2R^5$, or —$C(=O)R^5$;

$R^z$ is H or $CH_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

$R^5$ is H, cycloalkyl, lower alkyl, lower haloalkyl, lower alkoxy, cycloalkylalkyl, heterocyclyl, or —O-heterocyclyl;

$R^6$ is cycloalkyl, heterocyclyl, or —$C(=O)R^7$;

$R^7$ is H, lower alkyl, or lower haloalkyl;

n is 0, 1, or 2;

q is 0, 1, or 2;

t is 0, 1, or 2;

m is 0, 1, 2, 3, 4, 5, or 6; and p is 0, 1, or 2.

In one embodiment, compounds are provided having the structure of Formula (II-a), or a pharmaceutically acceptable isomer, racemate, hydrate, solvate, isotope, or salt thereof:

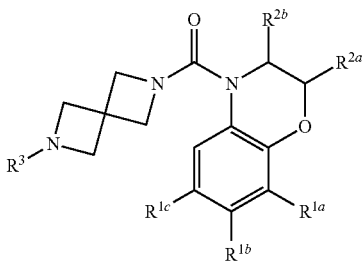

(II-a)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^3$ is —$(CHR^z)_m$-Q-$(R^4)_p$, —$S(=O)_2R^5$, or —$C(=O)R^5$;

$R^z$ is H or $CH_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

$R^5$ is H, cycloalkyl, lower alkyl, lower haloalkyl, lower alkoxy, aryl, heteroaryl, cycloalkylalkyl, heterocyclyl, or —O-heterocyclyl;

m is 0, 1, 2, 3, 4, 5, or 6; and p is 0, 1, or 2.

In one embodiment, compounds are provided having the structure of Formula (II-b), or a pharmaceutically acceptable isomer, racemate, hydrate, solvate, isotope, or salt thereof:

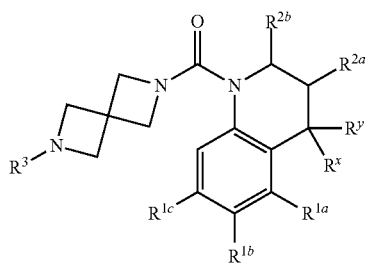

(II-b)

wherein:

$R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^3$ is —$(CHR^z)_m$-Q-$(R^4)_p$, —$S(=O)_2R^5$, or —$C(=O)R^5$;

$R^z$ is H or $CH_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

$R^5$ is H, cycloalkyl, lower alkyl, lower haloalkyl, lower alkoxy, aryl, heteroaryl, cycloalkylalkyl, heterocyclyl, or —O-heterocyclyl;

m is 0, 1, 2, 3, 4, 5, or 6; and p is 0, 1, or 2.

In one embodiment, compounds are provided having the structure of Formula (II-c), or a pharmaceutically acceptable isomer, racemate, hydrate, solvate, isotope, or salt thereof:

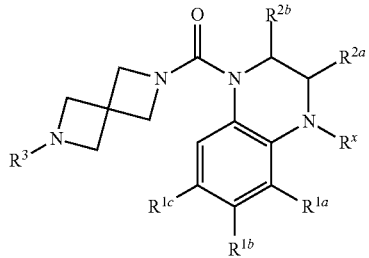

(II-c)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^3$ is —$(CHR^z)_m$-Q-$(R^4)_p$, —$S(=O)_2R^5$, or —$C(=O)R^5$;

$R^z$ is H or $CH_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

$R^5$ is H, cycloalkyl, lower alkyl, lower haloalkyl, lower alkoxy, aryl, heteroaryl, cycloalkylalkyl, heterocyclyl, or —O-heterocyclyl;

m is 0, 1, 2, 3, 4, 5, or 6; and p is 0, 1, or 2.

In one embodiment, compounds are provided having the structure of Formula (II-d), or a pharmaceutically acceptable isomer, racemate, hydrate, solvate, isotope, or salt thereof:

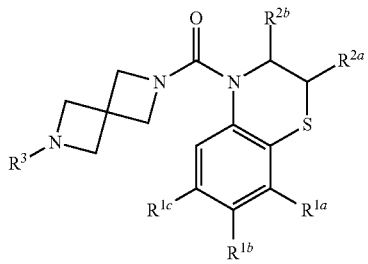

(II-d)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^3$ is —$(CHR^z)_m$-Q-$(R^4)_p$, —$S(=O)_2R^5$, or —$C(=O)R^5$;

$R^z$ is H or $CH_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

$R^5$ is H, cycloalkyl, lower alkyl, lower haloalkyl, lower alkoxy, aryl, heteroaryl, cycloalkylalkyl, heterocyclyl, or —O-heterocyclyl;

m is 0, 1, 2, 3, 4, 5, or 6; and p is 0, 1, or 2.

In one embodiment, compounds are provided having the structure of Formula (II-e), or a pharmaceutically acceptable isomer, racemate, hydrate, solvate, isotope, or salt thereof:

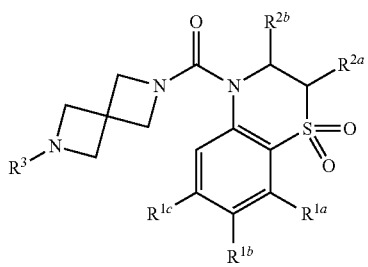

(II-e)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^3$ is —$(CHR^z)_m$-Q-$(R^4)_p$, —$S(=O)_2R^5$, or —$C(=O)R^5$;

$R^z$ is H or $CH_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

$R^5$ is H, cycloalkyl, lower alkyl, lower haloalkyl, lower alkoxy, aryl, heteroaryl, cycloalkylalkyl, heterocyclyl, or —O-heterocyclyl;

m is 0, 1, 2, 3, 4, 5, or 6; and p is 0, 1, or 2.

In one embodiment, compounds are provided having the structure of Formula (II-f), or a pharmaceutically acceptable isomer, racemate, hydrate, solvate, isotope, or salt thereof:

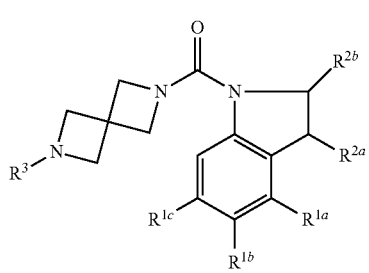

(II-f)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^3$ is —$(CHR^z)_m$-Q-$(R^4)_p$, —$S(=O)_2R^5$, or —$C(=O)R^5$;

$R^z$ is H or $CH_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

$R^5$ is H, cycloalkyl, lower alkyl, lower haloalkyl, lower alkoxy, aryl, heteroaryl, cycloalkylalkyl, heterocyclyl, or —O-heterocyclyl;

m is 0, 1, 2, 3, 4, 5, or 6; and p is 0, 1, or 2.

In one embodiment, compounds are provided having the structure of Formula (II-g), or a pharmaceutically acceptable isomer, racemate, hydrate, solvate, isotope, or salt thereof:

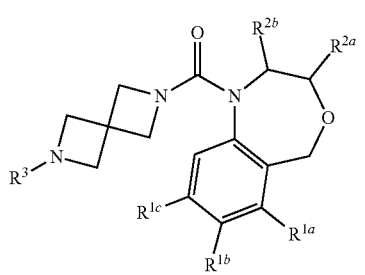

(II-g)

wherein:
R$^{1a}$, R$^{1b}$, and R$^{1c}$ are each, independently, H, lower alkyl, lower haloalkyl, lower alkoxy, cyano, or halo;
R$^{2a}$ and R$^{2b}$ are each, independently, H, lower alkyl, lower haloalkyl, or lower alkoxy;
R$^3$ is —(CHR$^z$)$_m$-Q-(R$^4$)$_p$, —S(=O)$_2$R$^5$, or —C(=O)R$^5$;
R$^z$ is H or CH$_3$
Q is aryl or heteroaryl;
R$^4$ is, at each occurrence, independently H, —OH, =O, cycloalkyl, lower alkyl, lower haloalkyl, lower alkoxy, lower haloalkoxy, halo, or cyano;
R$^5$ is H, cycloalkyl, lower alkyl, lower haloalkyl, lower alkoxy, aryl, heteroaryl, cycloalkylalkyl, heterocyclyl, or —O-heterocyclyl;
m is 0, 1, 2, 3, 4, 5, or 6; and
p is 0, 1, or 2.

In one embodiment, compounds are provided having the structure of Formula (II-h), or a pharmaceutically acceptable isomer, racemate, hydrate, solvate, isotope, or salt thereof:

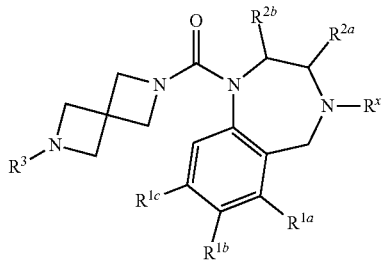

(II-h)

wherein:
R$^x$ is, at each occurrence, independently H, lower alkyl, lower haloalkyl, or halo;
R$^{1a}$, R$^{1b}$, and R$^{1c}$ are each, independently, H, lower alkyl, lower haloalkyl, lower alkoxy, cyano, or halo;
R$^{2a}$ and R$^{2b}$ are each, independently, H, lower alkyl, lower haloalkyl, or lower alkoxy;
R$^3$ is —(CHR$^z$)$_m$-Q-(R$^4$)$_p$, —S(=O)$_2$R$^5$, or —C(=O)R$^5$;
R$^z$ is H or CH$_3$
Q is aryl or heteroaryl;
R$^4$ is, at each occurrence, independently H, —OH, =O, cycloalkyl, lower alkyl, lower haloalkyl, lower alkoxy, lower haloalkoxy, halo, or cyano;
R$^5$ is H, cycloalkyl, lower alkyl, lower haloalkyl, lower alkoxy, aryl, heteroaryl, cycloalkylalkyl, heterocyclyl, or —O-heterocyclyl;
m is 0, 1, 2, 3, 4, 5, or 6; and
p is 0, 1, or 2.

In one embodiment, compounds are provided having the structure of Formula (II-i), or a pharmaceutically acceptable isomer, racemate, hydrate, solvate, isotope, or salt thereof:

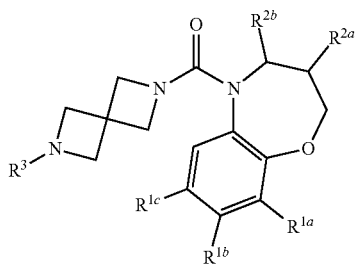

(II-i)

wherein:
R$^{1a}$, R$^{1b}$, and R$^{1c}$ are each, independently, H, lower alkyl, lower haloalkyl, lower alkoxy, cyano, or halo;
R$^{2a}$ and R$^{2b}$ are each, independently, H, lower alkyl, lower haloalkyl, or lower alkoxy;
R$^3$ is —(CHR$^z$)$_m$-Q-(R$^4$)$_p$, —S(=O)$_2$R$^5$, or —C(=O)R$^5$;
R$^z$ is H or CH$_3$
Q is aryl or heteroaryl;
R$^4$ is, at each occurrence, independently H, —OH, =O, cycloalkyl, lower alkyl, lower haloalkyl, lower alkoxy, lower haloalkoxy, halo, or cyano;
R$^5$ is H, cycloalkyl, lower alkyl, lower haloalkyl, lower alkoxy, aryl, heteroaryl, cycloalkylalkyl, heterocyclyl, or —O-heterocyclyl;
m is 0, 1, 2, 3, 4, 5, or 6; and
p is 0, 1, or 2.

In one embodiment, compounds are provided having the structure of Formula (II-j), or a pharmaceutically acceptable isomer, racemate, hydrate, solvate, isotope, or salt thereof:

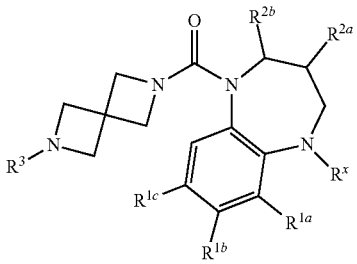

(II-j)

wherein:
R$^x$ is, at each occurrence, independently H, lower alkyl, lower haloalkyl, or halo;
R$^{1a}$, R$^{1b}$, and R$^{1c}$ are each, independently, H, lower alkyl, lower haloalkyl, lower alkoxy, cyano, or halo;
R$^{2a}$ and R$^{2b}$ are each, independently, H, lower alkyl, lower haloalkyl, or lower alkoxy;
R$^3$ is —(CHR$^z$)$_m$-Q-(R$^4$)$_p$, —S(=O)$_2$R$^5$, or —C(=O)R$^5$;
R$^z$ is H or CH$_3$
Q is aryl or heteroaryl;
R$^4$ is, at each occurrence, independently H, —OH, =O, cycloalkyl, lower alkyl, lower haloalkyl, lower alkoxy, lower haloalkoxy, halo, or cyano;
R$^5$ is H, cycloalkyl, lower alkyl, lower haloalkyl, lower alkoxy, aryl, heteroaryl, cycloalkylalkyl, heterocyclyl, or —O-heterocyclyl;
m is 0, 1, 2, 3, 4, 5, or 6; and
p is 0, 1, or 2.

In one embodiment, compounds are provided having the structure of Formula (II-k), or a pharmaceutically acceptable isomer, racemate, hydrate, solvate, isotope, or salt thereof:

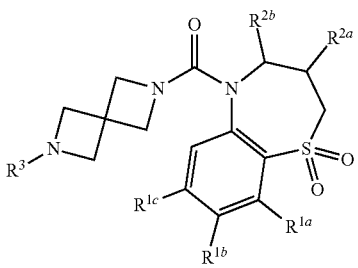

(II-k)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^3$ is —(CHR$^z$)$_m$-Q-(R$^4$)$_p$, —S(=O)$_2$R$^5$, or —C(=O)R$^5$;

R$^z$ is H or CH$_3$

Q is aryl or heteroaryl;

R$^4$ is, at each occurrence, independently H, —OH, =O, cycloalkyl, lower alkyl, lower haloalkyl, lower alkoxy, lower haloalkoxy, halo, or cyano;

R$^5$ is H, cycloalkyl, lower alkyl, lower haloalkyl, lower alkoxy, aryl, heteroaryl, cycloalkylalkyl, heterocyclyl, or —O-heterocyclyl;

m is 0, 1, 2, 3, 4, 5, or 6; and p is 0, 1, or 2.

In one embodiment, compounds are provided having the structure of Formula (III), or a pharmaceutically acceptable isomer, racemate, hydrate, solvate, isotope, or salt thereof:

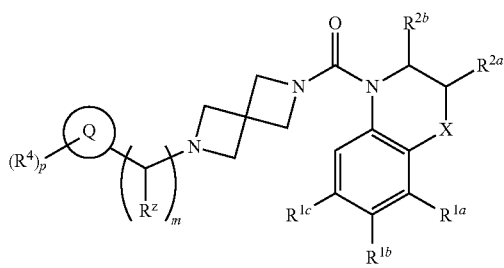

(III)

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—,

R$^x$ is, at each occurrence, independently H, lower alkyl, lower haloalkyl, or halo;

R$^y$ is, at each occurrence, independently H, —OH, lower alkyl, lower alkoxy, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^z$ is H or CH$_3$

Q is aryl or heteroaryl;

R$^4$ is, at each occurrence, independently H, —OH, =O, cycloalkyl, lower alkyl, lower haloalkyl, lower alkoxy, lower haloalkoxy, halo, or cyano;

n is 0, 1, or 2;

q is 0, 1, or 2;

t is 0, 1, or 2;

m is 0, 1, 2, 3, 4, 5, or 6; and p is 0, 1, or 2.

In one embodiment, compounds are provided having the structure of Formula (III-a), or a pharmaceutically acceptable isomer, racemate, hydrate, solvate, isotope, or salt thereof:

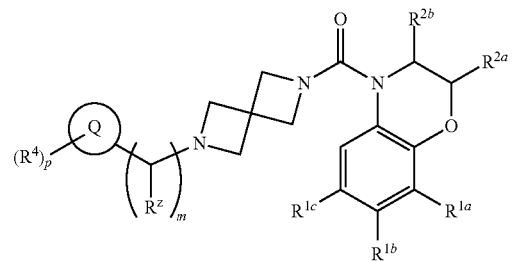

(III-a)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^z$ is H or CH$_3$

Q is aryl or heteroaryl;

R$^4$ is, at each occurrence, independently H, —OH, =O, cycloalkyl, lower alkyl, lower haloalkyl, lower alkoxy, lower haloalkoxy, halo, or cyano;

m is 0, 1, 2, 3, 4, 5, or 6; and p is 0, 1, or 2.

In one embodiment, compounds are provided having the structure of Formula (III-b), or a pharmaceutically acceptable isomer, racemate, hydrate, solvate, isotope, or salt thereof:

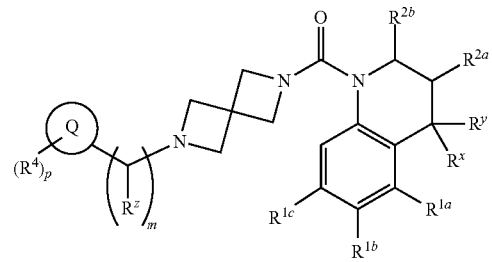

(III-b)

wherein:

R$^x$ is, at each occurrence, independently H, lower alkyl, lower haloalkyl, or halo;

R$^y$ is, at each occurrence, independently H, —OH, lower alkyl, lower alkoxy, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^z$ is H or CH$_3$

Q is aryl or heteroaryl;

R$^4$ is, at each occurrence, independently H, —OH, =O, cycloalkyl, lower alkyl, lower haloalkyl, lower alkoxy, lower haloalkoxy, halo, or cyano;

m is 0, 1, 2, 3, 4, 5, or 6; and p is 0, 1, or 2.

In one embodiment, compounds are provided having the structure of Formula (III-c), or a pharmaceutically acceptable isomer, racemate, hydrate, solvate, isotope, or salt thereof:

(III-c)

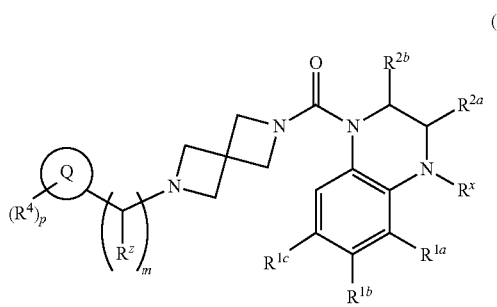

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^z$ is H or $CH_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

m is 0, 1, 2, 3, 4, 5, or 6; and p is 0, 1, or 2.

In one embodiment, compounds are provided having the structure of Formula (III-d), or a pharmaceutically acceptable isomer, racemate, hydrate, solvate, isotope, or salt thereof:

(III-d)

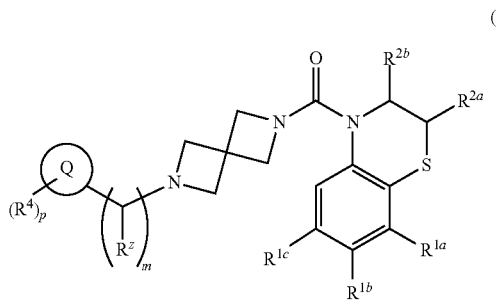

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^z$ is H or $CH_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

m is 0, 1, 2, 3, 4, 5, or 6; and p is 0, 1, or 2.

In one embodiment, compounds are provided having the structure of Formula (III-e), or a pharmaceutically acceptable isomer, racemate, hydrate, solvate, isotope, or salt thereof:

(III-e)

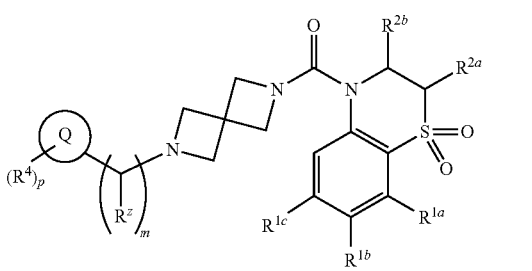

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^z$ is H or $CH_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

m is 0, 1, 2, 3, 4, 5, or 6; and p is 0, 1, or 2.

In one embodiment, compounds are provided having the structure of Formula (III-f), or a pharmaceutically acceptable isomer, racemate, hydrate, solvate, isotope, or salt thereof:

(III-f)

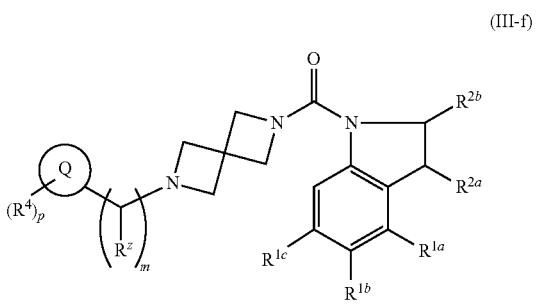

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^z$ is H or $CH_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

m is 0, 1, 2, 3, 4, 5, or 6; and p is 0, 1, or 2.

In one embodiment, compounds are provided having the structure of Formula (III-g), or a pharmaceutically acceptable isomer, racemate, hydrate, solvate, isotope, or salt thereof:

(III-g)

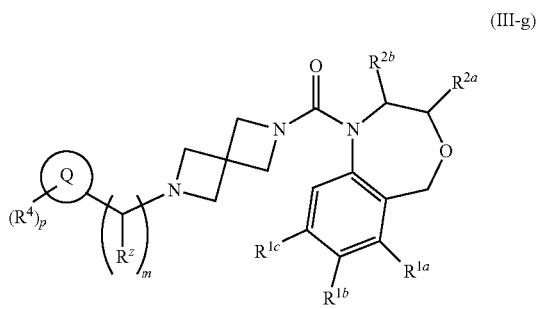

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^z$ is H or $CH_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

m is 0, 1, 2, 3, 4, 5, or 6; and p is 0, 1, or 2.

In one embodiment, compounds are provided having the structure of Formula (III-h), or a pharmaceutically acceptable isomer, racemate, hydrate, solvate, isotope, or salt thereof:

(III-h)

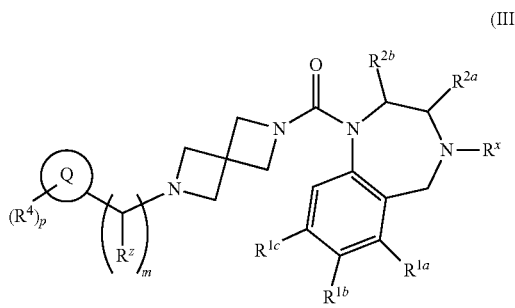

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^z$ is H or $CH_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

m is 0, 1, 2, 3, 4, 5, or 6; and p is 0, 1, or 2.

In one embodiment, compounds are provided having the structure of Formula (III-i), or a pharmaceutically acceptable isomer, racemate, hydrate, solvate, isotope, or salt thereof:

(III-i)

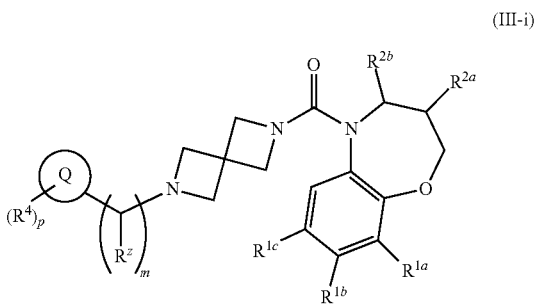

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^z$ is H or $CH_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

m is 0, 1, 2, 3, 4, 5, or 6; and p is 0, 1, or 2.

In one embodiment, compounds are provided having the structure of Formula (III-j), or a pharmaceutically acceptable isomer, racemate, hydrate, solvate, isotope, or salt thereof:

(III-j)

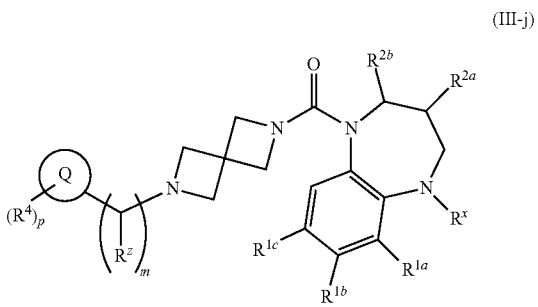

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^z$ is H or $CH_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

m is 0, 1, 2, 3, 4, 5, or 6; and p is 0, 1, or 2.

In one embodiment, compounds are provided having the structure of Formula (III-k), or a pharmaceutically acceptable isomer, racemate, hydrate, solvate, isotope, or salt thereof:

(III-k)

wherein:
R$^{1a}$, R$^{1b}$, and R$^{1c}$ are each, independently, H, lower alkyl, lower haloalkyl, lower alkoxy, cyano, or halo;
R$^{2a}$ and R$^{2b}$ are each, independently, H, lower alkyl, lower haloalkyl, or lower alkoxy;
R$^z$ is H or CH$_3$
Q is aryl or heteroaryl;
R$^4$ is, at each occurrence, independently H, —OH, =O, cycloalkyl, lower alkyl, lower haloalkyl, lower alkoxy, lower haloalkoxy, halo, or cyano;
m is 0, 1, 2, 3, 4, 5, or 6; and
p is 0, 1, or 2.

In one embodiment, compounds are provided having the structure of Formula (IV), or a pharmaceutically acceptable isomer, racemate, hydrate, solvate, isotope, or salt thereof:

(IV)

wherein:
X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—,
R$^x$ is, at each occurrence, independently H, lower alkyl, lower haloalkyl, or halo;
R$^y$ is, at each occurrence, independently H, —OH, lower alkyl, lower alkoxy, or halo;
R$^{1a}$, R$^{1b}$, and R$^{1c}$ are each, independently, H, lower alkyl, lower haloalkyl, lower alkoxy, cyano, or halo;
R$^{2a}$ and R$^{2b}$ are each, independently, H, lower alkyl, lower haloalkyl, or lower alkoxy;
R$^z$ is H or CH$_3$
J$^1$, J$^2$, J$^3$, and J$^4$ are each, independently, N, O, CH, or CR$^4$;
R$^4$ is, at each occurrence, independently H, —OH, =O, cycloalkyl, lower alkyl, lower haloalkyl, lower alkoxy, lower haloalkoxy, halo, or cyano;
n is 0, 1, or 2;
q is 0, 1, or 2;
t is 0, 1, or 2;
p is 0, 1, or 2.

In one embodiment, compounds are provided having the structure of Formula (IV-a), or a pharmaceutically acceptable isomer, racemate, hydrate, solvate, isotope, or salt thereof:

(IV-a)

wherein:
R$^{1a}$, R$^{1b}$, and R$^{1c}$ are each, independently, H, lower alkyl, lower haloalkyl, lower alkoxy, cyano, or halo;
R$^{2a}$ and R$^{2b}$ are each, independently, H, lower alkyl, lower haloalkyl, or lower alkoxy;
R$^z$ is H or CH$_3$
J$^1$, J$^2$, J$^3$, and J$^4$ are each, independently, N, O, CH, or CR$^4$;
R$^4$ is, at each occurrence, independently H, —OH, =O, cycloalkyl, lower alkyl, lower haloalkyl, lower alkoxy, lower haloalkoxy, halo, or cyano; and
p is 0, 1, or 2.

In one embodiment, compounds are provided having the structure of Formula (IV-b), or a pharmaceutically acceptable isomer, racemate, hydrate, solvate, isotope, or salt thereof:

(IV-b)

wherein:
R$^x$ is, at each occurrence, independently H, lower alkyl, lower haloalkyl, or halo;
R$^y$ is, at each occurrence, independently H, —OH, lower alkyl, lower alkoxy, or halo;
R$^{1a}$, R$^{1b}$, and R$^{1c}$ are each, independently, H, lower alkyl, lower haloalkyl, lower alkoxy, cyano, or halo;
R$^{2a}$ and R$^{2b}$ are each, independently, H, lower alkyl, lower haloalkyl, or lower alkoxy;
R$^z$ is H or CH$_3$
J$^1$, J$^2$, J$^3$, and J$^4$ are each, independently, N, O, CH, or CR$^4$;
R$^4$ is, at each occurrence, independently H, —OH, =O, cycloalkyl, lower alkyl, lower haloalkyl, lower alkoxy, lower haloalkoxy, halo, or cyano; and
p is 0, 1, or 2.

In one embodiment, compounds are provided having the structure of Formula (IV-c), or a pharmaceutically acceptable isomer, racemate, hydrate, solvate, isotope, or salt thereof:

(IV-c)

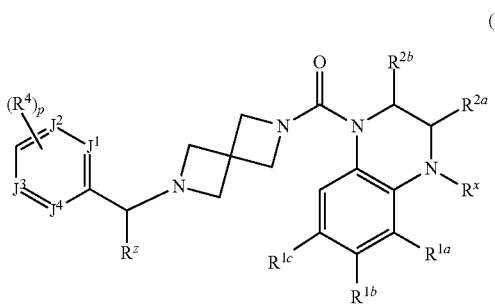

(IV-e)

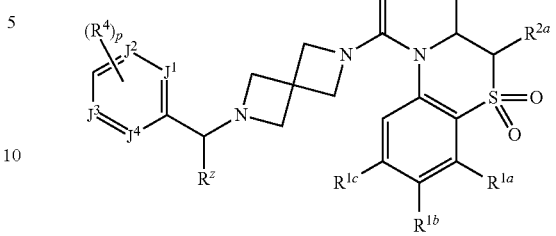

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^z$ is H or $CH_3$ $J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (IV-d), or a pharmaceutically acceptable isomer, racemate, hydrate, solvate, isotope, or salt thereof:

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^z$ is H or $CH_3$ $J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (IV-f), or a pharmaceutically acceptable isomer, racemate, hydrate, solvate, isotope, or salt thereof:

(IV-d)

(IV-f)

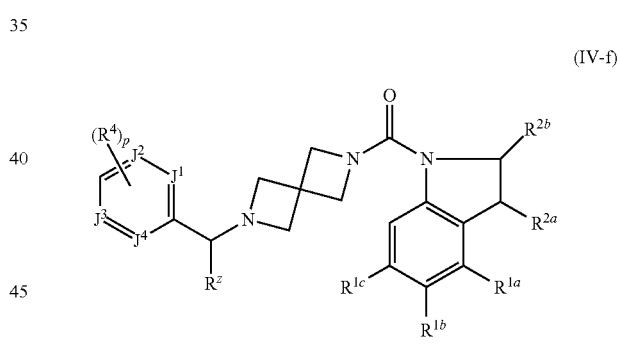

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^z$ is H or $CH_3$ $J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (IV-e), or a pharmaceutically acceptable isomer, racemate, hydrate, solvate, isotope, or salt thereof:

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^z$ is H or $CH_3$ $J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (IV-g), or a pharmaceutically acceptable isomer, racemate, hydrate, solvate, isotope, or salt thereof:

(IV-g)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^z$ is H or $CH_3$ $J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (IV-h), or a pharmaceutically acceptable isomer, racemate, hydrate, solvate, isotope, or salt thereof:

(IV-h)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^z$ is H or $CH_3$ $J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (IV-i), or a pharmaceutically acceptable isomer, racemate, hydrate, solvate, isotope, or salt thereof:

(IV-i)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^z$ is H or $CH_3$ $J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (IV-j), or a pharmaceutically acceptable isomer, racemate, hydrate, solvate, isotope, or salt thereof:

(IV-j)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^z$ is H or $CH_3$ $J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (IV-k), or a pharmaceutically acceptable isomer, racemate, hydrate, solvate, isotope, or salt thereof:

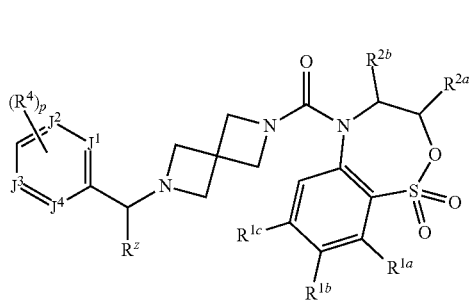

(IV-k)

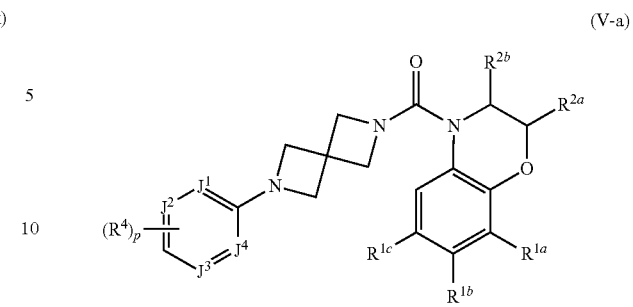

(V-a)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^z$ is H or $CH_3$ $J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (V), or a pharmaceutically acceptable isomer, racemate, hydrate, solvate, isotope, or salt thereof:

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (V-b), or a pharmaceutically acceptable isomer, racemate, hydrate, solvate, isotope, or salt thereof:

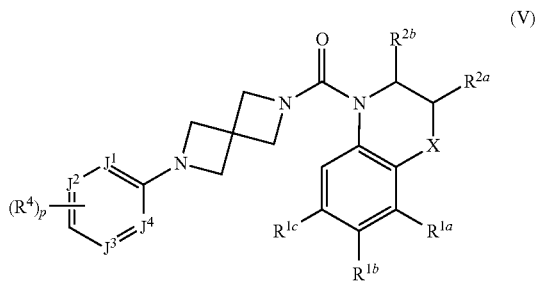

(V)

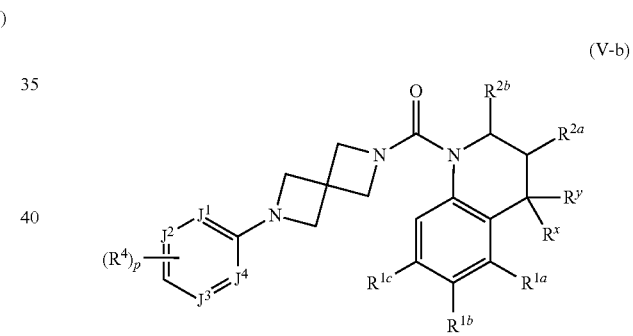

(V-b)

wherein:

X is —$(CR^xR^y)_nO(CR^xR^y)_q$—, —$(CR^xR^y)_nS(O)_t(CR^xR^y)_q$—, —$(CR^xR^y)_nN(R^x)(CR^xR^y)_q$—, or —$(CR^xR^y)_n$—, $R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano;

n is 0, 1, or 2;

q is 0, 1, or 2;

t is 0, 1, or 2;

p is 0, 1, or 2.

In one embodiment, compounds are provided having the structure of Formula (V-a), or a pharmaceutically acceptable isomer, racemate, hydrate, solvate, isotope, or salt thereof:

wherein:

$R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (V-c), or a pharmaceutically acceptable isomer, racemate, hydrate, solvate, isotope, or salt thereof:

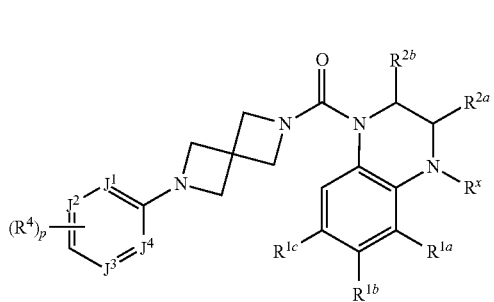

(V-c)

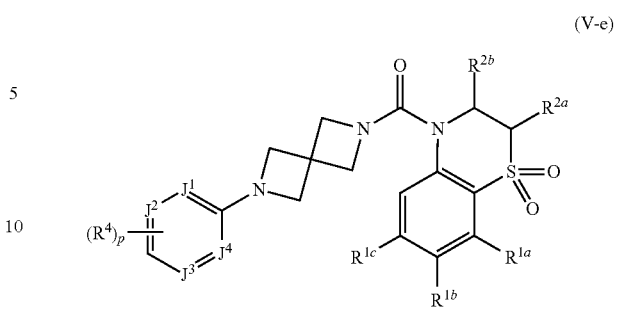

(V-e)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (V-d), or a pharmaceutically acceptable isomer, racemate, hydrate, solvate, isotope, or salt thereof:

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (V-f), or a pharmaceutically acceptable isomer, racemate, hydrate, solvate, isotope, or salt thereof:

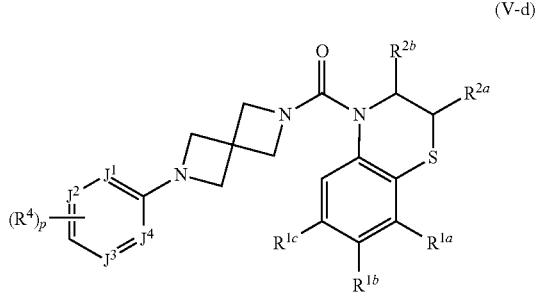

(V-d)

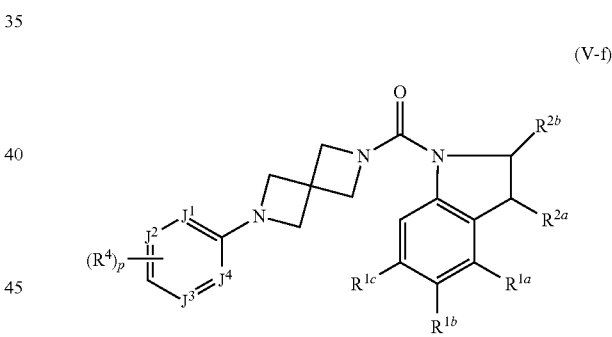

(V-f)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (V-e), or a pharmaceutically acceptable isomer, racemate, hydrate, solvate, isotope, or salt thereof:

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (V-g), or a pharmaceutically acceptable isomer, racemate, hydrate, solvate, isotope, or salt thereof:

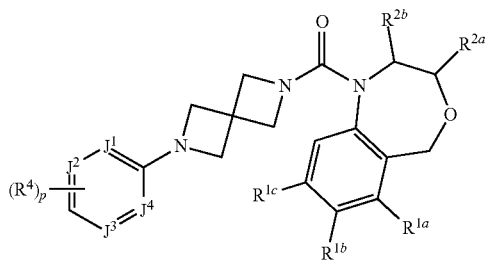

(V-g)

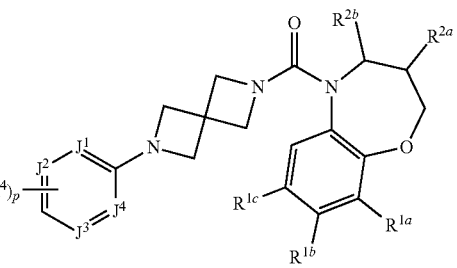

(V-i)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (V-h), or a pharmaceutically acceptable isomer, racemate, hydrate, solvate, isotope, or salt thereof:

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (V-j), or a pharmaceutically acceptable isomer, racemate, hydrate, solvate, isotope, or salt thereof:

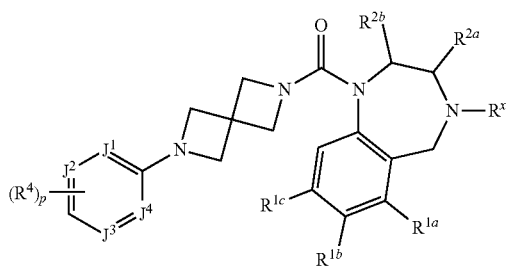

(V-h)

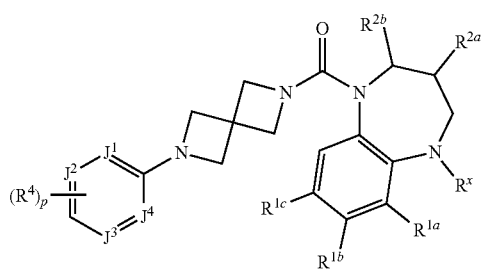

(V-j)

wherein:

$R^x$ is, at each occurrence, independently H, lower alkyl, lower haloalkyl, or halo;

$T^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (V-i), or a pharmaceutically acceptable isomer, racemate, hydrate, solvate, isotope, or salt thereof:

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (V-k), or a pharmaceutically acceptable isomer, racemate, hydrate, solvate, isotope, or salt thereof:

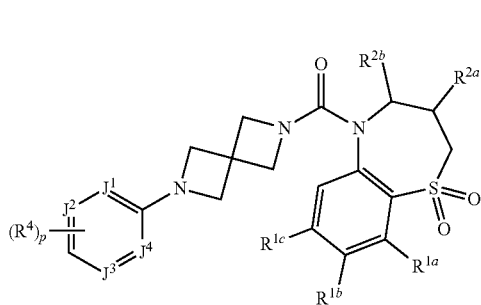

(V-k)

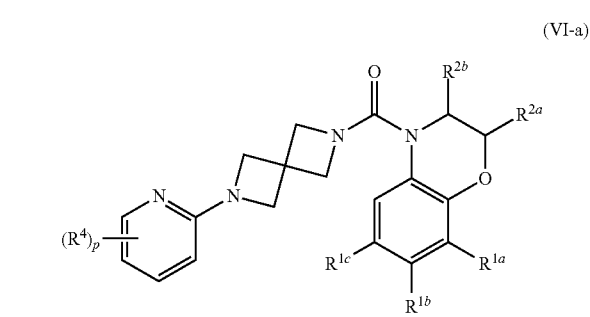

(VI-a)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VI), or a pharmaceutically acceptable isomer, racemate, hydrate, solvate, isotope, or salt thereof:

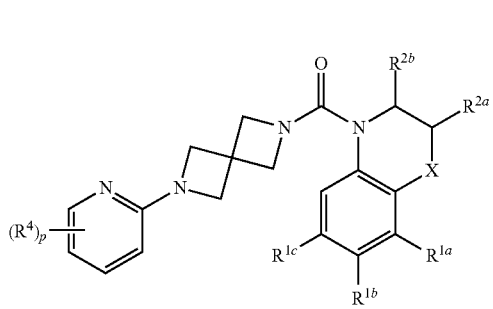

(VI)

wherein:

X is —$(CR^xR^y)_nO(CR^xR^y)_q$—, —$(CR^xR^y)_nS(O)_t(CR^xR^y)_q$—, —$(CR^xR^y)_nN(R^x)(CR^xR^y)_q$—, or —$(CR^xR^y)_n$—, $R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano;

n is 0, 1, or 2;

q is 0, 1, or 2;

t is 0, 1, or 2;

p is 0, 1, or 2.

In one embodiment, compounds are provided having the structure of Formula (VI-a), or a pharmaceutically acceptable isomer, racemate, hydrate, solvate, isotope, or salt thereof:

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VI-b), or a pharmaceutically acceptable isomer, racemate, hydrate, solvate, isotope, or salt thereof:

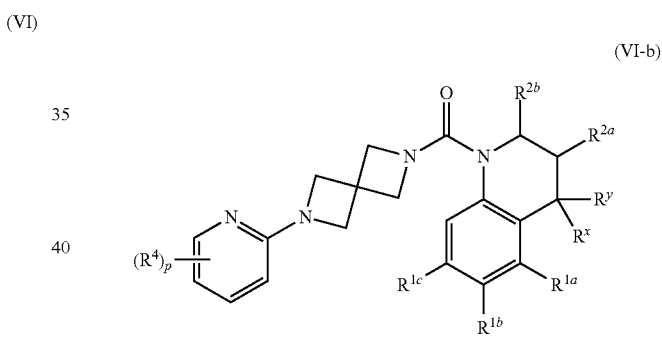

(VI-b)

wherein:

$R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VI-c), or a pharmaceutically acceptable isomer, racemate, hydrate, solvate, isotope, or salt thereof:

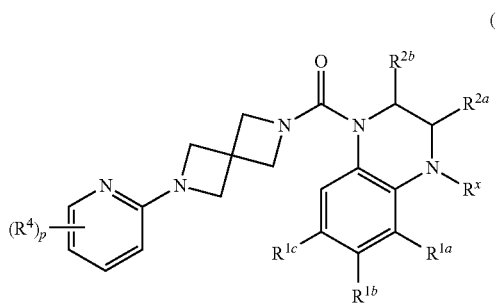

(VI-c)

wherein:

R$^x$ is, at each occurrence, independently H, lower alkyl, lower haloalkyl, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VI-d), or a pharmaceutically acceptable isomer, racemate, hydrate, solvate, isotope, or salt thereof:

(VI-d)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VI-e), or a pharmaceutically acceptable isomer, racemate, hydrate, solvate, isotope, or salt thereof:

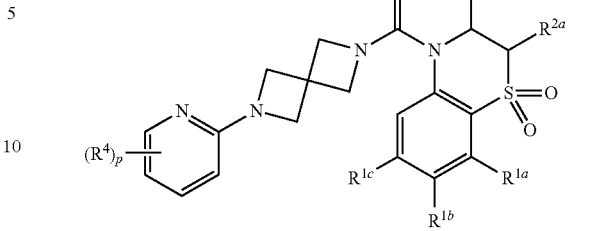

(VI-e)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VI-f), or a pharmaceutically acceptable isomer, racemate, hydrate, solvate, isotope, or salt thereof:

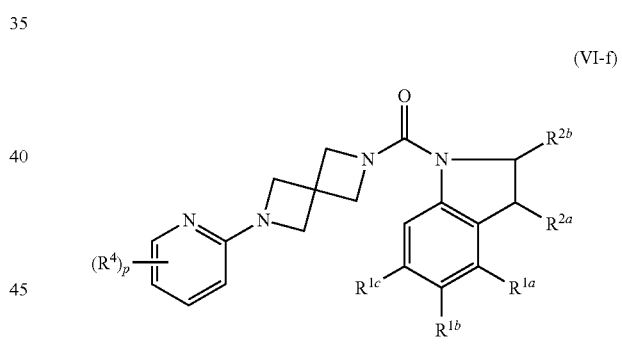

(VI-f)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VI-g), or a pharmaceutically acceptable isomer, racemate, hydrate, solvate, isotope, or salt thereof:

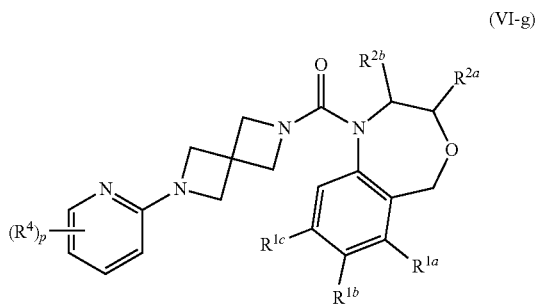

(VI-g)

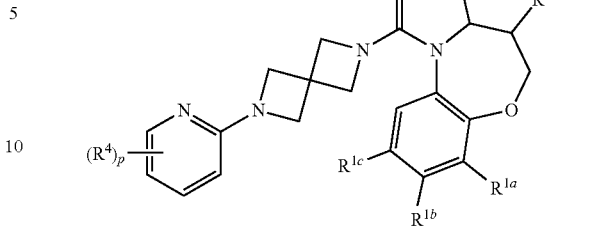

(VI-i)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, ═O, cycloalkyl, lower alkyl, lower haloalkyl, lower alkoxy, lower haloalkoxy, halo, or cyano; and p is 0, 1, or 2.

In one embodiment, compounds are provided having the structure of Formula (VI-h), or a pharmaceutically acceptable isomer, racemate, hydrate, solvate, isotope, or salt thereof:

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, ═O, cycloalkyl, lower alkyl, lower haloalkyl, lower alkoxy, lower haloalkoxy, halo, or cyano; and p is 0, 1, or 2.

In one embodiment, compounds are provided having the structure of Formula (VI-j), or a pharmaceutically acceptable isomer, racemate, hydrate, solvate, isotope, or salt thereof:

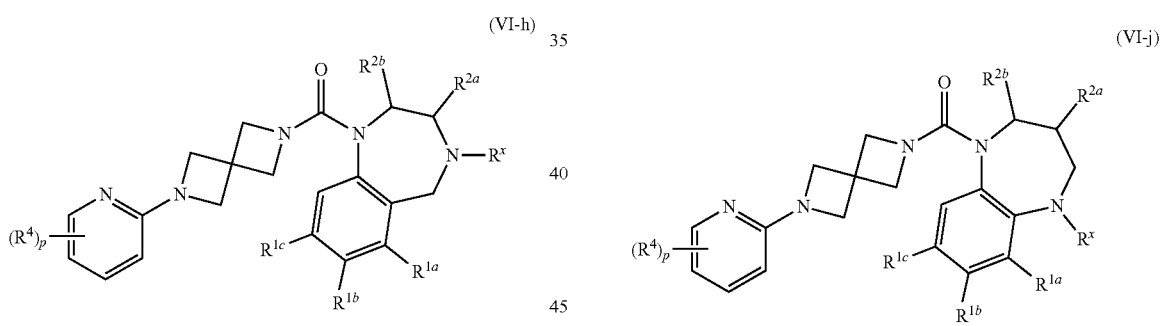

(VI-h)

(VI-j)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, ═O, cycloalkyl, lower alkyl, lower haloalkyl, lower alkoxy, lower haloalkoxy, halo, or cyano; and p is 0, 1, or 2.

In one embodiment, compounds are provided having the structure of Formula (VI-i), or a pharmaceutically acceptable isomer, racemate, hydrate, solvate, isotope, or salt thereof:

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, ═O, cycloalkyl, lower alkyl, lower haloalkyl, lower alkoxy, lower haloalkoxy, halo, or cyano; and p is 0, 1, or 2.

In one embodiment, compounds are provided having the structure of Formula (VI-k), or a pharmaceutically acceptable isomer, racemate, hydrate, solvate, isotope, or salt thereof:

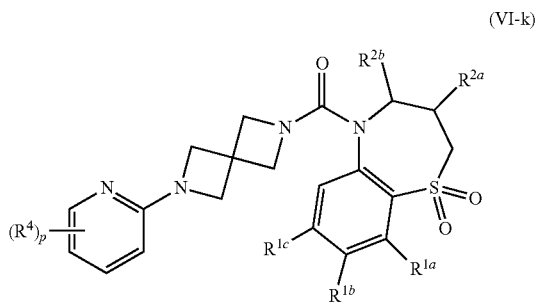

(VI-k)

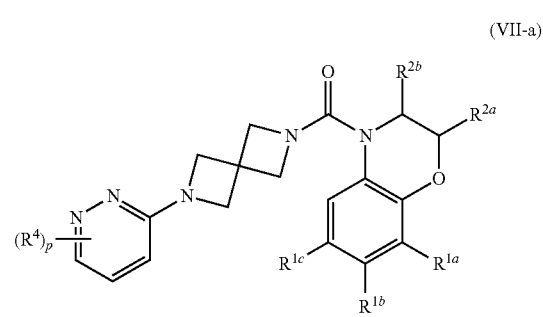

(VII-a)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VII), or a pharmaceutically acceptable isomer, racemate, hydrate, solvate, isotope, or salt thereof:

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VII-b), or a pharmaceutically acceptable isomer, racemate, hydrate, solvate, isotope, or salt thereof:

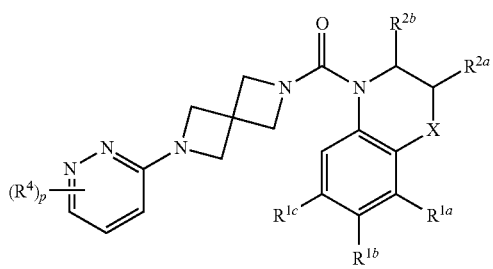

(VII)

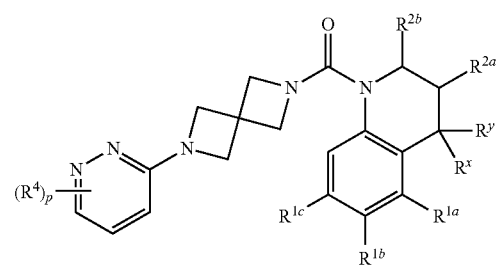

(VII-b)

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—, $R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano;

n is 0, 1, or 2;

q is 0, 1, or 2;

t is 0, 1, or 2;

p is 0, 1, or 2.

In one embodiment, compounds are provided having the structure of Formula (VII-a), or a pharmaceutically acceptable isomer, racemate, hydrate, solvate, isotope, or salt thereof:

wherein:

$R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VII-c), or a pharmaceutically acceptable isomer, racemate, hydrate, solvate, isotope, or salt thereof:

(VII-c)

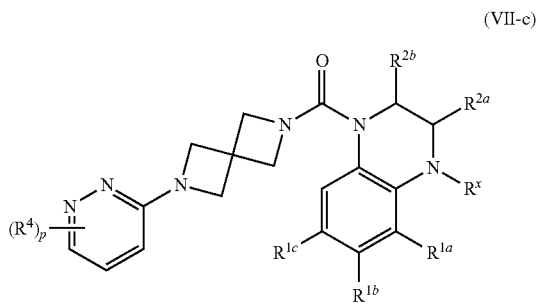

wherein:

R$^x$ is, at each occurrence, independently H, lower alkyl, lower haloalkyl, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VII-d), or a pharmaceutically acceptable isomer, racemate, hydrate, solvate, isotope, or salt thereof:

(VII-d)

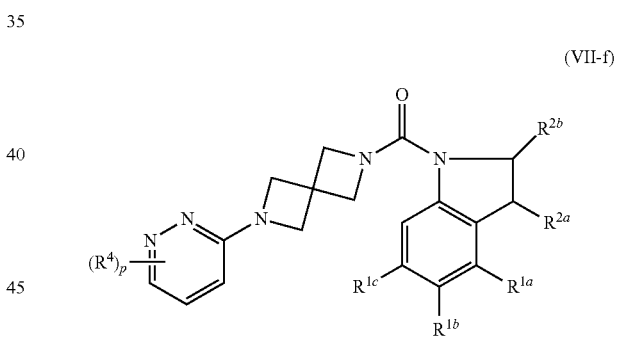

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VII-e), or a pharmaceutically acceptable isomer, racemate, hydrate, solvate, isotope, or salt thereof:

(VII-e)

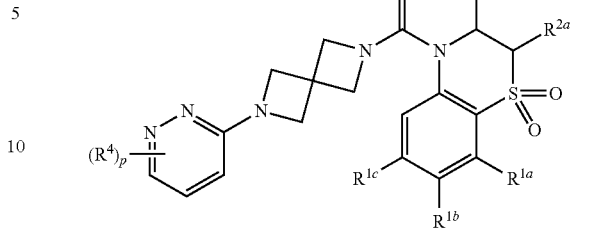

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VII-f), or a pharmaceutically acceptable isomer, racemate, hydrate, solvate, isotope, or salt thereof:

(VII-f)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VII-g), or a pharmaceutically acceptable isomer, racemate, hydrate, solvate, isotope, or salt thereof:

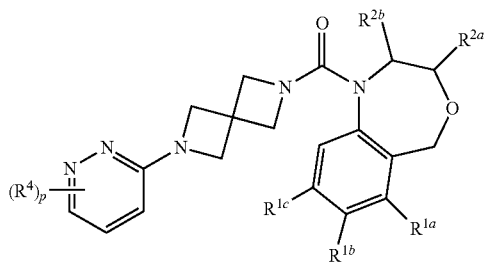

(VII-g)

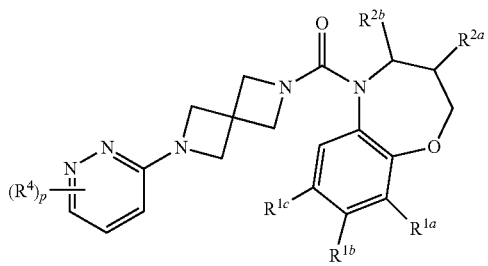

(VII-i)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VII-h), or a pharmaceutically acceptable isomer, racemate, hydrate, solvate, isotope, or salt thereof:

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VII-j), or a pharmaceutically acceptable isomer, racemate, hydrate, solvate, isotope, or salt thereof:

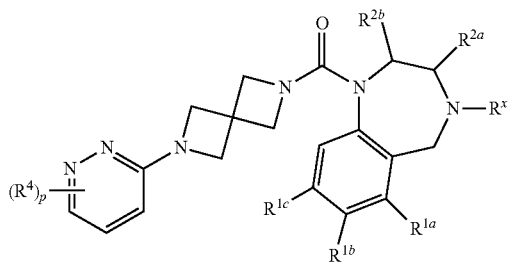

(VII-h)

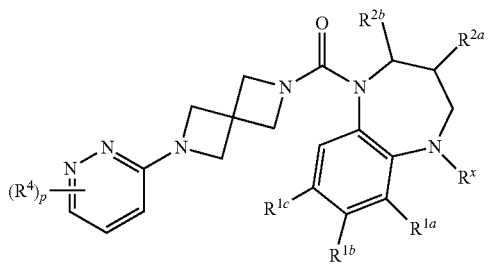

(VII-j)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VII-i), or a pharmaceutically acceptable isomer, racemate, hydrate, solvate, isotope, or salt thereof:

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VII-k), or a pharmaceutically acceptable isomer, racemate, hydrate, solvate, isotope, or salt thereof:

(VII-k)

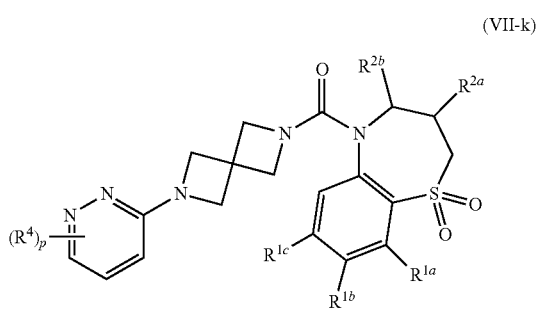

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In further embodiments, compounds are provided having the structure of Formula (VII-a), or a pharmaceutically acceptable isomer, racemate, hydrate, solvate, isotope, or salt thereof, wherein p is zero. In more specific embodiments, compounds are provided having the structure of Formula (VII-a) or a pharmaceutically acceptable isomer, racemate, hydrate, solvate, isotope, or salt thereof, wherein $R^{1b}$ is halo; $R^{1a}$ and $R^{1c}$ are each, independently, H, lower alkyl, lower alkoxy; and $R^{2a}$ and $R^{2b}$ are each, independently, H, lower alkyl, or lower alkoxy.

In one embodiment, compounds are provided having the structure of Formula (VIII), or a pharmaceutically acceptable isomer, racemate, hydrate, solvate, isotope, or salt thereof:

(VIII)

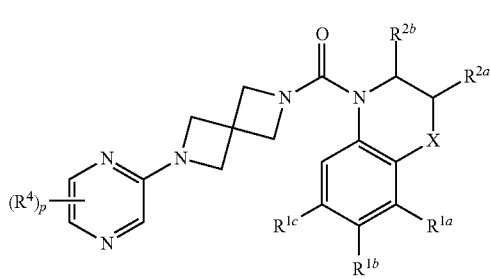

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—, $R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano;

n is 0, 1, or 2;
q is 0, 1, or 2;
t is 0, 1, or 2;
p is 0, 1, or 2.

In one embodiment, compounds are provided having the structure of Formula (VIII-a), or a pharmaceutically acceptable isomer, racemate, hydrate, solvate, isotope, or salt thereof:

(VIII-a)

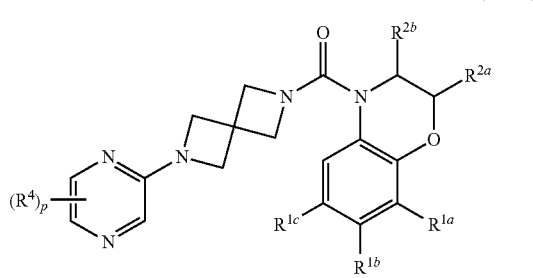

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VIII-b), or a pharmaceutically acceptable isomer, racemate, hydrate, solvate, isotope, or salt thereof:

(VIII-b)

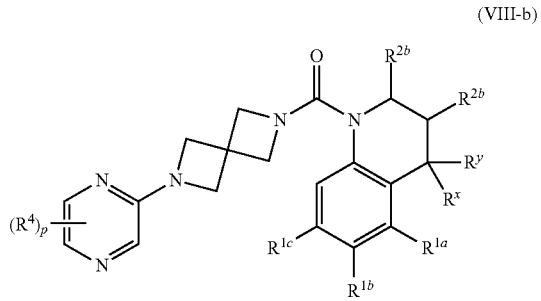

wherein:

$R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VIII-c), or a pharmaceutically acceptable isomer, racemate, hydrate, solvate, isotope, or salt thereof:

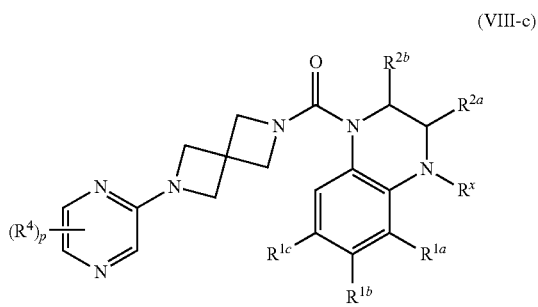

(VIII-c)

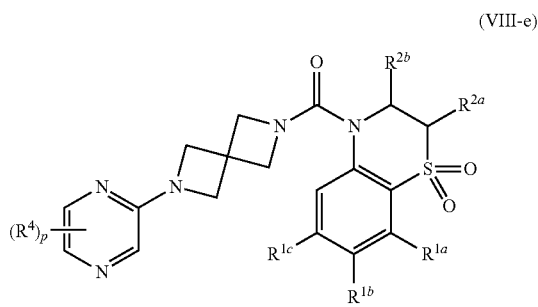

(VIII-e)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VIII-d), or a pharmaceutically acceptable isomer, racemate, hydrate, solvate, isotope, or salt thereof:

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VIII-f), or a pharmaceutically acceptable isomer, racemate, hydrate, solvate, isotope, or salt thereof:

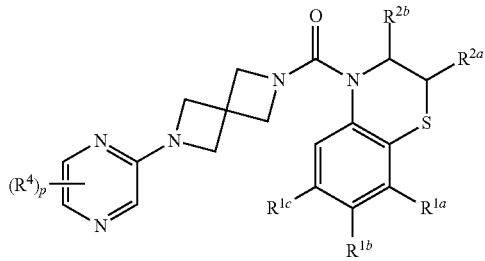

(VIII-d)

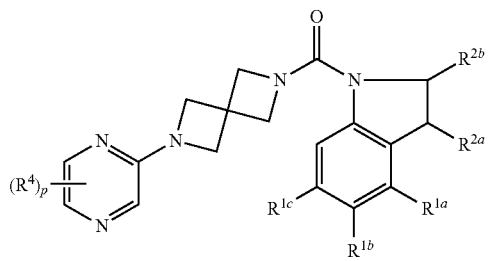

(VIII-f)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VIII-e), or a pharmaceutically acceptable isomer, racemate, hydrate, solvate, isotope, or salt thereof:

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VIII-g), or a pharmaceutically acceptable isomer, racemate, hydrate, solvate, isotope, or salt thereof:

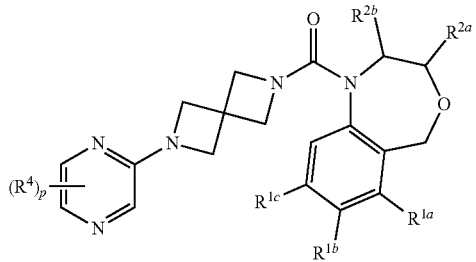

(VIII-g)

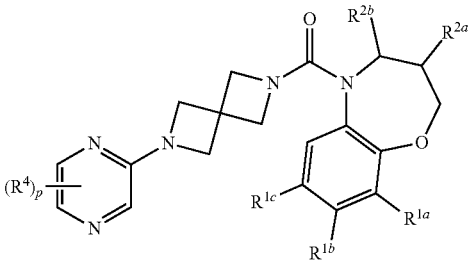

(VIII-i)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VIII-h), or a pharmaceutically acceptable isomer, racemate, hydrate, solvate, isotope, or salt thereof:

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VIII-j), or a pharmaceutically acceptable isomer, racemate, hydrate, solvate, isotope, or salt thereof:

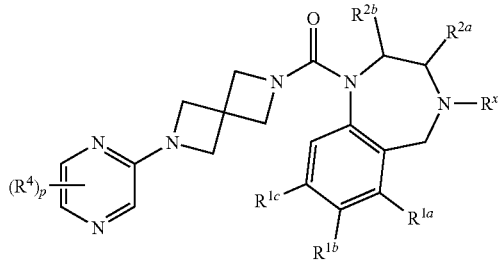

(VIII-h)

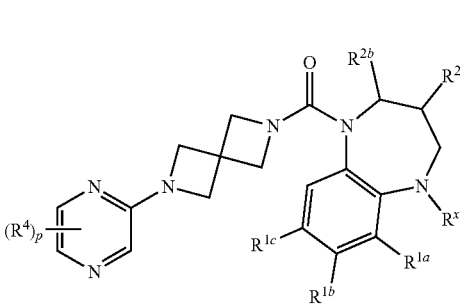

(VIII-j)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VIII-i), or a pharmaceutically acceptable isomer, racemate, hydrate, solvate, isotope, or salt thereof:

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (VIII-k), or a pharmaceutically acceptable isomer, racemate, hydrate, solvate, isotope, or salt thereof:

(VIII-k)

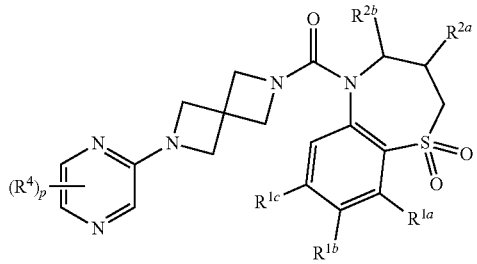

(IX-a)

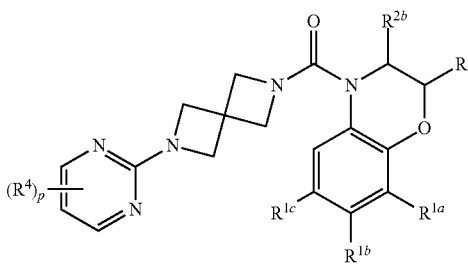

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (IX), or a pharmaceutically acceptable isomer, racemate, hydrate, solvate, isotope, or salt thereof:

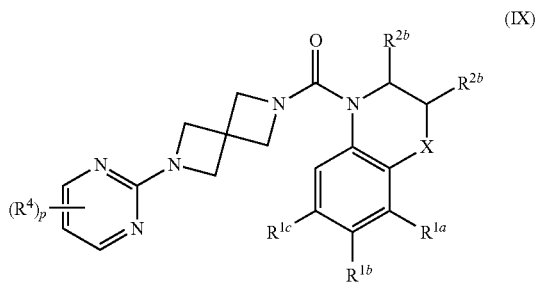

(IX)

wherein:

X is $-(CR^xR^y)_nO(CR^xR^y)_q-$, $-(CR^xR^y)_nS(O)_t(CR^xR^y)_q-$, $-(CR^xR^y)_nN(R^x)(CR^xR^y)_q-$, or $-(CR^xR^y)_n-$;

$R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano;

n is 0, 1, or 2;

q is 0, 1, or 2;

t is 0, 1, or 2;

p is 0, 1, or 2.

In one embodiment, compounds are provided having the structure of Formula (IX-a), or a pharmaceutically acceptable isomer, racemate, hydrate, solvate, isotope, or salt thereof:

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In further embodiments, compounds are provided having the structure of Formula (IX-a), or a pharmaceutically acceptable isomer, racemate, hydrate, solvate, isotope, or salt thereof, wherein p is zero. In more specific embodiments, compounds are provided having the structure of Formula (IX-a) or a pharmaceutically acceptable isomer, racemate, hydrate, solvate, isotope, or salt thereof, wherein $R^{1b}$ is halo; $R^{1a}$ and $R^{1c}$ are each, independently, H, lower alkyl, lower alkoxy; and $R^{2a}$ and $R^{2b}$ are each, independently, H, lower alkyl, or lower alkoxy. In more specific embodiments, compounds are provided having the structure of Formula (IX-a) or a pharmaceutically acceptable isomer, racemate, hydrate, solvate, isotope, or salt thereof, wherein $R^{1b}$ is halo; $R^{1a}$ and $R^{1c}$ are each, independently, H, lower alkyl, lower alkoxy or halo; and $R^{2a}$ and $R^{2b}$ are each, independently, H, lower alkyl, or lower alkoxy.

In one embodiment, compounds are provided having the structure of Formula (IX-b), or a pharmaceutically acceptable isomer, racemate, hydrate, solvate, isotope, or salt thereof:

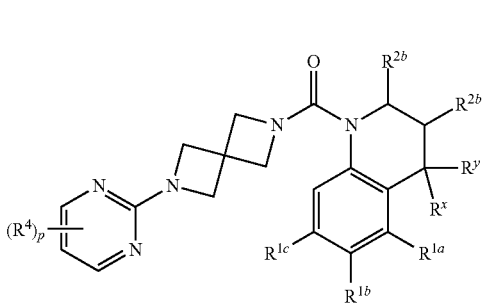

(IX-b)

wherein:

$R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (IX-c), or a pharmaceutically acceptable isomer, racemate, hydrate, solvate, isotope, or salt thereof:

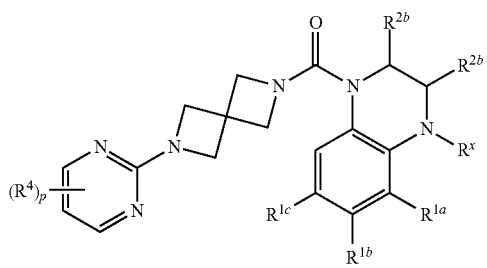

(IX-c)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (IX-d), or a pharmaceutically acceptable isomer, racemate, hydrate, solvate, isotope, or salt thereof:

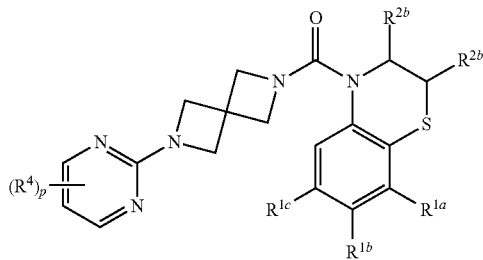

(IX-d)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (IX-e), or a pharmaceutically acceptable isomer, racemate, hydrate, solvate, isotope, or salt thereof:

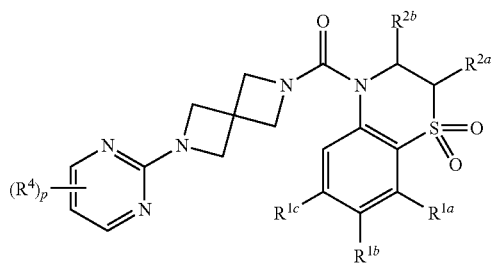

(IX-e)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (IX-f), or a pharmaceutically acceptable isomer, racemate, hydrate, solvate, isotope, or salt thereof:

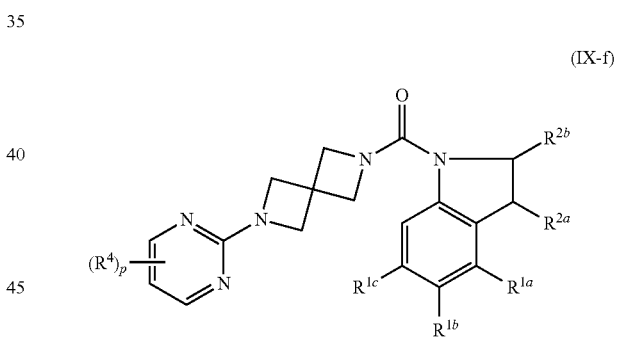

(IX-f)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (IX-g), or a pharmaceutically acceptable isomer, racemate, hydrate, solvate, isotope, or salt thereof:

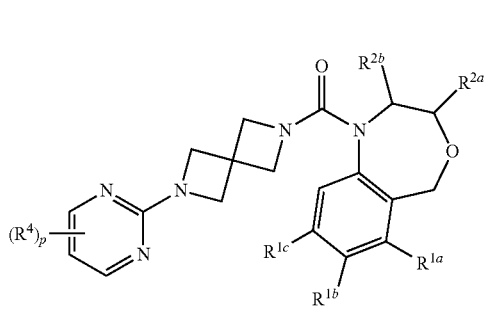
(IX-g)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (IX-h), or a pharmaceutically acceptable isomer, racemate, hydrate, solvate, isotope, or salt thereof:

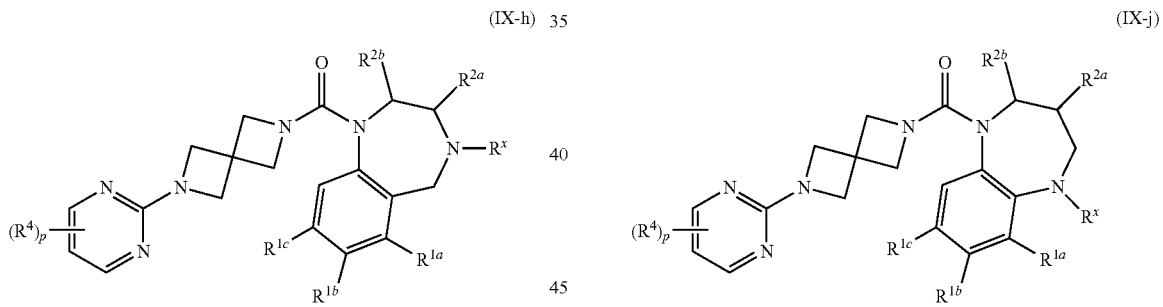
(IX-h)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano;

p is 0, 1, or 2.

In one embodiment, compounds are provided having the structure of Formula (IX-i), or a pharmaceutically acceptable isomer, racemate, hydrate, solvate, isotope, or salt thereof:

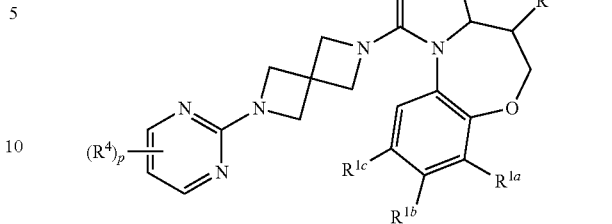
(IX-i)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (IX-j), or a pharmaceutically acceptable isomer, racemate, hydrate, solvate, isotope, or salt thereof:

(IX-j)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano;

p is 0, 1, or 2.

In one embodiment, compounds are provided having the structure of Formula (IX-k), or a pharmaceutically acceptable isomer, racemate, hydrate, solvate, isotope, or salt thereof:

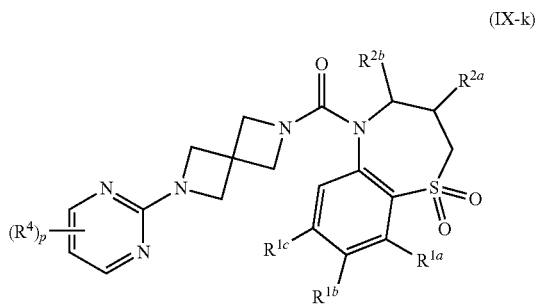

(IX-k)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (X), or a pharmaceutically acceptable isomer, racemate, hydrate, solvate, isotope, or salt thereof:

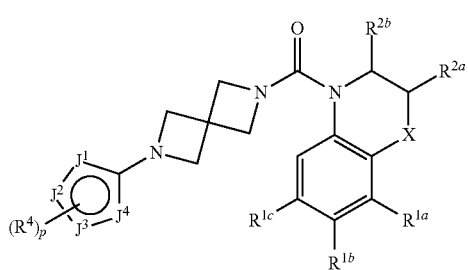

(X)

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—, $R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or CR$^4$;

$R^4$ is, at each occurrence, independently H, —OH, =O, cycloalkyl, lower alkyl, lower haloalkyl, lower alkoxy, lower haloalkoxy, halo, or cyano;

n is 0, 1, or 2;

q is 0, 1, or 2;

t is 0, 1, or 2;

p is 0, 1, or 2.

In one embodiment, compounds are provided having the structure of Formula (X-a), or a pharmaceutically acceptable isomer, racemate, hydrate, solvate, isotope, or salt thereof:

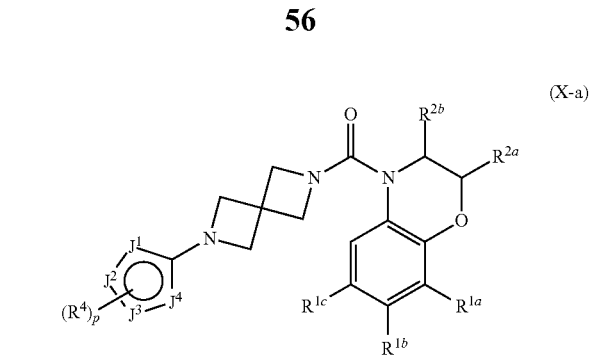

(X-a)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or CR$^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (X-b), or a pharmaceutically acceptable isomer, racemate, hydrate, solvate, isotope, or salt thereof:

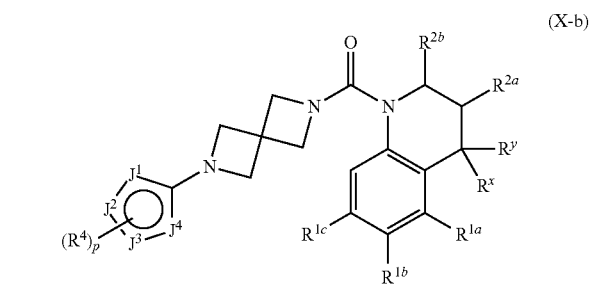

(X-b)

wherein:

$R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or CR$^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (Xc-), or a pharmaceutically acceptable isomer, racemate, hydrate, solvate, isotope, or salt thereof:

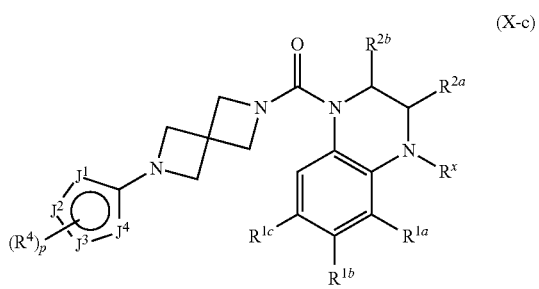

(X-c)

wherein:

R$^x$ is, at each occurrence, independently H, lower alkyl, lower haloalkyl, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

J$^1$, J$^2$, J$^3$, and J$^4$ are each, independently, N, O, CH, or CR$^4$;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (Xd-), or a pharmaceutically acceptable isomer, racemate, hydrate, solvate, isotope, or salt thereof:

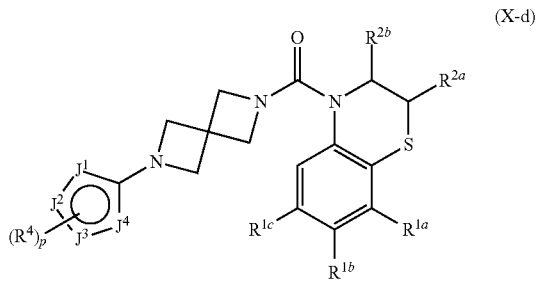

(X-d)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

J$^1$, J$^2$, J$^3$, and J$^4$ are each, independently, N, O, CH, or CR$^4$;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (Xe-), or a pharmaceutically acceptable isomer, racemate, hydrate, solvate, isotope, or salt thereof:

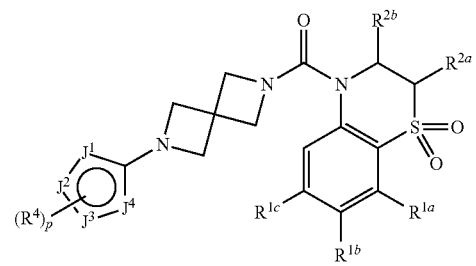

(X-e)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

J$^1$, J$^2$, J$^3$, and J$^4$ are each, independently, N, O, CH, or CR$^4$;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (X-f), or a pharmaceutically acceptable isomer, racemate, hydrate, solvate, isotope, or salt thereof:

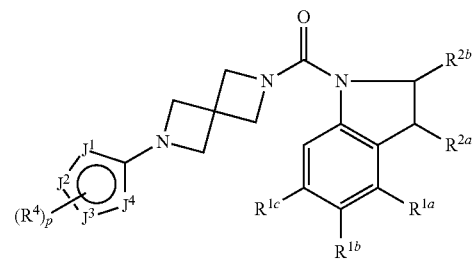

(X-f)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

J$^1$, J$^2$, J$^3$, and J$^4$ are each, independently, N, O, CH, or CR$^4$;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (Xg-), or a pharmaceutically acceptable isomer, racemate, hydrate, solvate, isotope, or salt thereof:

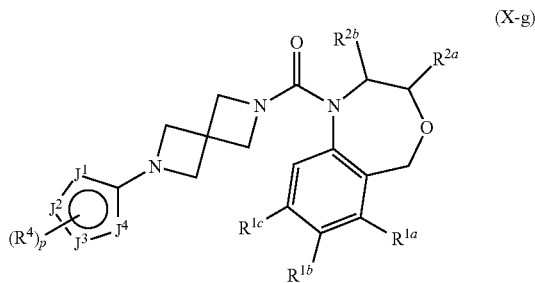

(X-g)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (Xh-), or a pharmaceutically acceptable isomer, racemate, hydrate, solvate, isotope, or salt thereof:

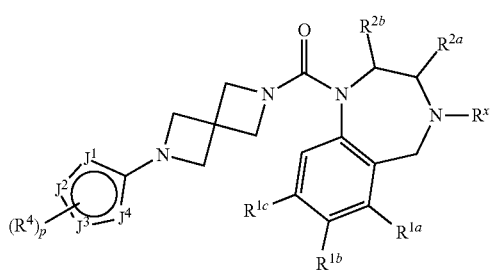

(X-h)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (X-i), or a pharmaceutically acceptable isomer, racemate, hydrate, solvate, isotope, or salt thereof:

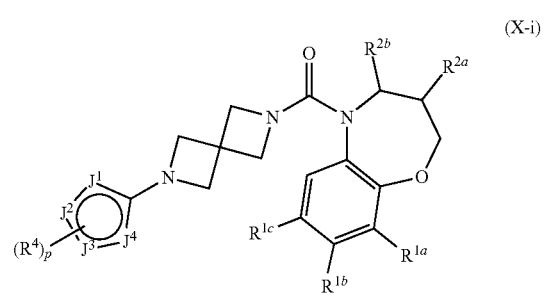

(X-i)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (Xj-), or a pharmaceutically acceptable isomer, racemate, hydrate, solvate, isotope, or salt thereof:

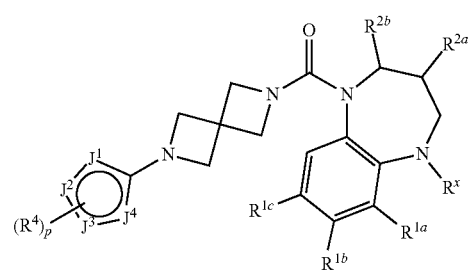

(X-j)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (Xk-), or a pharmaceutically acceptable isomer, racemate, hydrate, solvate, isotope, or salt thereof:

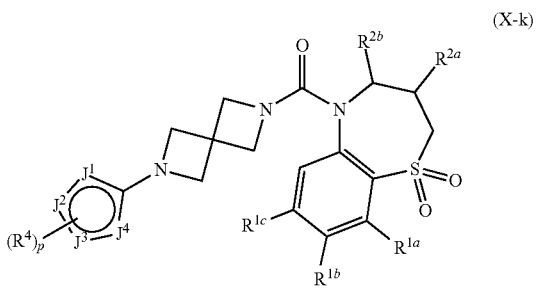

(X-k)

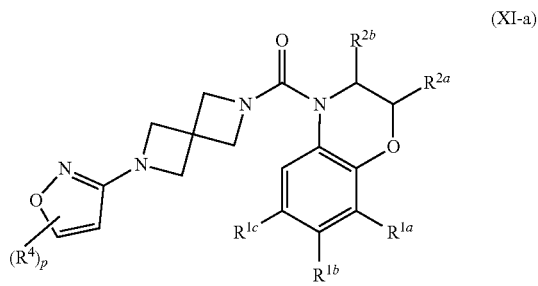

(XI-a)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or $CR^4$;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XI), or a pharmaceutically acceptable isomer, racemate, hydrate, solvate, isotope, or salt thereof:

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0 or 1.

In one embodiment, compounds are provided having the structure of Formula (XI-b), or a pharmaceutically acceptable isomer, racemate, hydrate, solvate, isotope, or salt thereof:

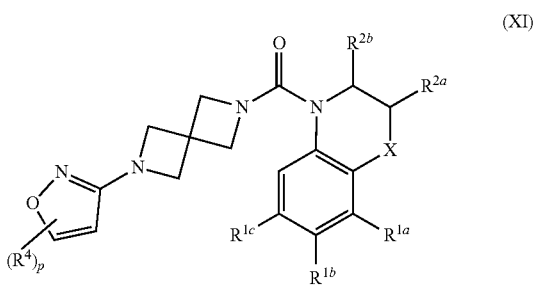

(XI)

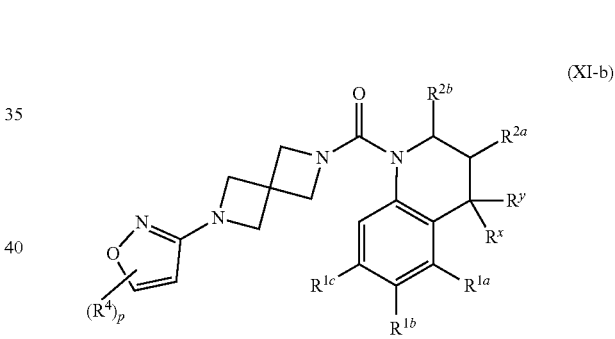

(XI-b)

wherein:

X is —$(CR^xR^y)_nO(CR^xR^y)_q$—, —$(CR^xR^y)_nS(O)_t(CR^xR^y)_q$—, —$(CR^xR^y)_nN(R^x)(CR^xR^y)_q$—, or —$(CR^xR^y)_n$—, $R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano;

n is 0, 1, or 2;

q is 0, 1, or 2;

t is 0, 1, or 2; and p is 0, 1, or 2.

In one embodiment, compounds are provided having the structure of Formula (XI-a), or a pharmaceutically acceptable isomer, racemate, hydrate, solvate, isotope, or salt thereof:

wherein:

$R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XI-c), or a pharmaceutically acceptable isomer, racemate, hydrate, solvate, isotope, or salt thereof:

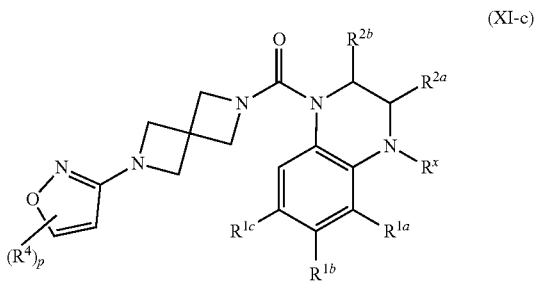

(XI-c)

wherein:

R$^x$ is, at each occurrence, independently H, lower alkyl, lower haloalkyl, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XI-d), or a pharmaceutically acceptable isomer, racemate, hydrate, solvate, isotope, or salt thereof:

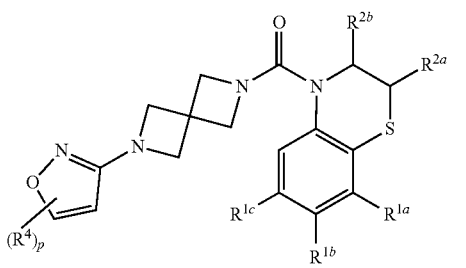

(XI-d)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XI-e), or a pharmaceutically acceptable isomer, racemate, hydrate, solvate, isotope, or salt thereof:

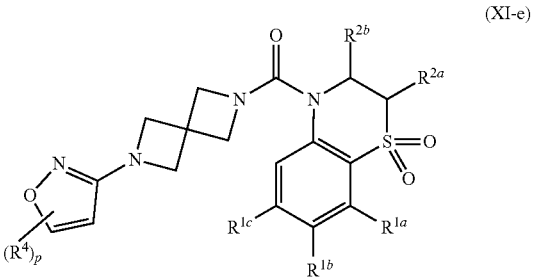

(XI-e)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XI-f), or a pharmaceutically acceptable isomer, racemate, hydrate, solvate, isotope, or salt thereof:

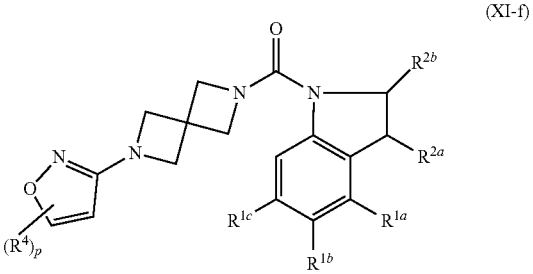

(XI-f)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XI-g), or a pharmaceutically acceptable isomer, racemate, hydrate, solvate, isotope, or salt thereof:

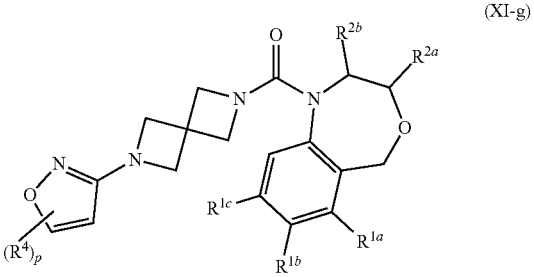

(XI-g)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XI-h), or a pharmaceutically acceptable isomer, racemate, hydrate, solvate, isotope, or salt thereof:

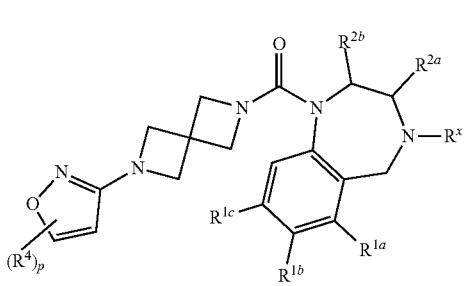

(XI-h)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XI-i), or a pharmaceutically acceptable isomer, racemate, hydrate, solvate, isotope, or salt thereof:

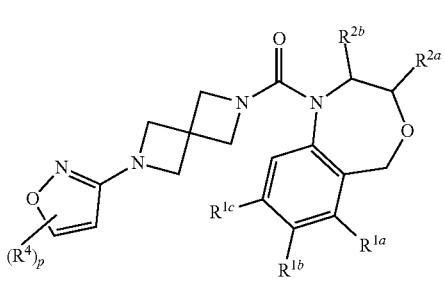

(XI-i)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XI-j), or a pharmaceutically acceptable isomer, racemate, hydrate, solvate, isotope, or salt thereof:

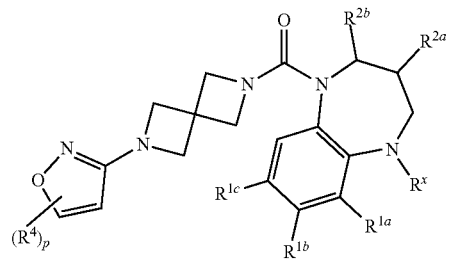

(XI-j)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIk-), or a pharmaceutically acceptable isomer, racemate, hydrate, solvate, isotope, or salt thereof:

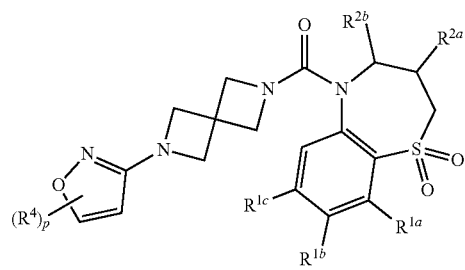

(XI-k)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XII), or a pharmaceutically acceptable isomer, racemate, hydrate, solvate, isotope, or salt thereof:

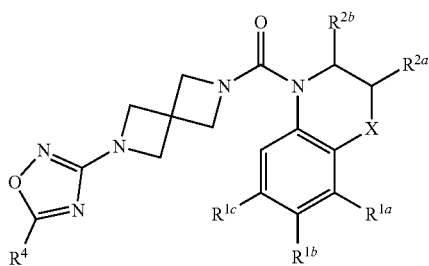

(XII)

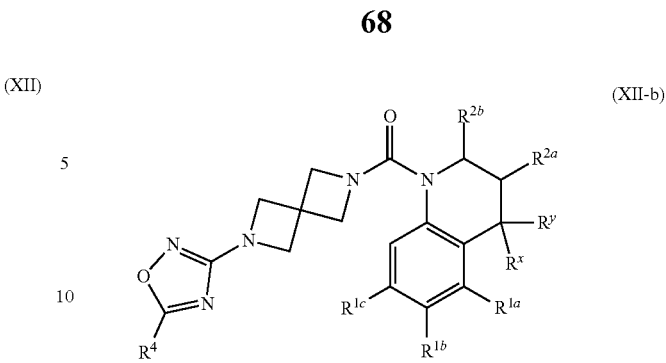

(XII-b)

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—,

R$^x$ is, at each occurrence, independently H, lower alkyl, lower haloalkyl, or halo;

R$^y$ is, at each occurrence, independently H, —OH, lower alkyl, lower alkoxy, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano;

n is 0, 1, or 2;

q is 0, 1, or 2;

t is 0, 1, or 2; and p is 0, 1, or 2.

In one embodiment, compounds are provided having the structure of Formula (XII-a), or a pharmaceutically acceptable isomer, racemate, hydrate, solvate, isotope, or salt thereof:

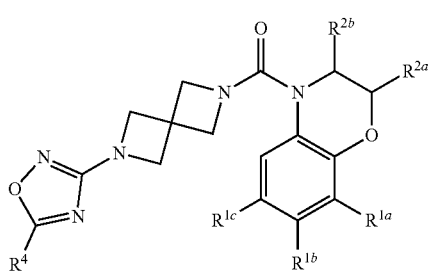

(XII-a)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XII-b), or a pharmaceutically acceptable isomer, racemate, hydrate, solvate, isotope, or salt thereof:

wherein:

R$^x$ is, at each occurrence, independently H, lower alkyl, lower haloalkyl, or halo;

R$^y$ is, at each occurrence, independently H, —OH, lower alkyl, lower alkoxy, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XII-c), or a pharmaceutically acceptable isomer, racemate, hydrate, solvate, isotope, or salt thereof:

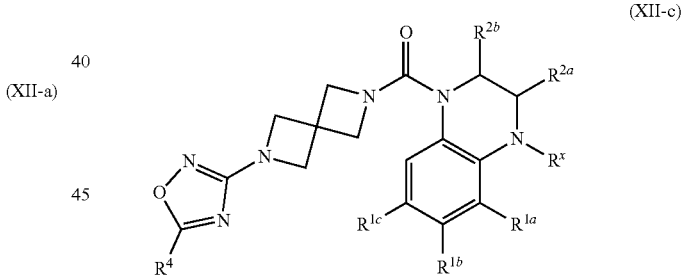

(XII-c)

wherein:

R$^x$ is, at each occurrence, independently H, lower alkyl, lower haloalkyl, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XII-d), or a pharmaceutically acceptable isomer, racemate, hydrate, solvate, isotope, or salt thereof:

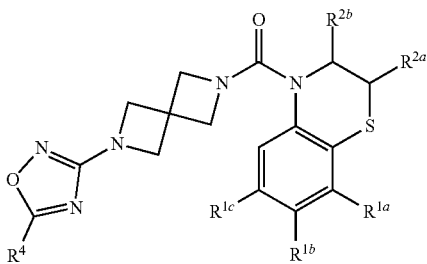

(XII-d)

wherein:
$R^{1a}$, $R^{1b}$, and $R^{1c}$ are each, independently, H, lower alkyl, lower haloalkyl, lower alkoxy, cyano, or halo;
$R^{2a}$ and $R^{2b}$ are each, independently, H, lower alkyl, lower haloalkyl, or lower alkoxy;
$R^4$ is, at each occurrence, independently H, —OH, =O, cycloalkyl, lower alkyl, lower haloalkyl, lower alkoxy, lower haloalkoxy, halo, or cyano; and
p is 0, 1, or 2.

In one embodiment, compounds are provided having the structure of Formula (XII-e), or a pharmaceutically acceptable isomer, racemate, hydrate, solvate, isotope, or salt thereof:

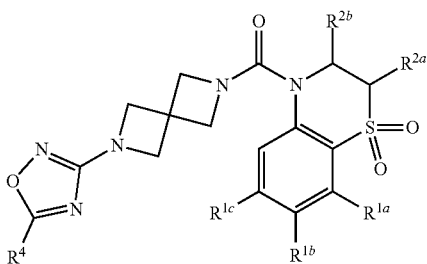

(XII-e)

wherein:
$R^{1a}$, $R^{1b}$, and $R^{1c}$ are each, independently, H, lower alkyl, lower haloalkyl, lower alkoxy, cyano, or halo;
$R^{2a}$ and $R^{2b}$ are each, independently, H, lower alkyl, lower haloalkyl, or lower alkoxy;
$R^4$ is, at each occurrence, independently H, —OH, =O, cycloalkyl, lower alkyl, lower haloalkyl, lower alkoxy, lower haloalkoxy, halo, or cyano; and
p is 0, 1, or 2.

In one embodiment, compounds are provided having the structure of Formula (XII-f), or a pharmaceutically acceptable isomer, racemate, hydrate, solvate, isotope, or salt thereof:

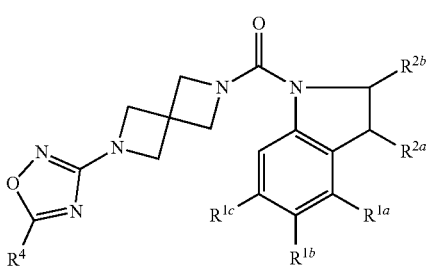

(XII-f)

wherein:
$R^{1a}$, $R^{1b}$, and $R^{1c}$ are each, independently, H, lower alkyl, lower haloalkyl, lower alkoxy, cyano, or halo;
$R^{2a}$ and $R^{2b}$ are each, independently, H, lower alkyl, lower haloalkyl, or lower alkoxy;
$R^4$ is, at each occurrence, independently H, —OH, =O, cycloalkyl, lower alkyl, lower haloalkyl, lower alkoxy, lower haloalkoxy, halo, or cyano; and
p is 0, 1, or 2.

In one embodiment, compounds are provided having the structure of Formula (XII-g), or a pharmaceutically acceptable isomer, racemate, hydrate, solvate, isotope, or salt thereof:

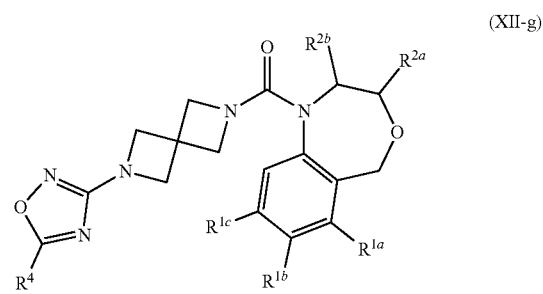

(XII-g)

wherein:
$R^{1a}$, $R^{1b}$, and $R^{1c}$ are each, independently, H, lower alkyl, lower haloalkyl, lower alkoxy, cyano, or halo;
$R^{2a}$ and $R^{2b}$ are each, independently, H, lower alkyl, lower haloalkyl, or lower alkoxy;
$R^4$ is, at each occurrence, independently H, —OH, =O, cycloalkyl, lower alkyl, lower haloalkyl, lower alkoxy, lower haloalkoxy, halo, or cyano; and
p is 0, 1, or 2.

In one embodiment, compounds are provided having the structure of Formula (XII-h), or a pharmaceutically acceptable isomer, racemate, hydrate, solvate, isotope, or salt thereof:

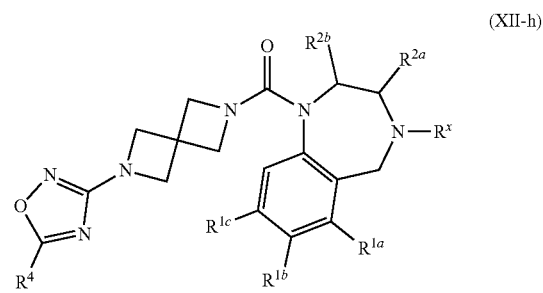

(XII-h)

wherein:
$R^x$ is, at each occurrence, independently H, lower alkyl, lower haloalkyl, or halo;
$R^{1a}$, $R^{1b}$, and $R^{1c}$ are each, independently, H, lower alkyl, lower haloalkyl, lower alkoxy, cyano, or halo;
$R^{2a}$ and $R^{2b}$ are each, independently, H, lower alkyl, lower haloalkyl, or lower alkoxy;
$R^4$ is, at each occurrence, independently H, —OH, =O, cycloalkyl, lower alkyl, lower haloalkyl, lower alkoxy, lower haloalkoxy, halo, or cyano; and
p is 0, 1, or 2.

In one embodiment, compounds are provided having the structure of Formula (XII-i), or a pharmaceutically acceptable isomer, racemate, hydrate, solvate, isotope, or salt thereof:

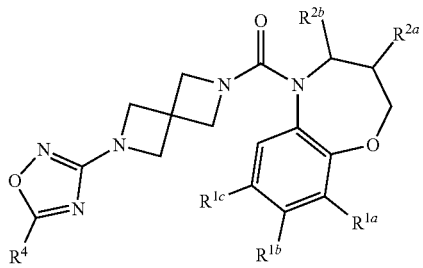

(XII-i)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XII-j), or a pharmaceutically acceptable isomer, racemate, hydrate, solvate, isotope, or salt thereof:

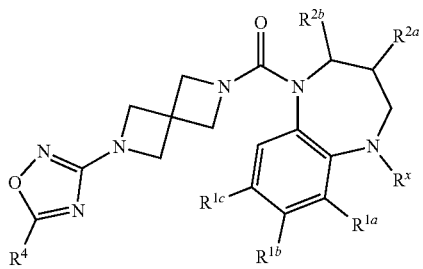

(XII-j)

wherein:

$R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XII-k), or a pharmaceutically acceptable isomer, racemate, hydrate, solvate, isotope, or salt thereof:

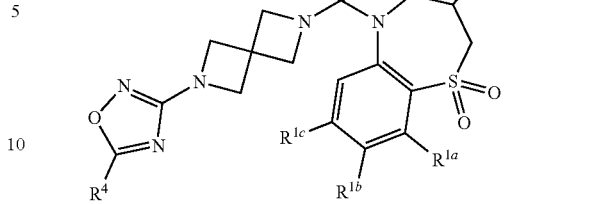

(XII-k)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIII), or a pharmaceutically acceptable isomer, racemate, hydrate, solvate, isotope, or salt thereof:

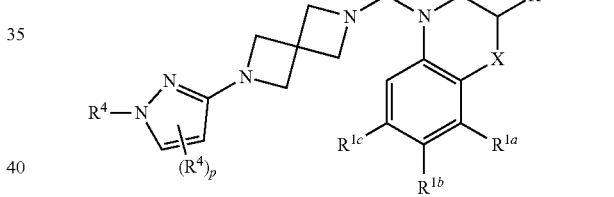

(XIII)

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—, $R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano;

n is 0, 1, or 2;

q is 0, 1, or 2;

t is 0, 1, or 2; and p is 0, 1, or 2.

In one embodiment, compounds are provided having the structure of Formula (XIII-a), or a pharmaceutically acceptable isomer, racemate, hydrate, solvate, isotope, or salt thereof:

(XIII-a)

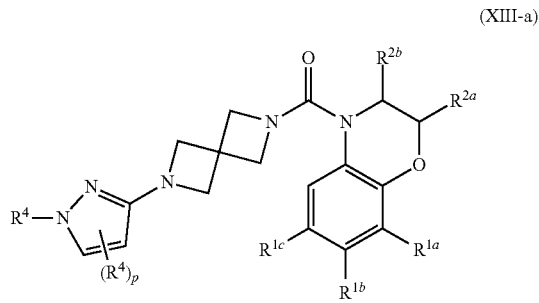

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIII-b), or a pharmaceutically acceptable isomer, racemate, hydrate, solvate, isotope, or salt thereof:

(XIII-b)

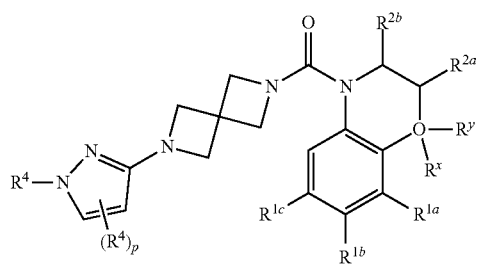

wherein:

$R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIII-c), or a pharmaceutically acceptable isomer, racemate, hydrate, solvate, isotope, or salt thereof:

(XIII-c)

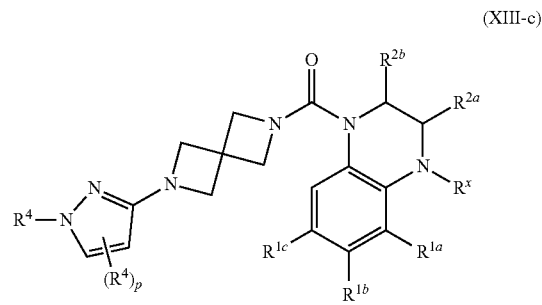

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIII-d), or a pharmaceutically acceptable isomer, racemate, hydrate, solvate, isotope, or salt thereof:

(XIII-d)

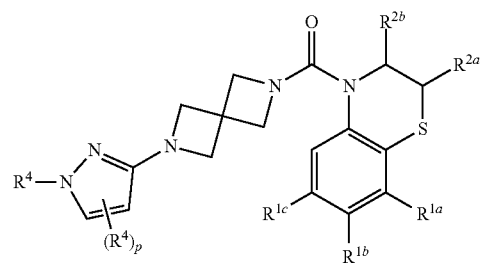

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIII-e), or a pharmaceutically acceptable isomer, racemate, hydrate, solvate, isotope, or salt thereof:

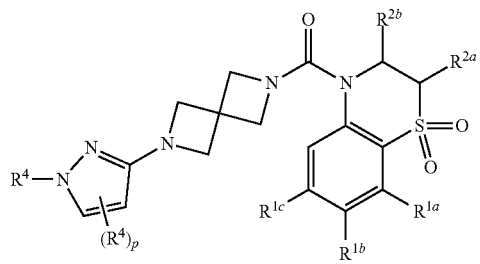

(XIII-e)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIII-f), or a pharmaceutically acceptable isomer, racemate, hydrate, solvate, isotope, or salt thereof:

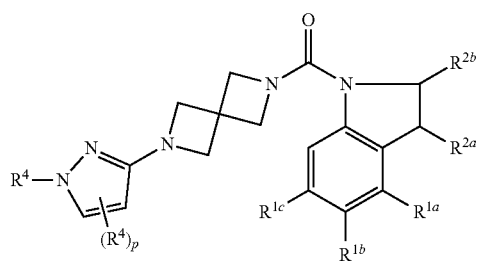

(XIII-f)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIII-g), or a pharmaceutically acceptable isomer, racemate, hydrate, solvate, isotope, or salt thereof:

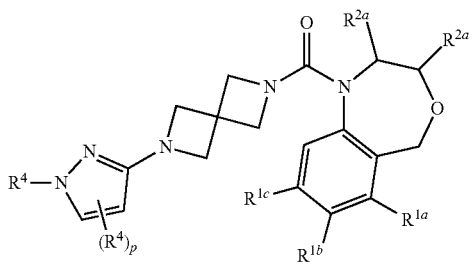

(XIII-g)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIII-h), or a pharmaceutically acceptable isomer, racemate, hydrate, solvate, isotope, or salt thereof:

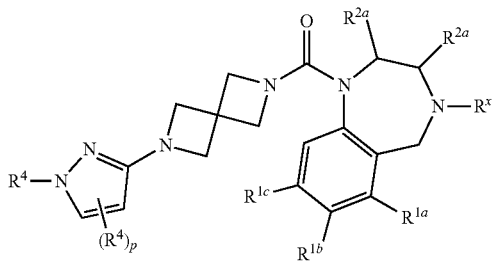

(XIII-h)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIII-i), or a pharmaceutically acceptable isomer, racemate, hydrate, solvate, isotope, or salt thereof:

(XIII-i)

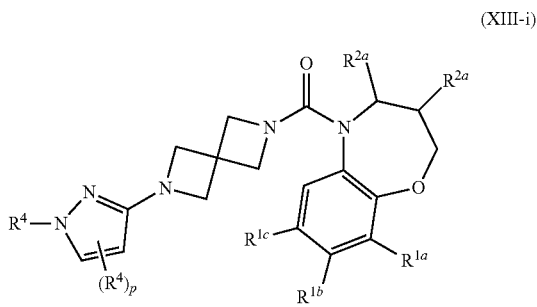

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIII-j), or a pharmaceutically acceptable isomer, racemate, hydrate, solvate, isotope, or salt thereof:

(XIII-j)

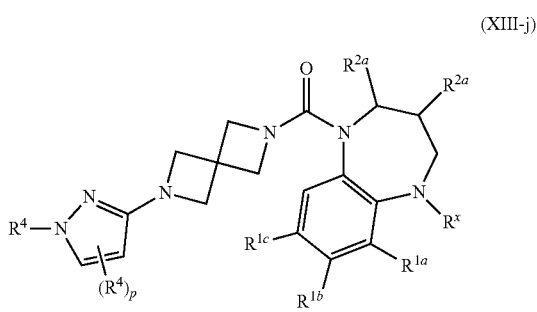

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIII-k), or a pharmaceutically acceptable isomer, racemate, hydrate, solvate, isotope, or salt thereof:

(XIII-k)

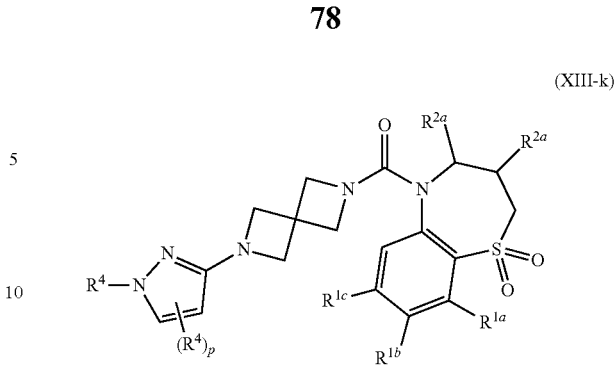

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIV), or a pharmaceutically acceptable isomer, racemate, hydrate, solvate, isotope, or salt thereof:

(XIV)

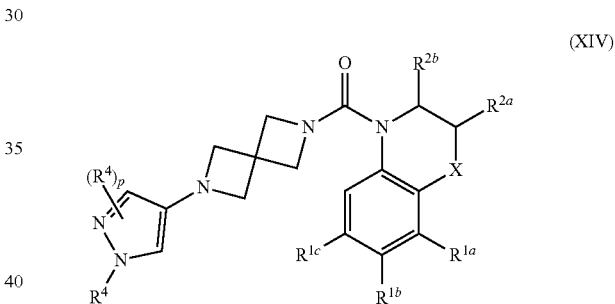

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—, $R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano;

n is 0, 1, or 2;

q is 0, 1, or 2;

t is 0, 1, or 2; and p is 0, 1, or 2.

In one embodiment, compounds are provided having the structure of Formula (XIV-a), or a pharmaceutically acceptable isomer, racemate, hydrate, solvate, isotope, or salt thereof:

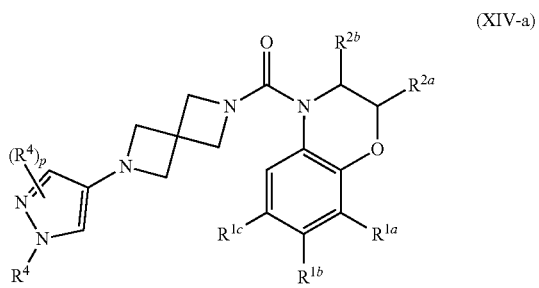

(XIV-a)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIV-b), or a pharmaceutically acceptable isomer, racemate, hydrate, solvate, isotope, or salt thereof:

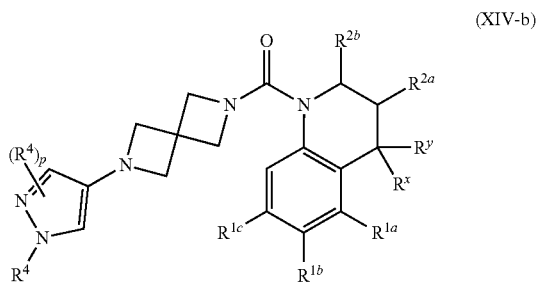

(XIV-b)

wherein:

$R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIV-c), or a pharmaceutically acceptable isomer, racemate, hydrate, solvate, isotope, or salt thereof:

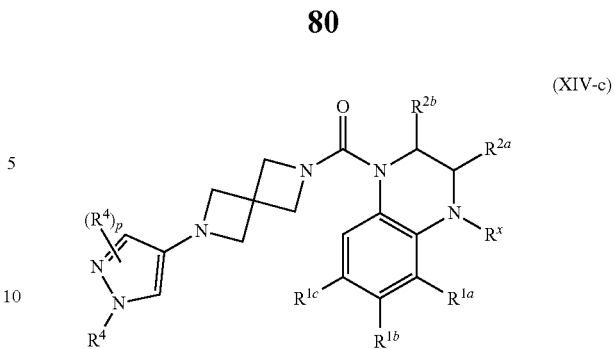

(XIV-c)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIV-d), or a pharmaceutically acceptable isomer, racemate, hydrate, solvate, isotope, or salt thereof:

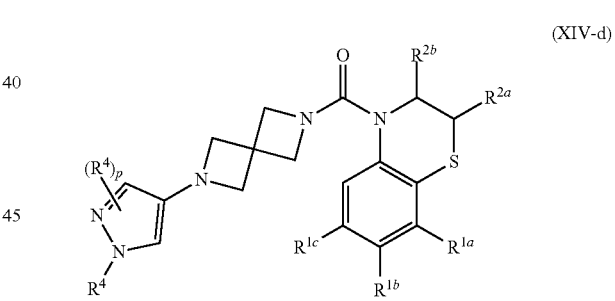

(XIV-d)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIV-e), or a pharmaceutically acceptable isomer, racemate, hydrate, solvate, isotope, or salt thereof:

(XIV-e)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIV-h), or a pharmaceutically acceptable isomer, racemate, hydrate, solvate, isotope, or salt thereof:

(XIV-h)

wherein:

R$^x$ is, at each occurrence, independently H, lower alkyl, lower haloalkyl, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIV-f), or a pharmaceutically acceptable isomer, racemate, hydrate, solvate, isotope, or salt thereof:

(XIV-f)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIV-i), or a pharmaceutically acceptable isomer, racemate, hydrate, solvate, isotope, or salt thereof:

(XIV-i)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIV-g), or a pharmaceutically acceptable isomer, racemate, hydrate, solvate, isotope, or salt thereof:

(XIV-g)

In one embodiment, compounds are provided having the structure of Formula (XIV-j), or a pharmaceutically acceptable isomer, racemate, hydrate, solvate, isotope, or salt thereof:

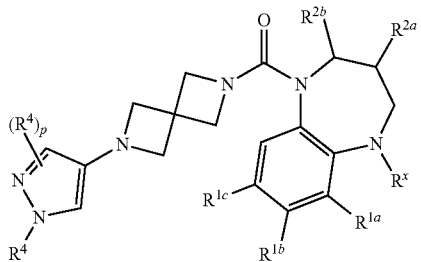

(XIV-j)

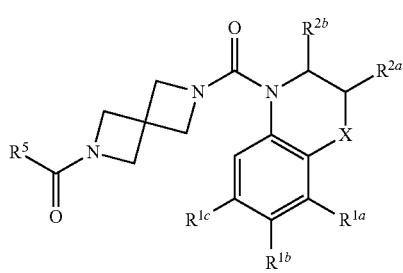

(XV)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XIV-k), or a pharmaceutically acceptable isomer, racemate, hydrate, solvate, isotope, or salt thereof:

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—, $R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^5$ is H, cycloalkyl, lower alkyl, lower haloalkyl, lower alkoxy, aryl, heteroaryl, cycloalkylalkyl, heterocyclyl, or —O-heterocyclyl;

n is 0, 1, or 2;

q is 0, 1, or 2; and t is 0, 1, or 2.

In one embodiment, compounds are provided having the structure of Formula (XV-a), or a pharmaceutically acceptable isomer, racemate, hydrate, solvate, isotope, or salt thereof:

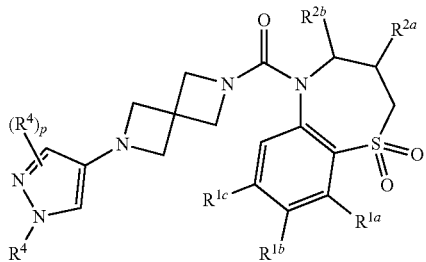

(XIV-k)

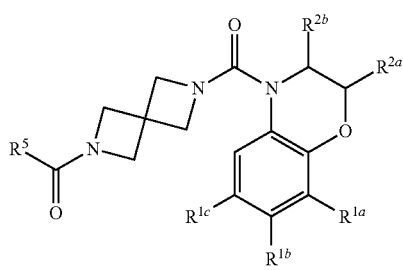

(XV-a)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano; and p is 0, 1, or 2.

In one embodiment, compounds are provided having the structure of Formula (XV), or a pharmaceutically acceptable isomer, racemate, hydrate, solvate, isotope, or salt thereof:

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy; and $R^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XV-b), or a pharmaceutically acceptable isomer, racemate, hydrate, solvate, isotope, or salt thereof:

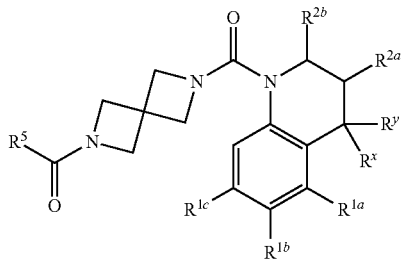

(XV-b)

wherein:

$R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy; and $R^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XV-c), or a pharmaceutically acceptable isomer, racemate, hydrate, solvate, isotope, or salt thereof:

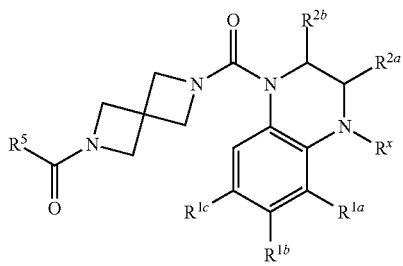

(XV-c)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy; and $R^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XV-d), or a pharmaceutically acceptable isomer, racemate, hydrate, solvate, isotope, or salt thereof:

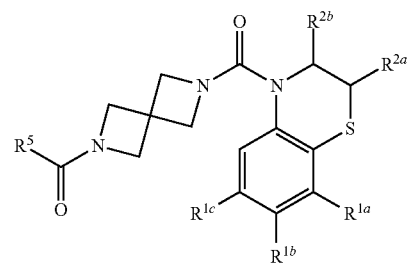

(XV-d)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy; and $R^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XV-e), or a pharmaceutically acceptable isomer, racemate, hydrate, solvate, isotope, or salt thereof:

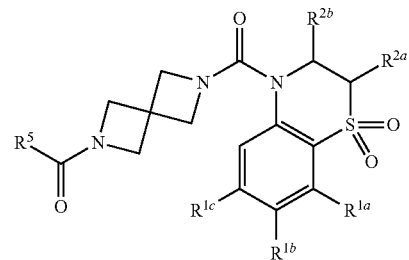

(XV-e)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy; and $R^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XV-f), or a pharmaceutically acceptable isomer, racemate, hydrate, solvate, isotope, or salt thereof:

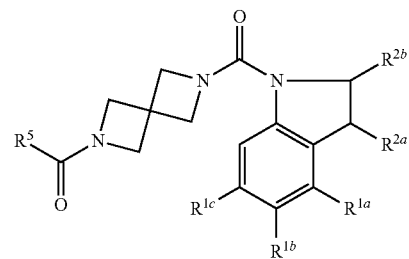

(XV-f)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy; and R$^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XV-g), or a pharmaceutically acceptable isomer, racemate, hydrate, solvate, isotope, or salt thereof:

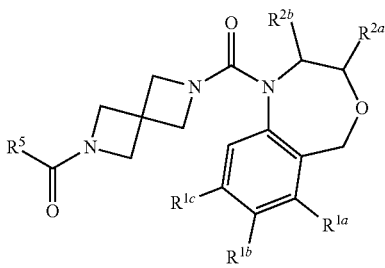

(XIV-g)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy; and R$^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XV-h), or a pharmaceutically acceptable isomer, racemate, hydrate, solvate, isotope, or salt thereof:

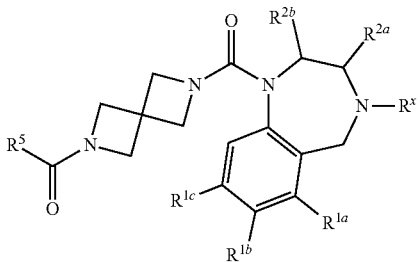

(XV-h)

wherein:

R$^x$ is, at each occurrence, independently H, lower alkyl, lower haloalkyl, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy; and R$^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XV-i), or a pharmaceutically acceptable isomer, racemate, hydrate, solvate, isotope, or salt thereof:

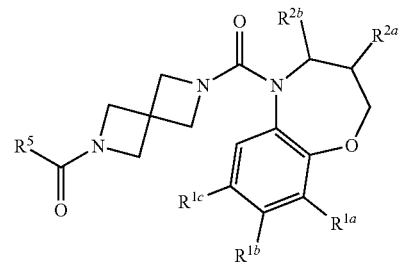

(XV-i)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy; and R$^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XV-j), or a pharmaceutically acceptable isomer, racemate, hydrate, solvate, isotope, or salt thereof:

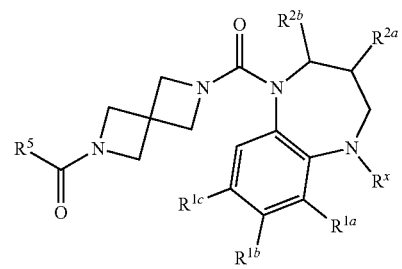

(XV-j)

wherein:

R$^x$ is, at each occurrence, independently H, lower alkyl, lower haloalkyl, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy; and R$^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XV-k), or a pharmaceutically acceptable isomer, racemate, hydrate, solvate, isotope, or salt thereof:

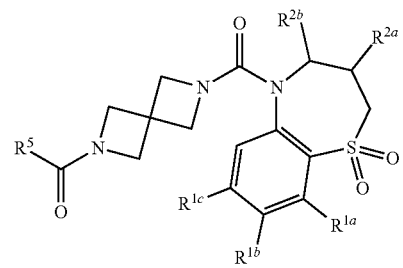

(XV-k)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy; and $R^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XVI), or a pharmaceutically acceptable isomer, racemate, hydrate, solvate, isotope, or salt thereof:

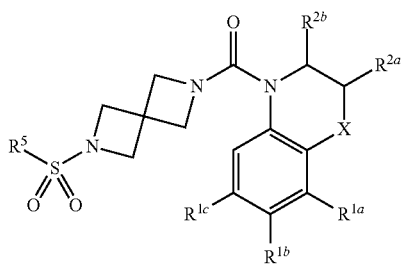

(XVI)

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—, $R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^5$ is H, cycloalkyl, lower alkyl, lower haloalkyl, lower alkoxy, aryl, heteroaryl, cycloalkylalkyl, heterocyclyl, or —O-heterocyclyl;

n is 0, 1, or 2;

q is 0, 1, or 2; and t is 0, 1, or 2.

In one embodiment, compounds are provided having the structure of Formula (XVI-a), or a pharmaceutically acceptable isomer, racemate, hydrate, solvate, isotope, or salt thereof:

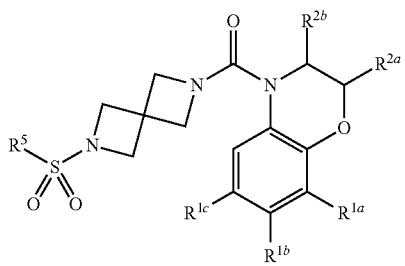

(XVI-a)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy; and $R^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XVI-b), or a pharmaceutically acceptable isomer, racemate, hydrate, solvate, isotope, or salt thereof:

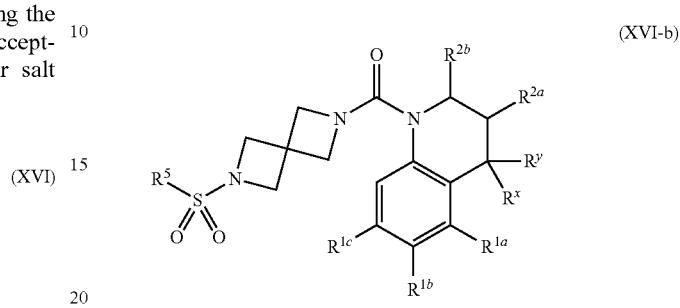

(XVI-b)

wherein:

$R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy; and $R^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XVI-c), or a pharmaceutically acceptable isomer, racemate, hydrate, solvate, isotope, or salt thereof:

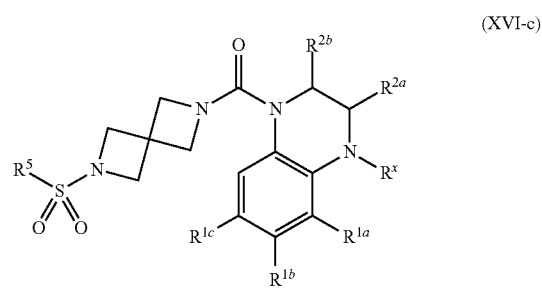

(XVI-c)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy; and $R^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XVI-d), or a pharmaceutically acceptable isomer, racemate, hydrate, solvate, isotope, or salt thereof:

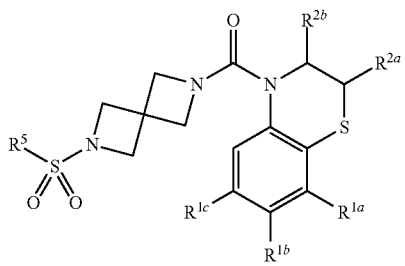

(XVI-d)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy; and $R^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XVI-e), or a pharmaceutically acceptable isomer, racemate, hydrate, solvate, isotope, or salt thereof:

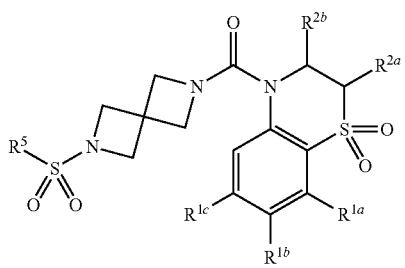

(XVI-e)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy; and $R^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XVI-f), or a pharmaceutically acceptable isomer, racemate, hydrate, solvate, isotope, or salt thereof:

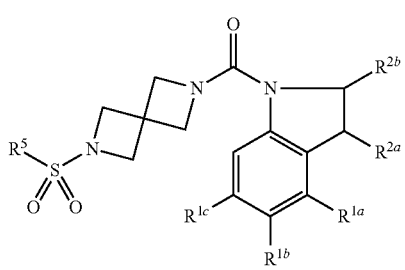

(XVI-f)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy; and $R^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XVI-g), or a pharmaceutically acceptable isomer, racemate, hydrate, solvate, isotope, or salt thereof:

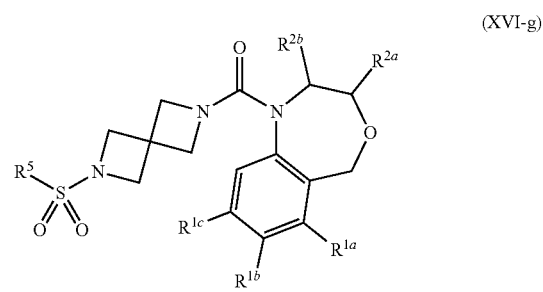

(XVI-g)

wherein:

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy; and $R^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XVI-h), or a pharmaceutically acceptable isomer, racemate, hydrate, solvate, isotope, or salt thereof:

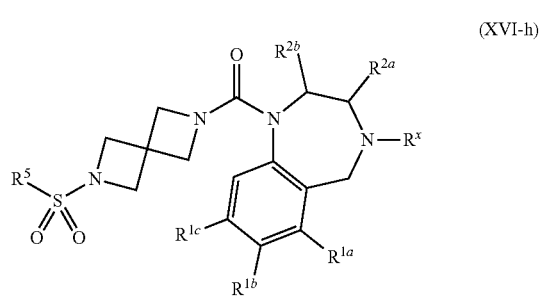

(XVI-h)

wherein:

$R^x$ is, at each occurrence, independently H, lower alkyl, lower haloalkyl, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy; and $R^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XVI-i), or a pharmaceutically acceptable isomer, racemate, hydrate, solvate, isotope, or salt thereof:

(XVI-i)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy; and R$^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XVI-j), or a pharmaceutically acceptable isomer, racemate, hydrate, solvate, isotope, or salt thereof:

(XVI-j)

wherein:

R$^x$ is, at each occurrence, independently H, lower alkyl, lower haloalkyl, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy; and R$^5$ is H, cycloalkyl, lower alkyl, lower haloalkyl, lower alkoxy, aryl, heteroaryl, cycloalkylalkyl, heterocyclyl, or —O-heterocyclyl.

In one embodiment, compounds are provided having the structure of Formula (XVI-k), or a pharmaceutically acceptable isomer, racemate, hydrate, solvate, isotope, or salt thereof:

(XVI-k)

wherein:

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy; and R$^5$ is H, cycloalkyl, lower alkyl, lower haloalkyl, lower alkoxy, aryl, heteroaryl, cycloalkylalkyl, heterocyclyl, or —O-heterocyclyl.

In the following more specific embodiments, the various substituents (e.g., R$^{1a}$, R$^{1b}$, R$^{1c}$, R$^{2a}$, R$^{2b}$, R$^3$, R$^4$, R$^5$, and X) are set forth in more detail with respect to the compounds of each of Formulas (I) through (XVI-k) above, as applicable to the substituents being further defined. For example, reference to Q$^1$ below is intended to further limit the compounds of Formulas (I) above, but not Formulas (II) through (XVI-k) since the Q$^1$ substituent has already been further defined in the same. Thus, reference to the substituents below is intended to further modify Formulas (I) through (XVI-k) to the extent such formulas recite that particular substituent as a variable.

In further embodiments, compounds are provided having the structure of any one of Formulas (I) through (XVI-k) or a pharmaceutically acceptable isomer, racemate, hydrate, solvate, isotope, or salt thereof, wherein R$^{1b}$ is halogen. In more specific embodiments, compounds are provided having the structure of any one of Formulas (I) through (XVI-k) or a pharmaceutically acceptable isomer, racemate, hydrate, solvate, isotope, or salt thereof, wherein R$^{1b}$ is Cl, F, or Br. In more specific embodiments, compounds are provided having the structure of any one of Formulas (I) through (XVI-k) or a pharmaceutically acceptable isomer, racemate, hydrate, solvate, isotope, or salt thereof, wherein R$^{1b}$ is Cl.

In further embodiments, compounds are provided having the structure of any one of Formulas (I) through (XVI-k), or a pharmaceutically acceptable isomer, racemate, hydrate, solvate, isotope, or salt thereof, wherein R$^{1b}$ is lower alkyl. In more specific embodiments, compounds are provided having the structure of any one of Formulas (I) through (XVI-k), or a pharmaceutically acceptable isomer, racemate, hydrate, solvate, isotope, or salt thereof, wherein R$^{1b}$ is methyl, ethyl, or isopropyl.

In further embodiments, compounds are provided having the structure of any one of Formulas (I) through (XVI-k), or a pharmaceutically acceptable isomer, racemate, hydrate, solvate, isotope, or salt thereof, wherein R$^{1b}$ is lower haloalkyl. In more specific embodiments, compounds are provided having the structure of any one of Formulas (I) through (XVI-k), or a pharmaceutically acceptable isomer, racemate, hydrate, solvate, isotope, or salt thereof, wherein R$^{1b}$ is —CF$_3$.

In further embodiments, compounds are provided having the structure of any one of Formulas (I) through (XVI-k), or a pharmaceutically acceptable isomer, racemate, hydrate, solvate, isotope, or salt thereof, wherein R$^{1b}$ is lower alkoxy. In more specific embodiments, compounds are provided having the structure of any one of Formulas (I) through (XVI-k), or a pharmaceutically acceptable isomer, racemate, hydrate, solvate, isotope, or salt thereof, wherein R$^{1b}$ is methoxy, ethoxy, isopropoxy, or t-butoxy.

In further embodiments, compounds are provided having the structure of any one of Formulas (I) through (XVI-k), or a pharmaceutically acceptable isomer, racemate, hydrate, solvate, isotope, or salt thereof, wherein R$^{1b}$ is cyano.

In further embodiments, compounds are provided having the structure of any one of Formulas (I) through (XVI-k), or a pharmaceutically acceptable isomer, racemate, hydrate, solvate, isotope, or salt thereof, wherein R$^x$ is hydrogen.

In further embodiments, compounds are provided having the structure of any one of Formulas (I) through (XVI-k), or a pharmaceutically acceptable isomer, racemate, hydrate, solvate, isotope, or salt thereof, wherein $R^x$ is lower alkyl. In more specific embodiments, compounds are provided having the structure of any one of Formulas (I) through (XVI-k), or a pharmaceutically acceptable isomer, racemate, hydrate, solvate, isotope, or salt thereof, wherein $R^x$ is methyl, ethyl, or isopropyl.

In further embodiments, compounds are provided having the structure of any one of Formulas (I) through (XVI-k), or a pharmaceutically acceptable isomer, racemate, hydrate, solvate, isotope, or salt thereof, wherein $R^x$ is lower alkoxy. In more specific embodiments, compounds are provided having the structure of any one of Formulas (I) through (XVI-k) or a pharmaceutically acceptable isomer, racemate, hydrate, solvate, isotope, or salt thereof, wherein $R^x$ is methoxy, ethoxy, isopropoxy, or t-butoxy.

In further embodiments, compounds are provided having the structure of any one of Formulas (I) through (XVI-k), or a pharmaceutically acceptable isomer, racemate, hydrate, solvate, isotope, or salt thereof, wherein $R^x$ is cycloalkyl. In more specific embodiments, compounds are provided having the structure of any one of Formulas (I) through (XVI-k), or a pharmaceutically acceptable isomer, racemate, hydrate, solvate, isotope, or salt thereof, wherein $R^x$ is cyclopropyl or cyclobutyl.

In further embodiments, compounds are provided having the structure of any one of Formulas (I) through (XVI-k), or a pharmaceutically acceptable isomer, racemate, hydrate, solvate, isotope, or salt thereof, wherein $R^3$ is $-Q-(R^4)_p$. In further embodiments, p is 0. In further embodiments, p is 1 or 2. In further embodiments, p is 1.

In further embodiments, compounds are provided having the structure of any one of Formulas (I) through (XVI-k) wherein $R^3$ is $-Q-(R^4)_p$ and $R^4$ is halogen. In more specific embodiments, compounds are provided wherein $R^4$ is F or Cl.

In further embodiments compounds are provided having the structure of any one of Formulas (I) through (XVI-k) wherein $R^2$ is $-Q-(R^4)_p$ and $R^4$ is lower alkyl. In more specific embodiments, compounds are provided wherein $R^4$ is methyl or ethyl.

In further embodiments compounds are provided having the structure of any one of Formulas (I) through (XVI-k) wherein $R^3$ is $-Q-(R^4)_p$ and $R^4$ is lower alkoxy. In more specific embodiments, compounds are provided wherein $R^4$ is methoxy or ethoxy.

In further embodiments compounds are provided having the structure of any one of Formulas (I) through (XVI-k) wherein $R^3$ is $-Q-(R^4)_p$ and $R^4$ is cyano.

In further embodiments compounds are provided having the structure of any one of Formulas (I) through (XVI-k) wherein $R^3$ is $-Q-(R^4)_n$ and $R^4$ is hydroxy.

In further embodiments, compounds are provided having the structure of any one of Formulas (I) through (XVI-k) wherein $R^3$ is $-S(=O)_2R^5$ or $-C(=O)R^5$ and $R^5$ is lower alkyl. In more specific embodiments, compounds are provided wherein $R^5$ is methyl, ethyl, or isopropyl.

In further embodiments, compounds are provided having the structure of any one of Formulas (I) through (XVI-k) wherein $R^3$ is $-S(=O)_2R^5$ or $-C(=O)R^5$ and $R^5$ is lower alkoxy. In more specific embodiments, compounds are provided wherein $R^5$ is t-butoxy.

Representative compounds of Formula (I), and Formulas (II) through (XVI-k) as applicable, include the compounds listed in Table 1 below, as well as pharmaceutically acceptable isomers, racemates, hydrates, solvates, isotopes, and salts thereof. To this end, representative compounds are identified herein by their respective "Compound Number", which is sometimes abbreviated as "Compound No.", "Cpd. No." or "No."

TABLE 1

Representative Compounds

| No. | Structure |
|---|---|
| 1-1 | 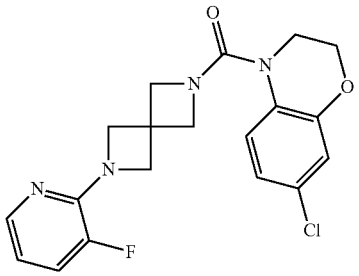 [SMILES: O=C(N1CC2(C1)CN(c1ncccc1F)C2)N1CCOc2cc(Cl)ccc21] |
| 1-2 | 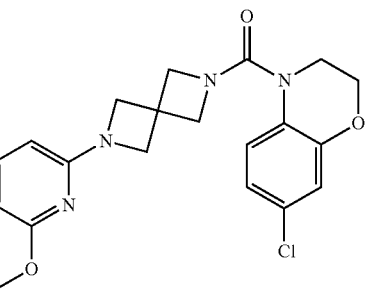 |
| 1-3 | 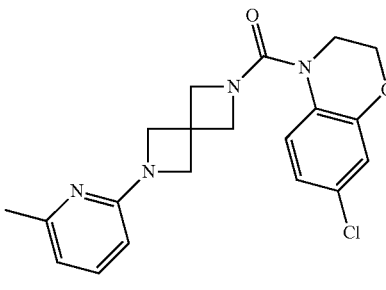 |
| 1-4 | 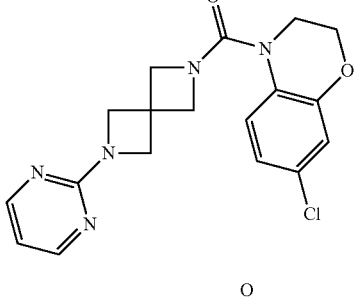 |
| 1-5 | 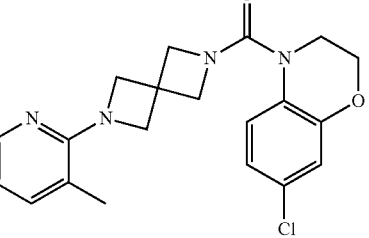 |

TABLE 1-continued

Representative Compounds

| No. | Structure |
|---|---|
| 1-6 | 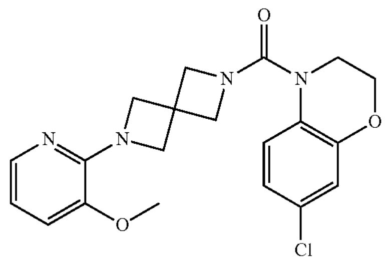 [SMILES: COc1cccnc1N1CC2(CN(C(=O)N3CCOc4cc(Cl)ccc43)C2)C1] |
| 1-7 | 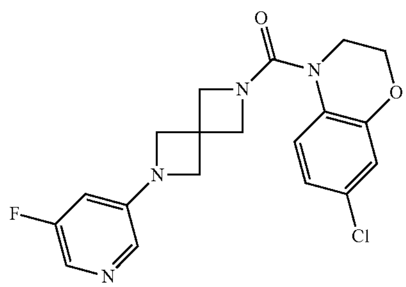 [SMILES: O=C(N1CC2(C1)CN(c1cncc(F)c1)C2)N1CCOc2cc(Cl)ccc21] |
| 1-8 | 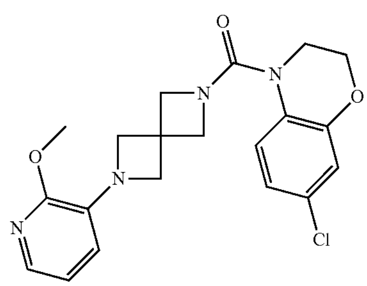 [SMILES: COc1ncccc1N1CC2(CN(C(=O)N3CCOc4cc(Cl)ccc43)C2)C1] |
| 1-9 | 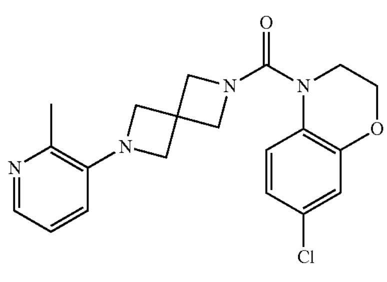 [SMILES: Cc1ncccc1N1CC2(CN(C(=O)N3CCOc4cc(Cl)ccc43)C2)C1] |
| 1-10 | 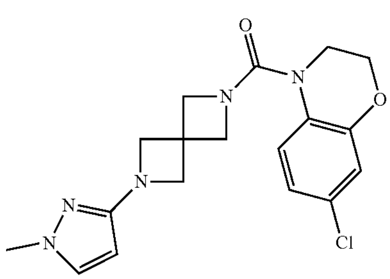 [SMILES: Cn1ccc(N2CC3(CN(C(=O)N4CCOc5cc(Cl)ccc54)C3)C2)n1] |

TABLE 1-continued

Representative Compounds

| No. | Structure |
|---|---|
| 1-11 | 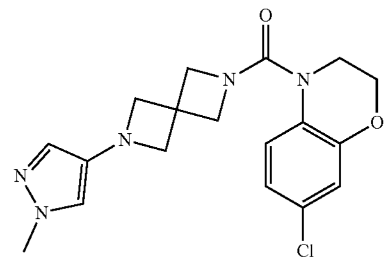 [SMILES: Cn1cc(N2CC3(CN(C(=O)N4CCOc5cc(Cl)ccc54)C3)C2)cn1] |
| 1-12 | 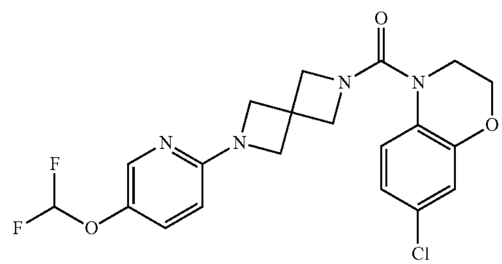 [SMILES: O=C(N1CC2(C1)CN(c1ccc(OC(F)F)cn1)C2)N1CCOc2cc(Cl)ccc21] |
| 1-13 | 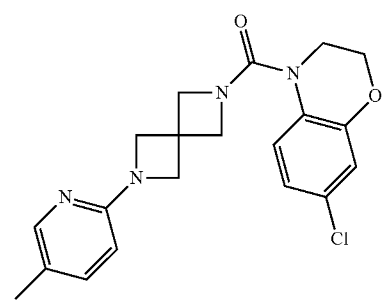 [SMILES: Cc1ccc(N2CC3(CN(C(=O)N4CCOc5cc(Cl)ccc54)C3)C2)nc1] |
| 1-14 | 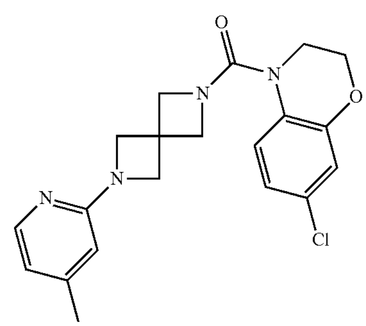 [SMILES: Cc1ccnc(N2CC3(CN(C(=O)N4CCOc5cc(Cl)ccc54)C3)C2)c1] |
| 1-15 | 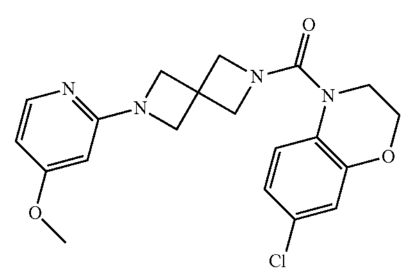 [SMILES: COc1ccnc(N2CC3(CN(C(=O)N4CCOc5cc(Cl)ccc54)C3)C2)c1] |

TABLE 1-continued

Representative Compounds

| No. | Structure |
|---|---|
| 1-16 | 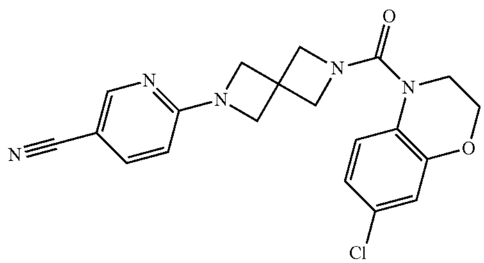 [SMILES: N#Cc1ccc(N2CC3(CN(C(=O)N4CCOc5cc(Cl)ccc54)C3)C2)nc1] |
| 1-17 | 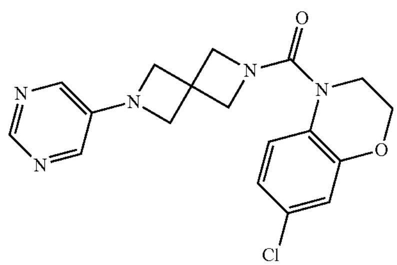 [SMILES: O=C(N1CC2(C1)CN(c1cncnc1)C2)N1CCOc2cc(Cl)ccc21] |
| 1-18 | 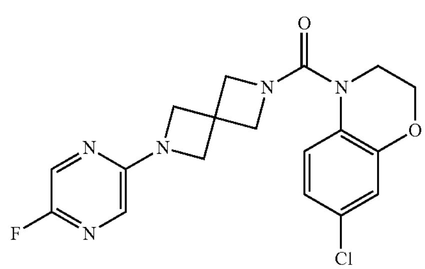 |
| 1-19 | 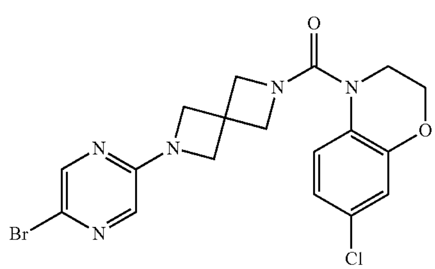 [SMILES: O=C(N1CC2(C1)CN(c1cnc(Br)cn1)C2)N1CCOc2cc(Cl)ccc21] |
| 1-20 | 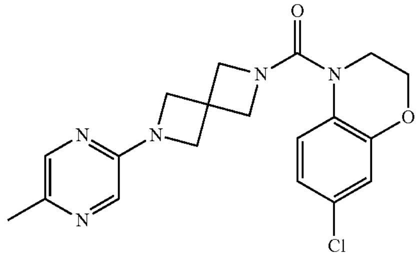 |

TABLE 1-continued

Representative Compounds

| No. | Structure |
|---|---|
| 1-21 | 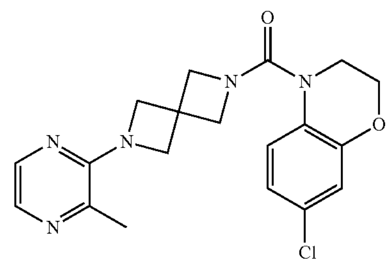 [SMILES: Cc1nccnc1N1CC2(CN(C(=O)N3CCOc4cc(Cl)ccc43)C2)C1] |
| 1-22 | 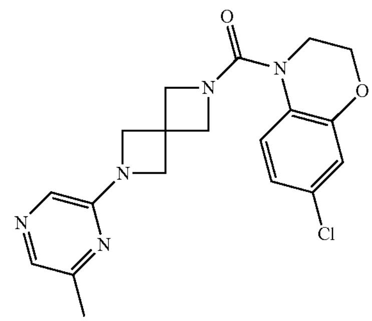 [SMILES: Cc1cncc(N2CC3(CN(C(=O)N4CCOc5cc(Cl)ccc54)C3)C2)n1] |
| 1-23 | 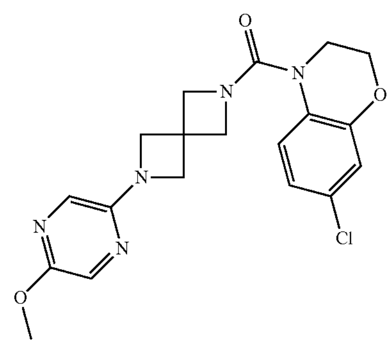 [SMILES: COc1cnc(N2CC3(CN(C(=O)N4CCOc5cc(Cl)ccc54)C3)C2)cn1] |
| 1-24 | 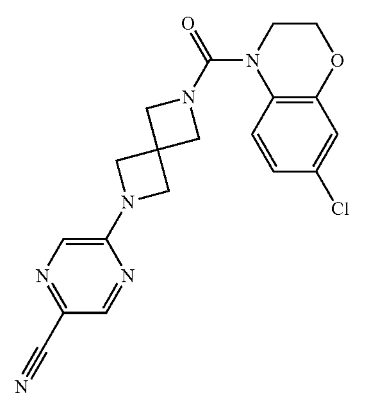 [SMILES: N#Cc1cnc(N2CC3(CN(C(=O)N4CCOc5cc(Cl)ccc54)C3)C2)cn1] |

TABLE 1-continued

Representative Compounds

| No. | Structure |
|---|---|
| 1-25 | 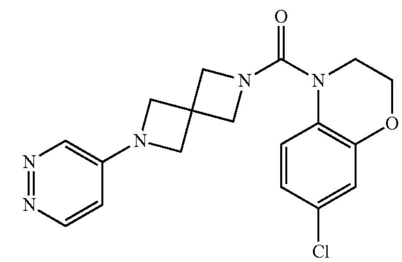 [SMILES: O=C(N1CC2(C1)CN(c1ccnnc1)C2)N1CCOc2cc(Cl)ccc21] |
| 1-26 | 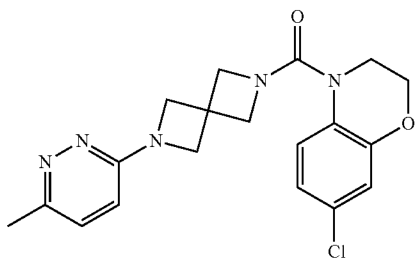 [SMILES: Cc1ccc(N2CC3(CN(C(=O)N4CCOc5cc(Cl)ccc54)C3)C2)nn1] |
| 1-27 | 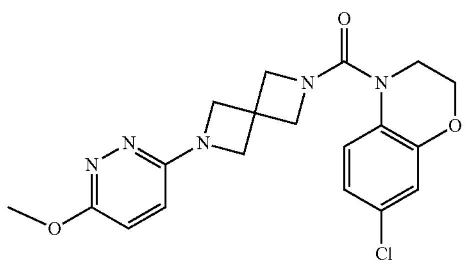 [SMILES: COc1ccc(N2CC3(CN(C(=O)N4CCOc5cc(Cl)ccc54)C3)C2)nn1] |
| 1-28 | 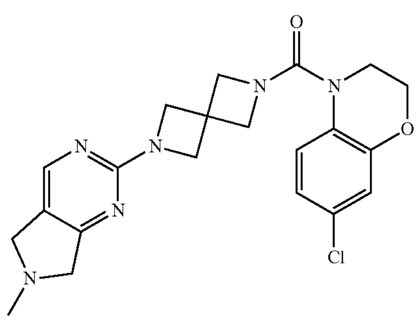 [SMILES: CN1Cc2cnc(N3CC4(CN(C(=O)N5CCOc6cc(Cl)ccc65)C4)C3)nc2C1] |
| 1-29 | 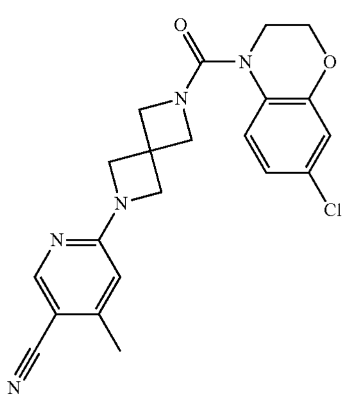 [SMILES: Cc1cc(N2CC3(CN(C(=O)N4CCOc5cc(Cl)ccc54)C3)C2)ncc1C#N] |
| 1-30 | |
| 1-31 | |
| 1-32 | |
| 1-33 | |

103

TABLE 1-continued

Representative Compounds

| No. | Structure |
|---|---|
| 1-34 | 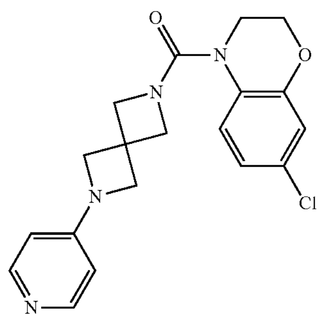 [SMILES: O=C(N1CC2(C1)CN(c1ccncc1)C2)N1CCOc2cc(Cl)ccc21] |
| 1-35 | 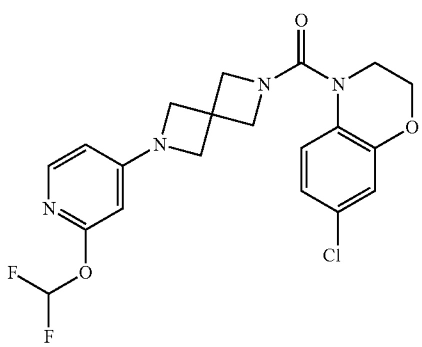 [SMILES: O=C(N1CC2(C1)CN(c1ccnc(OC(F)F)c1)C2)N1CCOc2cc(Cl)ccc21] |
| 1-36 | 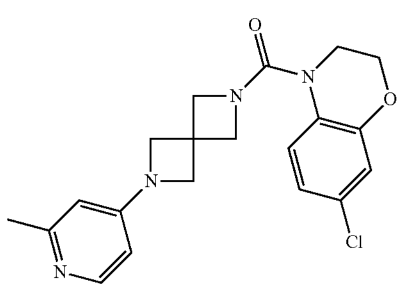 |
| 1-37 | 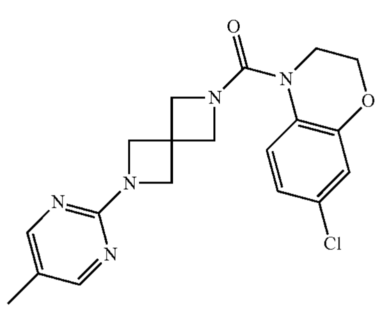 [SMILES: Cc1cnc(N2CC3(CN(C(=O)N4CCOc5cc(Cl)ccc54)C3)C2)nc1] |

104

TABLE 1-continued

Representative Compounds

| No. | Structure |
|---|---|
| 1-38 | 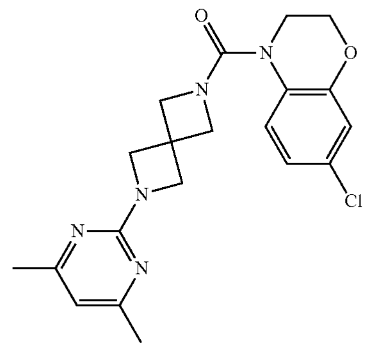 [SMILES: Cc1cc(C)nc(N2CC3(CN(C(=O)N4CCOc5cc(Cl)ccc54)C3)C2)n1] |
| 1-39 | 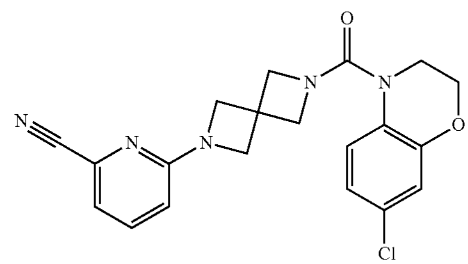 [SMILES: N#Cc1cccc(N2CC3(CN(C(=O)N4CCOc5cc(Cl)ccc54)C3)C2)n1] |
| 1-40 | 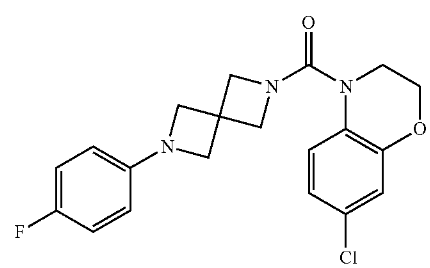 |
| 1-41 | 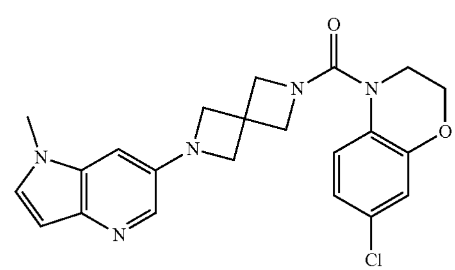 [SMILES: Cn1ccc2ncc(N3CC4(CN(C(=O)N5CCOc6cc(Cl)ccc65)C4)C3)cc21] |
| 1-42 | 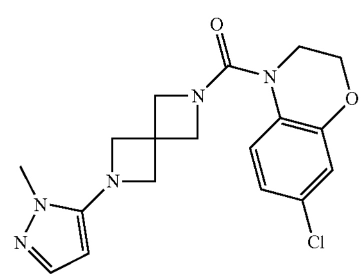 [SMILES: Cn1nccc1N1CC2(CN(C(=O)N3CCOc4cc(Cl)ccc43)C2)C1] |

TABLE 1-continued

Representative Compounds

| No. | Structure |
|-----|-----------|
| 1-43 | 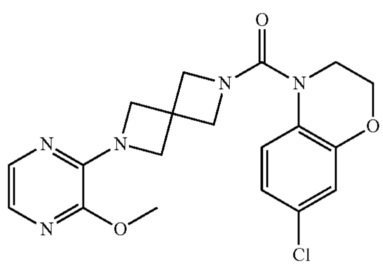 [SMILES: COc1nccnc1N1CC2(CN(C(=O)N3CCOc4cc(Cl)ccc43)C2)C1] |
| 1-44 | 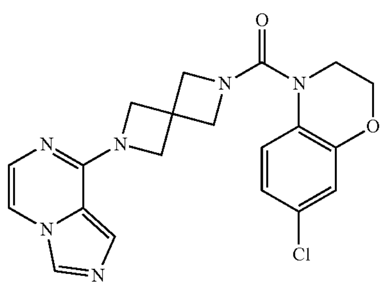 [SMILES: O=C(N1CC2(C1)CN(c1nccn3cncc13)C2)N1CCOc2cc(Cl)ccc21] |
| 1-45 | 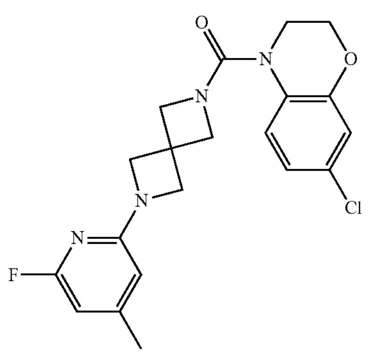 [SMILES: Cc1cc(F)nc(N2CC3(CN(C(=O)N4CCOc5cc(Cl)ccc54)C3)C2)c1] |
| 1-46 | 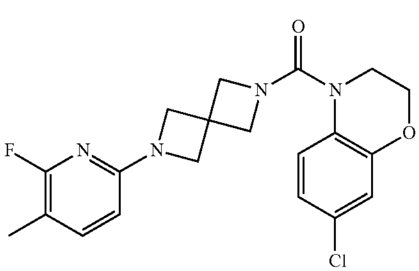 [SMILES: Cc1ccc(N2CC3(CN(C(=O)N4CCOc5cc(Cl)ccc54)C3)C2)nc1F] |
| 1-47 | 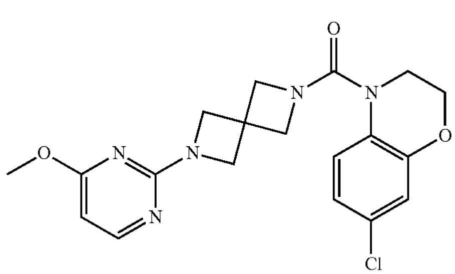 [SMILES: COc1ccnc(N2CC3(CN(C(=O)N4CCOc5cc(Cl)ccc54)C3)C2)n1] |
| 1-48 | |
| 1-49 | |
| 1-50 | |
| 1-51 | |
| 1-52 | |

TABLE 1-continued

Representative Compounds

| No. | Structure |
|-----|-----------|
| 1-53 | |
| 1-54 | |
| 1-55 | |
| 1-56 | |
| 1-57 | |
| 1-58 | 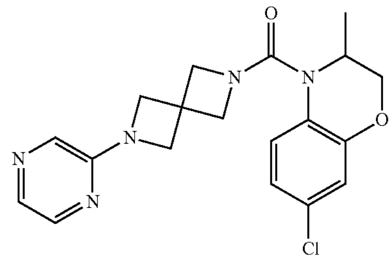 [SMILES: CC1COc2cc(Cl)ccc2N1C(=O)N1CC2(C1)CN(c1cnccn1)C2] |
| 1-59 | 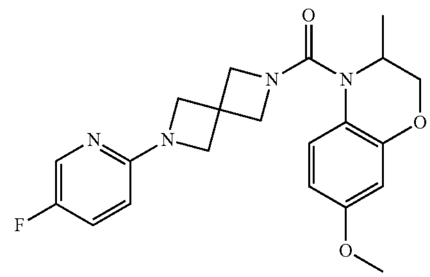 |
| 1-60 | 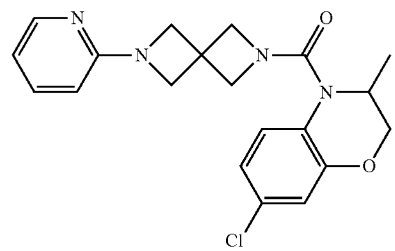 [SMILES: CC1COc2cc(Cl)ccc2N1C(=O)N1CC2(C1)CN(c1ccccn1)C2] |
| 1-61 | 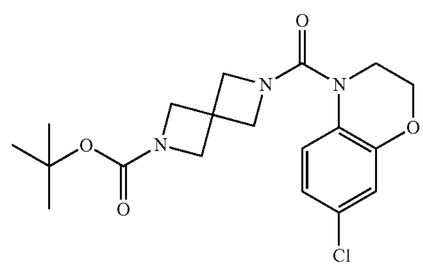 [SMILES: CC(C)(C)OC(=O)N1CC2(C1)CN(C(=O)N1CCOc3cc(Cl)ccc31)C2] |
| 1-62 | 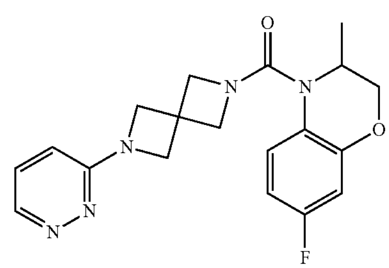 [SMILES: CC1COc2cc(F)ccc2N1C(=O)N1CC2(C1)CN(c1cccnn1)C2] |
| 1-63 | 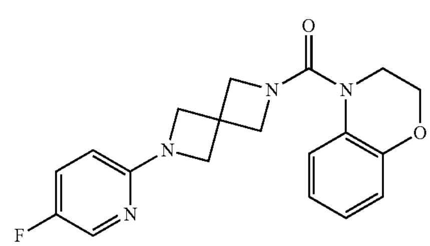 |

TABLE 1-continued

Representative Compounds

| No. | Structure |
|---|---|
| 1-64 | 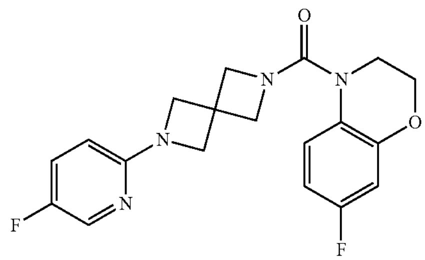 |
| 1-65 | 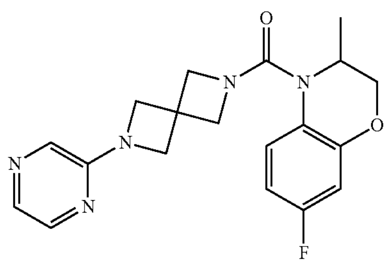 [SMILES: CC1COc2cc(F)ccc2N1C(=O)N1CC2(C1)CN(c1cnccn1)C2] |
| 1-66 | 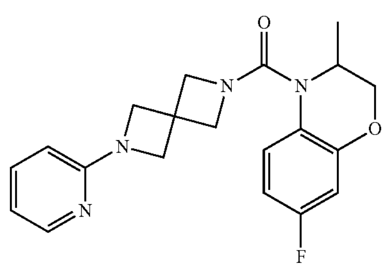 [SMILES: CC1COc2cc(F)ccc2N1C(=O)N1CC2(C1)CN(c1ccccn1)C2] |
| 1-67 | 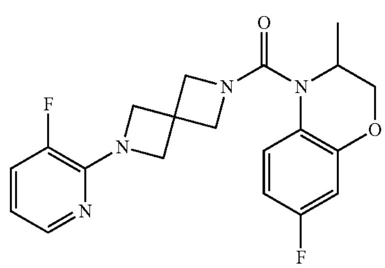 [SMILES: CC1COc2cc(F)ccc2N1C(=O)N1CC2(C1)CN(c1ncccc1F)C2] |
| 1-68 | 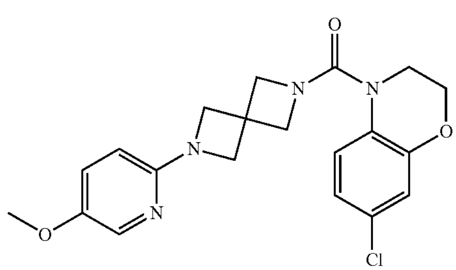 [SMILES: COc1ccc(N2CC3(CN(C(=O)N4CCOc5cc(Cl)ccc54)C3)C2)nc1] |
| 1-69 | 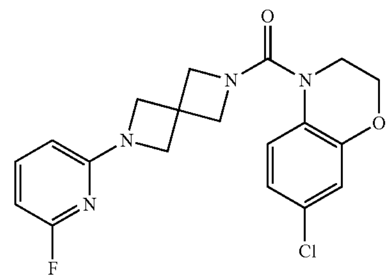 [SMILES: O=C(N1CC2(C1)CN(c1cccc(F)n1)C2)N1CCOc2cc(Cl)ccc21] |
| 1-70 | 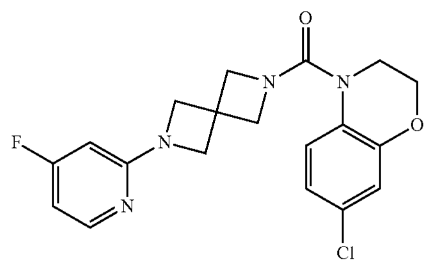 [SMILES: O=C(N1CC2(C1)CN(c1cc(F)ccn1)C2)N1CCOc2cc(Cl)ccc21] |
| 1-71 | 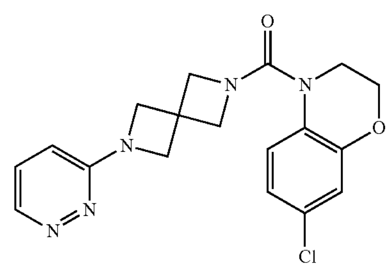 |
| 1-72 | 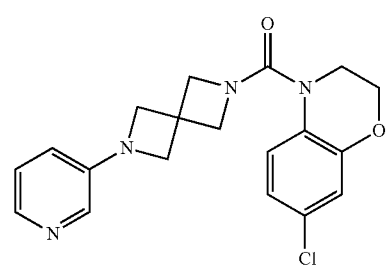 [SMILES: O=C(N1CC2(C1)CN(c1cccnc1)C2)N1CCOc2cc(Cl)ccc21] |
| 1-73 | 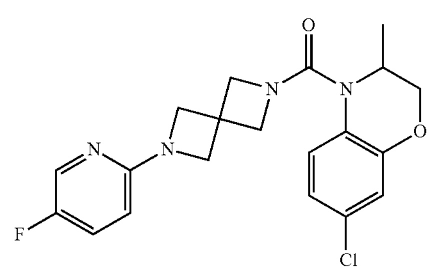 [SMILES: CC1COc2cc(Cl)ccc2N1C(=O)N1CC2(C1)CN(c1ccc(F)cn1)C2] |

TABLE 1-continued

Representative Compounds

| No. | Structure |
|---|---|
| 1-74 | 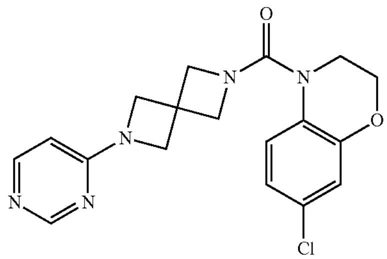 [SMILES: O=C(N1CC2(C1)CN(c1ccncn1)C2)N1CCOc2cc(Cl)ccc21] |
| 1-75 | 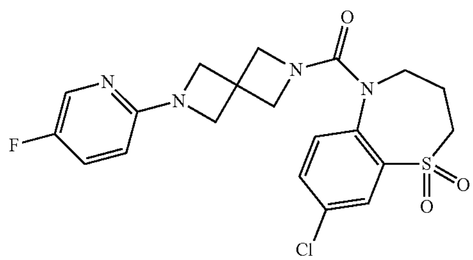 [SMILES: O=C(N1CC2(C1)CN(c1ccc(F)cn1)C2)N1CCCS(=O)(=O)c2cc(Cl)ccc21] |
| 1-76 | 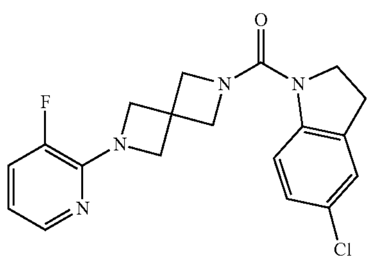 [SMILES: O=C(N1CC2(C1)CN(c1ncccc1F)C2)N1CCc2cc(Cl)ccc21] |
| 1-77 | 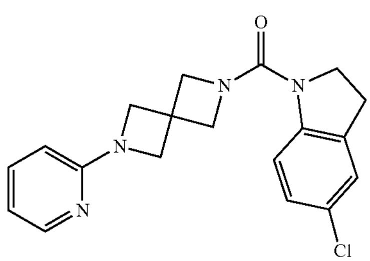 [SMILES: O=C(N1CC2(C1)CN(c1ccccn1)C2)N1CCc2cc(Cl)ccc21] |
| 1-78 | 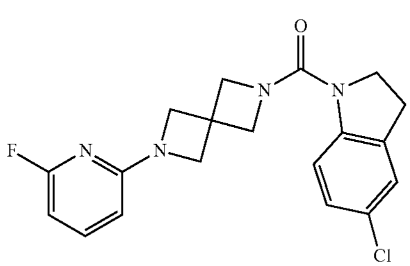 [SMILES: O=C(N1CC2(C1)CN(c1cccc(F)n1)C2)N1CCc2cc(Cl)ccc21] |

TABLE 1-continued

Representative Compounds

| No. | Structure |
|---|---|
| 1-79 | 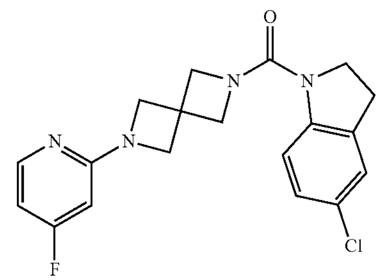 [SMILES: O=C(N1CC2(C1)CN(c1cc(F)ccn1)C2)N1CCc2cc(Cl)ccc21] |
| 1-80 | 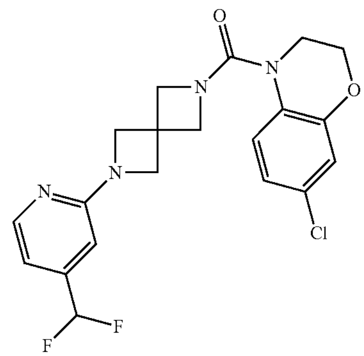 [SMILES: O=C(N1CC2(C1)CN(c1cc(C(F)F)ccn1)C2)N1CCOc2cc(Cl)ccc21] |
| 1-81 | 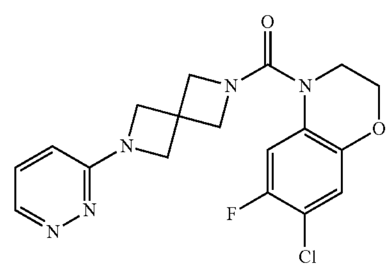 [SMILES: O=C(N1CC2(C1)CN(c1cccnn1)C2)N1CCOc2cc(Cl)c(F)cc21] |
| 1-82 | 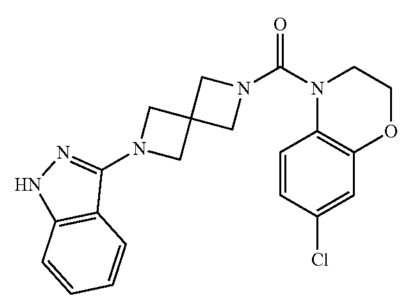 [SMILES: O=C(N1CC2(C1)CN(c1n[nH]c3ccccc13)C2)N1CCOc2cc(Cl)ccc21] |
| 1-83 | 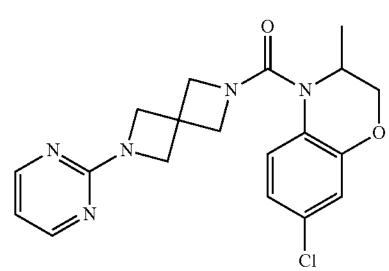 [SMILES: CC1COc2cc(Cl)ccc2N1C(=O)N1CC2(C1)CN(c1ncccn1)C2] |

TABLE 1-continued
Representative Compounds
| No. | Structure |
|---|---|
| 1-84 | 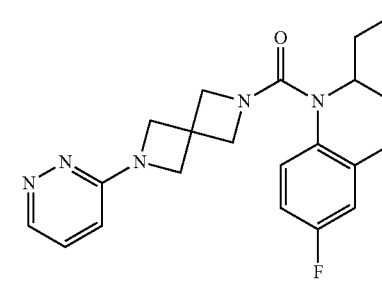 |
| 1-85 | 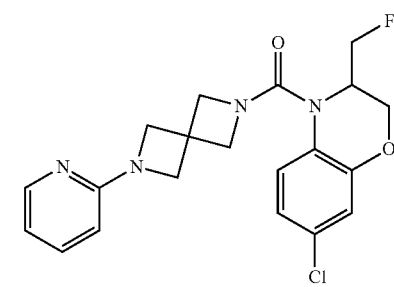 [SMILES: O=C(N1CC2(C1)CN(c1ccccn1)C2)N1c2ccc(Cl)cc2OCC1CF] |
| 1-86 | 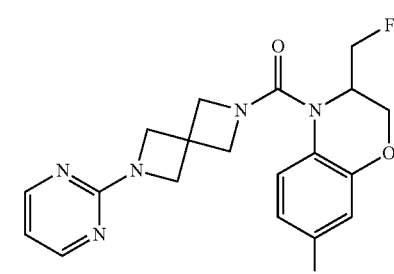 |
| 1-87 | 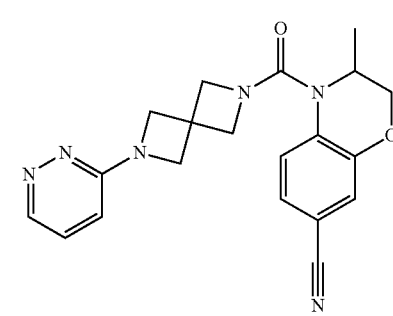 |
| 1-88 | 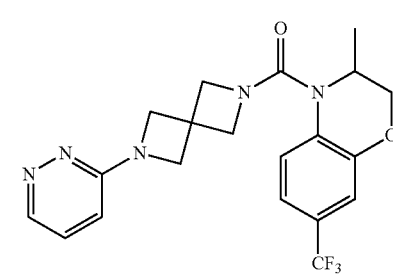 |
| 1-89 | 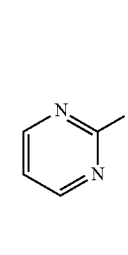 |
| 1-90 | 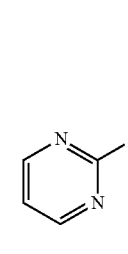 |
| 2-1 |  |
| 2-2 | 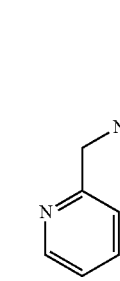 |
| 2-3 | |

TABLE 1-continued

Representative Compounds

| No. | Structure |
|---|---|
| 2-4 | 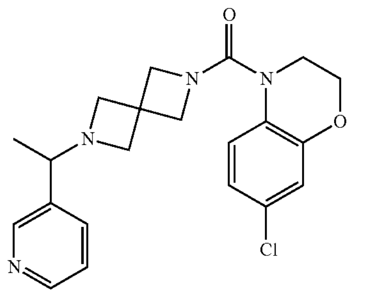 [SMILES: CC(c1cccnc1)N1CC2(CN(C(=O)N3CCOc4cc(Cl)ccc43)C2)C1] |
| 2-5 | 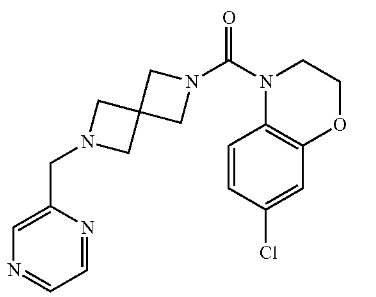 [SMILES: O=C(N1CC2(CN(Cc3cnccn3)C2)C1)N1CCOc2cc(Cl)ccc21] |
| 2-6 | 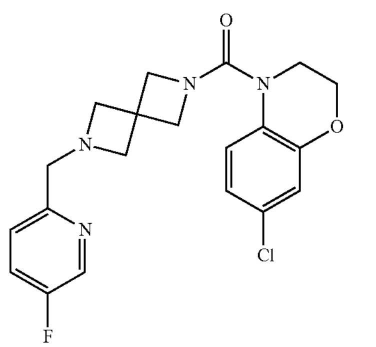 [SMILES: O=C(N1CC2(CN(Cc3ccc(F)cn3)C2)C1)N1CCOc2cc(Cl)ccc21] |
| 3-1 | 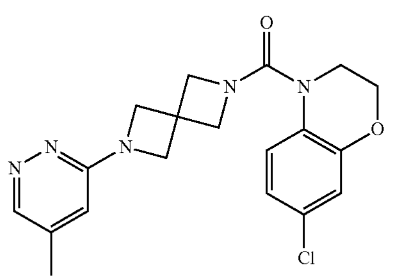 [SMILES: Cc1cnnc(N2CC3(CN(C(=O)N4CCOc5cc(Cl)ccc54)C3)C2)c1] |
| 4-1 | 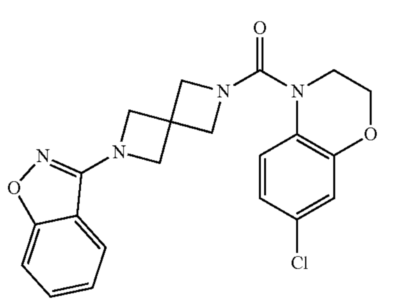 [SMILES: O=C(N1CC2(C1)CN(c1noc3ccccc13)C2)N1CCOc2cc(Cl)ccc21] |
| 4-2 | |
| 4-3 | |
| 5-1 | |
| 6-1 | |
| 6-2 | |

TABLE 1-continued

Representative Compounds

| No. | Structure |
|---|---|
| 6-3 | 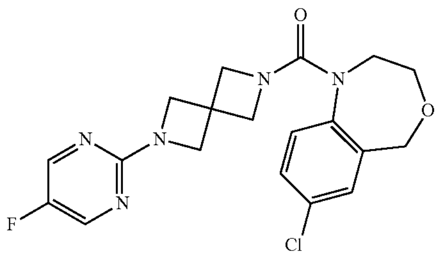 [SMILES: O=C(N1CC2(C1)CN(c1ncc(F)cn1)C2)N1CCOCc2cc(Cl)ccc21] |
| 6-4 | 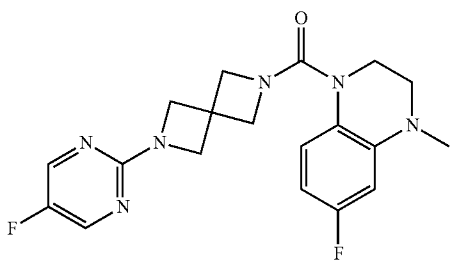 [SMILES: CN1CCN(C(=O)N2CC3(C2)CN(c2ncc(F)cn2)C3)c2ccc(F)cc21] |
| 6-5 | 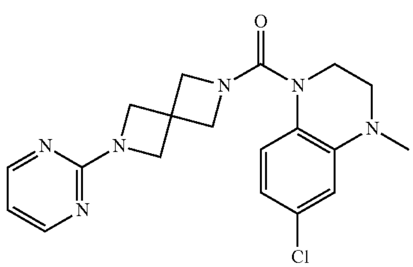 [SMILES: CN1CCN(C(=O)N2CC3(C2)CN(c2ncccn2)C3)c2ccc(Cl)cc21] |
| 6-6 | 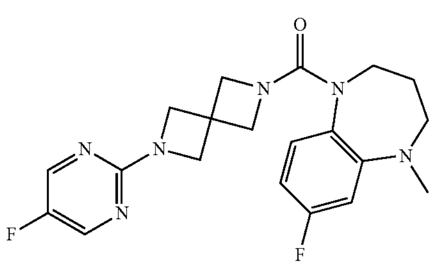 [SMILES: CN1CCCN(C(=O)N2CC3(C2)CN(c2ncc(F)cn2)C3)c2ccc(F)cc21] |
| 6-7 | 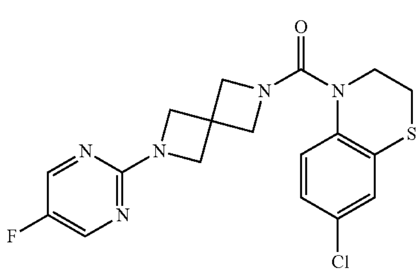 [SMILES: O=C(N1CC2(C1)CN(c1ncc(F)cn1)C2)N1CCSc2cc(Cl)ccc21] |
| 6-8 | |
| 7-1 | |
| 8-1 | |
| 8-2 | |
| 8-3 | |

TABLE 1-continued

Representative Compounds

| No. | Structure |
|---|---|
| 8-4 | (structure) |
| 8-5 | (structure) |
| 8-6 | (structure) |
| 8-7 | (structure) |
| 8-8 | (structure) |
| 8-9 | (structure) |
| 8-10 | (structure) |
| 8-11 | (structure) |
| 8-12 | (structure) |
| 8-13 | (structure) |
| 8-14 | (structure) |

TABLE 1-continued

Representative Compounds

| No. | Structure |
|---|---|
| 8-15 | 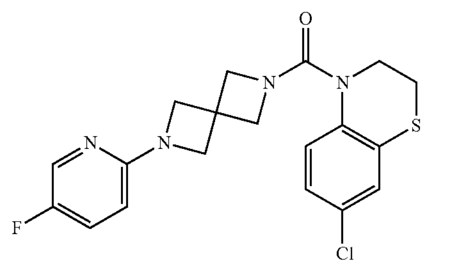 [SMILES: O=C(N1CC2(C1)CN(c1ccc(F)cn1)C2)N1CCSc2cc(Cl)ccc21] |
| 8-16 | 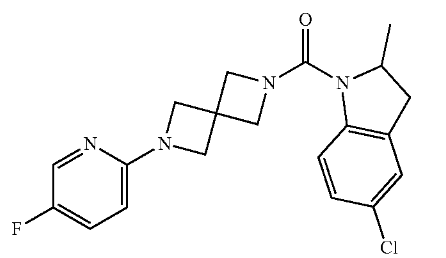 [SMILES: CC1Cc2cc(Cl)ccc2N1C(=O)N1CC2(C1)CN(c1ccc(F)cn1)C2] |
| 8-17 | 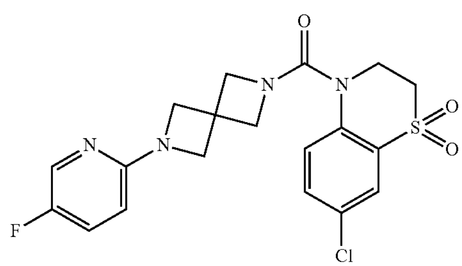 [SMILES: O=C(N1CC2(C1)CN(c1ccc(F)cn1)C2)N1CCS(=O)(=O)c2cc(Cl)ccc21] |
| 8-18 | 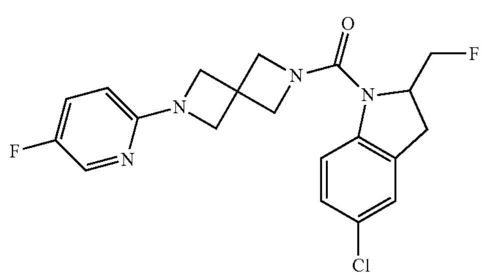 [SMILES: O=C(N1CC2(C1)CN(c1ccc(F)cn1)C2)N1c2ccc(Cl)cc2CC1CF] |
| 8-19 | 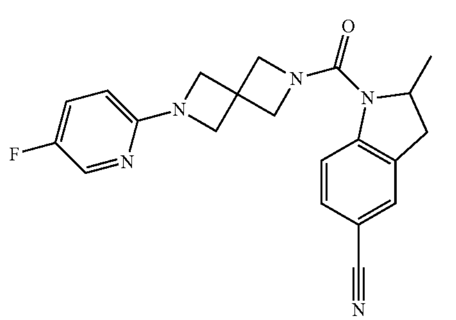 [SMILES: CC1Cc2cc(C#N)ccc2N1C(=O)N1CC2(C1)CN(c1ccc(F)cn1)C2] |
| 8-20 | |
| 9-1 | |
| 9-2 | |
| 9-3 | |
| 9-4 | |

TABLE 1-continued
Representative Compounds
| No. | Structure |
|---|---|
| 9-5 | 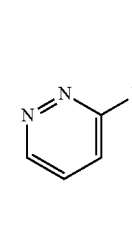 |
| 9-6 | 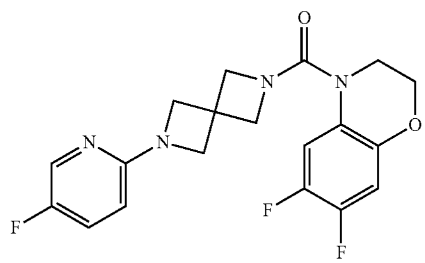 [SMILES: O=C(N1CC2(C1)CN(c1ccc(F)cn1)C2)N1CCOc2cc(F)c(F)cc21] |
| 9-7 | 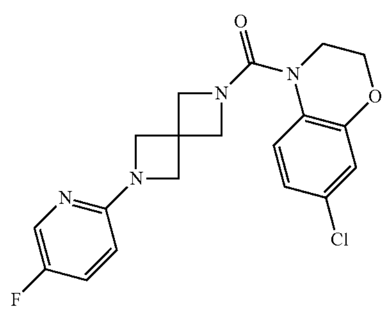 [SMILES: O=C(N1CC2(C1)CN(c1ccc(F)cn1)C2)N1CCOc2cc(Cl)ccc21] |
| 9-8 | 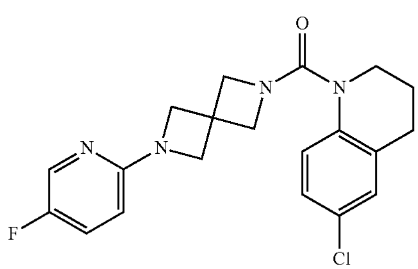 [SMILES: O=C(N1CC2(C1)CN(c1ccc(F)cn1)C2)N1CCCc2cc(Cl)ccc21] |
| 9-9 | 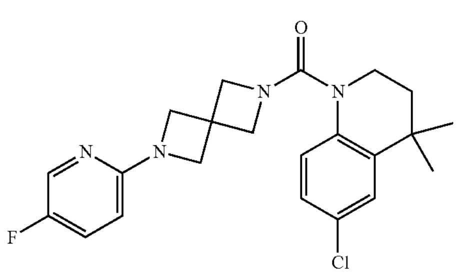 [SMILES: CC1(C)CCN(C(=O)N2CC3(C2)CN(c2ccc(F)cn2)C3)c2ccc(Cl)cc21] |
| 9-10 |  |
| 9-11 | |
| 9-12 | |
| 9-13 | |
| 9-14 | |

TABLE 1-continued
Representative Compounds
| No. | Structure |
|---|---|
| 9-15 | 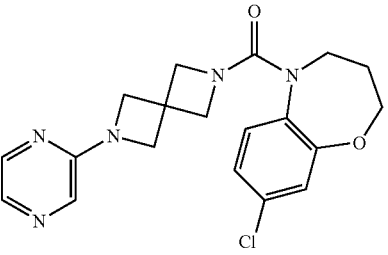 [SMILES: O=C(N1CC2(C1)CN(c1cnccn1)C2)N1CCCOc2cc(Cl)ccc21] |
| 9-16 | 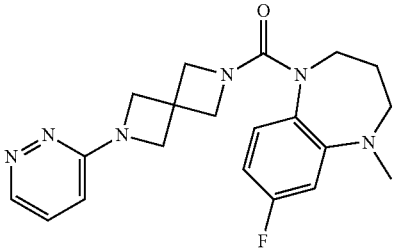 [SMILES: CN1CCCN(C(=O)N2CC3(C2)CN(c2cccnn2)C3)c2ccc(F)cc21] |
| 9-17 | 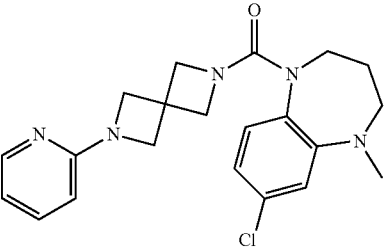 [SMILES: CN1CCCN(C(=O)N2CC3(C2)CN(c2ccccn2)C3)c2ccc(Cl)cc21] |
| 9-18 | 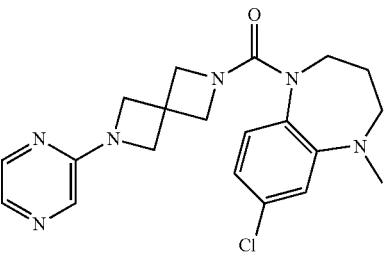 [SMILES: CN1CCCN(C(=O)N2CC3(C2)CN(c2cnccn2)C3)c2ccc(Cl)cc21] |
| 9-19 | 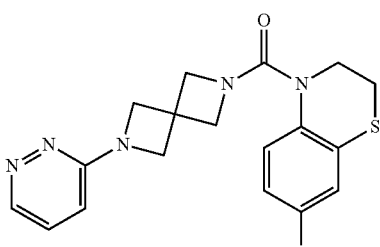 |
| 9-20 | 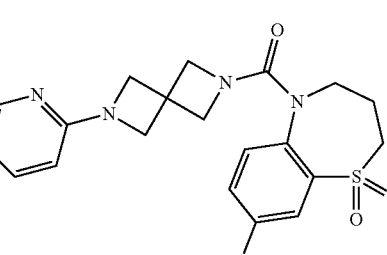 |
| 9-21 | 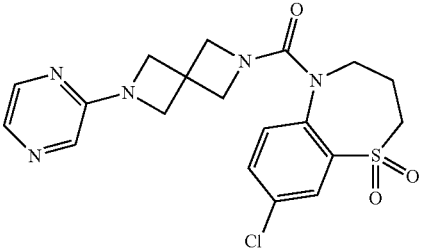 [SMILES: O=C(N1CC2(C1)CN(c1cnccn1)C2)N1CCCS(=O)(=O)c2cc(Cl)ccc21] |
| 9-22 | 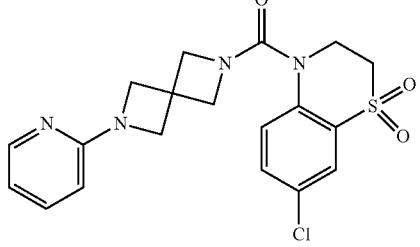 |
| 9-23 | 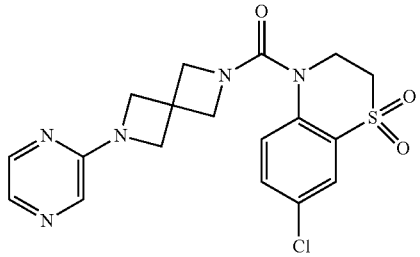 [SMILES: O=C(N1CC2(C1)CN(c1cnccn1)C2)N1CCS(=O)(=O)c2cc(Cl)ccc21] |
| 9-24 | 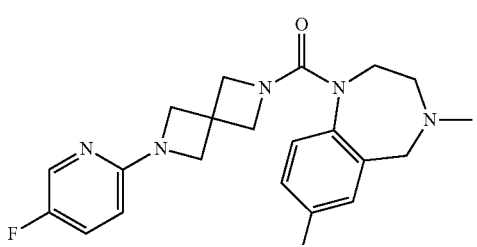 |
| 9-25 | 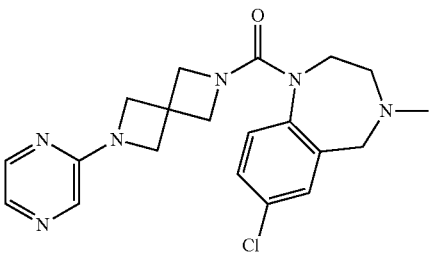 [SMILES: CN1CCN(C(=O)N2CC3(C2)CN(c2cnccn2)C3)c2ccc(Cl)cc2C1] |

TABLE 1-continued

Representative Compounds

| No. | Structure |
|---|---|
| 9-26 | 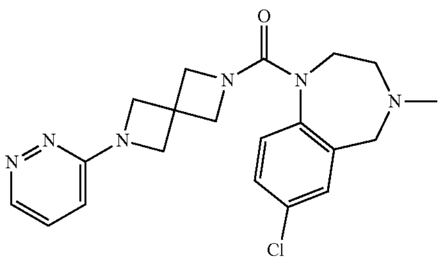 [SMILES: CN1CCN(C(=O)N2CC3(C2)CN(c2cccnn2)C3)c2ccc(Cl)cc2C1] |
| 9-27 | 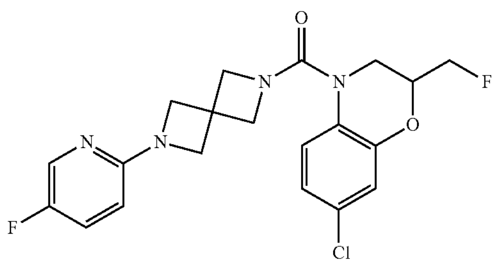 [SMILES: O=C(N1CC2(C1)CN(c1ccc(F)cn1)C2)N1CC(CF)Oc2cc(Cl)ccc21] |
| 9-28 | 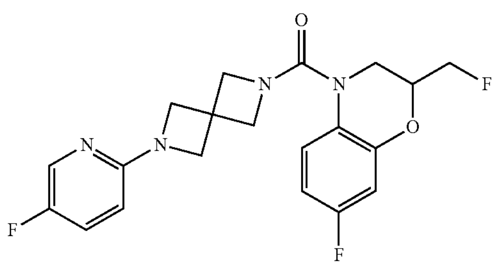 [SMILES: O=C(N1CC2(C1)CN(c1ccc(F)cn1)C2)N1CC(CF)Oc2cc(F)ccc21] |
| 9-29 | 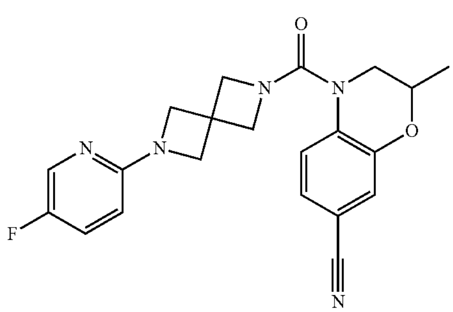 [SMILES: CC1CN(C(=O)N2CC3(C2)CN(c2ccc(F)cn2)C3)c2ccc(C#N)cc2O1] |
| 9-30 | 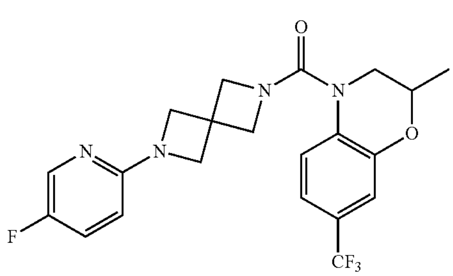 [SMILES: CC1CN(C(=O)N2CC3(C2)CN(c2ccc(F)cn2)C3)c2ccc(C(F)(F)F)cc2O1] |
| 9-31 | |
| 9-32 | |
| 10-1 | |
| 10-2 | |
| 10-3 | |

TABLE 1-continued
Representative Compounds
| No. | Structure |
|---|---|
| 10-4 | 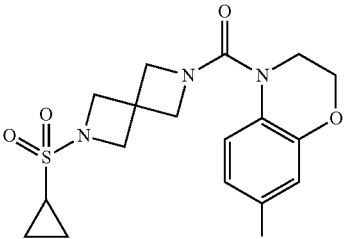 |
| 10-5 | 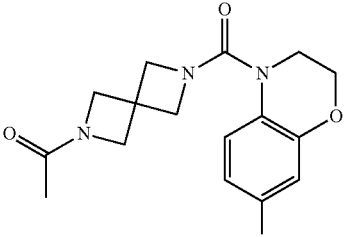 |
| 10-6 | 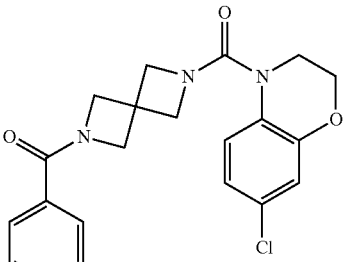 |
| 10-7 | 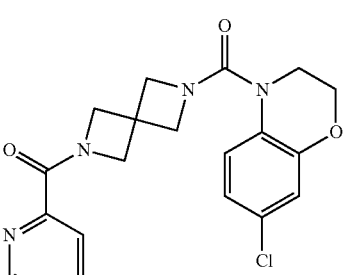 |
| 10-8 | 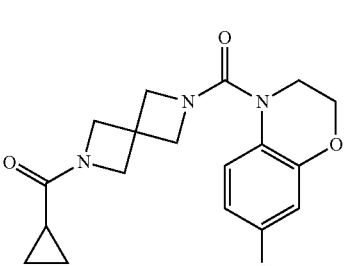 |
TABLE 1-continued
Representative Compounds
| No. | Structure |
|---|---|
| 11-1 | 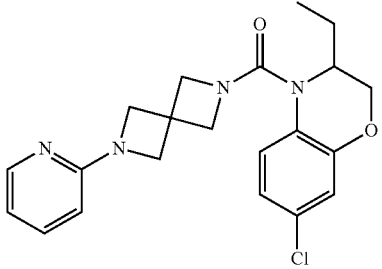 [SMILES: CCC1COc2cc(Cl)ccc2N1C(=O)N1CC2(C1)CN(c1ccccn1)C2] |
| 12-1 | 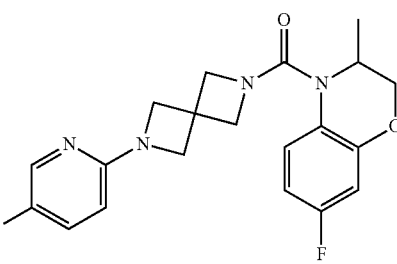 |
| 13-1 | 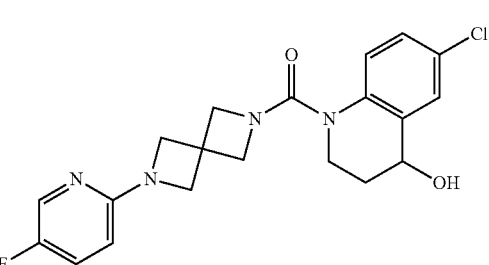 |
| 13-2 | 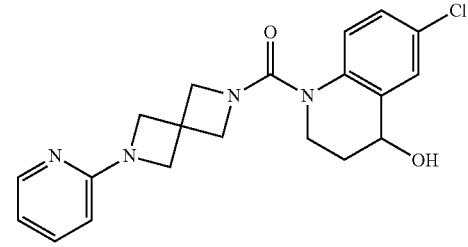 [SMILES: O=C(N1CC2(C1)CN(c1ccccn1)C2)N1CCC(O)c2cc(Cl)ccc21] |
| 13-3 | 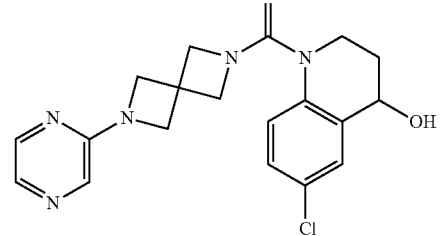 |

TABLE 1-continued
Representative Compounds
| No. | Structure |
|---|---|
| 13-4 | 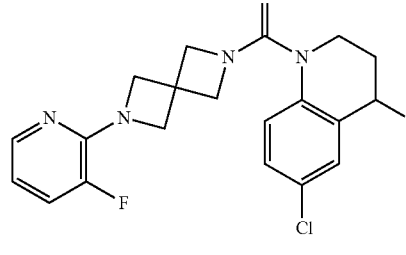 |
| 13-5 | 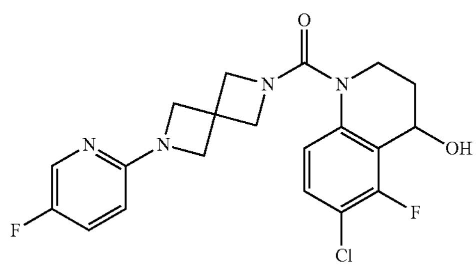 [SMILES: O=C(N1CC2(C1)CN(c1ccc(F)cn1)C2)N1CCC(O)c2c1ccc(Cl)c2F] |
| 13-6 | 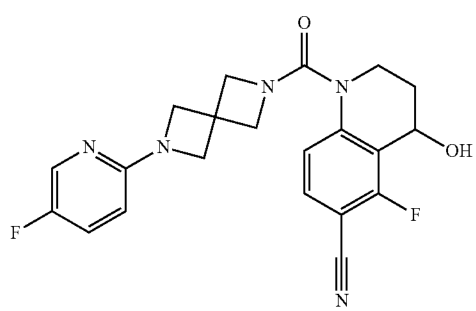 [SMILES: N#Cc1ccc2c(c1F)C(O)CCN2C(=O)N1CC2(C1)CN(c1ccc(F)cn1)C2] |
| 13-7 | 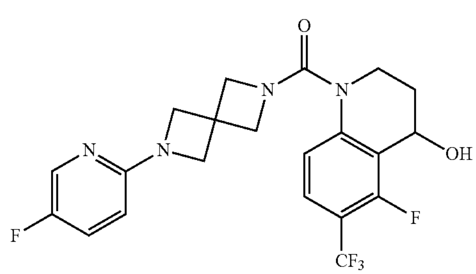 [SMILES: O=C(N1CC2(C1)CN(c1ccc(F)cn1)C2)N1CCC(O)c2c1ccc(C(F)(F)F)c2F] |
| 14-1 | 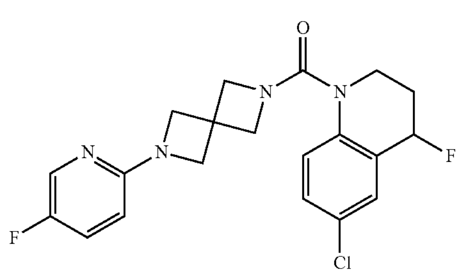 [SMILES: O=C(N1CC2(C1)CN(c1ccc(F)cn1)C2)N1CCC(F)c2cc(Cl)ccc21] |
TABLE 1-continued
Representative Compounds
| No. | Structure |
|---|---|
| 15-1 | 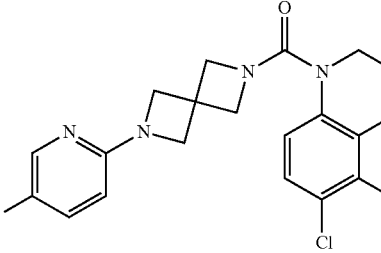 |
| 16-1 | 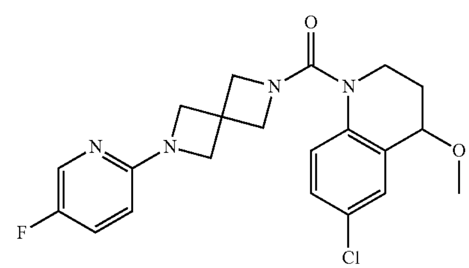 [SMILES: COC1CCN(C(=O)N2CC3(C2)CN(c2ccc(F)cn2)C3)c2ccc(Cl)cc21] |
| 17-1 | 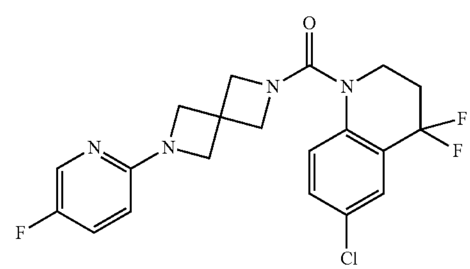 [SMILES: O=C(N1CC2(C1)CN(c1ccc(F)cn1)C2)N1CCC(F)(F)c2cc(Cl)ccc21] |
| 18-1 | 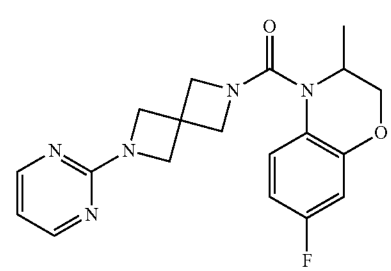 [SMILES: CC1COc2cc(F)ccc2N1C(=O)N1CC2(C1)CN(c1ncccn1)C2] |
| 18-2 | 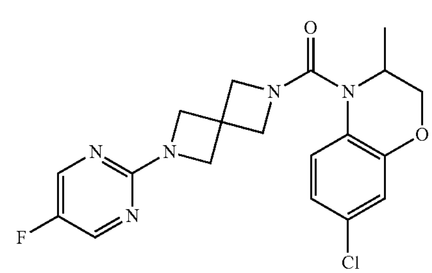 |

TABLE 1-continued

Representative Compounds

| No. | Structure |
|---|---|
| 18-3 | 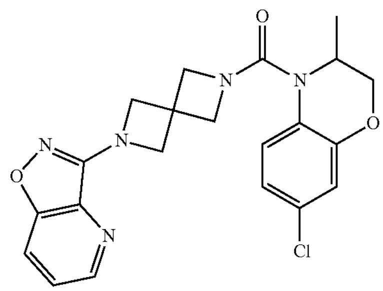 [SMILES: CC1COc2cc(Cl)ccc2N1C(=O)N1CC2(C1)CN(c1noc3cccnc13)C2] |
| 18-4 | 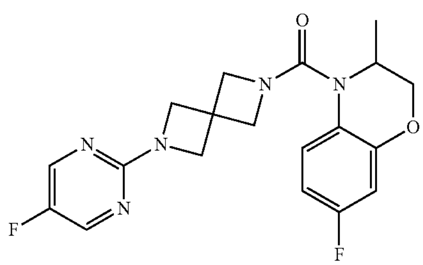 |
| 18-5 | 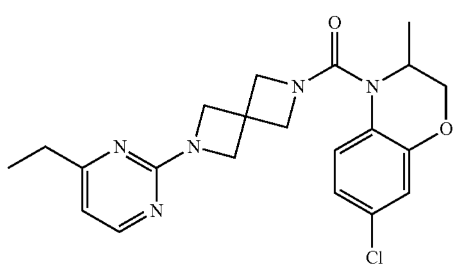 [SMILES: CCc1ccnc(N2CC3(CN(C(=O)N4c5ccc(Cl)cc5OCC4C)C3)C2)n1] |
| 19-1 | 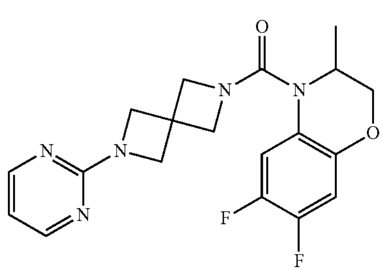 [SMILES: CC1COc2cc(F)c(F)cc2N1C(=O)N1CC2(C1)CN(c1ncccn1)C2] |
| 19-2 | 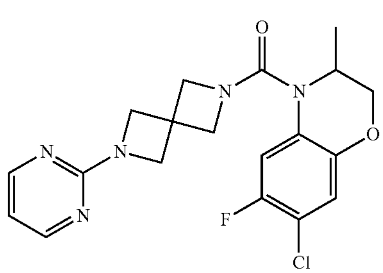 [SMILES: CC1COc2cc(Cl)c(F)cc2N1C(=O)N1CC2(C1)CN(c1ncccn1)C2] |
| 19-3 | |
| 19-4 | |
| 19-5 | |
| 19-6 | |
| 19-7 | |

TABLE 1-continued

Representative Compounds

| No. | Structure |
|---|---|
| 19-8 | 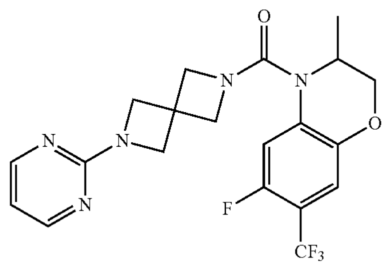 |
| 19-9 | 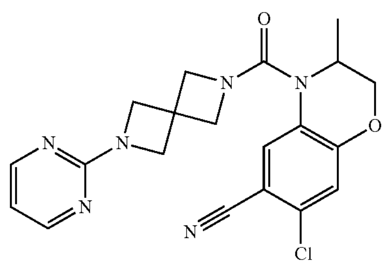 [SMILES: CC1COc2cc(Cl)c(C#N)cc2N1C(=O)N1CC2(C1)CN(c1ncccn1)C2] |
| 19-10 | 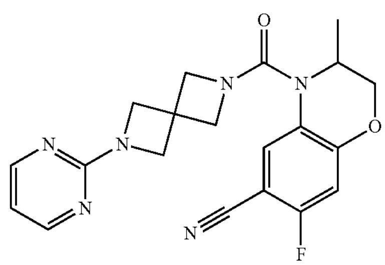 [SMILES: CC1COc2cc(F)c(C#N)cc2N1C(=O)N1CC2(C1)CN(c1ncccn1)C2] |
| 19-11 | 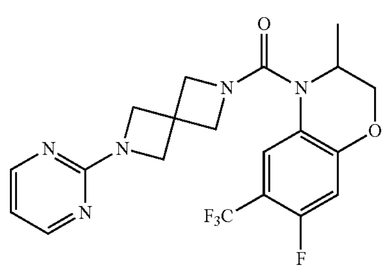 [SMILES: CC1COc2cc(F)c(C(F)(F)F)cc2N1C(=O)N1CC2(C1)CN(c1ncccn1)C2] |
| 19-12 | 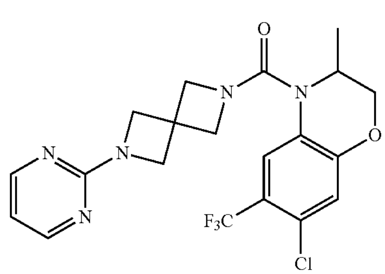 [SMILES: CC1COc2cc(Cl)c(C(F)(F)F)cc2N1C(=O)N1CC2(C1)CN(c1ncccn1)C2] |

TABLE 1-continued

Representative Compounds

| No. | Structure |
|---|---|
| 19-13 | 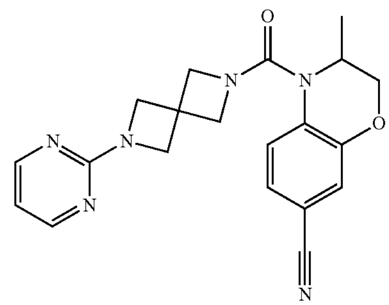 [SMILES: CC1COc2cc(C#N)ccc2N1C(=O)N1CC2(C1)CN(c1ncccn1)C2] |
| 19-14 | 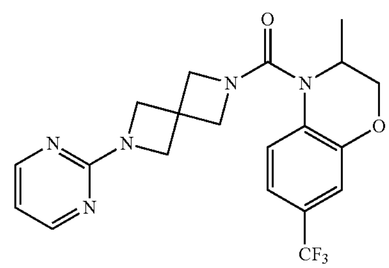 [SMILES: CC1COc2cc(C(F)(F)F)ccc2N1C(=O)N1CC2(C1)CN(c1ncccn1)C2] |
| 19-15 | 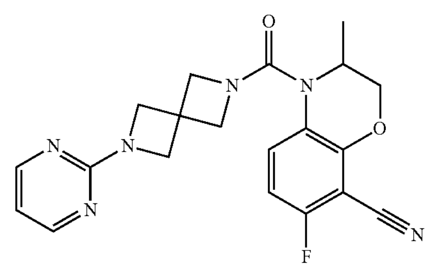 |
| 19-16 | 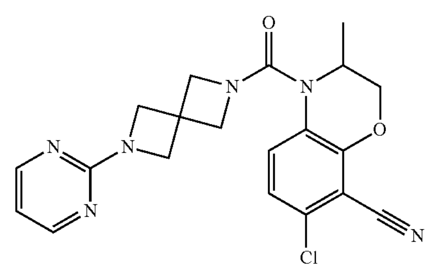 [SMILES: CC1COc2c(ccc(F)c2C#N)N1C(=O)N1CC2(C1)CN(c1ncccn1)C2] |
| 19-17 | 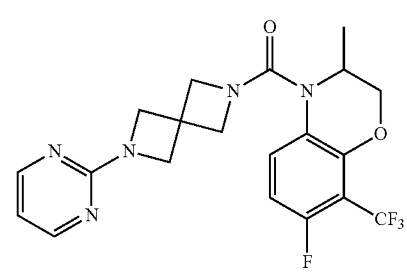 [SMILES: CC1COc2c(ccc(F)c2C(F)(F)F)N1C(=O)N1CC2(C1)CN(c1ncccn1)C2] |

TABLE 1-continued

Representative Compounds

| No. | Structure |
|---|---|
| 19-18 | (structure) |
| 20-1 | (structure) |
| 20-2 | (structure) |
| 20-3 | (structure) |
| 20-4 | (structure) |
| 20-5 | (structure) |
| 20-6 | (structure) |
| 20-7 | (structure) |
| 20-8 | (structure) |
| 20-9 | (structure) |

TABLE 1-continued
Representative Compounds
| No. | Structure |
|---|---|
| 20-10 | 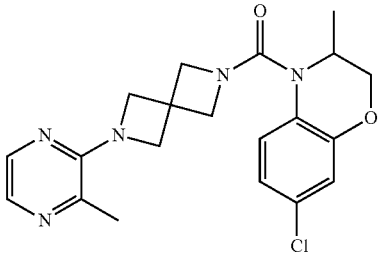 |
| 20-11 | 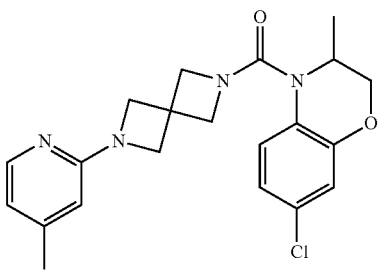 [SMILES: Cc1ccnc(N2CC3(CN(C(=O)N4c5ccc(F)cc5OCC4C)C3)C2)c1] |
| 20-12 | 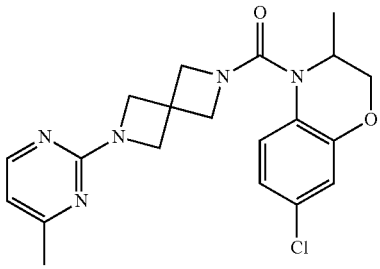 [SMILES: Cc1ccnc(N2CC3(CN(C(=O)N4c5ccc(Cl)cc5OCC4C)C3)C2)n1] |
| 20-13 | 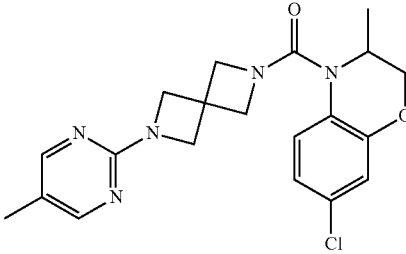 |
| 20-14 | 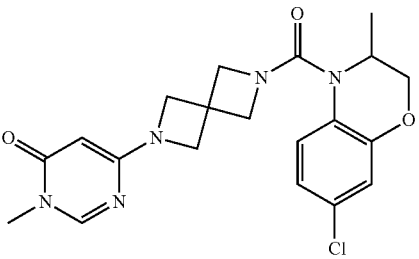 [SMILES: CC1COc2cc(Cl)ccc2N1C(=O)N1CC2(C1)CN(c1cc(=O)n(C)cn1)C2] |
| 20-15 | 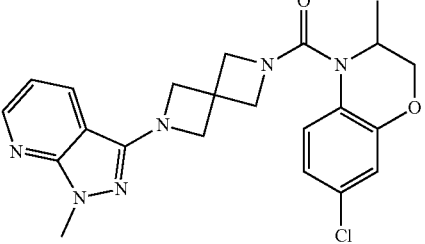 |
| 20-16 | 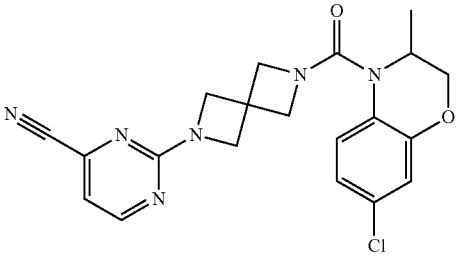 [SMILES: CC1COc2cc(Cl)ccc2N1C(=O)N1CC2(C1)CN(c1nccc(C#N)n1)C2] |
| 21-1 | 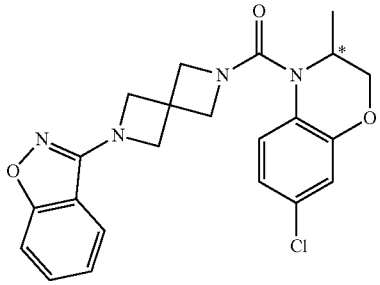 |
| 21-2 | 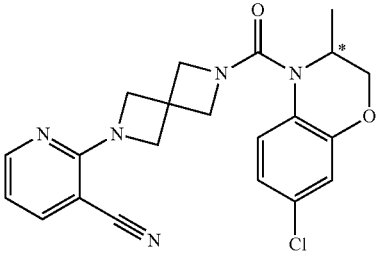 [SMILES: CC1COc2cc(Cl)ccc2N1C(=O)N1CC2(C1)CN(c1ncccc1C#N)C2] |
| 21-3 | 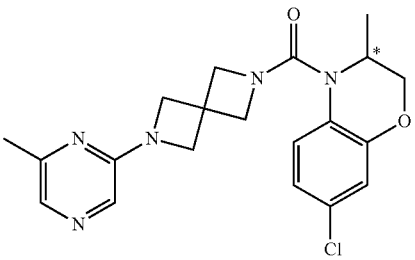 |

TABLE 1-continued

Representative Compounds

| No. | Structure |
|---|---|
| 21-4 | 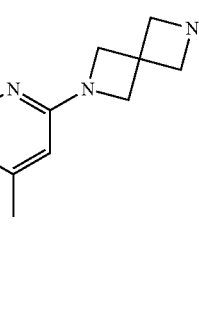 |
| 21-5 | 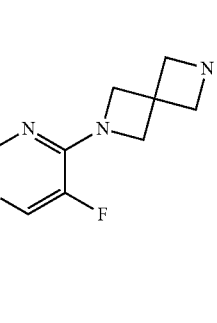 |
| 21-6 | 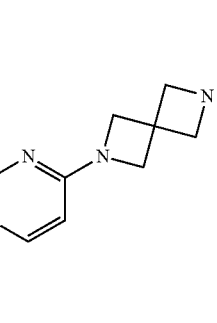 |
| 21-7 | 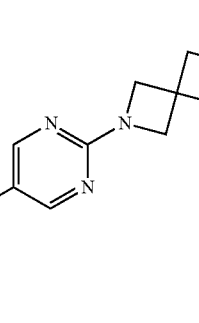 |
| 21-8 | 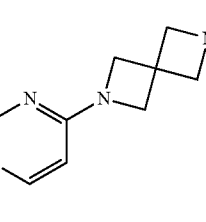 |
| 21-9 | 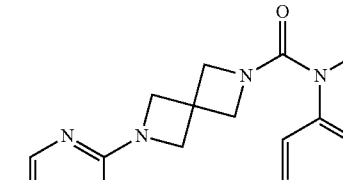 |
| 21-10 | 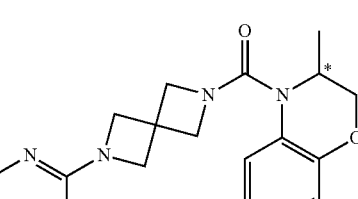 |
| 21-11 | 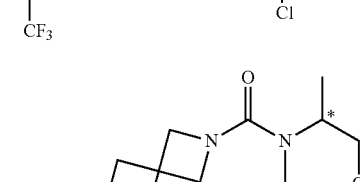 |

In one embodiment, substantially enantiomerically pure compounds are provided having the structure of Formula (XVII-S), or a pharmaceutically acceptable hydrate, solvate, isotope, or salt thereof:

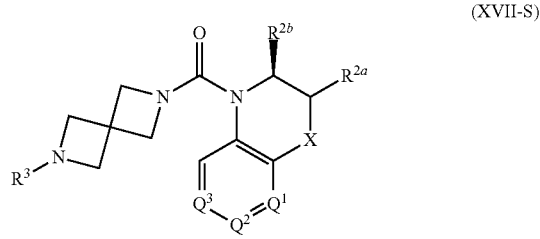

(XVII-S)

wherein:
X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—, R$^x$ is, at each occurrence, independently H, lower alkyl, lower haloalkyl, halo, or R$^6$;

R$^y$ is, at each occurrence, independently H, —OH, lower alkyl, lower alkoxy, or halo;

Q$^1$ is N or CR$^{1a}$, Q$^2$ is N or CR$^{1b}$, and Q$^3$ is N or CR$^{1c}$, wherein at least one Q$^1$, Q$^2$, or Q$^3$ is not N;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

$R^3$ is —$(CHR^z)_m$-Q-$(R^4)_p$, —$S(=O)_2R^5$, or —$C(=O)R^5$;
$R^z$ is H or $CH_3$
Q is aryl or heteroaryl;
$R^4$ is, at each occurrence, independently H, —OH, =O, cycloalkyl, lower alkyl, lower haloalkyl, lower alkoxy, lower haloalkoxy, halo, or cyano;
$R^5$ is H, cycloalkyl, lower alkyl, lower haloalkyl, lower alkoxy, aryl, heteroaryl, cycloalkylalkyl, heterocyclyl, or —O-heterocyclyl;
$R^6$ is cycloalkyl, heterocyclyl, or —$C(=O)R^7$;
$R^7$ is H, lower alkyl, or lower haloalkyl;
n is 0, 1, or 2;
q is 0, 1, or 2;
t is 0, 1, or 2;
m is 0, 1, 2, 3, 4, 5, or 6; and
p is 0, 1, or 2.

In one embodiment, substantially enantiomerically pure compounds are provided having the structure of Formula (XVII-R), or a pharmaceutically acceptable hydrate, solvate, isotope, or salt thereof:

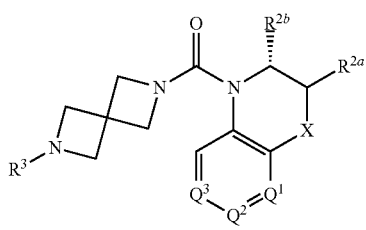

(XVII-R)

wherein:
X is —$(CR^xR^y)_nO(CR^xR^y)_q$—, —$(CR^xR^y)_nS(O)_t(CR^xR^y)_q$—, —$(CR^xR^y)_nN(R^x)(CR^xR^y)_q$—, or —$(CR^xR^y)_n$—,
$R^x$ is, at each occurrence, independently H, lower alkyl, lower haloalkyl, halo, or $R^6$;
$R^y$ is, at each occurrence, independently H, —OH, lower alkyl, lower alkoxy, or halo;
$Q^1$ is N or $CR^{1a}$, $Q^2$ is N or $CR^{1b}$, and $Q^3$ is N or $CR^{1c}$, wherein at least one $Q^1$, $Q^2$, or $Q^3$ is not N;
$R^{1a}$, $R^{1b}$, and $R^{1c}$ are each, independently, H, lower alkyl, lower haloalkyl, lower alkoxy, cyano, or halo;
$R^{2a}$ and $R^{2b}$ are each, independently, H, lower alkyl, lower haloalkyl, or lower alkoxy;
$R^3$ is —$(CHR^z)_m$-Q-$(R^4)_p$, —$S(=O)_2R^5$, or —$C(=O)R^5$;
$R^z$ is H or $CH_3$
Q is aryl or heteroaryl;
$R^4$ is, at each occurrence, independently H, —OH, =O, cycloalkyl, lower alkyl, lower haloalkyl, lower alkoxy, lower haloalkoxy, halo, or cyano;
$R^5$ is H, cycloalkyl, lower alkyl, lower haloalkyl, lower alkoxy, aryl, heteroaryl, cycloalkylalkyl, heterocyclyl, or —O-heterocyclyl;
$R^6$ is cycloalkyl, heterocyclyl, or —$C(=O)R^7$;
$R^7$ is H, lower alkyl, or lower haloalkyl;
n is 0, 1, or 2;
q is 0, 1, or 2;
t is 0, 1, or 2;
m is 0, 1, 2, 3, 4, 5, or 6; and
p is 0, 1, or 2.

In one embodiment, substantially enantiomerically pure compounds are provided having the structure of Formula (XVIII-S), or a pharmaceutically acceptable hydrate, solvate, isotope, or salt thereof:

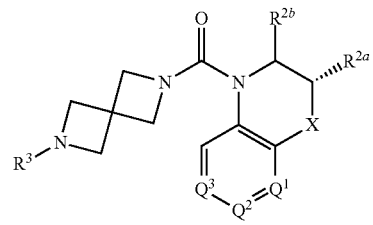

(XVIII-S)

wherein:
X is —$(CR^xR^y)_nO(CR^xR^y)_q$—, —$(CR^xR^y)_nS(O)_t(CR^xR^y)_q$—, —$(CR^xR^y)_nN(R^x)(CR^xR^y)_q$—, or —$(CR^xR^y)_n$—,
$R^x$ is, at each occurrence, independently H, lower alkyl, lower haloalkyl, halo, or $R^6$;
$R^y$ is, at each occurrence, independently H, —OH, lower alkyl, lower alkoxy, or halo;
$Q^1$ is N or $CR^{1a}$, $Q^2$ is N or $CR^{1b}$, and $Q^3$ is N or $CR^{1c}$, wherein at least one $Q^1$, $Q^2$, or $Q^3$ is not N;
$R^{1a}$, $R^{1b}$, and $R^{1c}$ are each, independently, H, lower alkyl, lower haloalkyl, lower alkoxy, cyano, or halo;
$R^{2a}$ and $R^{2b}$ are each, independently, H, lower alkyl, lower haloalkyl, or lower alkoxy;
$R^3$ is —$(CHR^z)_m$-Q-$(R^4)_p$, —$S(=O)_2R^5$, or —$C(=O)R^5$;
$R^z$ is H or $CH_3$
Q is aryl or heteroaryl;
$R^4$ is, at each occurrence, independently H, —OH, =O, cycloalkyl, lower alkyl, lower haloalkyl, lower alkoxy, lower haloalkoxy, halo, or cyano;
$R^5$ is H, cycloalkyl, lower alkyl, lower haloalkyl, lower alkoxy, aryl, heteroaryl, cycloalkylalkyl, heterocyclyl, or —O-heterocyclyl;
$R^6$ is cycloalkyl, heterocyclyl, or —$C(=O)R^7$;
$R^7$ is H, lower alkyl, or lower haloalkyl;
n is 0, 1, or 2;
q is 0, 1, or 2;
t is 0, 1, or 2;
m is 0, 1, 2, 3, 4, 5, or 6; and
p is 0, 1, or 2.

In one embodiment, substantially enantiomerically pure compounds are provided having the structure of Formula (XVIII-R), or a pharmaceutically acceptable hydrate, solvate, isotope, or salt thereof:

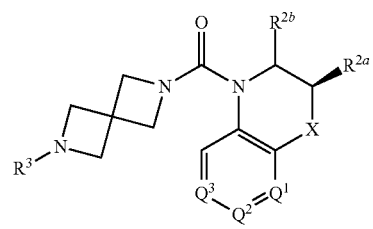

(XVIII-R)

wherein:
X is —$(CR^xR^y)_nO(CR^xR^y)_q$—, —$(CR^xR^y)_nS(O)_t(CR^xR^y)_q$—, —$(CR^xR^y)_nN(R^x)(CR^xR^y)_q$—, or —$(CR^xR^y)_n$—,
$R^x$ is, at each occurrence, independently H, lower alkyl, lower haloalkyl, halo, or $R^6$;
$R^y$ is, at each occurrence, independently H, —OH, lower alkyl, lower alkoxy, or halo;
$Q^1$ is N or $CR^{1a}$, $Q^2$ is N or $CR^{1b}$, and $Q^3$ is N or $CR^{1c}$, wherein at least one $Q^1$, $Q^2$, or $Q^3$ is not N;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^3$ is —$(CHR^z)_m$-Q-$(R^4)_p$, —S(=O)$_2R^5$, or —C(=O)$R^5$;

$R^z$ is H or $CH_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

$R^5$ is H, cycloalkyl, lower alkyl, lower haloalkyl, lower alkoxy, aryl, heteroaryl, cycloalkylalkyl, heterocyclyl, or —O-heterocyclyl;

$R^6$ is cycloalkyl, heterocyclyl, or —C(=O)$R^7$;

$R^7$ is H, lower alkyl, or lower haloalkyl;

n is 0, 1, or 2;

q is 0, 1, or 2;

t is 0, 1, or 2;

m is 0, 1, 2, 3, 4, 5, or 6; and p is 0, 1, or 2.

Representative compounds of Formula (XVII-R), (XVII-S), (XVIII-R), and (XVIII-S) as applicable, include the compounds listed in Table 2 below, as well as pharmaceutically acceptable hydrates, solvates, isotopes, and salts thereof.

TABLE 2

Representative Stereoisomers

| No. | Structure | Chiral Center |
|---|---|---|
| 1-55-A | 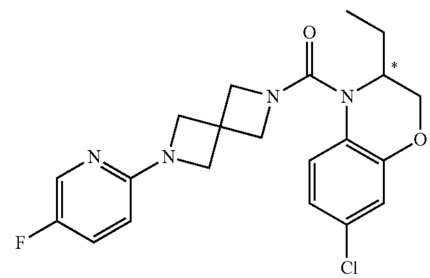 [SMILES: CCC1COc2cc(Cl)ccc2N1C(=O)N1CC2(C1)CN(c1ccc(F)cn1)C2] | Isomer A |
| 1-55-B | 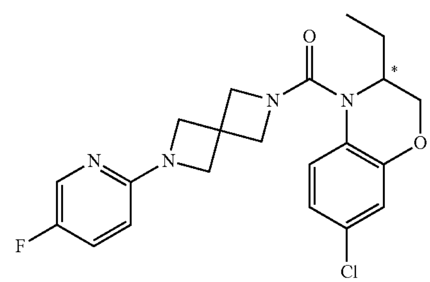 [SMILES: CCC1COc2cc(Cl)ccc2N1C(=O)N1CC2(C1)CN(c1ccc(F)cn1)C2] | Isomer B |
| 1-57-A | 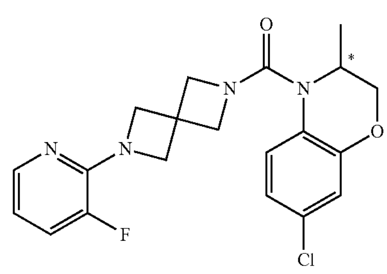 [SMILES: CC1COc2cc(Cl)ccc2N1C(=O)N1CC2(C1)CN(c1ncccc1F)C2] | Isomer A |
| 1-57-B | 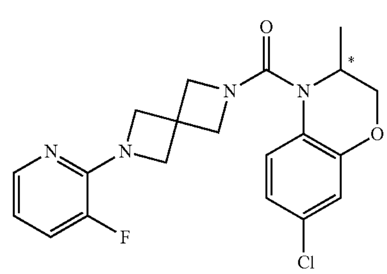 [SMILES: CC1COc2cc(Cl)ccc2N1C(=O)N1CC2(C1)CN(c1ncccc1F)C2] | Isomer B |

TABLE 2-continued

| | Representative Stereoisomers | |
|---|---|---|
| No. | Structure | Chiral Center |
| 1-58-A | | Isomer A |
| 1-58-B | | Isomer B |
| 1-59-A | | Isomer A |
| 1-59-B | | Isomer B |
| 1-60-A | | Isomer A |

TABLE 2-continued

| | Representative Stereoisomers | |
|---|---|---|
| No. | Structure | Chiral Center |
| 1-60-B | | Isomer B |
| 1-62-A | | Isomer A |
| 1-62-B | | Isomer B |
| 1-65-A | | Isomer A |
| 1-65-B | | Isomer B |

TABLE 2-continued

Representative Stereoisomers

| No. | Structure | Chiral Center |
|---|---|---|
| 1-66-A | 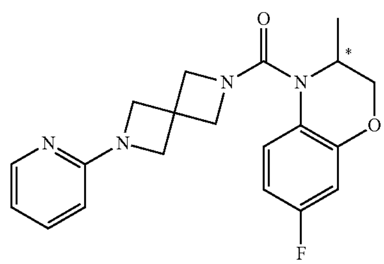 [SMILES: CC1COc2cc(F)ccc2N1C(=O)N1CC2(C1)CN(c1ccccn1)C2] | Isomer A |
| 1-66-B | 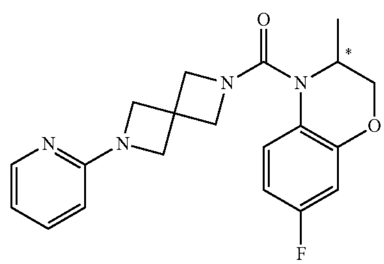 | Isomer B |
| 1-67-A | 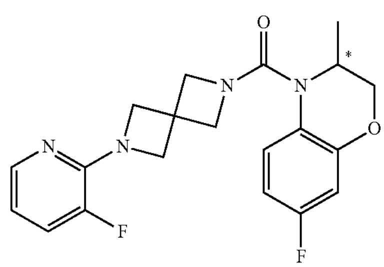 [SMILES: CC1COc2cc(F)ccc2N1C(=O)N1CC2(C1)CN(c1ncccc1F)C2] | Isomer A |
| 1-67-B | 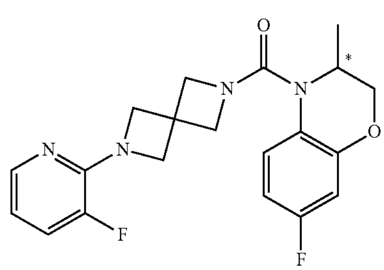 [SMILES: CC1COc2cc(F)ccc2N1C(=O)N1CC2(C1)CN(c1ncccc1F)C2] | Isomer B |
| 1-73-A | 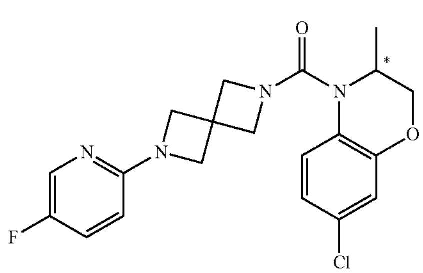 | Isomer A |

TABLE 2-continued

| | Representative Stereoisomers | |
|---|---|---|
| No. | Structure | Chiral Center |
| 1-73-B | [structure] | Isomer B |
| 1-83-A | [structure] | Isomer A |
| 1-83-B | [structure] | Isomer B |
| 9-1-A | [structure] | Isomer A |
| 9-1-B | [structure] | Isomer B |

TABLE 2-continued

Representative Stereoisomers

| No. | Structure | Chiral Center |
|---|---|---|
| 9-3-A | 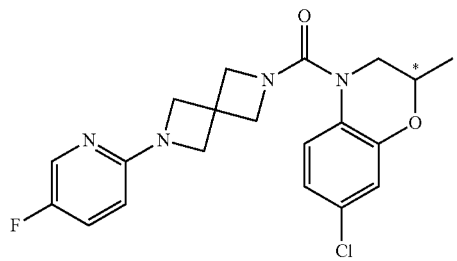 | Isomer A |
| 9-3-B | 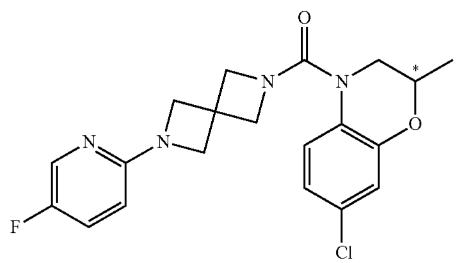 | Isomer B |
| 9-4-A | 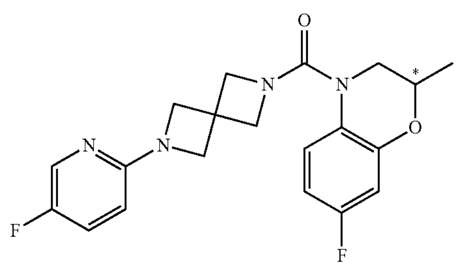 [SMILES: CC1CN(C(=O)N2CC3(C2)CN(c2ccc(F)cn2)C3)c2ccc(F)cc2O1] | Isomer A |
| 9-4-B | 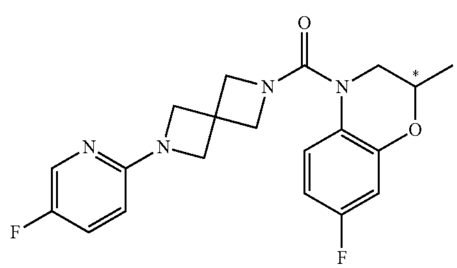 | Isomer B |
| 12-1-A | 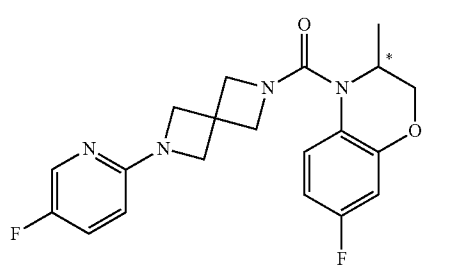 | Isomer A |

TABLE 2-continued

| | Representative Stereoisomers | |
|---|---|---|
| No. | Structure | Chiral Center |
| 12-1-B | [structure] | Isomer B |
| 13-1-A | [structure] | Isomer A |
| 13-1-B | [structure] | Isomer B |
| 13-2-A | [structure] | Isomer A |
| 13-2-B | [structure] | Isomer B |

TABLE 2-continued

| | Representative Stereoisomers | |
|---|---|---|
| No. | Structure | Chiral Center |
| 13-3-A | | Isomer A |
| 13-3-B | | Isomer B |
| 13-4-A | | Isomer A |
| 13-4-B | | Isomer B |
| 13-5-A | | Isomer A |

TABLE 2-continued

| No. | Structure | Chiral Center |
|---|---|---|
| 13-5-B | 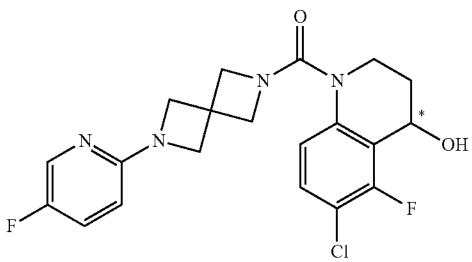 [SMILES: O=C(N1CC2(C1)CN(c1ccc(F)cn1)C2)N1CCC(O)c2c1ccc(Cl)c2F] | Isomer B |
| 18-2-A | 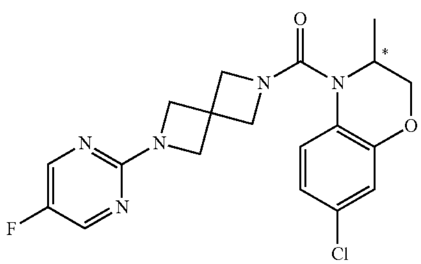 | Isomer A |
| 18-2-B | 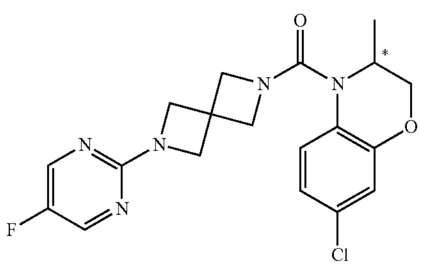 | Isomer B |
| 18-3-A | 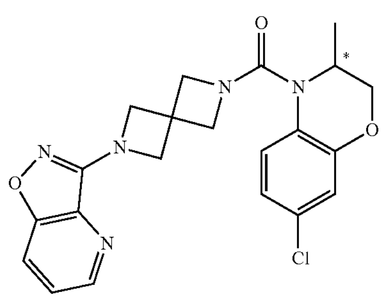 [SMILES: CC1COc2cc(Cl)ccc2N1C(=O)N1CC2(C1)CN(c1noc3cccnc13)C2] | Isomer A |
| 18-3-B | 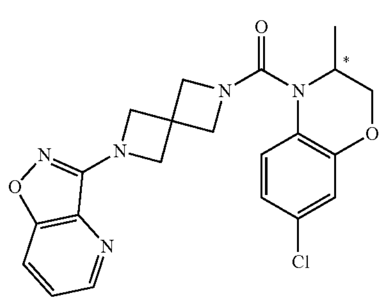 [SMILES: CC1COc2cc(Cl)ccc2N1C(=O)N1CC2(C1)CN(c1noc3cccnc13)C2] | Isomer B |

TABLE 2-continued
Representative Stereoisomers
| No. | Structure | Chiral Center |
|---|---|---|
| 18-4-A | 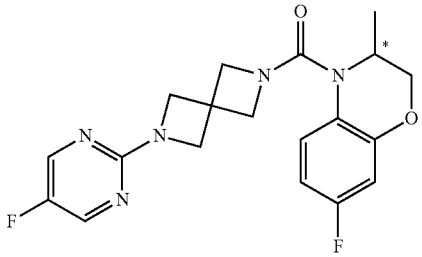 | Isomer A |
| 18-4-B | 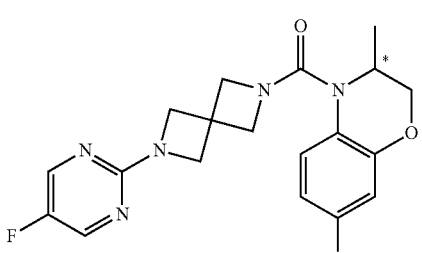 | Isomer B |
| 18-5-A | 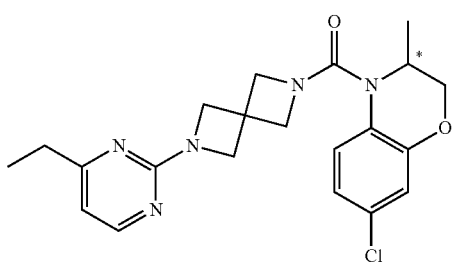 [SMILES: CCc1ccnc(N2CC3(CN(C(=O)N4c5ccc(Cl)cc5OCC4C)C3)C2)n1] | Isomer A |
| 18-5-B | 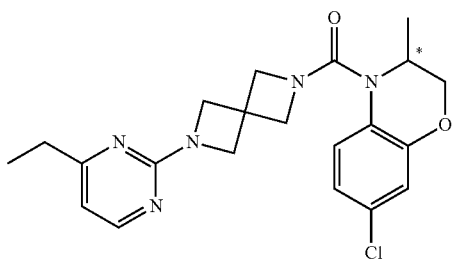 [SMILES: CCc1ccnc(N2CC3(CN(C(=O)N4c5ccc(Cl)cc5OCC4C)C3)C2)n1] | Isomer B |
| 19-1-A | 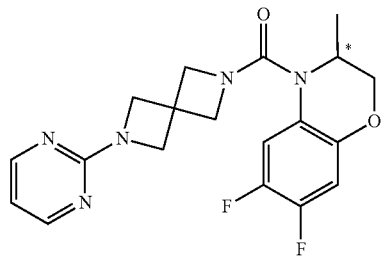 [SMILES: CC1COc2cc(F)c(F)cc2N1C(=O)N1CC2(C1)CN(c1ncccn1)C2] | Isomer A |

TABLE 2-continued

Representative Stereoisomers

| No. | Structure | Chiral Center |
|---|---|---|
| 19-1-B | 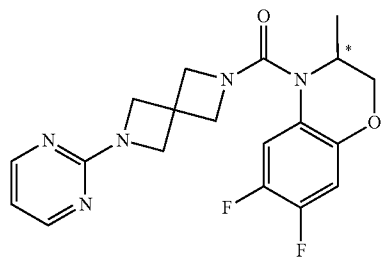 [SMILES: CC1COc2cc(F)c(F)cc2N1C(=O)N1CC2(C1)CN(c1ncccn1)C2] | Isomer B |
| 19-2-A | 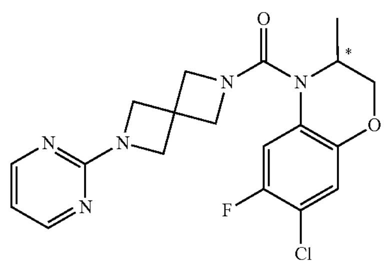 [SMILES: CC1COc2cc(Cl)c(F)cc2N1C(=O)N1CC2(C1)CN(c1ncccn1)C2] | Isomer A |
| 19-2-B | 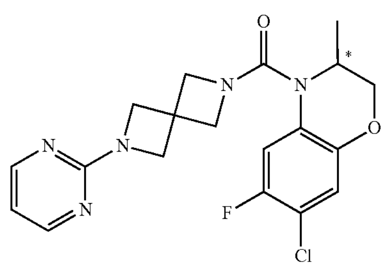 [SMILES: CC1COc2cc(Cl)c(F)cc2N1C(=O)N1CC2(C1)CN(c1ncccn1)C2] | Isomer B |
| 19-3-B | 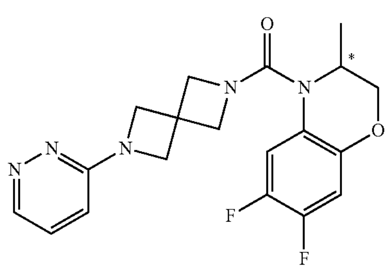 [SMILES: CC1COc2cc(F)c(F)cc2N1C(=O)N1CC2(C1)CN(c1cccnn1)C2] | Isomer B |
| 19-4-A | 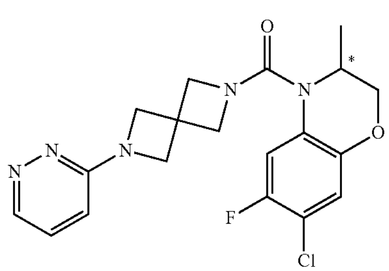 [SMILES: CC1COc2cc(Cl)c(F)cc2N1C(=O)N1CC2(C1)CN(c1cccnn1)C2] | Isomer A |

TABLE 2-continued

| | Representative Stereoisomers | |
|---|---|---|
| No. | Structure | Chiral Center |
| 19-4-B | | Isomer B |
| 19-5-A | | Isomer A |
| 19-5-B | | Isomer B |
| 20-1-A | | Isomer A |
| 20-1-B | | Isomer B |

TABLE 2-continued
| | Representative Stereoisomers | |
|---|---|---|
| No. | Structure | Chiral Center |
| 20-2-A | 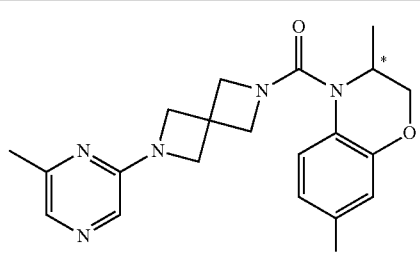 | Isomer A |
| 20-2-B | 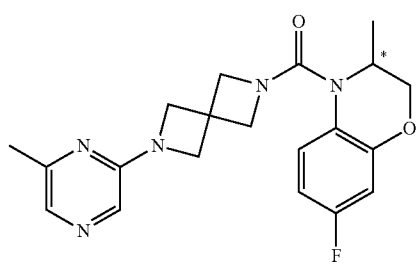 | Isomer B |
| 20-3-A | 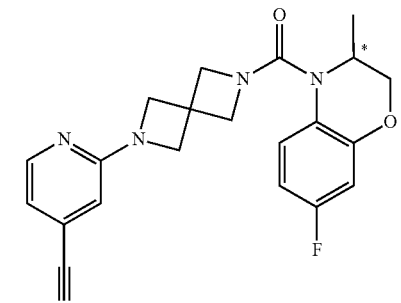 | Isomer A |
| 20-3-B | 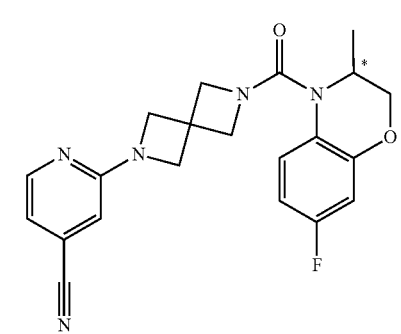 | Isomer B |
| 20-4-A | 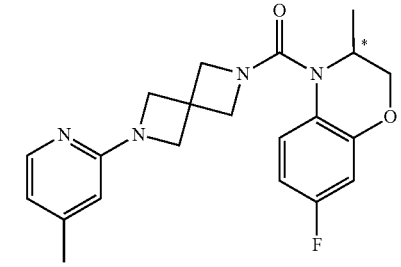 [SMILES: Cc1ccnc(N2CC3(CN(C(=O)N4c5ccc(F)cc5OCC4C)C3)C2)c1] | Isomer A |

TABLE 2-continued

| No. | Structure | Chiral Center |
|---|---|---|
| 20-4-B | 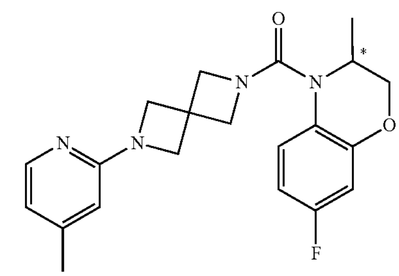 [SMILES: Cc1ccnc(N2CC3(CN(C(=O)N4c5ccc(F)cc5OCC4C)C3)C2)c1] | Isomer B |
| 20-5-A | 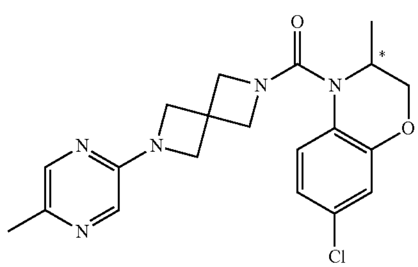 | Isomer A |
| 20-5-B | 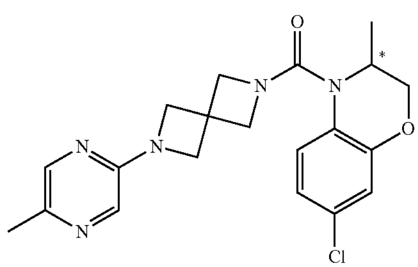 | Isomer B |
| 20-6-A | 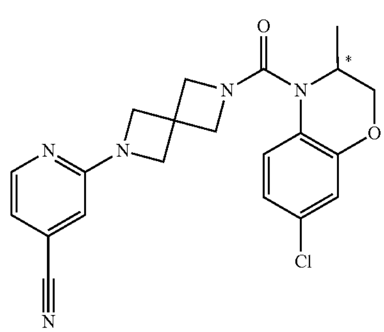 [SMILES: CC1COc2cc(Cl)ccc2N1C(=O)N1CC2(C1)CN(c1cc(C#N)ccn1)C2] | Isomer A |
| 20-6-B | 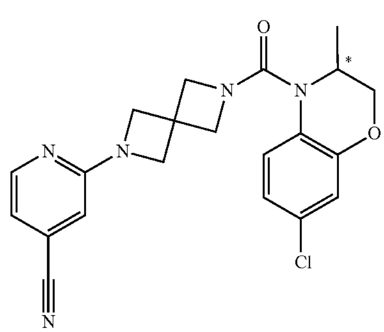 [SMILES: CC1COc2cc(Cl)ccc2N1C(=O)N1CC2(C1)CN(c1cc(C#N)ccn1)C2] | Isomer B |

TABLE 2-continued

| No. | Structure | Chiral Center |
|---|---|---|
| 20-7-A | 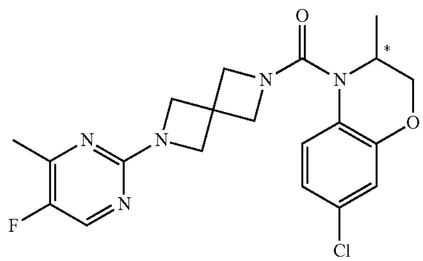 [SMILES: Cc1nc(N2CC3(CN(C(=O)N4c5ccc(Cl)cc5OCC4C)C3)C2)ncc1F] | Isomer A |
| 20-7-B | 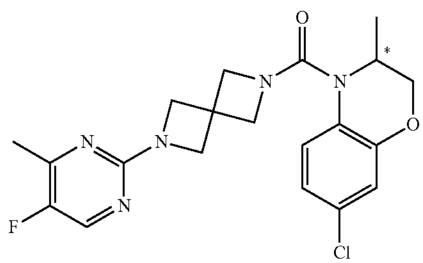 [SMILES: Cc1nc(N2CC3(CN(C(=O)N4c5ccc(Cl)cc5OCC4C)C3)C2)ncc1F] | Isomer B |
| 20-8-A | 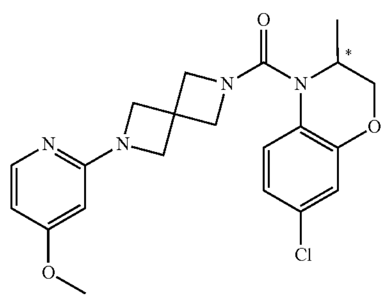 [SMILES: COc1ccnc(N2CC3(CN(C(=O)N4c5ccc(Cl)cc5OCC4C)C3)C2)c1] | Isomer A |
| 20-8-B | 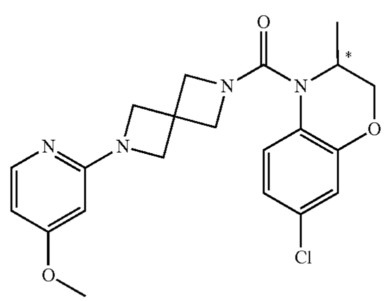 [SMILES: COc1ccnc(N2CC3(CN(C(=O)N4c5ccc(Cl)cc5OCC4C)C3)C2)c1] | Isomer B |
| 20-9-A | 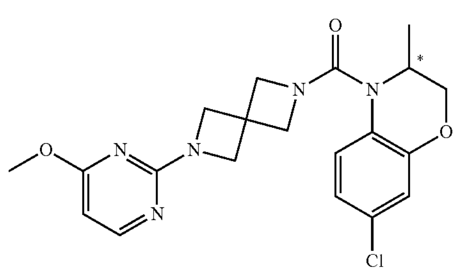 [SMILES: COc1ccnc(N2CC3(CN(C(=O)N4c5ccc(Cl)cc5OCC4C)C3)C2)n1] | Isomer A |

TABLE 2-continued
Representative Stereoisomers
| No. | Structure | Chiral Center |
|---|---|---|
| 20-9-B | 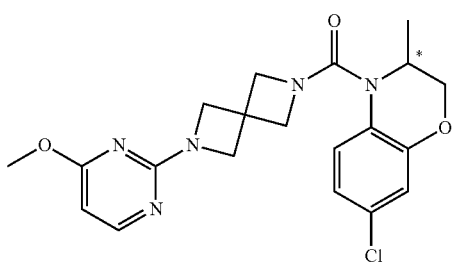 [SMILES: COc1ccnc(N2CC3(CN(C(=O)N4c5ccc(Cl)cc5OCC4C)C3)C2)n1] | Isomer B |
| 20-10-A | 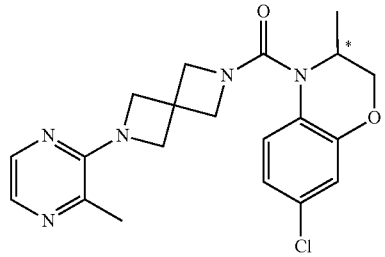 [SMILES: Cc1nccnc1N1CC2(CN(C(=O)N3c4ccc(Cl)cc4OCC3C)C2)C1] | Isomer A |
| 20-10-B | 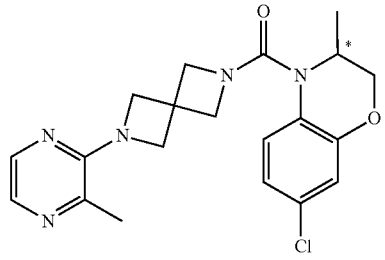 [SMILES: Cc1nccnc1N1CC2(CN(C(=O)N3c4ccc(Cl)cc4OCC3C)C2)C1] | Isomer B |
| 20-11-A | 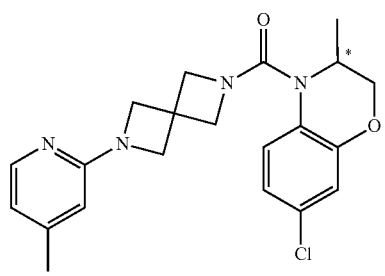 [SMILES: Cc1ccnc(N2CC3(CN(C(=O)N4c5ccc(Cl)cc5OCC4C)C3)C2)c1] | Isomer A |
| 20-11-B | 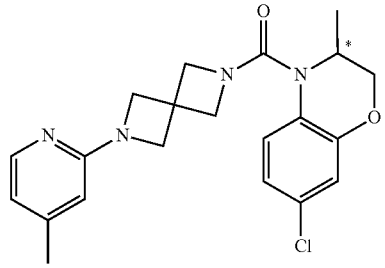 | Isomer B |

TABLE 2-continued

| | Representative Stereoisomers | |
|---|---|---|
| No. | Structure | Chiral Center |
| 20-12-A | | Isomer A |
| 20-12-B | | Isomer B |
| 20-13-A | | Isomer A |
| 20-13-B | | Isomer B |
| 20-14-A | | Isomer A |

TABLE 2-continued

Representative Stereoisomers

| No. | Structure | Chiral Center |
|---|---|---|
| 20-14-B | 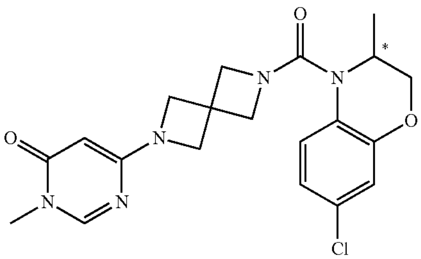 [SMILES: CC1COc2cc(Cl)ccc2N1C(=O)N1CC2(C1)CN(c1cc(=O)n(C)cn1)C2] | Isomer B |
| 20-15-A | 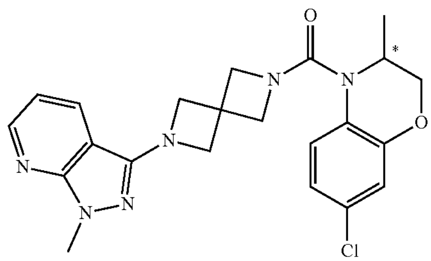 [SMILES: CC1COc2cc(Cl)ccc2N1C(=O)N1CC2(C1)CN(c1nn(C)c3ncccc13)C2] | Isomer A |
| 20-15-B | 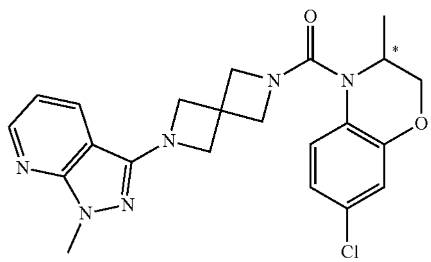 [SMILES: CC1COc2cc(Cl)ccc2N1C(=O)N1CC2(C1)CN(c1nn(C)c3ncccc13)C2] | Isomer B |
| 20-16-A | 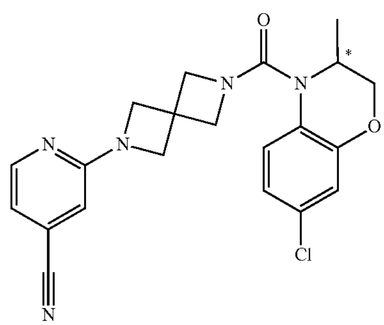 [SMILES: CC1COc2cc(Cl)ccc2N1C(=O)N1CC2(C1)CN(c1cc(C#N)ccn1)C2] | Isomer A |
| 20-16-B | 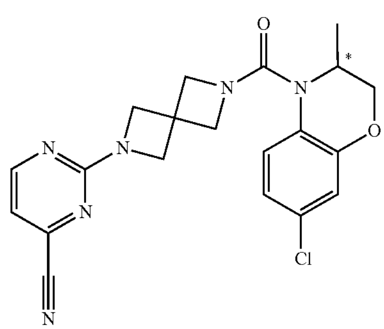 [SMILES: CC1COc2cc(Cl)ccc2N1C(=O)N1CC2(C1)CN(c1nccc(C#N)n1)C2] | Isomer B |

In certain embodiments, the invention provides a pharmaceutical composition comprising a compound of the invention together with at least one pharmaceutically acceptable carrier, diluent, or excipient. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid, or lower alkyl ethers of cellulose, silicic acid, fatty acids, fatty acid amines, fatty acid monoglycerides and diglycerides, pentaerythritol fatty acid esters, polyoxyethylene, hydroxymethyl cellulose, and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents, or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal, or parenteral, e.g., rectal, depot, subcutaneous, intravenous, intraurethral, intramuscular, intranasal, ophthalmic solution, or an ointment, the oral route being preferred.

For parenteral administration, the carrier will typically comprise sterile water, although other ingredients that aid solubility or serve as preservatives can also be included. Furthermore, injectable suspensions can also be prepared, in which case appropriate liquid carriers, suspending agents, and the like can be employed.

For topical administration, the compounds of the present invention can be formulated using bland, moisturizing bases such as ointments or creams.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule, or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is nonvolatile, including natural or synthetic oils, fatty acids, mono-, di-, or tri-glycerides.

For injection, the formulation can also be a powder suitable for reconstitution with an appropriate solution as described above. Examples of these include, but are not limited to, freeze dried, rotary dried, or spray dried powders, amorphous powders, granules, precipitates, or particulates. For injection, the formulations can optionally contain stabilizers, pH modifiers, surfactants, bioavailability modifiers, and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Dosage forms can be administered once a day, or more than once a day, such as twice or thrice daily. Alternatively, dosage forms can be administered less frequently than daily, such as every other day, or weekly, if found to be advisable by a prescribing physician. Dosing regimens include, for example, dose titration to the extent necessary or useful for the indication to be treated, thus allowing the patient's body to adapt to the treatment and/or to minimize or avoid unwanted side effects associated with the treatment. Other dosage forms include delayed or controlled-release forms. Suitable dosage regimens and/or forms include those set out, for example, in the latest edition of the *Physicians' Desk Reference*, incorporated herein by reference.

When used to prevent the onset of a malcondition, the compounds provided herein will be administered to a subject at risk for developing the same, typically on the advice and under the supervision of a physician, at the dosage levels described above. Subjects at risk for developing a particular malcondition generally include those that have a family history of the same, or those who have been identified by genetic testing or screening to be particularly susceptible to developing the malcondition.

Chronic administration refers to administration of a compound or pharmaceutical composition thereof over an extended period of time, e.g., for example, over 3 months, 6 months, 1 year, 2 years, 3 years, 5 years, etc., or may be continued indefinitely, for example, for the rest of the subject's life. In certain embodiments, the chronic administration is intended to provide a constant level of the compound in the blood, e.g., within the therapeutic window over the extended period of time.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

In another embodiment, a method is provided for antagonizing the V1a receptor, the method comprising contacting the receptor with an effective amount of a compound having the structure of Formula (I) through (XVI-k), or a pharmaceutically acceptable isomer, racemate, hydrate, solvate, isotope, or salt thereof, or a pharmaceutical composition comprising the same.

The term "antagonism" is used herein to encompass molecules that interact in some way with a receptor and thereby function as an antagonist, either by binding to the receptor at the binding site of its natural ligand or at locations other than the binding site. The phrase to "V1a antagonism" is used herein to encompass molecules that interact in some way with the V1a receptor and thereby function as an antagonist, either by binding to the V1a receptor at the binding site of its natural ligand, or at a location other than the binding site (i.e., allosteric binding).

In an embodiment, a method is provided for treatment of a malcondition in a subject for which antagonism of the V1a receptor is medically indicated. Such method comprises administering to the subject an effective amount of a compound having the structure of Formula (I) through (XVI-k), or a pharmaceutically acceptable isomer, racemate, hydrate, solvate, isotope, or salt thereof, or a pharmaceutical composition comprising the same, at a frequency and for duration sufficient to provide a beneficial effect to the subject.

As used herein, a "subject" means both mammals and non-mammals. Mammals include, for example: humans; non-human primates (e.g., apes and monkeys); cattle; horses; sheep; and goats. Non-mammals include, for example, fish and birds.

"Treating" or "treatment" within the meaning herein refers to an alleviation of symptoms associated with a malcondition, or inhibition of further progression or worsening of those symptoms, or prevention or prophylaxis of the malcondition in certain instances.

The expression "effective amount", when used to describe use of a compound for treating a subject suffering from a malcondition for which antagonism of the V1a receptor is medically indicated, refers to the amount of the compound sufficient to produce a beneficial therapeutic effect for the subject.

The phrase "malcondition" is intended to broadly encompass any and all diseases, disorders, syndromes and/or symptoms wherein the V1a receptor plays a role in the same, such that a therapeutically beneficial effect can be achieved by antagonism of the V1a receptor.

In certain embodiments, the present invention provides a method for antagonizing the V1a receptor with a compound of Formula (I) through (XVI-k), or a pharmaceutically acceptable isomer, racemate, hydrate, solvate, isotope, or salt thereof, by contacting the receptor with a suitable amount of the compound to antagonize the receptor. Such contacting can take place in vitro, for example in carrying out an assay to determine the V1a inhibition activity of a compound undergoing experimentation related to a submission for regulatory approval.

In certain embodiments, the method for antagonizing the V1a receptor can also be carried out in vivo, that is, within the living body of the subject. The compound of Formula (I) through (XVI-k), or a pharmaceutically acceptable isomer, racemate, hydrate, solvate, isotope, or salt thereof, can be supplied to the living organism via one of the routes as described above (e.g., orally) or can be provided locally within the body tissues. In the presence of the inventive compound, inhibition of the receptor takes place, and the effect thereof can be studied.

In another embodiment, a compound of Formula (I) through (XVI-k) is an imaging agent, wherein the compound contains an isotope, such as isotopes of F, O, N and C. In certain embodiments, the isotope is a fluorine isotope. The compounds may be used for therapeutic purposes, or to diagnose or assess the progression of a malcondition (a vasopressin-dependent condition) in a subject for which antagonism of the V1a receptor is medically indicated.

In some embodiments, imaging and/or diagnostic methods are provided comprising administering to a subject in need thereof the imaging agent described herein and detecting the compound comprised in the imaging agent in the subject. In some aspects, the amount of the compound in the subject is quantified. In further aspects, a vasopressin-dependent condition in the subject is detected via a detection of the compound in the subject. In certain embodiments, the imaging is effected by a radiodiagnostic method. The radiodiagnostic method may be performed by any instrument capable of detecting radiation by the compounds. Exemplary radiodiagnostic methods include, but not limited to, Positron Emission Tomography (PET), PET-Time-Activity Curve (TAC) or PET-Magnetic Resonance Imaging (MRI). In particular aspect, the radiodiagnostic method is PET. In one embodiment, methods of treatment are provided comprising administering a compound of Formula (I) through (XVI-k) or a pharmaceutically acceptable isomer, racemate, hydrate, solvate, isotope, or salt thereof, alone or in combination with another pharmacologically active agent or second medicament, to a subject having a malcondition for which antagonizing the V1a receptor is medically indicated.

As mentioned above, V1a receptor antagonists provide significant promise for the treatment of malconditions which benefit from antagonism of the V1a receptor. As summarized in the review article by Szczepanska-Sadowaska et al., *Current Drug Metabolism* 18:306-345, 2017 (incorporated by reference herein in its entirety), vasopressin has been associated with a wide range of regulatory functions in numerous organs and/or tissues and implicated in or with: (1) the cardiovascular system, (2) renal effects, (3) circadian rhythm, (4) food intake and metabolic and endocrine regulation, (5) uterus, (6) endotoxemia, and (7) stress, depression and psychiatric disorders. AVP is also involved in the regulation of several functions, such as, hepatic, pancreatic, and platelet-aggregating effects, and effects on the central and peripheral nervous system. The effects of the AVP receptors depends on where they are located.

In the cardiovascular system, vasopressin is associated with: (a) peripheral effects (e.g., it acts as a potent vasoconstrictor and plays a role in the regulation of carioca muscle differentiation, growth and contractility); (b) central cardiovascular control (e.g., buffering excessive increases and decreases in blood pressure); (c) regulation of cardiovascular reflexes (e.g., in the regulation of the baroreceptor reflex); (d) interaction with other factors (e.g., factors regulating blood pressure such as Ang II); (e) adaption to hemorrhage; and (f) cardiovascular diseases (e.g., hypertension and heart failure, intracranial hemorrhage and stroke).

As for renal effects, vasopressin has antidiuretic action, and interacts with Angiotensin II (AngII) in the regulation of urine excretion. Vasopressin also exerts a diposgenic action, manifested by reduction of the osmotic thirst threshold.

In the context of circadian rhythm, vasopressin neurons in the suprachiasmatic nuclei (SCN) of the hypothalamus manifest a distinct circadian rhythmicity, and studies have shown distinct circadian rhythmicity of vasopressin concentration in the cerebrospinal fluid (CSF). It has been suggested that SCN vasopressin neurons belong to the group of autonomous pacemakers and play a role in the regulation of the circadian rhythm, and studies have shown that circadian rhythmicity of vasopressin release has repercussions in the diurnal rhythmicity of other functions, such as corticosterone release, locomotor activity and body temperature.

With regard to food intake and metabolic and endocrine regulation, vasopressin has been associated with regulation of food intake and glucose homeostasis, and animal studies with V1a receptor knockout mice consuming high fat diet show that vasopressin acting on V1a receptor improves glucose tolerance and protects from the development of obesity. Studies have also shown that vasopressin plays a directed role in the regulation of glucagon and insulin release from the pancreatic cells. In the adrenal gland, vasopressin causes hypertrophy and hyperplasia of the adrenal cortex and stimulates secretion of aldosterone and glucocorticoids through stimulation of V1a receptors. Stimulation of the V1a receptor by vasopressin also influences release of luteinizing hormone releasing hormone (LHRL) and is believed to play a role in initiating the preovulatory LH surge.

The presence of V1a receptors has also been reported in the uterus, with the density of such receptors higher in the myometrium than in the endometrium, and they react with oxytocin (OT) receptors.

Endotoxemia is associated with the increased expression of the vasopressin gene in the hypothalamic nuclei and elevated concentration of vasopressin in the blood. Vasopressin exerts various effects on the cardiovascular system during endotoxemia, including reducing renal medullary blood flow aortic contractility is reduced. There is also evidence that vasopressin plays a role in the regulation of immunologic processes, and that it may play a role in the regeneration of the liver.

With regard to stress, depression and psychiatric disorders, the role of vasopressin in the regulation of behavior has been studied for many decades, with early studies showing that it facilitates conditioned avoidance responses in rats. Experimental studies have shown that vasopressin has long-lasting effects on learning and new memory acquisition as well as emotional and social behaviors, and clinical observations have shown that depression and other psychiatric disorders are associated with significant changes in vasopressin secretion. Neurogenic stress has also been shown to stimulate vasopressin release in the blood and CSF. A strong association has been shown between chronic stress, inappropriate activation of the vasopressinergic system and depression. Studies in humans have shown that patients with major depression manifested an elevated plasma vasopressin level, and in patients with unipolar depression there was a significant positive correlation between peripheral plasma vasopressin and hypercortisolemia. There is also evidence that vasopressin is an anxiogenic agent, and direct administration of V1a receptor antagonist into the paraventricular nucleus (PVN) of rats attenuated anxiety and depression behavior. Aggression has also been associated with an increased release of vasopressin into the CSF. Vasopressin plays a role in the regulation of pain, and its antinociceptive action has been shown in a number of studies. Inappropriate secretion of vasopressin has also been suggested in the disordered processing of psychosomatic stress which occurs in schizophrenia.

Due its wide and pivotal role for maintaining body homeostasis under a variety of conditions, vasopressin and its receptors, including V1a, have been recognized as an important target for diagnostic and therapeutic applications. To this end, vasopressin antagonists have shown efficacy in easing congestion symptoms and oedema and increasing plasma sodium ion concentration in clinical trials. In addition, the compounds of the present invention have utility across a broad spectrum of malconditions, including the following: heart failure, hepatic cirrhosis, psychiatric disorders (e.g., major depressive disorder or generalized anxiety disorder), brain injury, circadian rhythm disorders (e.g., associated with shift work or jet lag, resulting in sleep drifting later each day, abnormal nigh sleep patterns, and/or difficulty staying awake during the day), bone growth, diabetes mellitus, ovarian function, septic shock (e.g., maintaining haemodynamic parameters and preventing organ damage), and cancer and metastasis (e.g., decreasing dissemination of tumor cells and the spread of metastases by improving haemostasis and slowing of proliferation of carcinoma cells).

The compounds of the present invention selectively block the effects of V1a receptors, are orally bioavailable/effective, and demonstrate central nervous system (CNS)-penetrating effects. These compounds, (when acting peripherally and/or centrally) are useful in the treatment of vasopressin-dependent conditions or in the conditions related to inappropriate secretion of vasopressin, particularly in the response to chronic stress and in circuits that are dysregulated in affective disorders. These compounds reduce measures of stress, fear, aggression, depression, and anxiety.

In an embodiment, a method is provided for treatment or prevention of vasopressin-dependent conditions or in the conditions related to inappropriate secretion of vasopressin, comprising administering to a subject in need thereof an effective amount of a compound having the structure of Formulas (I) through (XVI-k), or a pharmaceutically acceptable isomer, racemate, hydrate, solvate, isotope or salt thereof, or a pharmaceutical composition comprising the same, at a frequency and for a duration sufficient to provide a beneficial effect to the subject.

In an embodiment, a method is provided for treatment of a vasopressin-dependent condition, whether organic, stress-induced or iatrogenic.

As used herein a "vasopressin-dependent condition" is defined as conditions related to inappropriate secretion of vasopressin, particularly in the response to chronic stress and in circuits that are dysregulated in affective disorders, such as disorders of stress, mood, and behavioral disorders, including stress-related affective disorders. Vasopressin-dependent conditions, include conditions such as cardiovascular conditions, for example hypertension, pulmonary hypertension, cardiac insufficiency, myocardial infarction or coronary vasospasm, in particular in smokers, Raynaud's syndrome, unstable angina and PTCA (percutaneous transluminal coronary angioplasty), cardiac ischemia, hemostasis disturbances or thrombosis; conditions of the central nervous system, such as migraine, cerebral vasospasm, cerebral hemorrhage, trauma and cerebral edema, depression, anxiety, stress, emotional disorders, obsessive-compulsive disorder, panic attacks, psychotic states, aggression, memory or sleep disorders, or cognitive disorders, for example disorders associated with impaired social cognition (e.g., schizophrenia, autism spectrum disorder); conditions of the renal system, such as renal vasospasm, necrosis of the renal cortex, nephrogenic diabetes insipidus or diabetic nephropathy; or conditions of the gastric system, such as gastric vasospasm, cirrhosis of the liver, ulcers or the pathology of vomiting, for example nausea, including nausea due to chemotherapy, or travel sickness; circadian rhythm-related disorders such as phase shift sleep disorders, jet-lag, sleep disorders and other chronobiological disorders. Additional examples of vasopressin-dependent conditions include but are not limited to neuropsychiatric disorders, neuropsychiatric symptoms in neurodegenerative diseases, PTSD, inappropriate aggression, anxiety, depressive disorders, major depression, obsessive compulsive disorder, autistic spectrum disorders, schizophrenia, and aggressive behavior, and other affective disorders.

In an embodiment, a method is provided for treatment of an autism spectrum disorder, comprising administering to a subject in need thereof an effective amount of a compound having the structure of Formulas (I) through (XVI-k), or a pharmaceutically acceptable isomer, racemate, hydrate, solvate, isotope or salt thereof, or a pharmaceutical composition comprising the same, at a frequency and for a duration sufficient to provide a beneficial effect to the subject.

Autism spectrum disorder (ASD), also referred to herein as autistic spectrum disorder, is a blanket term describing a complex developmental disorder that affects the brain's normal development of social and communication skills. Core symptoms of ASD include impaired social interactions such as social interaction difficulties, communication challenges including impaired verbal and nonverbal communication, problems processing information from the senses, and a tendency to engage in restricted and repetitive patterns of behavior. In one embodiment, the core symptoms of the autism spectrum disorder are impaired social interactions and communication challenges. In one embodiment, the core symptom of the autism spectrum disorder is impaired social interactions. In one embodiment, the core symptom of the autism spectrum disorder is impaired communication challenges. In one embodiment, the core symptom of the autism spectrum disorder is the tendency to engage in restricted and repetitive patterns of behavior.

In an embodiment, a method is provided for treatment of an anxiety disorder, comprising administering to a subject in need thereof an effective amount of a compound having the structure of Formulas (I) through (XVI-k), or a pharmaceutically acceptable isomer, racemate, hydrate, solvate, isotope or salt thereof, or a pharmaceutical composition comprising the same, at a frequency and for a duration sufficient to provide a beneficial effect to the subject.

Anxiety disorder is a blanket term covering several different forms of abnormal and pathological fear and anxiety. Current psychiatric diagnostic criteria recognize a wide variety of anxiety disorders, including generalized anxiety disorder, panic disorder, stress-related disorders, obsessive compulsive disorder, phobia, social anxiety disorder, separation anxiety disorder and post-traumatic stress disorder (PTSD). In one embodiment, the anxiety disorder is a social anxiety disorder. In one embodiment, the anxiety disorder is phobia. In one embodiment, the anxiety disorder is a stress-related disorder. In one embodiment, the anxiety related disorder is PTSD.

Generalized anxiety disorder is a common chronic disorder characterized by long-lasting anxiety that is not focused on any one object or situation. A person suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attack's potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of Phobia, which includes all cases in which fear and anxiety is triggered by a specific stimulus or situation. Sufferers typically anticipate terrifying consequences from encountering the object of their fear, which can be anything from social phobia, specific phobia, agoraphobia, phobia of an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

In an embodiment, a method is provided for treatment of a depressive disorder, depression, or depressive illness, comprising administering to a subject in need thereof an effective amount of a compound having the structure of Formulas (I) through (XVI-k), or a pharmaceutically acceptable isomer, racemate, hydrate, solvate, isotope or salt thereof, or a pharmaceutical composition comprising the same, at a frequency and for duration sufficient to provide a beneficial effect to the subject. Examples of such disorders include major depression, MDD, drug-resistant depression, dysthymia and bipolar disorder.

In an embodiment, a method is provided for treatment of a mood disorder, or an affective disorder comprising administering to a subject in need thereof an effective amount of a compound having the structure of Formulas (I) through (XVI-k), or a pharmaceutically acceptable isomer, racemate, hydrate, solvate, isotope or salt thereof, or a pharmaceutical composition comprising the same, at a frequency and for duration sufficient to provide a beneficial effect to the subject.

Examples of a mood disorder or an affective disorder include major depressive disorder (MDD); bipolar disorder; anhedonia; dysthymia; major depression, Psychotic major depression (PMD), or psychotic depression; postpartum depression; seasonal affective disorder (SAD); and catatonic depression is a rare and severe form of major depression involving disturbances of motor behavior and other symptoms.

The terms "anhedonia" and "anhedonic symptom" are used interchangeably and is defined as the inability to experience pleasure from activities usually found enjoyable, e.g. exercise, hobbies, music, sexual activities or social interactions. The terms "anhedonia" and "anhedonic symptom" are closely related to criterion of "depressive disorder with melancholic features" which is defined in DSM-5 as melancholic depression characterized by a loss of pleasure in most or all activities, a failure of reactivity to pleasurable stimuli, a quality of depressed mood more pronounced than that of grief or loss, a worsening of symptoms in the morning hours, early morning waking, psychomotor retardation, excessive weight loss, or excessive guilt. The term "treatment of depressive disorder with melancholic features" comprises treatment of both the depressive disorder and melancholic features associated herewith. In one embodiment, the mood disorder is anhedonia. In one embodiment, the mood disorder is major depression. In one embodiment, the mood disorder is seasonal affective disorder (SAD).

In an embodiment, a method is provided for treatment of an affective disorder, comprising administering to a subject in need thereof an effective amount of a compound having the structure of Formulas (I) through (XVI-k), or a pharmaceutically acceptable isomer, racemate, hydrate, solvate, isotope or salt thereof, or a pharmaceutical composition comprising the same, at a frequency and for a duration sufficient to provide a beneficial effect to the subject. Affective disorders such as disorders of stress, mood, and behavioral disorders, including stress-related affective disorders, obsessive compulsive disorder, autistic spectrum disorders, Personality disorders, ADHD, panic attacks and the like. As used herein, "autistic spectrum disorders" and "Autism spectrum disorders" are used interchangeably and refer to autism, monogenetic causes of autism such as synaptophathies, e.g., Rett syndrome, Fragile X syndrome, Angelman syndrome and the like.

In an embodiment, a method is provided for treatment of Anger, Aggression or Aggressive Disorder, or Impulse Control Disorders comprising administering to a subject in need thereof an effective amount of a compound having the structure of Formulas (I) through (XVI-k), or a pharmaceutically acceptable isomer, racemate, hydrate, solvate, isotope or salt thereof, or a pharmaceutical composition comprising the same, at a frequency and for a duration sufficient to provide a beneficial effect to the subject. Examples of Anger, Aggression or Aggressive Disorder, or Impulse Control Disorders include, but are not limited to, inappropriate aggression, aggressive behavior, aggression related to social isolation, for treatment of interpersonal violence co-occurring with such illness as ADHD, autism, bipolar disorder, emotional disorders, disorders of memory and/or cognition and cognitive disorders (such as Alzheimer's disease, Parkinson's disease, Huntington's disease and the like), and addictive disorder/substance abuse.

In an embodiment, a method is provided for treatment of Intermittent Explosive Disorder (sometimes abbreviated as IED) comprising administering to a subject in need thereof an effective amount of a compound having the structure of Formulas (I) through (XVI-k), or a pharmaceutically acceptable isomer, racemate, hydrate, solvate, isotope or salt thereof, or a pharmaceutical composition comprising the same, at a frequency and for a duration sufficient to provide a beneficial effect to the subject. Intermittent explosive disorder is a behavioral disorder characterized by explosive outbursts of anger and violence, often to the point of rage, that are disproportionate to the situation at hand (e.g., impulsive screaming triggered by relatively inconsequential events). Impulsive aggression is unpremeditated, and is defined by a disproportionate reaction to any provocation, real or perceived. Some individuals have reported affective changes prior to an outburst (e.g., tension, mood changes, energy changes, etc.). The disorder is currently categorized in the Diagnostic and Statistical Manual of Mental Disorders (DSM-5) under the "Disruptive, Impulse-Control, and Conduct Disorders" category. The disorder itself is not easily characterized and often exhibits comorbidity with other mood disorders, particularly bipolar disorder. Individuals diagnosed with IED report their outbursts as being brief (lasting less than an hour), with a variety of bodily symptoms (sweating, stuttering, chest tightness, twitching, palpitations) reported by a third of one sample. Aggressive acts are frequently reported accompanied by a sensation of relief and in some cases pleasure, but often followed by later remorse.

In other embodiments, a method is provided for treatment of a Schizophrenia spectrum disorders, comprising administering to a subject in need thereof an effective amount of a compound having the structure of Formulas (I) through (XVI-k), or a pharmaceutically acceptable isomer, racemate, hydrate, solvate, isotope or salt thereof, or a pharmaceutical composition comprising the same, at a frequency and for duration sufficient to provide a beneficial effect to the subject. Examples of Schizophrenia spectrum disorders include schizophrenia, schizoaffective disorder, psychotic states and memory disorders.

In other embodiments, a method is provided for treatment of a circadian rhythm related disorders, comprising administering to a subject in need thereof an effective amount of a compound having the structure of Formulas (I) through (XVI-k), or a pharmaceutically acceptable isomer, racemate, hydrate, solvate, isotope or salt thereof, or a pharmaceutical composition comprising the same, at a frequency and for duration sufficient to provide a beneficial effect to the subject. Circadian rhythm sleep disorders are caused by desynchronization or misalignment between internal sleep-wake rhythms (body clock) and the external light-darkness cycle. Circadian rhythm disorders (sometimes also referred to as phase shift disorders) include sleep disorders associated with jet lag, shift work, or altered sleep phase types, resulting in sleep drifting later each day, abnormal nigh sleep patterns, and/or difficulty staying awake during the day. The cause may be internal (e.g., delayed or advanced sleep phase syndrome, or Non-24-h sleep-wake syndrome) or external (e.g., jet lag, shift work). If the cause is external, other circadian body rhythms, including temperature and hormone secretion, can become out of sync with the light-darkness cycle (external desynchronization) and with one another (internal desynchronization); in addition to insomnia and excessive sleepiness, these alterations may cause nausea, malaise, irritability, and depression. Risk of cardiovascular and metabolic disorders may also be increased. Compounds of the invention are useful for treating circadian rhythm-related disorders, such as depression, jet-lag, work-shift syndrome, sleep disorders, glaucoma, reproduction, cancer, premenstrual syndrome, immune disorders, inflammatory articular diseases and neuroendocrine disorders, Non-24 Hour Disorder.

The compounds according to the invention may also be used in the treatment or prevention of Neuropsychiatric Disorders such as anorexia nervosa, bulimia, mood disorders, depression, anxiety, sleeping disorders, addictive disorders, panic attacks, phobias, obsession, pain-perception disorders (fibromyalgia), dependency on a substance, hemorrhagic stress, muscular spasms and hypoglycemia. Addictive disorder, including disorders related to substance abuse or addiction, and compulsive behavior.

The compounds according to the invention may also be used in the treatment or prevention of chronic stress states such as immunodepression, fertility disorders and dysfunctions of the hypothalamopituitaryadrenal axis.

The compounds according to the invention can also be used in the treatment of disorders such as primary or secondary dysmenorrhea, premature labor or endometriosis, male or female sexual dysfunction, hypertension, chronic heart failure, inappropriate secretion of vasopressin, liver cirrhosis and nephrotic syndrome.

The compounds according to the invention can also be used in the treatment or prevention of any pathology resulting from stress, such as fatigue and its syndromes, ACTH-dependent disorders, cardiac disorders, pain, modifications in gastric emptying, in fecal excretion (colitis, irritable bowel syndrome or Crohn's disease) or in acid secretion, hyperglycemia, immunosuppression, inflammatory processes (rheumatoid arthrit is and osteoarthritis), multiple infections, septic shock, cancers, asthma, psoriasis and allergies.

The compounds according to the invention may also be used as psychostimulants, bringing about an increase in consciousness/alertness and/or in emotional reactivity towards the environment and making adaptation easier.

The compounds according to the present invention can be used in healing, in analgesia, in anxiolysis, in the prevention of pain, in the prevention of anxiety, depression, schizophrenia, autism or obsessive-compulsive syndrome, in maternal behavior (facilitation of recognition and acceptance of the mother by the child) and social behavior, memory; regulation of food and drink intake, dependence on drugs, withdrawal and sexual motivation; hypertension, hyponatremia, cardiac insufficiency, atherosclerosis, angiogenesis, the proliferation of tumors, Kaposi's sarcoma, to regulate the storage of fat by the adipocyte, to control hyperlipidemia, triglyceridemia and metabolic syndrome.

The compounds according to the invention can also be used in the treatment of cancers, such as small cell lung cancers or breast cancers; hyponatremic encephalopathy; pulmonary syndrome; Meniere's disease; ocular hypertension; glaucoma; cataracts; obesity; type-I and type-II diabetes; atherosclerosis; metabolic syndrome; hyperlipidemia; insulin resistance; or hypertriglyceridemia; in post-operative treatments, in particular after abdominal surgery; autism; hypercortisolemia; hyperaldosteronemia; pheochromocytoma; Cushing's syndrome; preeclampsia; disorders of micturition; or premature ejaculation.

Compounds having the structure of Formula (I), as well as the sub-structures for Formulas (II) through (XVI-k), can be synthesized using standard synthetic techniques known to those of skill in the art. For examples, compounds of the present invention can be synthesized using the general synthetic procedures set forth in Reaction Schemes 1 through 5.

To this end, the reactions, processes, and synthetic methods described herein are not limited to the specific conditions described in the following experimental section, but rather are intended as a guide to one with suitable skill in this field. For example, reactions may be carried out in any suitable solvent, or other reagents to perform the transformation[s] necessary. Generally, suitable solvents are protic or aprotic solvents which are substantially non-reactive with the reactants, the intermediates or products at the temperatures at which the reactions are carried out (i.e., temperatures which may range from the freezing to boiling temperatures). A given reaction may be carried out in one solvent or a mixture of more than one solvent. Depending on the particular reaction, suitable solvents for a particular work-up following the reaction may be employed.

Reaction Scheme 1

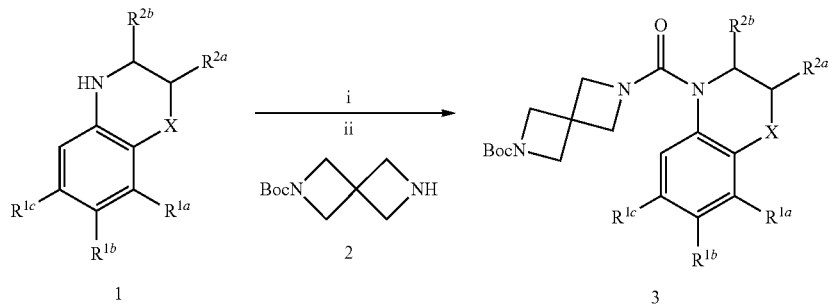

-continued

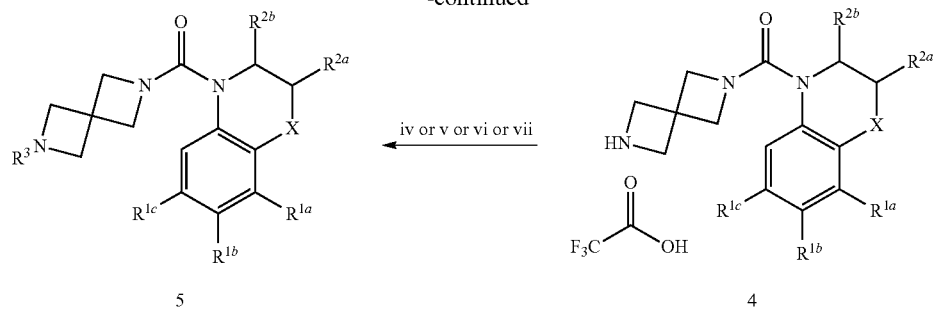

Reagents and conditions: i) Triphosgene, DIPEA, DCM; ii) 1, DIPEA, DMF; iii) TFA, DCM; iv) R³Br or R³Cl, Ruphos or Xantphos, Cs₂CO₃, Pd(OAc)₂, 1,4-dioxane; v) R³Br, BINAP, Pd₂(dba)₃, NaOᵗBu, 1,4-dioxane; vi) R³Cl, DIPEA, Dioxane; R³Cl, NaOᵗBu, Dioxane Reaction Scheme 2

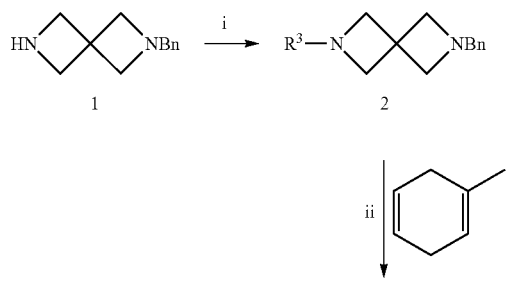

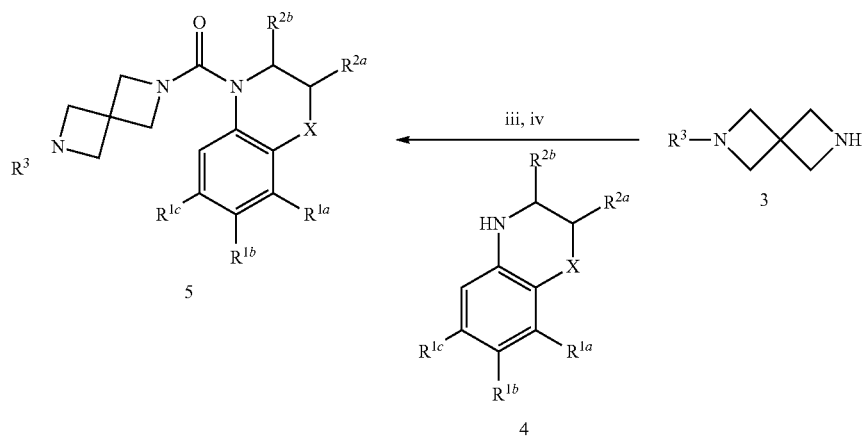

Reagents and conditions: i) R³Br or R³Cl, Ruphos, Cs₂CO₃, Pd(OAc)₂, 1,4-dioxane; ii) Pd/C, EtOH; iii) 4, triphosgene, DIPEA, DCM; iv) 3, DIPEA, DMF.

Reaction Scheme 3

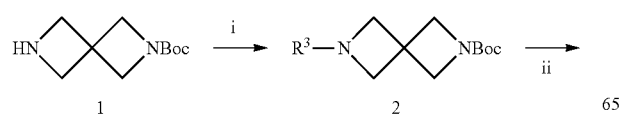

195
-continued
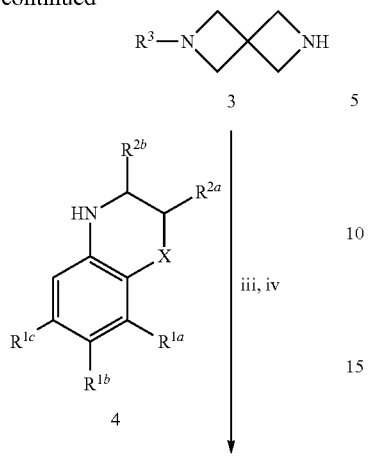
196
-continued
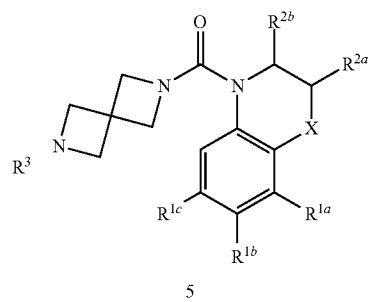
Reagents and conditions: i) R³Br or R³Cl, Ruphos, Cs₂CO₃, Pd(OAc)₂, 1,4-dioxane; ii) TFA, DCM; iii) 4, triphosgene, DIPEA, DCM; iv) 3, DIPEA, DMF.
Reaction Scheme 4
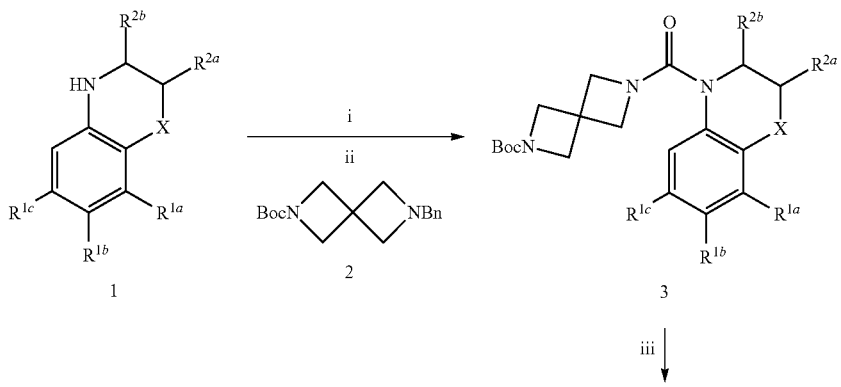
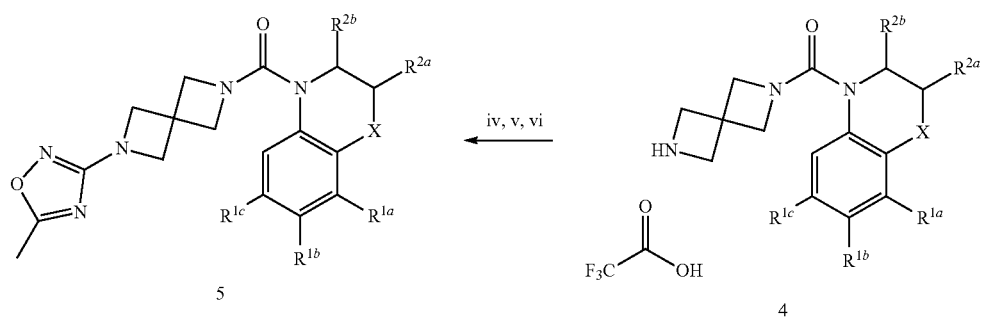
Reagents and conditions: i) Triphosgene, DIPEA, DCM; ii) 2, DIPEA, DMF; iii) TFA, DCM; iv) BrCN, DIPEA, DCM; v) HONH₃Cl, NEt₃, EtOH; vi) Ac₂O, Pyr

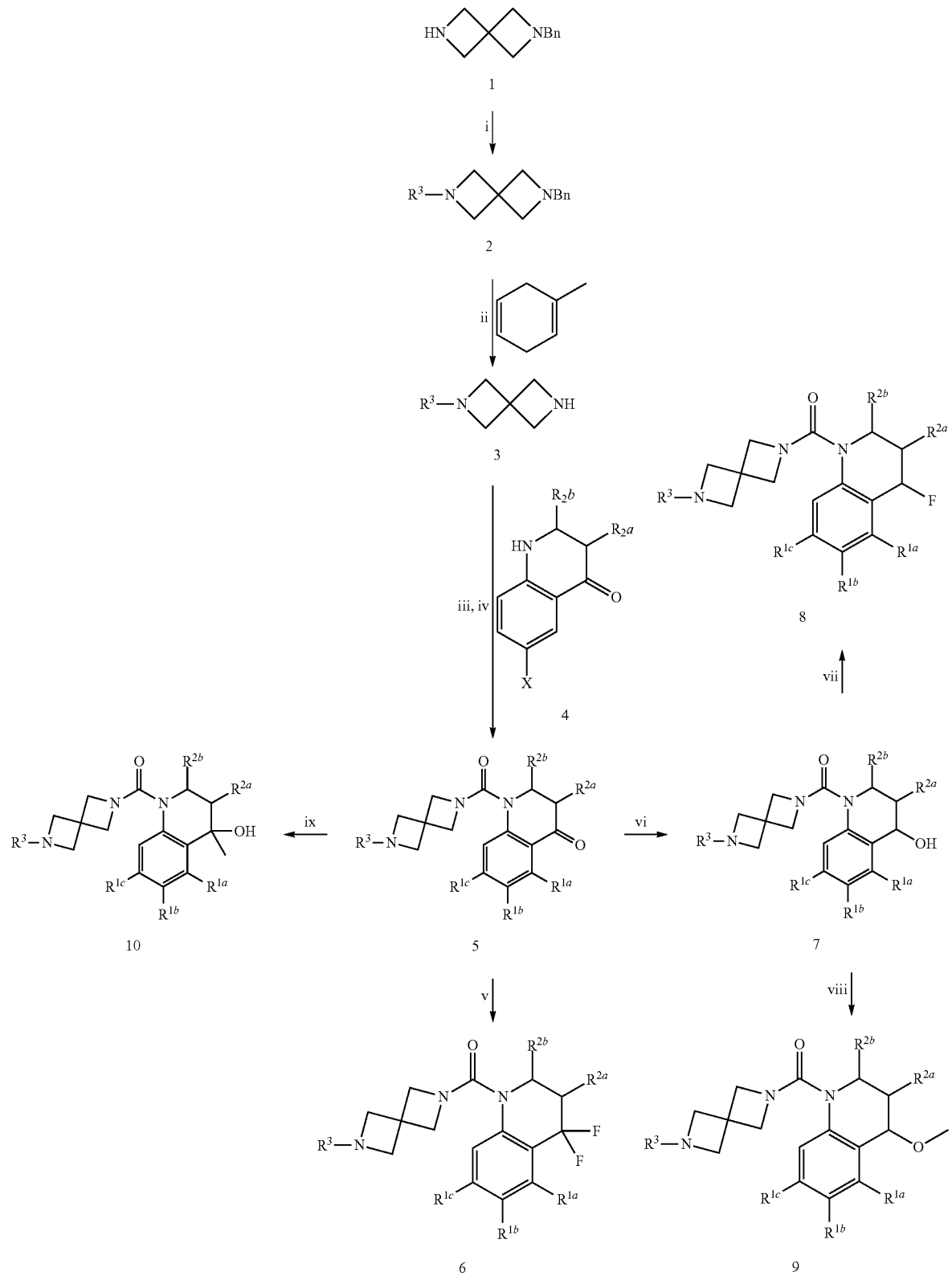
Reaction Scheme 5
Reagents and conditions: i) $R^3Br$ or $R^3Cl$, Ruphos, $Cs_2CO_3$, $Pd(OAc)_2$, 1,4-dioxane; ii) Pd/C, methylcyclohexane, EtOH; iii) 4, triphosgene, DIPEA, DCM; iv) 3, DIPEA, DMF; v) Deoxo-Fluor®, DCM; vi) $NaBH_4$, MeOH; vii) Deoxo-Fluor®, DCM; viii) NaH, MeI, DMF; ix) MeLi, THF.

EXAMPLES

The invention is further illustrated by the following examples. The examples below are non-limiting are merely representative of various aspects of the invention. Solid and dotted wedges within the structures herein disclosed illustrate relative stereochemistry, with absolute stereochemistry depicted only when specifically stated or delineated.

General Methods

All the starting materials and reagents are commercially available and were used as is. $^1$H Nuclear magnetic resonance (NMR) spectroscopy was carried out using a Bruker instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad. Preparative HPLC purification was performed by reverse phase HPLC using a Waters Fractionlynx preparative HPLC system (2525 pump, 2996/2998 UV/VIS detector, 2767 liquid handler) or an equivalent HPLC system such as a Gilson Trilution UV directed system. The Waters 2767 liquid handler acted as both auto-sampler and fraction collector. The columns used for the preparative purification of the compounds were a Waters Sunfire OBD Phenomenex Luna Phenyl Hexyl (10 μm 21.2×150 mm, 10 μm) or Waters Xbridge Phenyl (10 μm 19×150 mm, 5 μm). Appropriate focused gradients were selected based on acetonitrile and methanol solvent systems under either acidic or basic conditions. The modifiers used under acidic/basic conditions were formic acid (0.1% V/V) and ammonium bicarbonate (10 mM) respectively. The purification was controlled by Waters Fractionlynx software through monitoring at 210-400 nm, and triggered a threshold collection value at 260 nm and, when using the Fractionlynx, the presence of target molecular ion as observed under APi conditions. Collected fractions were analysed by LCMS (Waters Acquity systems with Waters SQD). Normal phase flash column chromatography was performed utilizing a Biotage Isolera system. The silica gel columns were purchased from either Interchim or Biotage. The mobile phase was either ethyl acetate in hexanes or methanol in dichloromethane with various ratios, and the fraction collection was triggered by UV absorbance at 254 nm. Analytical high-performance liquid chromatography-mass spectrometry (HPLC-MS) was performed utilizing HP or Waters DAD+Micromass ZQ, single quadrupole LC-MS or Quattro Micro LC-MS-MS. Method 1: The RP-HPLC column was Phenomenex Luna 5 μm C18 (2), (100×4.6 mm). Mobile phase 5-95% acetonitrile in water (0.1% formic acid) gradient, flow rate 2.0 mL/min, and 6.5 min run time. Method 2: The RP-HPLC column was Waters Xterra MS 5 μm C18, 100×4.6 mm. Mobile phase 5-95% acetonitrile in water (10 mM ammonium bicarbonate (ammonium hydrogen carbonate)).

Abbreviations

The following abbreviations are used in the examples:
BrettPhos: 2-(dicyclohexylphosphino)3,6-dimethoxy-2',4',6'-triisopropyl-1,1'-biphenyl
RuPhos: 2-Dicyclohexylphosphino-2',6'-diisopropoxybiphenylXantphos: 4,5-Bis(diphenylphosphino)-9,9-dimethylxanthene
CDCl$_3$: deuterochloroform
DMSO: dimethyl sulfoxide
DMA: N,N-Dimethylacetamide
ESI: electrospray ionisation
eq.: equivalent
g: gram
HATU: (1-[bis(dimethylamino)methylene]-1H-1,2,3-triazolo[4,5-b]pyridinium-3-oxidhexafluoro-phosphate
HPLC: high performance liquid chromatography
M: molar
mg: milligram
MHz: megahertz
ml: milliliter
mmol: millimole
MP: macroporous
MS: mass spectrometry
NMP: N-methyl-2-pyrrolidone
NMR: nuclear magnetic resonance
Pyr: pyridine
SFC: supercritical fluid chromatography
THF: tetrahydrofuran
μL: microliters
DCM: dichloromethane
EtOAc: ethyl acetate
NaHCO$_3$: sodium hydrogencarbonate
LiCl: lithium chloride
NEt$_3$: triethylamine
DMF: dimethylformamide
MeOH: methanol
DIPEA: diisopropylethylamine
Soln.: solution

Example 1

Synthesis of (7-chloro-2,3-dihydro-4H-benzo[b][1,4]oxazin-4-yl)(6-(3-fluoropyridin-2-yl)-2,6-diazaspiro[3.3]heptan-2-yl)methanone (Compound No. 1-1)

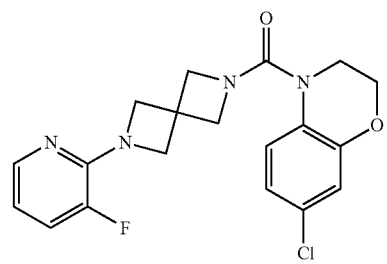 [SMILES: O=C(N1CC2(C1)CN(c1ncccc1F)C2)N1CCOc2cc(Cl)ccc21]

Step 1; tert-butyl 6-(7-chloro-3,4-dihydro-2H-benzo[b][1,4]oxazine-4-carbonyl)-2,6-diazaspiro[3.3]heptane-2-carboxylate

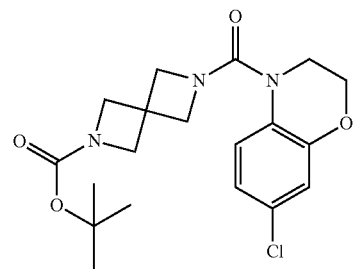 [SMILES: CC(C)(C)OC(=O)N1CC2(C1)CN(C(=O)N1CCOc3cc(Cl)ccc31)C2]

To a cooled solution of triphosgene (735 mg, 2.48 mmol, 1.10 eq.) at 0° C. in DCM (4 mL) was added a solution of 7-chloro-3,4-dihydro-2H-benzo[b][1,4]oxazine (382 mg, 2.25 mmol, 1.10 eq.), DIPEA (427 µL, 2.5 mmol, 1.2 eq.) in DCM dropwise. The reaction mixture was stirred at RT for 3 hours and concentrated in vacuo. To the residue in DMF (7 mL) was added tert-butyl 2,6-diazaspiro[3.3]heptane-2-carboxylate hemioxalate salt (500 mg, 2.05 mmol, 1.0 eq.), DIPEA (428 µL, 2.5 mmol, 1.2 eq.) and the mixture was stirred at RT overnight. The mixture was diluted with water and extracted with DCM. The organic layer was separated, concentrated in vacuo and the residue was purified using silica flash column chromatography eluting with 0-90% EtOAc in isohexane. Trituration in diethyl ether, followed by filtration afforded the titled compound. (438 mg, 49% yield). $^1$H NMR (400 MHz, CDCl$_3$) δ 7.26-7.20 (1H, m), 6.89-6.84 (2H, m), 4.28 (2H, dd, J=4.4, 4.4 Hz), 4.01 (8H, s), 3.75 (2H, dd, J=4.4, 4.4 Hz), 1.42 (9H, s)

Step 2; (7-chloro-2,3-dihydro-4H-benzo[b][1,4]oxazin-4-yl)(2,6-diazaspiro[3.3]heptan-2-yl)methanone 2,2,2-trifluoroacetate

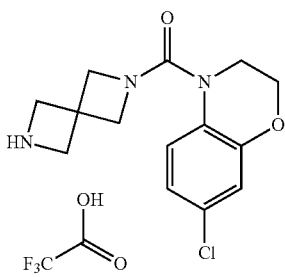

To a solution of tert-butyl 6-(7-chloro-3,4-dihydro-2H-benzo[b][1,4]oxazine-4-carbonyl)-2,6-diazaspiro[3.3]heptane-2-carboxylate (438 mg, 1.11 mmol, 1.10 eq.) in DCM (30 mL) was added TFA (3.0 mL) dropwise. The mixture was stirred at RT for 45 minutes, concentrated in vacuo and the residue was triturated with diethyl ether to afford the titled compound as a grey solid. (496 mg, quant.). $^1$H NMR (400 MHz, DMSO) δ 8.57-8.56 (2H, m), 7.35 (1H, dd, J=1.6, 10.2 Hz), 6.96-6.90 (2H, m), 4.25 (2H, t, J=4.5 Hz Hz), 4.11-4.03 (8H, m), 3.64 (2H, t, J=4.5 Hz Hz)

Step 3; (7-chloro-2,3-dihydro-4H-benzo[b][1,4]oxazin-4-yl)(6-(3-fluoropyridin-2-yl)-2,6-diazaspiro[3.3]heptan-2-yl)methanone (Compound No. 1-1)

A mixture of (7-chloro-2,3-dihydro-4H-benzo[b][1,4]oxazin-4-yl)(2,6-diazaspiro[3.3]heptan-2-yl)methanone 2,2,2-trifluoroacetate (62 mg, 0.152 mmol, 1.0 eq.), 2-bromo-3-fluoropyridine (37 mg, 0.21 mmol, 1.4 eq.), RuPhos (20 mg, 0.042 mmol, 0.3 eq.), cesium carbonate (274 mg, 0.84 mmol, 5.5 eq.) in 1,4-dioxane was degassed using nitrogen for 30 minutes. Palladium acetate (5 mg, 0.02 mmol, 0.1 eq.) was added and the mixture was heated to 80° C. overnight. The mixture was diluted with H$_2$O, extracted with DCM and the organic phase was concentrated in vacuo. The residue was purified using preparative HPLC to afford the titled compound. (20 mg, 24% yield). $^1$H NMR (400 MHz, CDCl$_3$) δ 7.92-7.90 (m, 1H), 7.30-7.27 (m, 1H), 7.18-7.11 (m, 1H), 6.88-6.85 (m, 2H), 6.64-6.59 (m, 1H), 4.29 (dd, J=4.7, 4.7 Hz, 2H), 4.23 (d, J=1.8 Hz, 4H), 4.09 (s, 4H), 3.77 (t, J=4.5 Hz, 2H). m/z 489 (M+H)$^+$.

Compound Nos. 1-2 through 1-83 listed in Table 3 below were prepared according to the methods described in Example 1 using the appropriately substituted or modified intermediates. Compound Nos. 1-84 and 1-90 are similarly prepared according to the methods described in Example 1 using appropriately substituted or modified intermediates.

TABLE 3

| No. | Structure | Data |
|---|---|---|
| 1-2 | 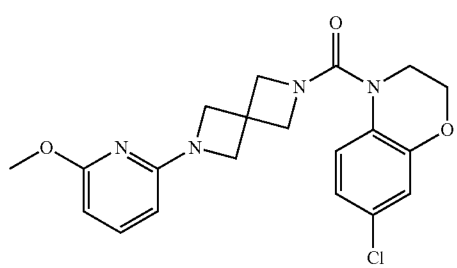 [SMILES: COc1cccc(N2CC3(CN(C(=O)N4CCOc5cc(Cl)ccc54)C3)C2)n1] | $^1$H NMR (400 MHz, CDCl$_3$) δ 7.30 (t, J = 7.9 Hz, 1H), 7.21-7.18 (m, 1H), 6.80-6.77 (m, 2H), 5.99 (d, J = 7.9 Hz, 1H), 5.75 (d, J = 7.8 Hz, 1H), 4.21 (t, J = 4.6 Hz, 2H), 4.02 (d, J = 6.4 Hz, 8H), 3.77 (s, 3H), 3.69 (t, J = 4.7 Hz, 2H). m/z 401 (M + H)$^+$. |
| 1-3 | 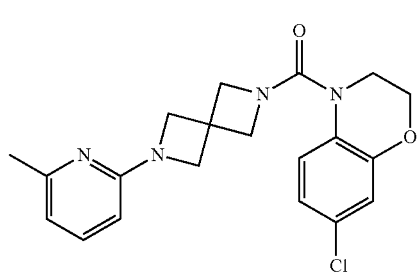 | $^1$H NMR (400 MHz, CDCl$_3$) δ 7.36-7.27 (m, 2H), 6.86 (d, J = 7.6 Hz, 2H), 6.49 (d, J = 7.3 Hz, 1H), 6.08 (d, J = 8.1 Hz, 1H), 4.29 (dd, J = 4.7, 4.7 Hz, 2H), 4.08 (d, J = 1.3 Hz, 8H), 3.77 (t, J = 4.5 Hz, 2H), 2.38 (s, 3H). m/z 485 (M + H)$^+$. |

TABLE 3-continued

| No. | Structure | Data |
|---|---|---|
| 1-4 | 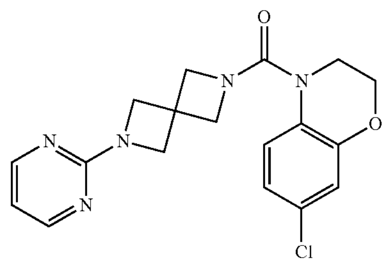 [SMILES: O=C(N1CC2(C1)CN(c1ncccn1)C2)N1CCOc2cc(Cl)ccc21] | $^1$H NMR (400 MHz, CDCl$_3$) δ 8.23 (d, J = 4.8 Hz, 2H), 7.24-7.19 (m, 1H), 6.82-6.77 (m, 2H), 6.49 (dd, J = 4.9, 4.9 Hz, 1H), 4.22 (dd, J = 4.7, 4.7 Hz, 2H), 4.15 (s, 4H), 4.03 (s, 4H), 3.70 (dd, J = 4.7, 4.7 Hz, 2H).<br>m/z 372 (M + H)$^+$. |
| 1-5 | 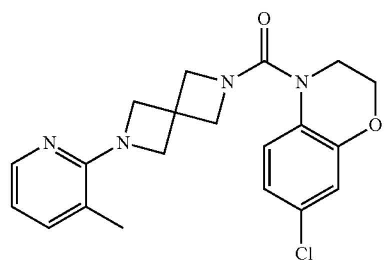 | $^1$H NMR (400 MHz, CDCl$_3$) δ 8.03 (1H, dd, J = 1.2, 5.0 Hz), 7.30-7.27 (1H, m), 7.23 (1H, d, J = 6.9 Hz), 6.88-6.85 (2H, m), 6.66 (1H, dd, J = 5.0, 7.2 Hz), 4.31-4.28 (2H, m), 4.18 (4H, s), 4.09 (4H, s), 3.77 (2H, t, J = 4.6 Hz), 2.15 (3H, s);<br>m/z 385 (M + H)$^+$. |
| 1-6 | 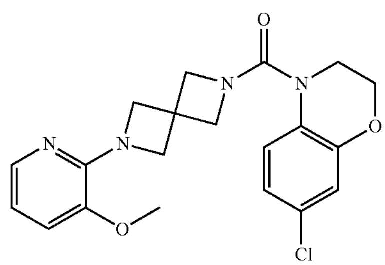 | $^1$H NMR (400 MHz, CDCl$_3$) δ 7.75 (1H, dd, J = 1.3, 5.0 Hz), 7.30-7.27 (1H, m), 6.90 (1H, dd, J = 1.3, 7.9 Hz), 6.87-6.84 (2H, m), 6.65 (1H, dd, J = 5.0, 7.8 Hz), 4.29 (2H, t, J = 4.6 Hz), 4.20 (4H, s), 4.07 (4H, s), 3.78-3.75 (5H, m);<br>m/z 401 (M + H)$^+$. |
| 1-7 | 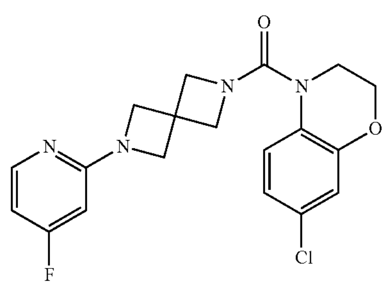 [SMILES: O=C(N1CC2(C1)CN(c1cc(F)ccn1)C2)N1CCOc2cc(Cl)ccc21] | $^1$H NMR (400 MHz, CDCl$_3$) δ 7.88 (d, J = 2.3 Hz, 1H), 7.63 (s, 1H), 7.27 (t, J = 4.5 Hz, 1H), 6.87 (d, J = 7.6 Hz, 2H), 6.41-6.38 (m, 1H), 4.29 (t, J = 4.4 Hz, 2H), 4.10 (s, 4H), 4.03 (s, 4H), 3.77 (t, J = 4.4 Hz, 2H).<br>m/z 389 (M + H)$^+$. |
| 1-8 | 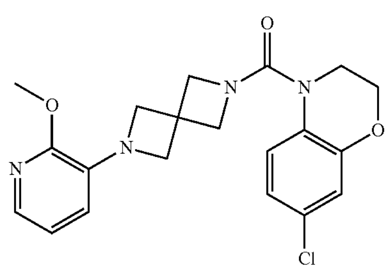 [SMILES: COc1ncccc1N1CC2(CN(C(=O)N3CCOc4cc(Cl)ccc43)C2)C1] | $^1$H NMR (400 MHz, CDCl$_3$) δ 7.61 (dd, J = 1.5, 5.1 Hz, 1H), 7.29-7.27 (m, 1H), 6.88-6.85 (m, 2H), 6.76 (dd, J = 5.1, 7.6 Hz, 1H), 6.56 (dd, J = 1.5, 7.6 Hz, 1H), 4.29 (t, J = 4.5 Hz, 2H), 4.07 (s, 4H), 3.99 (s, 4H), 3.92 (s, 3H), 3.76 (dd, J = 4.7, 4.7 Hz, 2H).<br>m/z 401 (M + H)$^+$. |
| 1-9 | 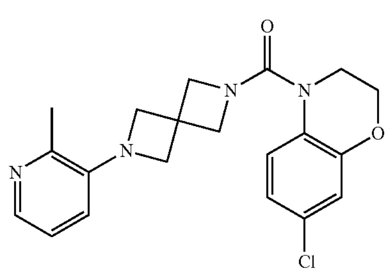 [SMILES: Cc1ncccc1N1CC2(CN(C(=O)N3CCOc4cc(Cl)ccc43)C2)C1] | $^1$H NMR (400 MHz, CDCl$_3$) δ 8.02 (1H, dd, J = 1.3, 4.8 Hz), 7.29-7.27 (1H, m), 7.02 (1H, dd, J = 4.8, 8.0 Hz), 6.89-6.86 (2H, m), 6.70 (1H, dd, J = 1.1, 8.0 Hz), 4.30 (2H, t, J = 4.6 Hz), 4.10 (4H, s), 4.00 (4H, s), 3.78 (2H, t, J = 4.6 Hz), 2.42 (3H, s);<br>m/z 385 (M + H)$^+$. |

TABLE 3-continued

| No. | Structure | Data |
|---|---|---|
| 1-10 | 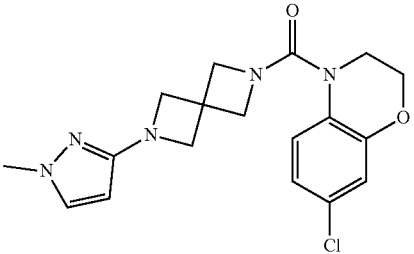 [SMILES: Cn1ccc(N2CC3(CN(C(=O)N4CCOc5cc(Cl)ccc54)C3)C2)n1] | $^1$H NMR (400 MHz, CDCl$_3$) δ 7.29-7.27 (m, 1H), 7.09 (d, J = 2.3 Hz, 1H), 6.86 (d, J = 7.6 Hz, 2H), 5.44 (d, J = 2.3 Hz, 1H), 4.28 (t, J = 4.5 Hz, 2H), 4.06 (s, 4H), 3.95 (s, 4H), 3.75 (dd, J = 4.7, 4.7 Hz, 2H), 3.72 (s, 3H). m/z 374 (M + H)$^+$. |
| 1-11 | 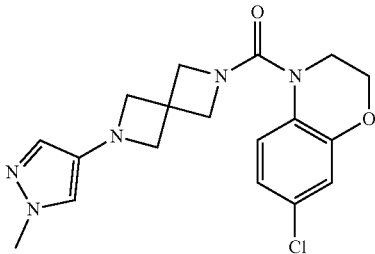 [SMILES: Cn1cc(N2CC3(CN(C(=O)N4CCOc5cc(Cl)ccc54)C3)C2)cn1] | $^1$H NMR (400 MHz, CDCl$_3$) δ 7.27-7.24 (1H, m), 6.99 (1H, d, J = 0.9 Hz), 6.87-6.84 (2H, m), 6.78 (1H, d, J = 0.8 Hz), 4.28 (2H, t, J = 4.6 Hz), 4.05 (4H, s), 3.79 (3H, s), 3.77 (4H, s), 3.77-3.74 (2H, m). m/z 374 (M + H)$^+$. |
| 1-12 | 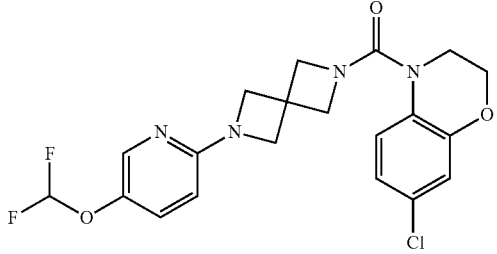 [SMILES: O=C(N1CC2(C1)CN(c1ccc(OC(F)F)cn1)C2)N1CCOc2cc(Cl)ccc21] | $^1$H NMR (400 MHz, CDCl$_3$) δ 8.01 (1H, d, J = 2.5 Hz), 7.32-7.27 (2H, m), 6.88-6.86 (2H, m), 6.38 (1H, t, J = 74.0 Hz), 6.25 (1H, d, J = 8.9 Hz), 4.31-4.28 (2H, m), 4.10 (8H, d, J = 1.5 Hz), 3.77 (2H, t, J = 4.6 Hz). m/z 437 (M + H)$^+$. |
| 1-13 | 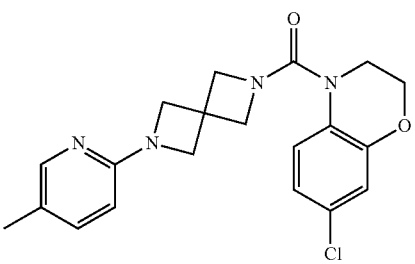 | $^1$H NMR (400 MHz, CDCl$_3$) δ 7.96 (d, J = 2.3 Hz, 1H), 7.30-7.27 (m, 2H), 6.88-6.84 (m, 2H), 6.22 (d, J = 8.3 Hz, 1H), 4.29 (dd, J = 4.7, 4.7 Hz, 2H), 4.07 (d, J = 9.1 Hz, 8H), 3.77 (dd, J = 4.7, 4.7 Hz, 2H), 2.18 (s, 3H). m/z 385 (M + H)$^+$. |
| 1-14 | 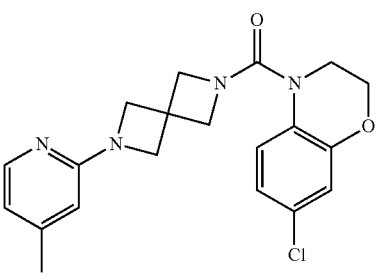 [SMILES: Cc1ccnc(N2CC3(CN(C(=O)N4CCOc5cc(Cl)ccc54)C3)C2)c1] | $^1$H NMR (400 MHz, CDCl$_3$) δ 8.00 (d, J = 5.3 Hz, 1H), 7.31-7.27 (m, 1H), 6.87 (d, J = 6.8 Hz, 2H), 6.48 (d, J = 5.3 Hz, 1H), 6.09 (s, 1H), 4.29 (t, J = 4.5 Hz, 2H), 4.09 (d, J = 1.5 Hz, 8H), 3.77 (t, J = 4.5 Hz, 2H), 2.25 (s, 3H). m/z 385 (M + H)$^+$. |

TABLE 3-continued

| No. | Structure | Data |
|---|---|---|
| 1-15 | 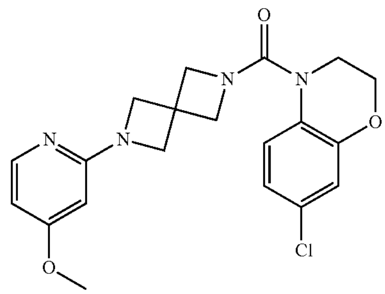 [SMILES: COc1ccnc(N2CC3(CN(C(=O)N4CCOc5cc(Cl)ccc54)C3)C2)c1] | ¹H NMR (400 MHz, CDCl₃) δ 8.00 (d, J = 6.3 Hz, 1H), 7.29-7.27 (m, 1H), 6.88-6.86 (m, 2H), 6.29 (dd, J = 2.3, 6.1 Hz, 1H), 5.69 (d, J = 2.3 Hz, 1H), 4.30 (dd, J = 4.7, 4.7 Hz, 2H), 4.17 (s, 4H), 4.10 (s, 4H), 3.82 (s, 3H), 3.77 (dd, J = 4.7, 4.7 Hz, 2H). m/z 401 (M + H)⁺. |
| 1-16 | 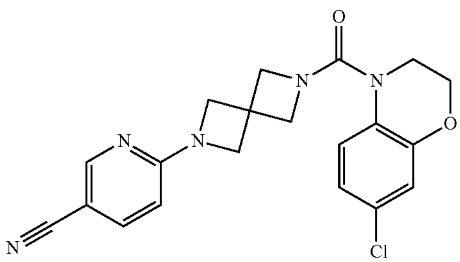 [SMILES: N#Cc1ccc(N2CC3(CN(C(=O)N4CCOc5cc(Cl)ccc54)C3)C2)nc1] | ¹H NMR (400 MHz, CDCl₃) δ 8.37 (d, J = 1.8 Hz, 1H), 7.59 (dd, J = 2.1, 8.7 Hz, 1H), 7.29-7.27 (m, 1H), 6.87 (d, J = 7.8 Hz, 2H), 6.21 (d, J = 8.8 Hz, 1H), 4.30 (t, J = 4.5 Hz, 2H), 4.21 (s, 4H), 4.11 (s, 4H), 3.78 (dd, J = 4.7, 4.7 Hz, 2H). m/z 396 (M + H)⁺. |
| 1-17 | 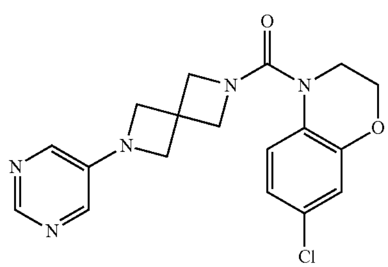 [SMILES: O=C(N1CC2(C1)CN(c1cncnc1)C2)N1CCOc2cc(Cl)ccc21] | ¹H NMR (400 MHz, CDCl₃) δ 8.67 (s, 1H), 7.94 (s, 2H), 7.29-7.27 (m, 1H), 6.87 (d, J = 7.8 Hz, 2H), 4.30 (dd, J = 4.7, 4.7 Hz, 2H), 4.10 (d, J = 13.6 Hz, 8H), 3.78 (t, J = 4.5 Hz, 2H). m/z 372 (M + H)⁺. |
| 1-18 | 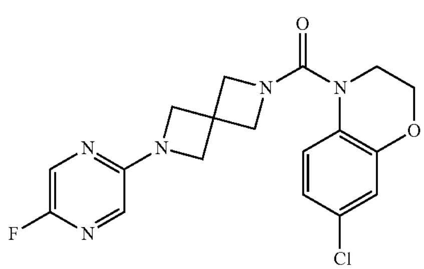 | ¹H NMR (400 MHz, CDCl₃) δ 7.91 (1H, dd, J = 1.4, 8.0 Hz), 7.31-7.28 (2H, m), 6.88-6.86 (2H, m), 4.32-4.28 (2H, m), 4.15 (4H, s), 4.11 (4H, s), 3.78 (2H, t, J = 4.6 Hz); m/z 390 (M + H)⁺. |
| 1-19 | 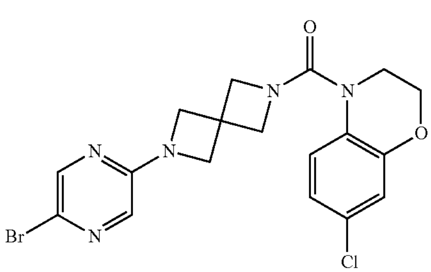 [SMILES: O=C(N1CC2(C1)CN(c1cnc(Br)cn1)C2)N1CCOc2cc(Cl)ccc21] | ¹H NMR (400 MHz, CDCl₃) δ 8.10 (1H, d, J = 1.3 Hz), 7.52 (1H, d, J = 1.3 Hz), 7.31-7.27 (1H, m), 6.87 (2H, d, J = 7.6 Hz), 4.30 (2H, t, J = 4.5 Hz Hz), 4.16 (4H, s), 4.11 (4H, s), 3.78 (2H, dd, J = 4.7, 4.7 Hz); m/z 452 (M + H)⁺. |

TABLE 3-continued

| No. | Structure | Data |
|---|---|---|
| 1-20 | 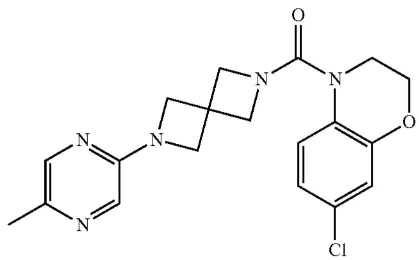 | $^1$H NMR (400 MHz, CDCl$_3$) δ 7.91 (1H, s), 7.70 (1H, d, J = 1.5 Hz), 7.29-7.27 (1H, m), 6.88-6.85 (2H, m), 4.30 (2H, t, J = 4.6 Hz), 4.14 (4H, s), 4.10 (4H, s), 3.77 (2H, t, J = 4.6 Hz), 2.40 (3H, s); m/z 386 (M + H)$^+$. |
| 1-21 | 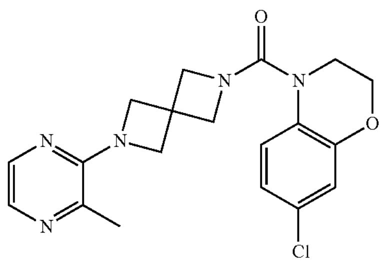 [SMILES: Cc1nccnc1N1CC2(CN(C(=O)N3CCOc4cc(Cl)ccc43)C2)C1] | $^1$H NMR (400 MHz, CDCl$_3$) δ 7.92 (1H, d, J = 2.8 Hz), 7.85 (1H, d, J = 2.8 Hz), 7.29-7.27 (1H, m), 6.89-6.86 (2H, m), 4.30 (2H, t, J = 4.6 Hz), 4.22 (4H, s), 4.10 (4H, s), 3.78 (2H, t, J = 4.6 Hz), 2.41 (3H, s); m/z 386 (M + H)$^+$. |
| 1-22 | 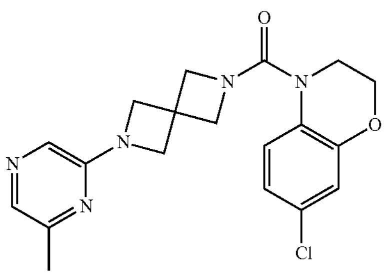 [SMILES: Cc1cncc(N2CC3(CN(C(=O)N4CCOc5cc(Cl)ccc54)C3)C2)n1] | $^1$H NMR (400 MHz, CDCl$_3$) δ 7.77 (s, 1H), 7.57 (s, 1H), 7.29 (t, J = 1.9 Hz, 1H), 6.88-6.86 (m, 2H), 4.29 (dd, J = 4.7, 4.7 Hz, 2H), 4.16 (s, 4H), 4.10 (s, 4H), 3.77 (dd, J = 4.7, 4.7 Hz, 2H), 2.36 (s, 3H). m/z 386 (M + H)$^+$. |
| 1-23 | 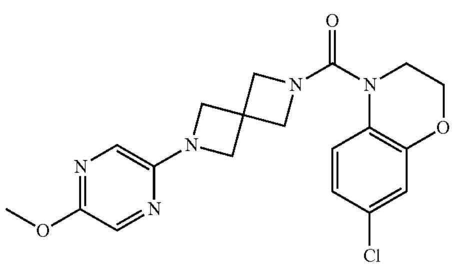 [SMILES: COc1cnc(N2CC3(CN(C(=O)N4CCOc5cc(Cl)ccc54)C3)C2)cn1] | $^1$H NMR (400 MHz, CDCl$_3$) δ 7.81 (d, J = 1.5 Hz, 1H), 7.32 (d, J = 1.3 Hz, 1H), 7.28 (t, J = 3.3 Hz, 1H), 6.88-6.85 (m, 2H), 4.29 (t, J = 4.5 Hz, 2H), 4.08 (d, J = 10.1 Hz, 8H), 3.87 (s, 3H), 3.77 (dd, J = 4.7, 4.7 Hz, 2H). m/z 402 (M + H)$^+$. |
| 1-24 | 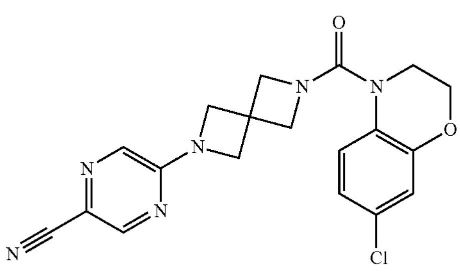 [SMILES: N#Cc1cnc(N2CC3(CN(C(=O)N4CCOc5cc(Cl)ccc54)C3)C2)cn1] | $^1$H NMR (400 MHz, DMSO) δ 8.57 (d, J = 1.5 Hz, 1H), 7.99 (d, J = 1.5 Hz, 1H), 7.46 (d, J = 9.1 Hz, 1H), 6.99-6.95 (m, 2H), 4.37 (s, 4H), 4.30 (t, J = 4.4 Hz, 2H), 4.17 (s, 4H), 3.70 (t, J = 4.4 Hz, 2H). m/z 397 (M + H)$^+$. |
| 1-25 | 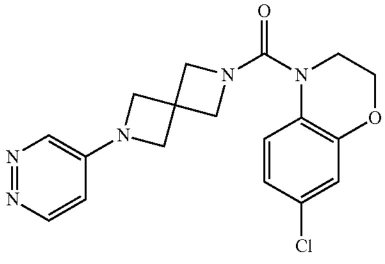 [SMILES: O=C(N1CC2(C1)CN(c1ccnnc1)C2)N1CCOc2cc(Cl)ccc21] | $^1$H NMR (400 MHz, CDCl$_3$) δ 8.68 (1H, d, J = 6.0 Hz), 8.39 (1H, d, J = 2.8 Hz), 7.26 (1H, dd, J = 1.0, 8.0 Hz), 6.87 (2H, d, J = 8.3 Hz), 6.31 (1H, dd, J = 3.1, 6.1 Hz), 4.30 (2H, t, J = 4.6 Hz), 4.17 (4H, s), 4.13 (4H, s), 3.78 (2H, t, J = 4.6 Hz); m/z 372 (M + H)$^+$. |

TABLE 3-continued

| No. | Structure | Data |
|---|---|---|
| 1-26 | 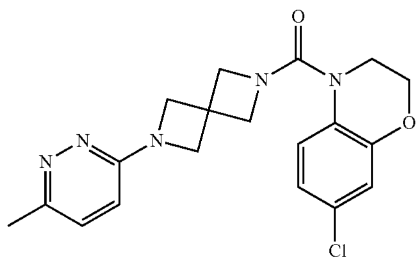 [SMILES: Cc1ccc(N2CC3(CN(C(=O)N4CCOc5cc(Cl)ccc54)C3)C2)nn1] | ¹H NMR (400 MHz, CDCl₃) δ 7.29-7.27 (1H, m), 7.07 (1H, d, J = 9.0 Hz), 6.88-6.85 (2H, m), 6.48 (1H, d, J = 8.9 Hz), 4.30 (2H, t, J = 4.6 Hz), 4.19 (4H, s), 4.11 (4H, s), 3.79-3.71 (2H, m), 2.53 (3H, s); m/z 386 (M + H)⁺. |
| 1-27 | 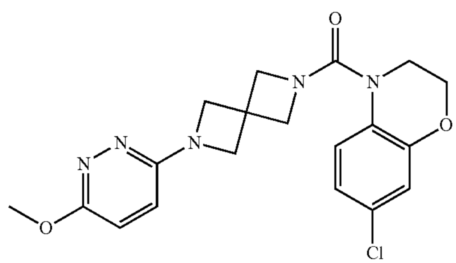 [SMILES: COc1ccc(N2CC3(CN(C(=O)N4CCOc5cc(Cl)ccc54)C3)C2)nn1] | ¹H NMR (400 MHz, CDCl₃) δ 7.29-7.27 (1H, m), 6.88-6.85 (2H, m), 6.83 (1H, d, J = 9.5 Hz), 6.60 (1H, d, J = 9.3 Hz), 4.30 (2H, t, J = 4.6 Hz), 4.15 (4H, s), 4.10 (4H, s), 4.01 (3H, s), 3.77 (2H, t, J = 4.6 Hz); m/z 402 (M + H)⁺. |
| 1-28 | 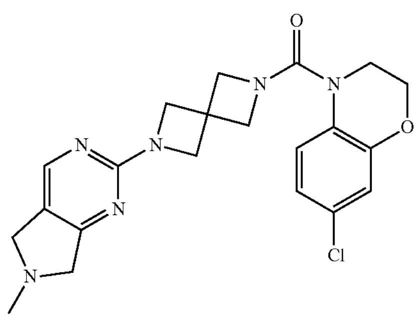 [SMILES: CN1Cc2cnc(N3CC4(CN(C(=O)N5CCOc6cc(Cl)ccc65)C4)C3)nc2C1] | ¹H NMR (400 MHz, DMSO) δ 8.22 (1H, s), 7.47 (1H, d, J = 9.1 Hz), 6.96 (2H, d, J = 8.1 Hz), 4.29 (2H, dd, J = 4.3, 4.3 Hz), 4.18 (4H, s), 4.15 (4H, s), 3.75 (2H, s), 3.37 (4H, s), 2.50 (3H, s); m/z 427 (M + H)⁺. |
| 1-29 | 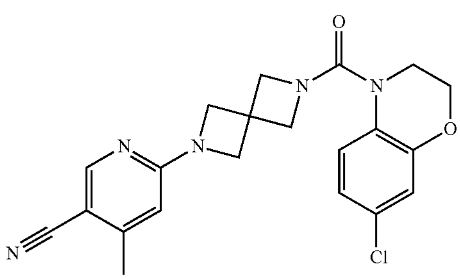 [SMILES: Cc1cc(N2CC3(CN(C(=O)N4CCOc5cc(Cl)ccc54)C3)C2)ncc1C#N] | ¹H NMR (400 MHz, CDCl₃) δ 7.52 (1H, d, J = 8.6 Hz), 7.29-7.27 (1H, m), 6.87 (2H, d, J = 8.3 Hz), 6.05 (1H, d, J = 8.6 Hz), 4.29 (2H, t, J = 4.5 Hz), 4.18 (4H, s), 4.10 (4H, s), 3.78 (2H, t, J = 4.5 Hz Hz), 2.55 (3H, s); m/z 410 (M + H)⁺. |
| 1-30 | 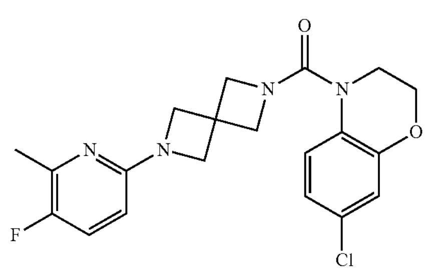 | ¹H NMR (400 MHz, CDCl₃): δ 7.30-7.29 (1H, m), 7.13 (1H, dd, J = 8.7, 8.7 Hz), 6.86 (2H, d, J = 7.6 Hz), 6.06 (1H, dd, J = 2.7, 8.7 Hz), 4.29 (2H, dd, J = 4.5, 4.5 Hz), 4.06 (8H, d, J = 11.4 Hz), 3.77 (2H, dd, J = 4.5, 4.5 Hz), 2.36 (3H, d, J = 2.8 Hz), m/z 403 (M + H)⁺. |

TABLE 3-continued

| No. | Structure | Data |
|---|---|---|
| 1-31 | 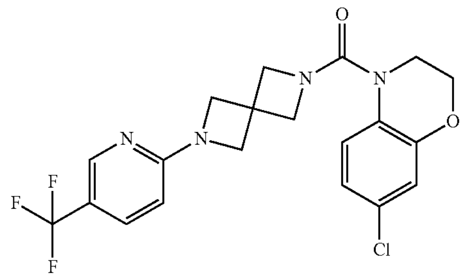 [SMILES: O=C(N1CC2(C1)CN(c1ccc(C(F)(F)F)cn1)C2)N1CCOc2cc(Cl)ccc21] | ¹H NMR (400 MHz, CDCl₃) δ 8.35 (s, 1H), 7.61 (dd, J = 2.4, 8.7 Hz, 1H), 7.30-7.26 (m, 1H), 6.88-6.86 (m, 2H), 6.26 (d, J = 8.6 Hz, 1H), 4.30 (dd, J = 4.7, 4.7 Hz, 2H), 4.18 (s, 4H), 4.11 (s, 4H), 3.78 (dd, J = 4.7, 4.7 Hz, 2H). m/z 439 (M + H)⁺. |
| 1-32 | 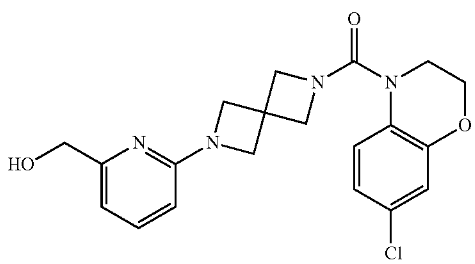 [SMILES: O=C(N1CC2(C1)CN(c1cccc(CO)n1)C2)N1CCOc2cc(Cl)ccc21] | ¹H NMR (400 MHz, CDCl₃) δ 7.46-7.41 (1H, m), 7.30-7.27 (1H, m), 6.88-6.85 (2H, m), 6.53 (1H, d, J = 7.0 Hz), 6.16 (1H, d, J = 8.5 Hz), 4.59 (2H, s), 4.30 (2H, t, J = 4.6 Hz), 4.12 (4H, s), 4.10 (4H, s), 3.77 (2H, t, J = 4.6 Hz); m/z 401 (M + H)⁺. |
| 1-33 | 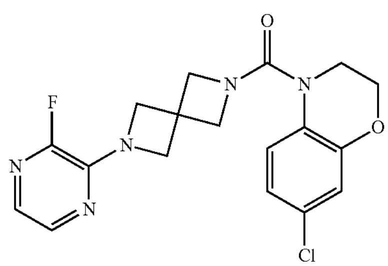 [SMILES: O=C(N1CC2(C1)CN(c1nccnc1F)C2)N1CCOc2cc(Cl)ccc21] | ¹H NMR (400 MHz, CDCl₃) δ 7.89 (dd, J = 2.9, 4.7 Hz, 1H), 7.39 (dd, J = 2.7, 2.7 Hz, 1H), 7.29-7.27 (m, 1H), 6.89-6.86 (m, 2H), 4.32-4.28 (m, 6H), 4.11 (s, 4H), 3.78 (t, J = 4.5 Hz, 2H). m/z 390 (M + H)⁺. |
| 1-34 | 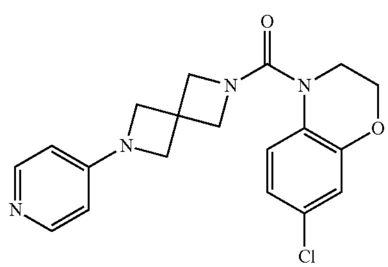 | ¹H NMR (400 MHz, CDCl₃) δ 8.25 (d, J = 6.8 Hz, 2H), 7.28-7.26 (m, 1H), 6.89-6.85 (m, 2H), 6.31-6.28 (m, 2H), 4.30 (dd, J = 4.7, 4.7 Hz, 2H), 4.16 (4H, s), 4.14 (4H, s), 3.78 (dd, J = 4.1, 5.1 Hz, 2H). m/z 371 (M + H)⁺. |
| 1-35 | 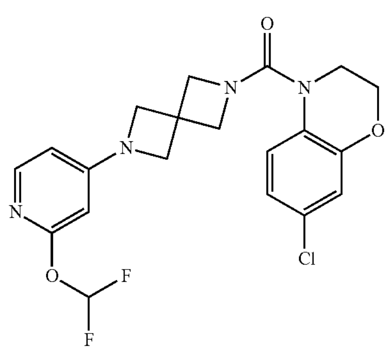 [SMILES: O=C(N1CC2(C1)CN(c1ccnc(OC(F)F)c1)C2)N1CCOc2cc(Cl)ccc21] | (400 MHz, CDCl₃) δ 7.82 (d, J = 5.8 Hz, 1H), 7.41 (t, J = 73.5 Hz, 1H), 7.29-7.27 (m, 1H), 6.87 (d, J = 7.8 Hz, 2H), 6.07 (dd, J = 2.0, 5.8 Hz, 1H), 5.75 (d, J = 2.0 Hz, 1H), 4.29 (t, J = 4.5 Hz, 2H), 4.12 (4H, s), 4.10 (4H, s), 3.77 (t, J = 4.5 Hz, 2H). m/z 371 (M + H)⁺. |

TABLE 3-continued

| No. | Structure | Data |
|---|---|---|
| 1-36 | 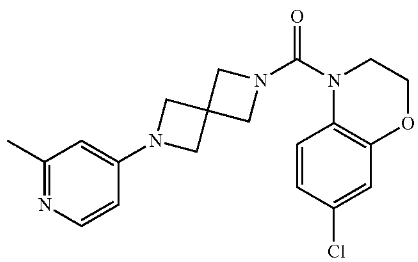 [SMILES: Cc1cc(N2CC3(CN(C(=O)N4CCOc5cc(Cl)ccc54)C3)C2)ccn1] | ¹H NMR (400 MHz, CDCl₃) δ 8.23 (d, J = 6.3 Hz, 1H), 7.26 (d, J = 8.7 Hz, 1H), 6.89-6.85 (m, 2H), 6.16 (dd, J = 2.5, 6.3 Hz, 1H), 6.09 (d, J = 2.3 Hz, 1H), 4.30 (dd, J = 4.7, 4.7 Hz, 2H), 4.14 (4H, s), 4.12 (4H, s), 3.78 (t, J = 4.5 Hz, 2H), 2.51 (s, 3H). m/z 385 (M + H)⁺. |
| 1-37 | 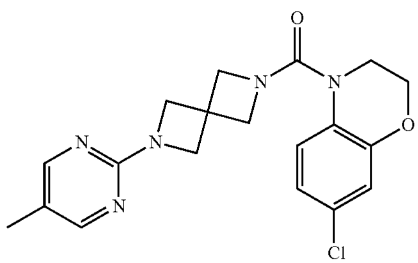 | ¹H NMR (400 MHz, CDCl₃) δ 8.16 (s, 2H), 7.31-7.27 (m, 1H), 6.89-6.85 (m, 2H), 4.29 (t, J = 4.5 Hz, 2H), 4.19 (s, 4H), 4.10 (s, 4H), 3.77 (t, J = 4.5 Hz, 2H), 2.13 (s, 3H). m/z 386 (M + H)⁺. |
| 1-38 | 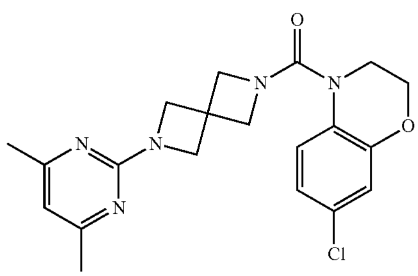 [SMILES: Cc1cc(C)nc(N2CC3(CN(C(=O)N4CCOc5cc(Cl)ccc54)C3)C2)n1] | ¹H NMR (400 MHz, CDCl₃) δ 7.31-7.27 (m, 1H), 6.86 (d, J = 7.6 Hz, 2H), 6.34 (s, 1H), 4.29 (t, J = 4.5 Hz, 2H), 4.20 (s, 4H), 4.08 (s, 4H), 3.77 (dd, J = 4.7, 4.7 Hz, 2H), 2.29 (s, 6H). m/z 400 (M + H)⁺. |
| 1-39 | 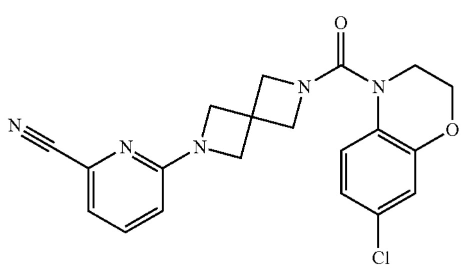 [SMILES: N#Cc1cccc(N2CC3(CN(C(=O)N4CCOc5cc(Cl)ccc54)C3)C2)n1] | ¹H NMR (400 MHz, CDCl₃) δ 7.49 (1H, dd, J = 7.3, 8.3 Hz), 7.29-7.27 (1H, m), 7.00 (1H, d, J = 7.1 Hz), 6.88-6.86 (2H, m), 6.42 (1H, d, J = 8.3 Hz), 4.30 (2H, dd, J = 4.7, 4.7 Hz), 4.14 (4H, s), 4.10 (4H, s), 3.78 (2H, dd, J = 4.7, 4.7 Hz); m/z 396 (M + H)⁺. |
| 1-40 | 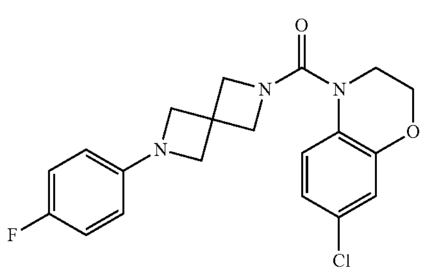 | ¹H NMR (400 MHz, CDCl₃) δ 7.28 (1H, d, J = 1.8 Hz), 6.93-6.85 (4H, m), 6.37-6.33 (2H, m), 4.29 (2H, dd, J = 4.7, 4.7 Hz), 4.08 (4H, s), 3.91 (4H, s), 3.77 (2H, dd, J = 4.7, 4.7 Hz); m/z 388 (M + H)⁺. |
| 1-41 | 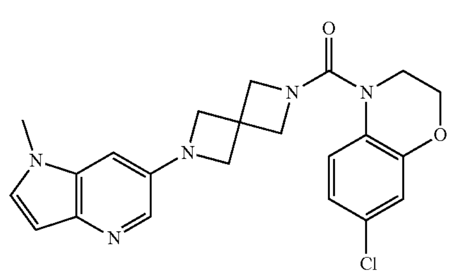 [SMILES: Cn1ccc2ncc(N3CC4(CN(C(=O)N5CCOc6cc(Cl)ccc65)C4)C3)cc21] | ¹H NMR (400 MHz, CDCl₃) δ 7.82 (1H, d, J = 2.3 Hz), 7.31-7.27 (1H, m), 7.09 (1H, d, J = 3.3 Hz), 6.90-6.86 (2H, m), 6.60-6.57 (2H, m), 4.30 (2H, t, J = 4.5 Hz Hz), 4.12 (4H, s), 4.04 (4H, s), 3.78 (2H, dd, J = 4.7, 4.7 Hz), 3.72 (3H, s); m/z 424 (M + H)⁺. |

TABLE 3-continued

| No. | Structure | Data |
|---|---|---|
| 1-42 | 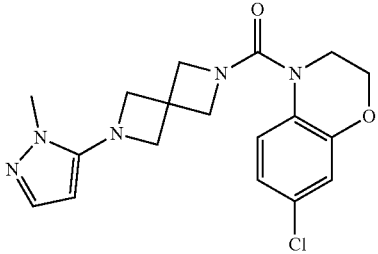 [SMILES: Cn1nccc1N1CC2(CN(C(=O)N3CCOc4cc(Cl)ccc43)C2)C1] | $^1$H NMR (400 MHz, CDCl$_3$) δ 7.24 (t, J = 1.9 Hz, 2H), 6.87 (d, J = 8.3 Hz, 2H), 5.49 (d, J = 1.8 Hz, 1H), 4.29 (dd, J = 4.7, 4.7 Hz, 2H), 4.08 (s, 4H), 3.92 (s, 4H), 3.77 (dd, J = 4.7, 4.7 Hz, 2H), 3.61 (s, 3H).<br>m/z 373 (M + H)$^+$. |
| 1-43 | 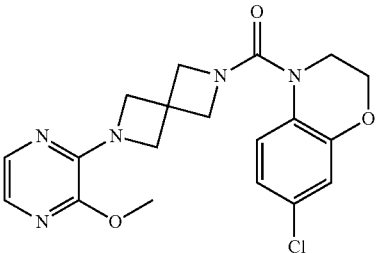 | $^1$H NMR (400 MHz, CDCl$_3$) δ 7.59 (d, J = 3.1 Hz, 1H), 7.39 (d, J = 3.0 Hz, 1H), 7.29-7.27 (m, 1H), 6.88-6.85 (m, 2H), 4.29 (t, J = 4.6 Hz, 2H), 4.25 (s, 4H), 4.08 (s, 4H), 3.90 (s, 3H), 3.77 (t, J = 4.6 Hz, 2H);<br>m/z 402 (M + H)$^+$. |
| 1-44 | 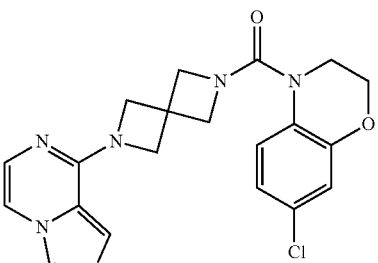 | $^1$H NMR (400 MHz, CDCl$_3$) δ 8.03 (s, 1H), 7.49 (s, 1H), 7.30-7.27 (m, 2H), 7.08 (d, J = 4.8 Hz, 1H), 6.90-6.86 (m, 2H), 4.47 (4H, s), 4.30 (t, J = 4.5 Hz, 2H), 4.14 (s, 4H), 3.78 (dd, J = 4.7, 4.7 Hz, 2H);<br>m/z 411 (M + H)$^+$. |
| 1-45 | 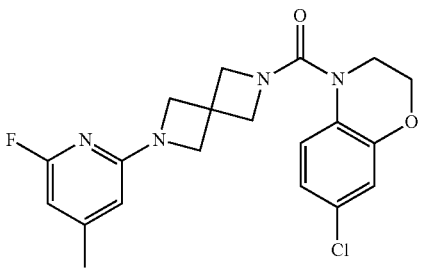 [SMILES: Cc1cc(F)nc(N2CC3(CN(C(=O)N4CCOc5cc(Cl)ccc54)C3)C2)c1] | $^1$H NMR (400 MHz, CDCl$_3$) δ 7.29-7.26 (m, 1H), 6.88-6.85 (m, 2H), 6.03 (s, 1H), 5.87 (s, 1H), 4.29 (dd, J = 4.7, 4.7 Hz, 2H), 4.08 (s, 8H), 3.77 (dd, J = 4.7, 4.7 Hz, 2H), 2.25 (s, 3H).<br>m/z 403 (M + H)$^+$. |
| 1-46 | 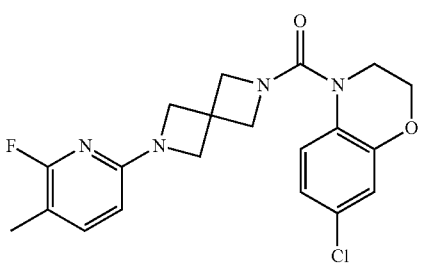 [SMILES: Cc1ccc(N2CC3(CN(C(=O)N4CCOc5cc(Cl)ccc54)C3)C2)nc1F] | $^1$H NMR (400 MHz, CDCl$_3$) δ 7.33 (1H, dd, J = 8.2, 9.8 Hz), 7.29-7.27 (1H, m), 6.88-6.85 (2H, m), 6.02 (1H, dd, J = 1.6, 8.0 Hz), 4.31-4.27 (2H, m), 4.08 (4H, s), 4.06 (4H, s), 3.77 (2H, t, J = 4.6 Hz), 2.12 (3H, s);<br>m/z 403 (M + H)$^+$. |

TABLE 3-continued

| No. | Structure | Data |
|---|---|---|
| 1-47 | 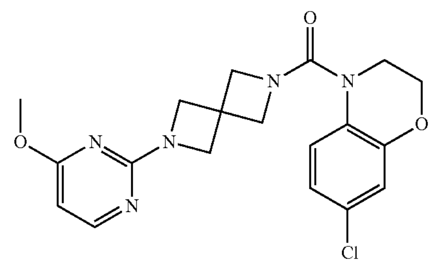 [SMILES: COc1ccnc(N2CC3(CN(C(=O)N4CCOc5cc(Cl)ccc54)C3)C2)n1] | $^1$H NMR (400 MHz, CDCl$_3$) δ 8.03 (1H, d, J = 5.6 Hz), 7.30-7.27 (1H, m), 6.88-6.85 (2H, m), 6.03 (1H, d, J = 5.8 Hz), 4.29 (2H, dd, J = 4.7, 4.7 Hz), 4.20 (4H, s), 4.09 (4H, s), 3.87 (3H, s), 3.77 (2H, dd, J = 4.7, 4.7 Hz); m/z 402 (M + H)$^+$. |
| 1-48 | 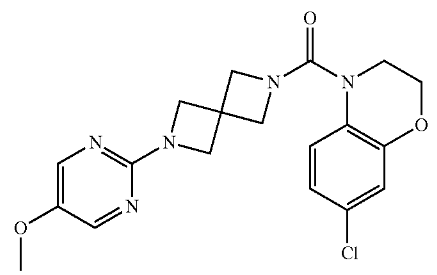 [SMILES: COc1cnc(N2CC3(CN(C(=O)N4CCOc5cc(Cl)ccc54)C3)C2)nc1] | $^1$H NMR (400 MHz, CDCl$_3$) δ 8.09 (2H, s), 7.31-7.27 (1H, m), 6.89-6.85 (2H, m), 4.29 (2H, dd, J = 4.7, 4.7 Hz), 4.17 (4H, s), 4.09 (4H, s), 3.80 (3H, s), 3.77 (2H, dd, J = 4.8, 4.8 Hz); m/z 402 (M + H)$^+$. |
| 1-49 | 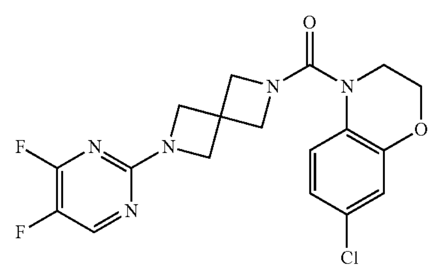 | $^1$H NMR (400 MHz, CDCl$_3$) δ 7.20 (ddd, J = 5.9, 8.3, 10.2 Hz, 1H), 6.88-6.86 (m, 2H), 6.11 (ddd, J = 1.8, 3.0, 8.3 Hz, 1H), 4.30-4.24 (m, 6H), 4.08 (s, 4H), 3.77 (t, J = 4.5 Hz, 2H); m/z 407 (M + H)$^+$. |
| 1-50 | 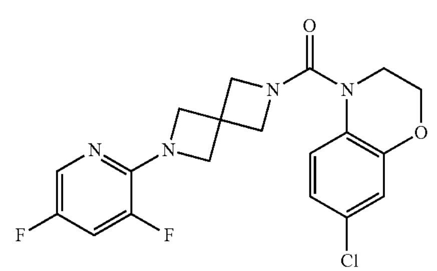 [SMILES: O=C(N1CC2(C1)CN(c1ncc(F)cc1F)C2)N1CCOc2cc(Cl)ccc21] | $^1$H NMR (400 MHz, CDCl$_3$) δ 7.85 (1H, d, J = 2.4 Hz), 7.29-7.27 (1H, m), 7.08-7.02 (1H, m), 6.88-6.85 (2H, m), 4.31-4.27 (2H, m), 4.18 (4H, d, J = 1.8 Hz), 4.09 (4H, s), 3.77 (2H, t, J = 4.6 Hz); m/z 407 (M + H)$^+$. |
| 1-51 | 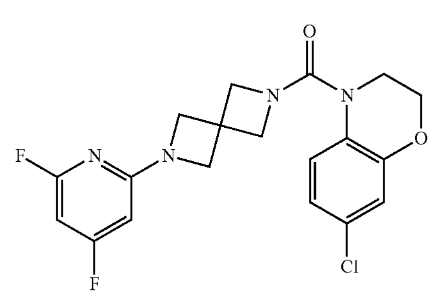 [SMILES: O=C(N1CC2(C1)CN(c1cc(F)cc(F)n1)C2)N1CCOc2cc(Cl)ccc21] | $^1$H NMR (400 MHz, CDCl$_3$) δ 7.27-7.25 (m, 1H), 6.89-6.84 (m, 2H), 5.95 (d, J = 8.5 Hz, 1H), 5.76-5.70 (m, 1H), 4.29 (t, J = 4.5 Hz, 2H), 4.11-4.07 (m, 8H), 3.77 (t, J = 4.5 Hz, 2H). m/z 407 (M + H)$^+$. |

TABLE 3-continued

| No. | Structure | Data |
|---|---|---|
| 1-52 | 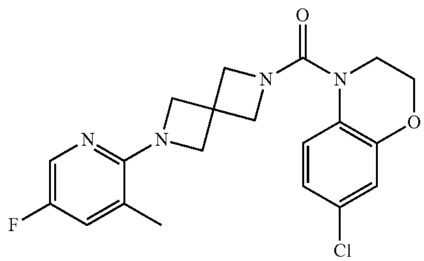 [SMILES: Cc1cc(F)cnc1N1CC2(CN(C(=O)N3CCOc4cc(Cl)ccc43)C2)C1] | $^1$H NMR (400 MHz, CDCl$_3$) δ 7.88 (1H, d, J = 2.8 Hz), 7.29-7.27 (1H, m), 7.05 (1H, dd, J = 2.4, 8.2 Hz), 6.88-6.85 (2H, m), 4.29 (2H, t, J = 4.5 Hz Hz), 4.12 (4H, s), 4.08 (4H, s), 3.77 (2H, dd, J = 4.7, 4.7 Hz), 2.15 (3H, s); m/z 403 (M + H)$^+$. |
| 1-53 | 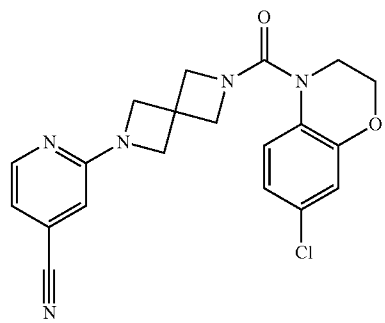 [SMILES: N#Cc1ccnc(N2CC3(CN(C(=O)N4CCOc5cc(Cl)ccc54)C3)C2)c1] | $^1$H NMR (400 MHz, CDCl$_3$) δ 8.24 (d, J = 4.3 Hz, 1H), 7.30-7.26 (m, 1H), 6.89-6.85 (m, 2H), 6.78 (dd, J = 1.3, 5.1 Hz, 1H), 6.43 (s, 1H), 4.30 (dd, J = 4.7, 4.7 Hz, 2H), 4.13 (d, J = 16.2 Hz, 8H), 3.78 (dd, J = 4.7, 4.7 Hz, 2H). m/z 396 (M + H)$^+$. |
| 1-54 | 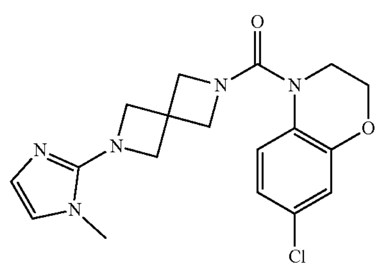 [SMILES: Cn1ccnc1N1CC2(CN(C(=O)N3CCOc4cc(Cl)ccc43)C2)C1] | $^1$H NMR (400 MHz, DMSO) δ 7.41 (d, J = 8.5 Hz, 1H), 6.94-6.90 (m, 2H), 6.72 (d, J = 1.4 Hz, 1H), 6.47 (d, J = 1.4 Hz, 1H), 4.24 (t, J = 4.4 Hz, 2H), 4.06 (d, J = 19.8 Hz, 8H), 3.65 (t, J = 4.4 Hz, 2H), 3.32 (s, 3H). m/z 374 (M + H)$^+$. |
| 1-55 | 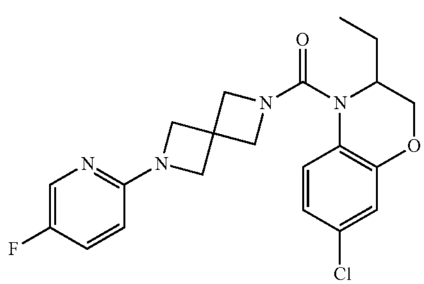 | $^1$H NMR (400 MHz, CDCl$_3$) δ 7.99 (d, J = 3.0 Hz, 1H), 7.25-7.19 (m, 2H), 6.89-6.85 (m, 2H), 6.22 (dd, J = 3.4, 9.0 Hz, 1H), 4.34-4.29 (m, 2H), 4.22-4.01 (m, 7H), 3.88 (d, J = 9.5 Hz, 2H), 1.55-1.46 (m, 2H), 0.96 (dd, J = 7.4, 7.4 Hz, 3H). m/z 417 (M + H)$^+$. |
| 1-56 | 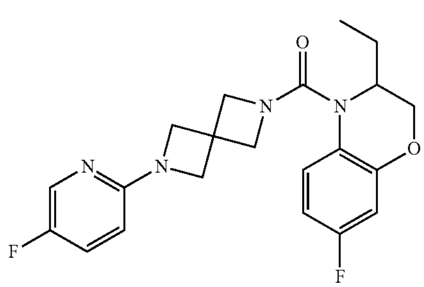 [SMILES: CCC1COc2cc(F)ccc2N1C(=O)N1CC2(C1)CN(c1ccc(F)cn1)C2] | $^1$H NMR (400 MHz, CDCl$_3$) δ 7.99 (d, J = 3.0 Hz, 1H), 7.25-7.19 (m, 2H), 6.63 (dq, J = 7.9, 3.9 Hz, 1H), 6.58 (dd, J = 2.9, 9.6 Hz, 1H), 6.22 (dd, J = 3.5, 9.0 Hz, 1H), 4.35-4.31 (m, 2H), 4.18 (d, J = 9.5 Hz, 2H), 4.14 (dd, J = 3.1, 11.0 Hz, 1H), 4.05 (dd, J = 8.4, 15.8 Hz, 4H), 3.87 (d, J = 9.4 Hz, 2H), 1.54-1.46 (m, 2H), 0.96 (dd, J = 7.4, 7.4 Hz, 3H). m/z 401 (M + H)$^+$. |

TABLE 3-continued

| No. | Structure | Data |
|---|---|---|
| 1-57 | 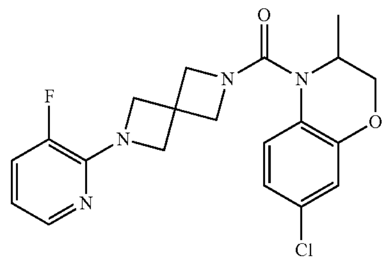 [SMILES: CC1COc2cc(Cl)ccc2N1C(=O)N1CC2(C1)CN(c1ncccc1F)C2] | $^1$H NMR (400 MHz, CDCl$_3$) δ 7.91 (d, J = 4.9 Hz, 1H), 7.22 (d, J = 9.3 Hz, 1H), 7.14 (ddd, J = 1.1, 7.9, 11.9 Hz, 1H), 6.90-6.86 (m, 2H), 6.64-6.59 (m, 1H), 4.49 (q, J = 6.9 Hz, 1H), 4.26-4.15 (m, 8H), 3.92 (d, J = 9.4 Hz, 2H), 1.22 (d, J = 6.9 Hz, 3H). m/z 403/405 (M + H)$^+$. |
| 1-58 | 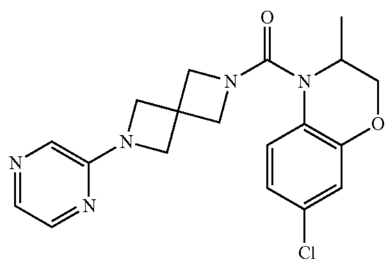 [SMILES: CC1COc2cc(Cl)ccc2N1C(=O)N1CC2(C1)CN(c1cnccn1)C2] | $^1$H NMR (400 MHz, CDCl$_3$) δ 8.02 (dd, 1=1.5, 2.8 Hz, 1H), 7.88 (d, J = 2.8 Hz, 1H), 7.77 (d, J = 1.5 Hz, 1H), 7.22 (d, J = 9.3 Hz, 1H), 6.90-6.87 (m, 2H), 4.52-4.47 (m, 1H), 4.28-4.15 (m, 8H), 3.94 (d, J = 9.5 Hz, 2H), 1.22 (d, J = 6.9 Hz, 3H). m/z 386/388 (M + H)$^+$. |
| 1-59 | 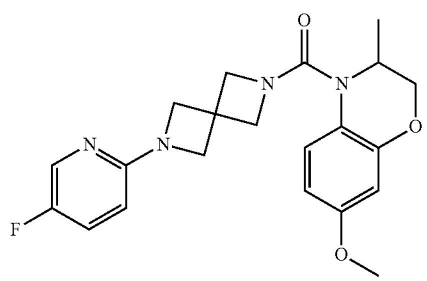 | $^1$H NMR (400 MHz, CDCl$_3$) δ 7.99 (d, J = 3.0 Hz, 1H), 7.23 (dd, J = 3.1, 8.5 Hz, 1H), 7.19 (d, J = 8.9 Hz, 1H), 6.50 (dd, J = 2.8, 8.9 Hz, 1H), 6.42 (d, J = 2.9 Hz, 1H), 6.22 (dd, J = 3.1, 9.0 Hz, 1H), 4.55-4.49 (m, 1H), 4.23-4.16 (m, 4H), 4.05 (q, J = 8.3 Hz, 4H), 3.88 (d, J = 9.5 Hz, 2H), 3.76 (s, 3H), 1.20 (d, J = 6.9 Hz, 3H). m/z 399 / 400 (M + H)$^+$. |
| 1-60 | 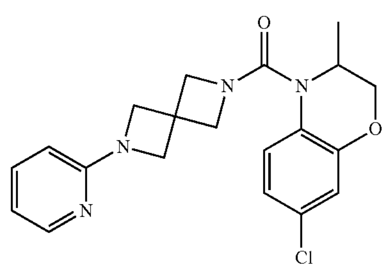 [SMILES: CC1COc2cc(Cl)ccc2N1C(=O)N1CC2(C1)CN(c1ccccn1)C2] | $^1$H NMR (400 MHz, CDCl$_3$) δ 8.14-8.13 (m, 1H), 7.47-7.42 (m, 1H), 7.22 (d, J = 9.3 Hz, 1H), 6.90-6.86 (m, 2H), 6.63 (dd, J = 5.4, 7.2 Hz, 1H), 6.27 (d, J = 8.4 Hz, 1H), 4.51-4.46 (m, 1H), 4.26-4.06 (m, 8H), 3.92 (d, J = 9.4 Hz, 2H), 1.22 (d, J = 6.8 Hz, 3H). m/z 385 (M + H)$^+$. |
| 1-61 | 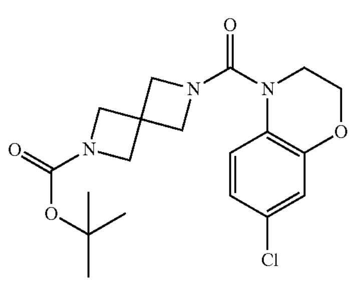 [SMILES: CC(C)(C)OC(=O)N1CC2(C1)CN(C(=O)N1CCOc3cc(Cl)ccc31)C2] | $^1$H NMR (400 MHz, CDCl$_3$) δ 7.25-7.23 (m, 1H) 6.88-6.83 (m, 2H), 4.28 (t, J = 4.6 Hz, 2H), 4.01 (s, 8H), 3.75 (t, J = 4.6 Hz, 2H). m/z 394/396 (M + H)$^+$. |
| 1-62 | 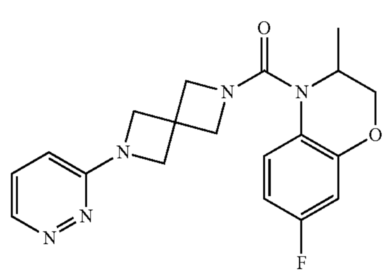 [SMILES: CC1COc2cc(F)ccc2N1C(=O)N1CC2(C1)CN(c1cccnn1)C2] | $^1$H NMR (400 MHz, CDCl$_3$) δ 8.60 (dd, J = 1.5, 4.5 Hz, 1H), 7.25-7.16 (m, 2H), 6.67-6.58 (m, 2H), 6.51 (dd, J = 1.4, 9.0 Hz, 1H), 4.55-4.49 (m, 1H), 4.28-4.16 (m, 8H), 3.94 (d, J = 9.3 Hz, 2H), 1.21 (d, J = 6.8 Hz, 3H). m/z 370 (M + H)$^+$. |

TABLE 3-continued

| No. | Structure | Data |
| --- | --- | --- |
| 1-63 | 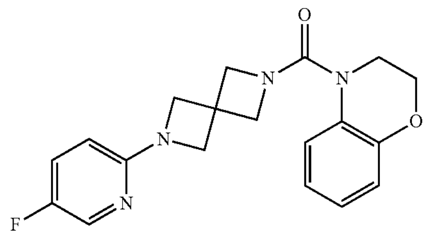 | $^1$H NMR (400 MHz, CDCl$_3$) δ 7.99 (d, J = 3.0 Hz, 1H), 7.33 (dd, J = 1.6, 8.0 Hz, 1H), 7.25-7.20 (m, 1H), 6.98-6.93 (m, 1H), 6.91-6.84 (m, 2H), 6.23 (dd, J = 3.5, 9.0 Hz, 1H), 4.32-4.29 (m, 2H), 4.07 (d, J = 7.5 Hz, 8H), 3.82-3.78 (m, 2H). m/z 355 (M + H)$^+$. |
| 1-64 | 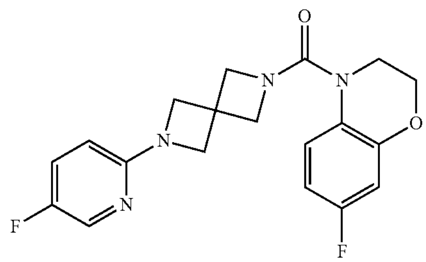 [SMILES: O=C(N1CC2(C1)CN(c1ccc(F)cn1)C2)N1CCOc2cc(F)ccc21] | $^1$H NMR (400 MHz, CDCl$_3$) δ 8.00 (d, J = 3.0 Hz, 1H), 7.31-7.21 (m, 2H), 6.65-6.57 (m, 2H), 6.23 (dd, J = 3.1, 9.0 Hz, 1H), 4.30 (t, J = 4.6 Hz, 2H), 4.07 (d, J = 3.3 Hz, 8H), 3.78 (t, J = 4.6 Hz, 2H). m/z 373 (M + H)$^+$. |
| 1-65 | 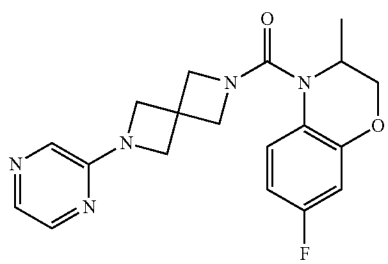 [SMILES: CC1COc2cc(F)ccc2N1C(=O)N1CC2(C1)CN(c1cnccn1)C2] | $^1$H NMR (400 MHz, CDCl$_3$) δ 8.05 (d, J = 1.4 Hz, 1H), 7.91 (d, J = 2.8 Hz, 1H), 7.81 (s, 1H), 7.29-7.24 (m, 1H) 6.70-6.61 (m, 2H), 4.55 (q, J = 6.9 Hz, 1H), 4.30-4.18 (m, 8H), 3.96 (d, J = 9.5 Hz, 2H), 1.23 (d, J = 6.9 Hz, 3H). m/z 370 (M + H)$^+$. |
| 1-66 | 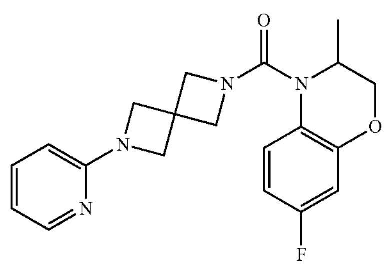 [SMILES: CC1COc2cc(F)ccc2N1C(=O)N1CC2(C1)CN(c1ccccn1)C2] | $^1$H NMR (400 MHz, CDCl$_3$) δ 8.17-8.15 (m, 1H), 7.51-7.45 (m, 1H), 7.29-7.25 (m, 1H) 6.70-6.61 (m, 3H), 6.30 (d, J = 8.4 Hz, 1H), 4.56-4.51 (m, 1H), 4.27-4.10 (m, 8H), 3.94 (d, J = 9.4 Hz, 2H), 1.24 (d, J = 6.9 Hz, 3H). m/z 369 (M + H)$^+$. |
| 1-67 | 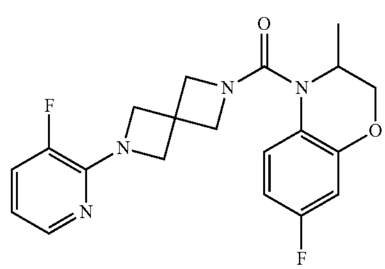 [SMILES: CC1COc2cc(F)ccc2N1C(=O)N1CC2(C1)CN(c1ncccc1F)C2] | $^1$H NMR (400 MHz, CDCl$_3$) δ 7.91 (d, J = 4.9 Hz, 1H), 7.26-7.21 (m, 1H), 7.14 (ddd, J = 1.4, 7.9, 11.9 Hz, 1H), 6.67-6.58 (m, 3H), 4.54-4.48 (m, 1H), 4.24-4.16 (m, 8H), 3.91 (d, J = 9.4 Hz, 2H), 1.21 (d, J = 6.9 Hz, 3H). m/z 387 (M + H)$^+$. |
| 1-68 | 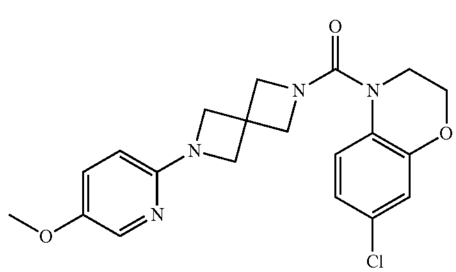 [SMILES: COc1ccc(N2CC3(CN(C(=O)N4CCOc5cc(Cl)ccc54)C3)C2)nc1] | $^1$H NMR (400 MHz, DMSO) δ 7.42 (d, J = 8.5 Hz, 1H), 7.37 (d, J = 2.6 Hz, 1H), 6.94-6.90 (m, 3H), 6.67 (d, J = 8.8 Hz, 1H), 4.25 (t, J = 4.4 Hz, 2H), 4.09 (s, 4H), 3.89 (s, 4H), 3.75 (s, 3H), 3.65 (t, J = 4.5 Hz, 2H). m/z 401 (M + H)$^+$. |

TABLE 3-continued

| No. | Structure | Data |
|---|---|---|
| 1-69 | 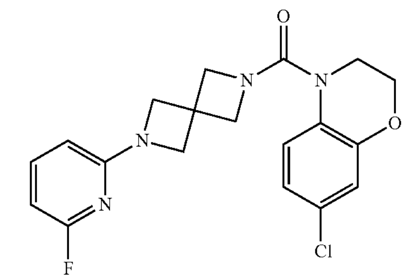 [SMILES: O=C(N1CC2(C1)CN(c1cccc(F)n1)C2)N1CCOc2cc(Cl)ccc21] | $^1$H NMR (400 MHz, DMSO) δ 7.64 (q, J = 8.2 Hz, 1H), 7.42 (d, J = 8.7 Hz, 1H), 6.93-6.90 (m, 2H), 6.25 (ddd, J = 2.2, 7.8, 14.7 Hz, 2H), 4.25 (t, J = 4.4 Hz, 2H), 4.09 (d, J = 12.3 Hz, 8H), 3.65 (t, J = 4.5 Hz, 2H). m/z 389 (M + H)$^+$. |
| 1-70 | 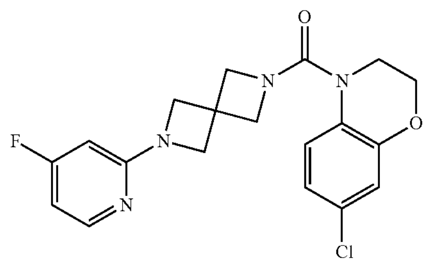 [SMILES: O=C(N1CC2(C1)CN(c1cc(F)ccn1)C2)N1CCOc2cc(Cl)ccc21] | $^1$H NMR (400 MHz, DMSO) δ 8.07 (dd, J = 5.8, 9.4 Hz, 1H), 7.43 (d, J = 8.7 Hz, 1H), 6.92 (d, J = 8.3 Hz, 2H), 6.56-6.50 (m, 1H), 6.23 (dd J = 2.3, 11.7 Hz, 1H), 4.25 (t, J = 4.5 Hz, 2H), 4.09 (d, J = 13.3 Hz, 8H), 3.65 (t, J = 4.5 Hz, 2H). m/z 389 (M + H)$^+$. |
| 1-71 | 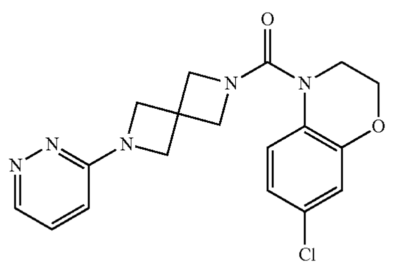 [SMILES: O=C(N1CC2(C1)CN(c1cccnn1)C2)N1CCOc2cc(Cl)ccc21] | $^1$H NMR (400 MHz, DMSO) δ 8.55 (dd, J = 1.3, 4.5 Hz, 1H), 7.43 (d, J = 9.2 Hz, 1H), 7.36 (dd, J = 4.5, 9.0 Hz, 1H), 6.92 (d, J = 7.9 Hz, 2H), 6.78 (dd, J = 1.4, 9.0 Hz, 1H), 4.25 (t, J = 4.4 Hz, 2H), 4.15 (d, J = 17.8 Hz, 8H), 3.66 (t, J = 4.5 Hz, 2H). m/z 372 (M + H)$^+$. |
| 1-72 | 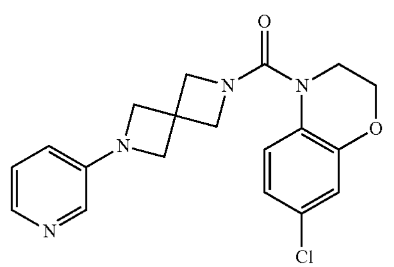 [SMILES: O=C(N1CC2(C1)CN(c1cccnc1)C2)N1CCOc2cc(Cl)ccc21] | $^1$H NMR (400 MHz, CDCl$_3$) δ 8.03 (d, J = 3.6 Hz, 1H), 7.84 (d, J = 2.8 Hz, 1H), 7.28-7.26 (m, 1H), 7.11 (dd, J = 4.8, 8.1 Hz, 1H), 6.88-6.86 (m, 2H), 6.73-6.69 (m, 1H), 4.31-4.28 (m, 2H), 4.10 (s, 4H), 4.01 (s, 4H), 3.77 (t, J = 4.6 Hz, 2H). m/z 371 (M + H)$^+$. |
| 1-73 | 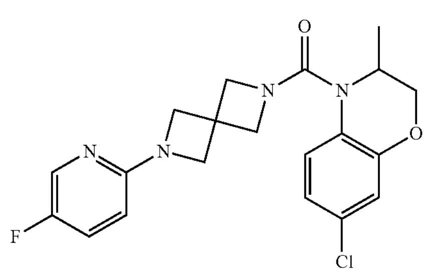 | $^1$H NMR (400 MHz, DMSO) δ 8.05 (d, J = 3.0 Hz, 1H), 7.52-7.46 (m, 1H), 7.28 (d, J = 8.5 Hz, 1H), 6.93 (d, J = 8.2 Hz, 2H), 6.42 (dd, J = 3.5, 9.0 Hz, 1H), 4.32 (q, J = 6.8 Hz, 1H), 4.23-4.09 (m, 4H), 4.04-3.98 (m, 6H), 1.10 (d, J = 7.0 Hz, 3H). m/z 403 (M + H)$^+$. |
| 1-74 | 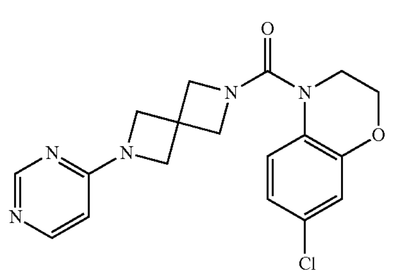 | $^1$H NMR (400 MHz, CDCl$_3$) δ 8.59 (s, 1H), 8.19 (d, J = 6.1 Hz, 1H), 7.27-7.25 (m, 1H), 6.88-6.86 (m, 2H), 6.17 (dd, J = 1.3, 6.1 Hz, 1H), 4.30 (t, J = 4.5 Hz, 2H), 4.19 (s, 4H), 4.11 (s, 4H), 3.78 (dd, J = 4.7, 4.7 Hz, 2H). m/z 372 (M + H)$^+$. |

TABLE 3-continued

| No. | Structure | Data |
|---|---|---|
| 1-75 | 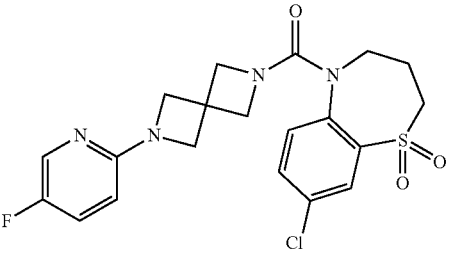 [SMILES: O=C(N1CC2(C1)CN(c1ccc(F)cn1)C2)N1CCCS(=O)(=O)c2cc(Cl)ccc21] | $^1$H NMR (400 MHz, DMSO) δ 8.06 (d, J = 3.0 Hz, 1H), 7.94-7.88 (m, 2H), 7.61 (d, J = 8.3 Hz, 1H), 7.54-7.48 (m, 1H), 6.41 (dd, J = 3.5, 9.1 Hz, 1H), 3.93 (s, 4H), 3.78-3.70 (m, 4H), 3.61 (dd, J = 5.1, 5.1 Hz, 2H), 3.41-3.38 (m, 2H), 2.06 (s, 2H). |
| 1-76 | 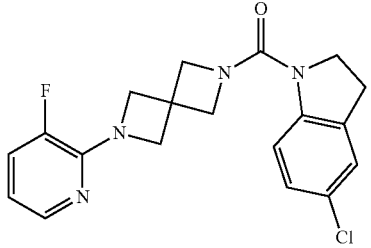 [SMILES: O=C(N1CC2(C1)CN(c1ncccc1F)C2)N1CCc2cc(Cl)ccc21] | $^1$H NMR (400 MHz, CDCl$_3$) δ 7.94-7.93 (m, 1H), 7.61 (d, J = 8.4 Hz, 1H), 7.19-7.10 (m, 3H), 6.65-6.61 (m, 1H), 4.29 (d, J = 2.2 Hz, 4H), 4.25 (s, 4H) 3.94 (dd, J = 8.6, 8.6 Hz, 2H), 3.12 (dd, J = 8.5, 8.5 Hz, 2H). |
| 1-77 | 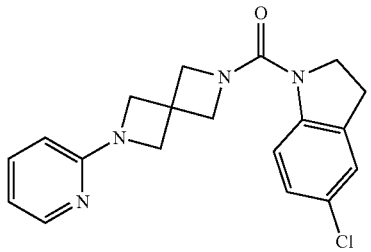 [SMILES: O=C(N1CC2(C1)CN(c1ccccn1)C2)N1CCc2cc(Cl)ccc21] | $^1$H NMR (400 MHz, DMSO) δ 8.12 (dd, J = 1.1, 4.9 Hz, 1H), 7.68 (d, J = 8.6 Hz, 1H), 7.59-7.54 (m, 1H), 7.28 (s, 1H), 7.20 (dd, J = 2.3, 8.6 Hz, 1H), 6.69 (dd, J = 5.1, 6.3 Hz, 1H), 6.44 (d, J = 8.3 Hz, 1H), 4.27 (s, 4H), 4.13 (s, 4H), 3.97 (t, J = 8.6 Hz, 2H), 3.16 (t, J = 8.6 Hz, 2H). |
| 1-78 | 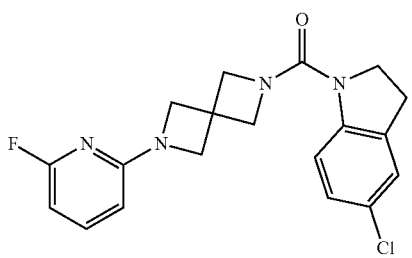 | $^1$H NMR (400 MHz, CDCl$_3$) δ 7.61 (d, J = 8.4 Hz, 1H), 7.52 (q, J = 8.0 Hz, 1H), 7.14-7.10 (m, 1H), 6.21 (dd, J = 2.0, 7.8 Hz, 1H), 6.09 (dd, J = 2.1, 7.8 Hz, 1H), 4.25 (s, 4H), 4.17 (s, 4H), 3.93 (t, J = 8.6 Hz, 2H), 3.12 (t, J = 8.5, Hz, 2H); |
| 1-79 | 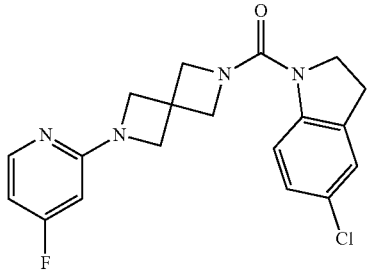 [SMILES: O=C(N1CC2(C1)CN(c1cc(F)ccn1)C2)N1CCc2cc(Cl)ccc21] | $^1$H NMR (400 MHz, CDCl$_3$) δ 8.10 (dd, J = 5.8. 8.9 Hz, 1H), 7.61 (d, J = 8.4 Hz, 1H), 7.15-7.11 (m, 2H), 6.43-6.38 (m, 1H), 5.96 (dd, J = 2.1, 10.8 Hz, 1H), 4.26 (s, 4H), 4.17 (s, 4H), 3.94 (t, J = 8.5 Hz, 2H), 3.12 (t, J = 8.5 Hz, 2H). |

TABLE 3-continued

| No. | Structure | Data |
|---|---|---|
| 1-80 | 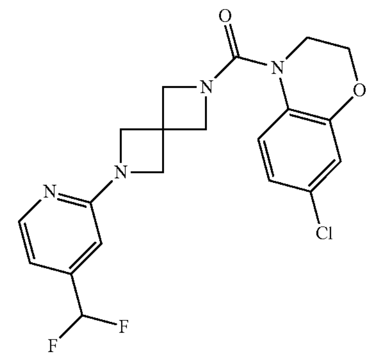 [SMILES: O=C(N1CC2(C1)CN(c1cc(C(F)F)ccn1)C2)N1CCOc2cc(Cl)ccc21] | ¹H NMR (400 MHz, CDCl₃) δ 8.22 (d, J = 5.1 Hz, 1H), 7.30-7.24 (m, 1H) 6.89-6.84 (m, 2H), 6.71 (d, J = 4.5 Hz, 1H), 6.51 (t, J = 56.1 Hz, 1H), 6.35 (s, 1H), 4.30 (t, J = 4.5 Hz, 2H), 4.16-4.09 (m, 8H), 3.78 (t, J = 4.5 Hz, 2H). |
| 1-81 | 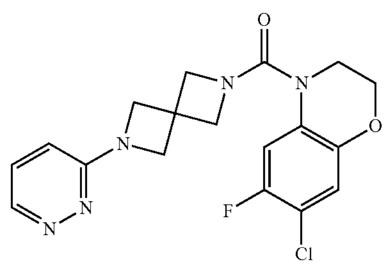 [SMILES: O=C(N1CC2(C1)CN(c1cccnn1)C2)N1CCOc2cc(Cl)c(F)cc21] | ¹H NMR (400 MHz, CDCl₃) δ 8.61 (d, J = 3.5 Hz, 1H), 7.30-7.20 (m, 2H), 6.90 (d, J = 7.1 Hz, 1H), 6.53 (d, J = 8.8 Hz, 1H), 4.28-4.24 (m, 6H), 4.18 (s, 4H), 3.75 (t, J = 4.5 Hz, 2H). |
| 1-82 | 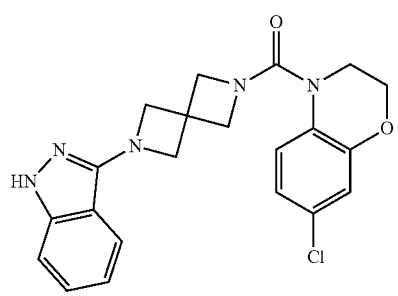 [SMILES: O=C(N1CC2(C1)CN(c1n[nH]c3ccccc13)C2)N1CCOc2cc(Cl)ccc21] | ¹H NMR (400 MHz, CDCl₃) δ 8.95 (s, 1H), 7.52 (d, J = 8.1 Hz, 1H), 7.35-7.27 (m, 3H), 7.06-7.01 (m, 1H), 6.89-6.85 (m, 2H), 4.32-4.27 (m, 6H), 4.13 (s, 4H), 3.77 (t, J = 4.5 Hz, 2H). |
| 1-83 | 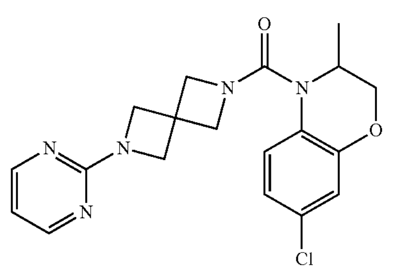 [SMILES: CC1COc2cc(Cl)ccc2N1C(=O)N1CC2(C1)CN(c1ncccn1)C2] | ¹H NMR (400 MHz, CDCl₃) δ 8.30 (d, J = 4.8 Hz, 2H), 7.25-7.21 (m, 1H), 6.89-6.86 (m, 2H), 6.56 (t, J = 4.4 Hz, 1H), 4.50-4.47 (m, 1H), 4.26-4.13 (m, 8H), 3.92 (d, J = 9.6 Hz, 2H), 1.22 (d, J = 6.7 Hz, 3H). |

Example 2

Synthesis of (7-chloro-2,3-dihydro-4H-benzo[b][1,4]oxazin-4-yl)(6-(pyridin-4-ylmethyl)-2,6-diazaspiro[3.3]heptan-2-yl)methanone (Compound No. 2-1)

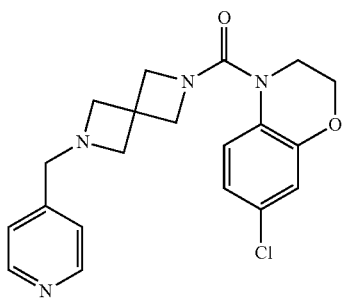 [SMILES: O=C(N1CC2(CN(Cc3ccncc3)C2)C1)N1CCOc2cc(Cl)ccc21]

A mixture of (7-chloro-2,3-dihydro-4H-benzo[b][1,4]oxazin-4-yl)(2,6-diazaspiro[3.3]heptan-2-yl)methanone 2,2,2-trifluoroacetate (110 mg, 0.27 mmol, 1.0 eq.), 4-pyridinecarboxaldehyde (34 mg, 0.32 mmol, 1.2 eq.), Et$_3$N (0.075 mL, 0.54 mmol, 2.0 eq.) in DCM (3 mL) was stirred at RT for 10 minutes. Sodium triacetoxyborohydride (131 mg, 0.62 mmol, 2.3 eq.) was added and the mixture was stirred at RT overnight. Reaction mixture was diluted with water and extracted with EtOAc (×2). The organic phases were combined, dried (MgSO$_4$) and concentrated in vacuo. The residue was purified using preparative HPLC to afford the titled compound. (71 mg, 68% yield). $^1$H NMR (400 MHz, CDCl$_3$) δ 8.53-8.51 (m, 2H), 7.23 (d, J=8.6 Hz, 1H), 7.16 (d, J=6.1 Hz, 2H), 6.87-6.83 (m, 2H), 4.27 (t, J=4.5 Hz, 2H), 3.99 (s, 4H), 3.74 (t, J=4.5 Hz, 2H), 3.53 (s, 2H), 3.32 (s, 4H). m/z 385 (M+H)$^+$.

Compound Nos. 2-2 through 2-6 listed in Table 4 below were prepared according to the methods described in Example 2 using the appropriately substituted or modified intermediates.

TABLE 4

| No. | Structure | Data |
|---|---|---|
| 2-2 | 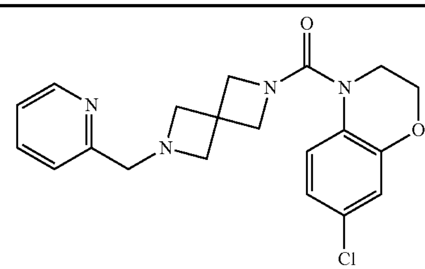 | $^1$H NMR (400 MHz, CDCl$_3$) δ 8.53 (1H, dd, J = 0.8, 3.8 Hz), 7.66-7.61 (1H, m), 7.23 (2H, d, J = 8.5 Hz), 7.15 (1H, dd, J = 5.2, 7.1 Hz), 6.87-6.82 (2H, m), 4.28-4.24 (2H, m), 3.99 (4H, s), 3.74 (2H, t, J = 4.6 Hz), 3.68 (2H, s), 3.39 (4H, s); m/z 385 (M + H)$^+$. |
| 2-3 | 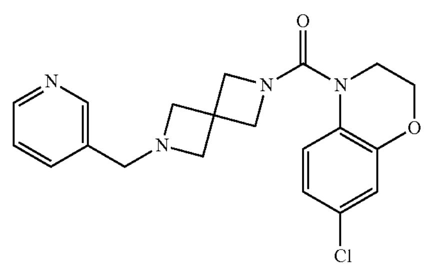 [SMILES: O=C(N1CC2(CN(Cc3cccnc3)C2)C1)N1CCOc2cc(Cl)ccc21] | $^1$H NMR (400 MHz, CDCl$_3$) δ 8.50 (1H, dd, J = 1.7, 4.8 Hz), 8.46 (1H, d, J = 1.8 Hz), 7.57 (1H, td, J = 2.0, 8.0 Hz), 7.25-7.21 (2H, m), 6.87-6.82 (2H, m), 4.26 (2H, t, J = 4.6 Hz), 3.98 (4H, s), 3.74 (2H, t, J = 4.6 Hz), 3.53 (2H, s), 3.30 (4H, s); m/z 385 (M + H)$^+$. |
| 2-4 | 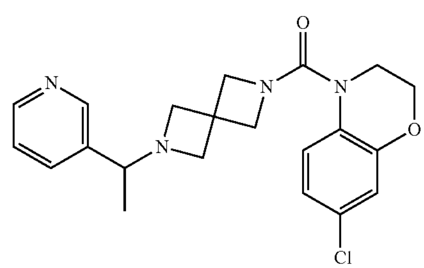 [SMILES: CC(c1cccnc1)N1CC2(CN(C(=O)N3CCOc4cc(Cl)ccc43)C2)C1] | $^1$H NMR (400 MHz, CDCl$_3$) δ 8.50-8.46 (2H, m), 7.61-7.58 (1H, m), 7.25-7.20 (2H, m), 6.87-6.82 (2H, m), 4.26 (2H, t, J = 4.6 Hz), 3.96 (4H, d, J = 2.3 Hz), 3.74 (2H, q, J = 4.2 Hz), 3.27-3.13 (5H, m), 1.18 (3H, d, J = 6.5 Hz); m/z 399 (M + H)$^+$. |
| 2-5 | 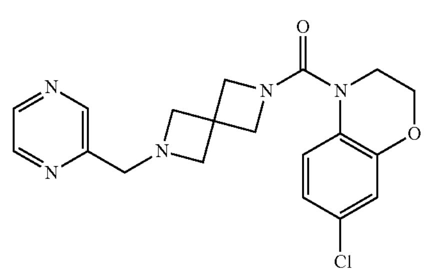 [SMILES: O=C(N1CC2(CN(Cc3cnccn3)C2)C1)N1CCOc2cc(Cl)ccc21] | $^1$H NMR (400 MHz, CDCl$_3$) δ 8.54 (d, J = 1.4 Hz, 1H), 8.50 (dd, J = 2.0, 2.0 Hz, 1H), 8.46 (d, J = 2.5 Hz, 1H), 7.23 (d, J = 8.7 Hz, 1H), 6.87-6.82 (m, 2H), 4.26 (t, J = 4.6 Hz, 2H), 4.00 (s, 4H), 3.76-3.72 (m, 4H), 3.42 (s, 4H); m/z 385 (M + H)$^+$. |

TABLE 4-continued

| No. | Structure | Data |
|---|---|---|
| 2-6 | 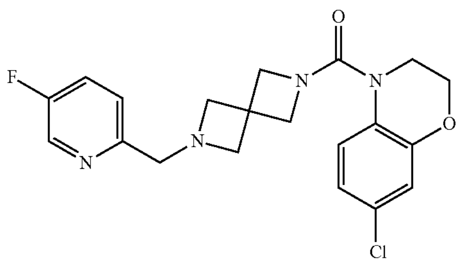 [SMILES: O=C(N1CC2(CN(Cc3ccc(F)cn3)C2)C1)N1CCOc2cc(Cl)ccc21] | $^1$H NMR (400 MHz, CDCl$_3$) δ 8.38 (d, J = 2.8 Hz, 1H), 7.38-7.32 (m, 1H), 7.26-7.22 (m, 2H), 6.87-6.82 (m, 2H), 4.26 (dd, J = 4.7, 4.7 Hz, 2H), 3.99 (s, 4H), 3.74 (t, J = 4.5 Hz, 2H), 3.66 (s, 2H), 3.37 (s, 4H). m/z 403 (M + H)$^+$. |

Example 3

Synthesis of (7-chloro-2,3-dihydro-4H-benzo[b][1,4]oxazin-4-yl)(6-(5-methylpyridazin-3-yl)-2,6-diazaspiro[3.3]heptan-2-yl)methanone (Compound No. 3-1)

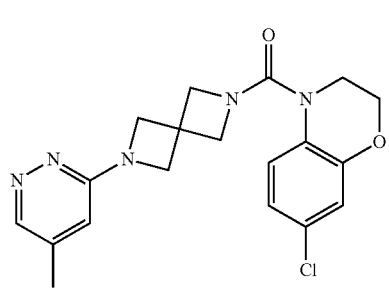

A mixture of (7-chloro-2,3-dihydro-4H-benzo[b][1,4]oxazin-4-yl)(2,6-diazaspiro[3.3]heptan-2-yl)methanone 2,2,2-trifluoroacetate (80 mg, 0.196 mmol, 1.0 eq.), Xantphos (24 mg, 0.04 mmol, 0.2 eq.), cesium carbonate (273 mg, 0.84 mmol, 4.3 eq.) and 3-chloro-5-methylpyridazine (81 mg, 0.21 mmol, 1.1 eq.) in 1,4-dioxane (2 mL) was degassed using nitrogen for 30 minutes. Pd$_2$(dba)$_3$ (19 mg, 0.02 mmol, 0.1 eq.) was added and the mixture was heated to 100° C. overnight. The mixture was filtered through a pad of celite and concentrated in vacuo. The residue partitioned between DCM and sat. NaHCO$_3$ soln., the organic phase was separated, dried and concentrated in vacuo. The residue was purified using preparative HPLC to afford the titled compound. (5 mg, 6% yield). $^1$H NMR (400 MHz, CDCl$_3$) δ 8.46 (1H, d, J=1.6 Hz), 7.30-7.27 (1H, m), 6.88-6.86 (2H, m), 6.31 (1H, ddd, J=0.9, 0.9, 0.9 Hz), 4.30 (2H, t, J=4.6 Hz), 4.21 (4H, s), 4.11 (4H, s), 3.78 (2H, t, J=4.6 Hz), 2.25 (3H, s). m/z 386 (M+H)$^+$.

Example 4

Synthesis of (6-(benzo[d]isoxazol-3-yl)-2,6-diazaspiro[3.3]heptan-2-yl)(7-chloro-2,3-dihydro-4H-benzo[b][1,4]oxazin-4-yl)methanone (Compound No. 4-1)

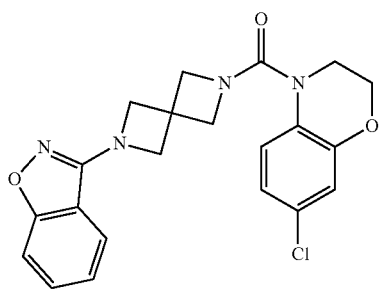

A mixture of (7-chloro-2,3-dihydro-4H-benzo[b][1,4]oxazin-4-yl)(2,6-diazaspiro[3.3]heptan-2-yl)methanone 2,2,2-trifluoroacetate (60 mg, 0.147 mmol, 1.0 eq.) and 3-chlorobenzo[d]isoxazole (59 mg, 0.2 mmol, 1.36 eq.) in pyridine was heated to 90° C. for 3 hours followed by 70° C. overnight. The reaction was diluted with water and extracted with DCM (×2). The organic phases were combined, washed with a 10% aq. solution of citric acid, dried (MgSO$_4$) and concentrated in vacuo. The residue was purified using preparative HPLC to afford the titled compound. (38 mg, 45% yield). $^1$H NMR (400 MHz, CDCl$_3$) δ 7.51-7.45 (m, 2H), 7.42 (d, J=8.6 Hz, 1H), 7.30-7.26 (m, 1H), 7.23-7.19 (m, 1H), 6.89-6.86 (m, 2H), 4.37 (s, 4H), 4.30 (dd, J=4.7, 4.7 Hz, 2H), 4.14 (s, 4H), 3.78 (dd, J=4.7, 4.7 Hz, 2H). m/z 411 (M+H)$^+$.

Compound Nos. 4-2 and 4-3 listed Table 5 below were prepared according to the methods described in Example 4 using the appropriately substituted or modified intermediates.

TABLE 5

| No. | Structure | Data |
|---|---|---|
| 4-2 | 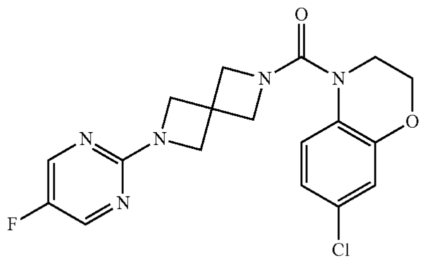 [SMILES: O=C(N1CC2(C1)CN(c1ncc(F)cn1)C2)N1CCOc2cc(Cl)ccc21] | $^1$H NMR (400 MHz, CDCl$_3$) δ 8.20 (2H, s), 7.30-7.27 (1H, m), 6.89-6.85 (2H, m), 4.31-4.28 (2H, m), 4.20 (4H, s), 4.10 (4H, s), 3.79-3.76 (2H, m); m/z 390 (M + H)$^+$. |
| 4-3 | 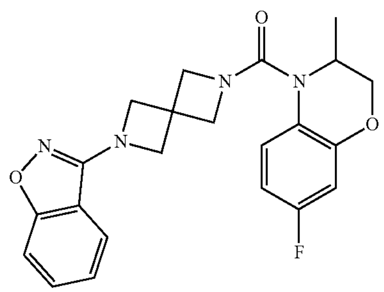 | $^1$H NMR (400 MHz, CDCl$_3$) δ 7.51-7.45 (m, 2H), 7.42 (d, J = 8.3 Hz, 1H), 7.26-7.18 (m, 2H), 6.68-6.59 (m, 2H), 4.55-4.49 (m, 1H), 4.40-4.25 (m, 6H), 4.23-4.16 (m, 2H), 3.95 (d, J = 9.5 Hz, 2H), 1.21 (d, J = 6.9 Hz, 3H). |

Example 5

Synthesis of (7-chloro-2,3-dihydro-4H-benzo[b][1,4]oxazin-4-yl)(6-(imidazo[1,2-a]pyridin-7-yl)-2,6-diazaspiro[3.3]heptan-2-yl)methanone Formate (Compound No. 5-1)

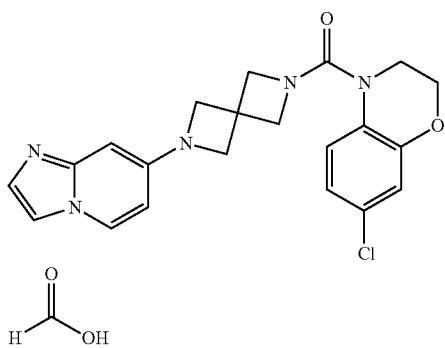

A mixture of (7-chloro-2,3-dihydro-4H-benzo[b][1,4]oxazin-4-yl)(2,6-diazaspiro[3.3]heptan-2-yl)methanone 2,2,2-trifluoroacetate (80 mg, 0.20 mmol, 1.0 eq.), 7-bromoimidazo[1,2-a]pyridine (41 mg, 0.21 mmol, 1.05 eq.), BINAP (17 mg, 0.03 mmol, 0.15 eq.), sodium tert-butoxide (60 mg, 0.63 mmol, 3.15 eq.) in 1,4-dioxane (1.5 mL) was degassed using nitrogen for 30 minutes. Pd$_2$(dba)$_3$ (6.0 mg, 0.01 mmol, 0.05 eq.) was added and the mixture was heated to 80° C. overnight. The mixture was filtered through a pad of celite and concentrated in vacuo. A solution of the residue in DCM was washed with sat. NaHCO$_3$ soln., dried (MgSO$_4$) and concentrated in vacuo. The residue was purified using preparative HPLC to afford the titled compound. (57 mg, 66% yield). $^1$H NMR (400 MHz, CDCl$_3$) δ 8.56 (1H, s), 7.89 (1H, d, J=7.7 Hz), 7.44 (1H, d, J=1.8 Hz), 7.30-7.28 (2H, m), 6.90-6.86 (2H, m), 6.58 (1H, d, J=2.1 Hz), 6.21 (1H, dd, J=2.3, 7.3 Hz), 4.30 (2H, t, J=4.6 Hz), 4.11 (4H, s), 4.09 (4H, s), 3.78 (2H, t, J=4.6 Hz). m/z 410 (M+H)$^+$.

Example 6

Synthesis of (7-chloro-2,3-dihydro-4H-benzo[b][1,4]oxazin-4-yl)(6-(5-fluoro-4-methylpyrimidin-2-yl)-2,6-diazaspiro[3.3]heptan-2-yl)methanone (Compound No. 6-1)

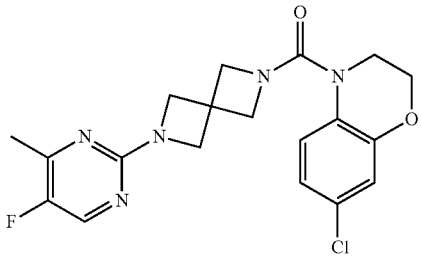

A mixture of 2-chloro-5-fluoro-4-methylpyrimidine (36 mg, 0.19 mmol, 1.4 eq.) and (7-chloro-2,3-dihydro-4H-benzo[b][1,4]oxazin-4-yl)(2,6-diazaspiro[3.3]heptan-2-yl) methanone 2,2,2-trifluoroacetate (42 mg, 0.10 mmol, 1.0 eq.) in 1,4-dioxane (2.5 mL) was heated to 120° C. for 20 minutes under microwave conditions. DIPEA (0.028 mL, 0.16 mmol, 1.6 eq.) was added and the mixture was heated to 150° C. for 1.5 hours under microwave conditions. The mixture was concentrated in vacuo, the residue was dissolved in DCM, washed with 10% aqueous citric acid soln. and concentrated in vacuo. The residue was purified using preparative HPLC to afford the titled compound. (17 mg, 30% yield). $^1$H NMR (400 MHz, CDCl$_3$) δ 8.04 (d, J=1.8 Hz, 1H), 7.29-7.26 (m, 1H), 6.89-6.83 (m, 2H), 4.32-4.26 (m, 2H), 4.17 (s, 4H), 4.08 (s, 4H), 3.77 (t, J=4.5 Hz, 2H), 2.35 (d, J=2.5 Hz, 3H). m/z 404 (M+H)$^+$.

Compound Nos. 6-2, 6-3, 6-4, 6-5, 6-6, 6-7 and 6-8 are prepared according to the method described in Example 6 using appropriately substituted or modified intermediates.

Example 7

Synthesis of (7-chloro-2,3-dihydro-4H-benzo[b][1,4]oxazin-4-yl)(6-(5-methyl-1,2,4-oxadiazol-3-yl)-2,6-diazaspiro[3.3]heptan-2-yl)methanone (Compound No. 7-1)

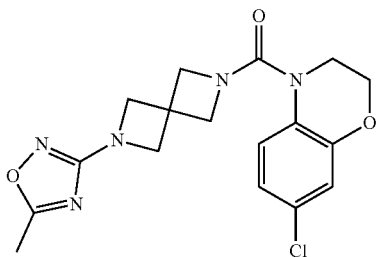 [SMILES: Cc1nc(N2CC3(CN(C(=O)N4CCOc5cc(Cl)ccc54)C3)C2)no1]

Step 1; 6-(7-chloro-3,4-dihydro-2H-benzo[b][1,4]oxazine-4-carbonyl)-2,6-diazaspiro[3.3]heptane-2-carbonitrile

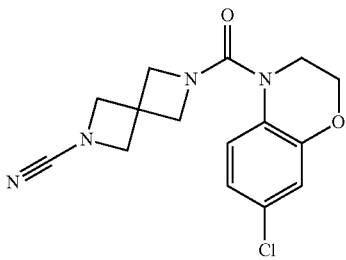 [SMILES: N#CN1CC2(C1)CN(C(=O)N1CCOc3cc(Cl)ccc31)C2]

To an ice cooled mixture of (7-chloro-2,3-dihydro-4H-benzo[b][1,4]oxazin-4-yl)(2,6-diazaspiro[3.3]heptan-2-yl)methanone 2,2,2-trifluoroacetate (280 mg, 0.69 mmol, 1.0 eq.), DIPEA (0.163 mL, 0.94 mmol, 1.4 eq.), in DCM (2 mL) was added cyanogen bromide (95 mg, 0.9 mmol, 1.3 eq.). The mixture was stirred in ice for 1 hour then water was added and the mixture was extracted with DCM (×2). The organic phases were combined, washed with sat. NaHCO$_3$ soln., dried (MgSO$_4$) and concentrated in vacuo. The crude residue was taken on to the next step without purification.

Step 2; (7-chloro-2,3-dihydro-4H-benzo[b][1,4]oxazin-4-yl)(6-(5-methyl-1,2,4-oxadiazol-3-yl)-2,6-diazaspiro[3.3]heptan-2-yl)methanone (Compound No. 7-1)

A suspension of the crude material 6-(7-chloro-3,4-dihydro-2H-benzo[b][1,4]oxazine-4-carbonyl)-2,6-diazaspiro[3.3]heptane-2-carbonitrile (85 mg, 0.27 mmol, 1.0 eq.), Et$_3$N (0.039 mL, 0.28 mmol, 1.05 eq.) and hydroxylamine hydrochloride (20 mg, 0.28 mmol, 1.05 eq.) in EtOH (1 mL) was heated to 80° C. for 1 hour. The mixture was concentrated in vacuo then pyridine (1 mL) and acetic anhydride (0.027 mL, 0.28 mmol, 1.05 eq.) were added. The resulting mixture was heated to 80° C. for 1 hour and concentrated in vacuo. The residue was purified using preparative HPLC to afford the titled compound. (15 mg, 14% yield). $^1$H NMR (400 MHz, CDCl$_3$) δ 7.28-7.24 (1H, m), 6.87 (2H, d, J=7.4 Hz), 4.29 (2H, t, J=4.6 Hz), 4.14 (4H, s), 4.08 (4H, s), 3.76 (2H, t, J=4.6 Hz), 2.45 (3H, s). m/z 376 (M+H)$^+$.

Example 8

Synthesis of (7-chloro-2,3-dihydro-4H-benzo[b][1,4]oxazin-4-yl)(6-(6-methoxypyridin-3-yl)-2,6-diazaspiro[3.3]heptan-2-yl)methanone (Compound No. 8-1)

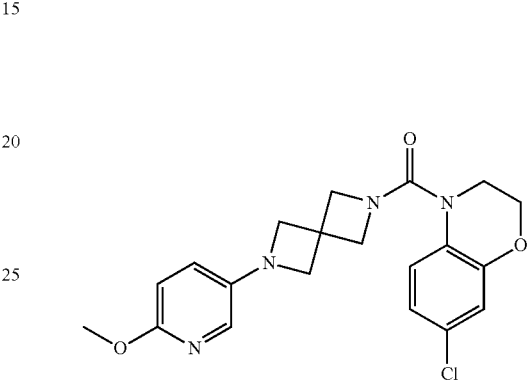

Step 1; 2-benzyl-6-(6-methoxypyridin-3-yl)-2,6-diazaspiro[3.3]heptane

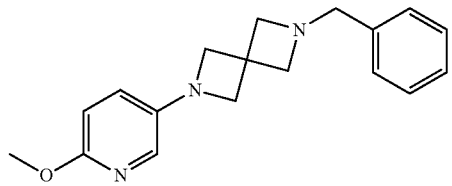 [SMILES: COc1ccc(N2CC3(CN(Cc4ccccc4)C3)C2)cn1]

A mixture of 2-benzyl-2,6-diazaspiro[3.3]heptane (400 mg, 1.44 mmol, 1.0 eq.), 5-bromo-2-methoxypyridine (188 µL, 1.44 mmol, 1.0 eq.), RuPhos (134 mg, 0.29 mmol, 0.2 eq.) and cesium carbonate (1.40 g, 4.32 mmol, 3 eq.) in 1,4-dioxane (8 mL) was degassed using nitrogen for 30 minutes and Pd(OAc)$_2$ (32 mg, 0.14 mmol. 0.1 eq.) was added. The mixture was heated to 80° C. for 2 hours. The mixture was diluted with EtOAc and filtered through celite. The organic phase was separated, washed with aq. LiCl soln., dried (MgSO$_4$), filtered and concentrated in vacuo to give a yellow oil. The crude material was purified by silica flash column chromatography 0-10% methanol in DCM to give the titled compound as a white solid (208 mg, 49% yield). $^1$H NMR (400 MHz, CDCl$_3$) δ 7.38 (d, J=2.8 Hz, 1H), 7.34-7.30 (m, 1H), 7.26 (d, J=7.4 Hz, 4H), 6.81 (dd, J=3.0, 8.8 Hz, 1H), 6.62 (d, J=8.4 Hz, 1H), 3.90 (s, 4H), 3.86 (s, 3H), 3.59 (s, 2H), 3.40 (s, 4H). m/z 296 (M+H)$^+$.

Step 2; 2-(6-methoxypyridin-3-yl)-2,6-diazaspiro[3.3]heptane

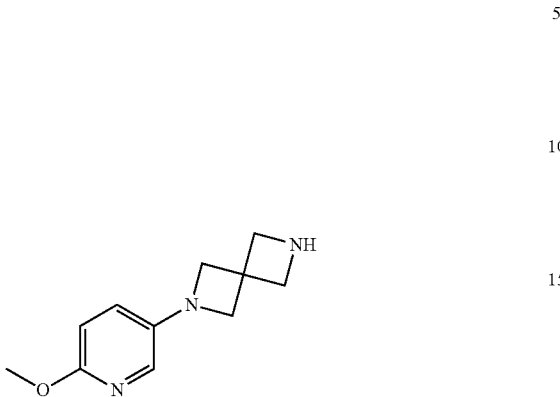

To a mixture of 2-benzyl-6-(6-methoxypyridin-3-yl)-2,6-diazaspiro[3.3]heptane (208 mg, 0.75 mmol, 1.0 eq.) and 1-methyl-1,4-cyclohexadiene (0.5 mL, 4.49 mmol, 6 eq.) in EtOH (6 mL) was added 10% palladium on carbon (120 mg, 50% water) and the mixture was heated to reflux for 4 h. Further palladium on carbon (100 mg, 50% water) and 1-methyl-1,4,-cyclohexadiene (0.5 mL, 4.49 mmol, 6 eq.) were added and the mixture heated to reflux for 3 h. The mixture was filtered through celite and concentrated in vacuo to give the title compound as an oily solid (167 mg, quant.). $^1$H NMR (400 MHz, CDCl$_3$) δ 7.39 (d, J=3.0 Hz, 1H), 6.83 (dd, J=3.0, 8.8 Hz, 1H), 6.63 (d, J=8.8 Hz, 1H), 3.92 (s, 4H), 3.86 (s, 3H), 3.82 (s, 4H).

Step 3; (7-chloro-2,3-dihydro-4H-benzo[b][1,4]oxazin-4-yl)(6-(6-methoxypyridin-3-yl)-2,6-diazaspiro[3.3]heptan-2-yl)methanone (Compound No. 8-1)

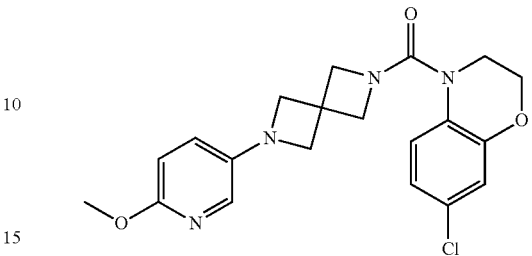

A mixture of 7-chloro-3,4-dihydro-2H-benzo[b][1,4]oxazine (33 mg, 0.2 mmol, 1.0 eq.) and DIPEA (122 μL, 0.22 mmol, 1.1 eq.) in DCM (1 mL) was added dropwise to a cooled solution of triphosgene (87.4 mg, 0.3 mmol, 1.5 eq.) in DCM (1 mL) at 0° C. and the mixture was stirred at 0° C. for 2 hours. Mixture was concentrated in vacuo, DMF (2 mL) was added followed by DIPEA (122 μL, 0.22 mmol, 1.1 eq.) and 2-(6-methoxypyridin-3-yl)-2,6-diazaspiro[3.3]heptane (50 mg, 0.2 mmol, 1.0 eq.) and the mixture was stirred at RT overnight. The mixture was concentrated in vacuo and the residue was purified by preparative HPLC to afford the titled compound. (26 mg, 35% yield). $^1$H NMR (400 MHz, CDCl$_3$) δ 7.37 (dd, J=0.6, 3.0 Hz, 1H), 7.28-7.26 (m, 1H), 6.88-6.51 (m, 2H), 6.80 (dd, J=2.8, 8.5 Hz, 1H), 6.63 (dd, J=0.7, 8.6 Hz, 1H), 4.29 (t, J=4.5 Hz, 2H), 4.08 (s, 4H), 3.91 (s, 4H), 3.86 (s, 3H), 3.77 (t, J=4.5 Hz, 2H). m/z 371 (M+H)$^+$.

Compound Nos. 8-2 through 8-17 listed in Table 6 below were prepared according to the methods described in Example 8 using the appropriately substituted or modified intermediates. Compound Nos. 8-18 through 8-20 are similarly prepared according to the methods described in Example 8 using appropriately substituted or modified intermediates.

TABLE 6

| No. | Structure | Data |
| --- | --- | --- |
| 8-2 | 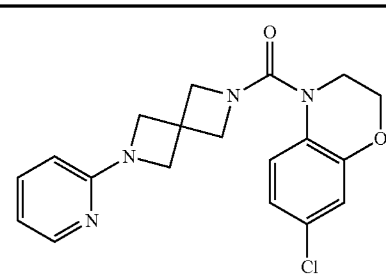 | $^1$H NMR (400 MHz, CDCl$_3$) δ 8.14-8.13 (m, 1H), 7.47-7.42 (m, 1H), 7.30-7.27 (m, 1H), 6.88-6.85 (m, 2H), 6.63 (dd, J = 5.1, 6.8 Hz, 1H), 6.27 (d, J = 8.3 Hz, 1H), 4.31-4.28 (m, 2H), 4.10 (d, J = 3.1 Hz, 8H), 3.77 (t, J = 4.6 Hz, 2H). m/z 371 (M + H)$^+$. |

TABLE 6-continued

| No. | Structure | Data |
|---|---|---|
| 8-3 | 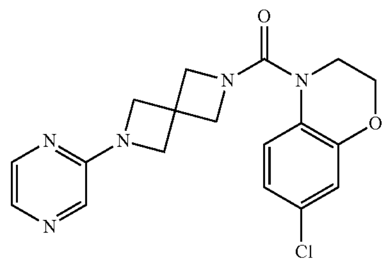 | $^1$H NMR (400 MHz, CDCl$_3$) δ 8.03-8.01 (m, 1H), 7.89 (d, J = 2.8 Hz, 1H), 7.77 (d, J = 1.4 Hz, 1H), 7.43-7.40 (m, 1H), 6.89-6.85 (m, 2H), 4.30 (t, J = 4.6 Hz, 2H), 4.19 (s, 4H), 4.12 (s, 4H), 3.78 (t, J = 4.6 Hz, 2H). m/z 372 (M + H)$^+$. |
| 8-4 | 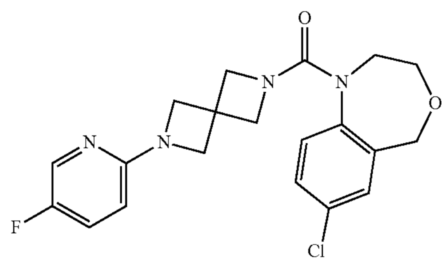 [SMILES: O=C(N1CC2(C1)CN(c1ccc(F)cn1)C2)N1CCOCc2cc(Cl)ccc21] | $^1$H NMR (400 MHz, DMSO) δ 7.98 (d, J = 2.9 Hz, 1H), 7.44-7.35 (m, 3H), 7.30 (d, J = 8.4 Hz, 1H), 6.34 (dd, J = 3.5, 9.0 Hz, 1H), 4.62 (s, 2H), 3.94 (s, 4H), 3.81-3.77 (m, 2H), 3.72 (s, 4H), 3.70-3.64 (m, 2H) |
| 8-5 | 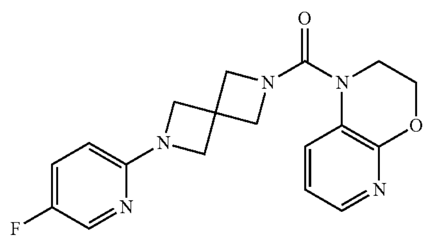 [SMILES: O=C(N1CC2(C1)CN(c1ccc(F)cn1)C2)N1CCOc2ncccc21] | $^1$H NMR (400 MHz, CDCl$_3$) δ 8.01 (d, J = 3.0 Hz, 1H), 7.92 (dd, J = 1.7, 4.8 Hz, 1H), 7.74 (dd, J = 1.7, 8.0 Hz, 1H), 7.25-7.21 (m, 1H), 6.94 (dd, J = 4.8, 8.0 Hz, 1H), 6.27-6.23 (m, 1H), 4.45 (dd, J = 4.2, 5.1 Hz, 2H), 4.13 (s, 4H), 4.10 (s, 4H), 3.80-3.77 (m, 2H) |
| 8-6 | 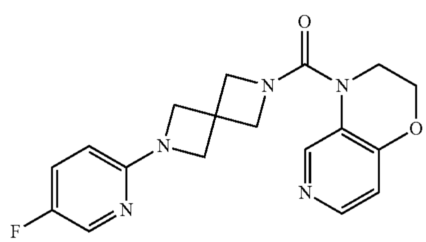 [SMILES: O=C(N1CC2(C1)CN(c1ccc(F)cn1)C2)N1CCOc2ccncc21] | $^1$H NMR (400 MHz, CDCl$_3$) δ 8.56 (s, 1H) 8.10 (d, J = 5.5 Hz, 1H), 8.00 (d, J = 3.0 Hz, 1H), 7.24 (d, J = 9.0 Hz, 1H), 7.25-7.21 (m, 1H), 6.79 (d, J = 5.5 Hz, 1H), 6.24 (dd, J = 3.4, 9.0 Hz, 1H), 4.37 (d, J = 9.2 Hz, 2H), 4.12 (s, 4H), 4.08 (s, 4H), 3.82 (d, J = 9.2 Hz, 2H) |
| 8-7 | 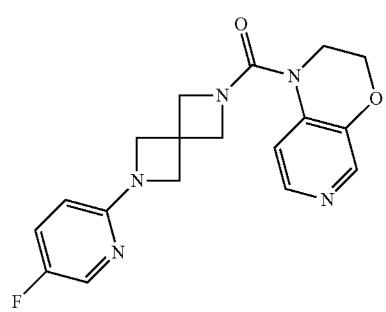 [SMILES: O=C(N1CC2(C1)CN(c1ccc(F)cn1)C2)N1CCOc2cnccc21] | $^1$H NMR (400 MHz, CDCl$_3$) δ 8.19 (1H, s), 8.08 (d, J = 5.5 Hz, 1H), 8.01 (d, J = 2.9 Hz, 1H), 7.34 (d, J = 5.6 Hz, 1H), 7.25-7.22 (m, 1H), 6.26 (dd, J = 3.1, 9.0 Hz, 1H), 4.34-4.31 (m, 2H), 4.19 (s, 4H), 4.11 (s, 4H), 3.79-3.76 (m, 2H) |
| 8-8 | 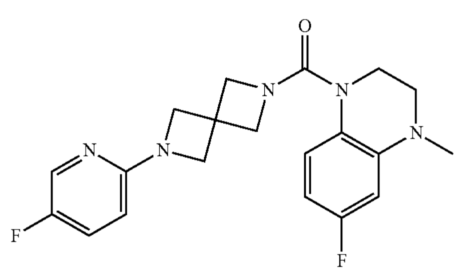 [SMILES: CN1CCN(C(=O)N2CC3(C2)CN(c2ccc(F)cn2)C3)c2ccc(F)cc21] | $^1$H NMR (400 MHz, CDCl$_3$) δ 8.19 (s, 1H), 8.08 (d, J = 5.5 Hz, 1H), 8.01 (d, J = 2.9 Hz, 1H), 7.34 (d, J = 5.6 Hz, 1H), 7.25-7.22 (m, 1H), 6.26 (dd, J = 3.1, 9.0 Hz, 1H), 4.34-4.31 (m, 2H), 4.19 (s, 4H), 4.11 (s, 4H), 3.79-3.76 (m, 2H); |

TABLE 6-continued

| No. | Structure | Data |
|---|---|---|
| 8-9 | 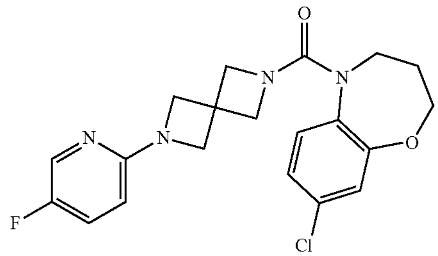 [SMILES: O=C(N1CC2(C1)CN(c1ccc(F)cn1)C2)N1CCCOc2cc(Cl)ccc21] | $^1$H NMR (400 MHz, DMSO) δ 8.01 (d, J = 3.0 Hz, 1H), 7.49-7.43 (m, 1H), 7.26 (q, J = 5.3 Hz, 1H), 7.16 (q, J = 5.4 Hz, 2H), 6.34 (dd, J = 3.6, 9.1 Hz, 1H), 4.09 (s, 2H), 3.90 (s, 4H), 3.66-3.60 (m, 6H), 1.93-1.84 (m, 2H); |
| 8-10 | 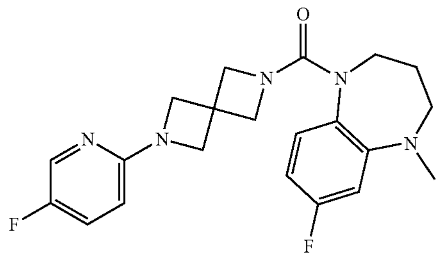 [SMILES: CN1CCCN(C(=O)N2CC3(C2)CN(c2ccc(F)cn2)C3)c2ccc(F)cc21] | $^1$H NMR (400 MHz, DMSO) δ 8.01 (d, J = 3.0 Hz, 1H), 7.49-7.43 (m, 1H), 7.08 (dd, J = 6.5, 8.5 Hz, 1H), 6.76-6.65 (m, 2H), 6.34 (dd, J = 3.4, 9.3 Hz, 1H), 3.86 (s, 4H), 3.50-3.00 (m, 8H), 2.83 (s, 3H), 1.73-1.68 (m, 2H). |
| 8-11 | 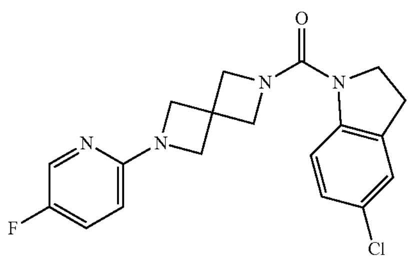 [SMILES: O=C(N1CC2(C1)CN(c1ccc(F)cn1)C2)N1CCc2cc(Cl)ccc21] | $^1$ $^1$H NMR (400 MHz, DMSO) δ 8.06 (d, J = 3.0 Hz, 1H), 7.63 (d, J = 8.5 Hz, 1H), 7.54-7.48 (m, 1H), 7.24 (d, J = 1.9 Hz, 1H), 7.15 (dd, J = 2.3, 8.5 Hz, 1H), 6.45 (dd, J = 3.6, 9.1 Hz, 1H), 4.22 (s, 4H), 4.07 (s, 4H), 3.93 (dd, J = 8.7, 8.7 Hz, 2H), 3.11 (dd, J = 8.7, 8.7 Hz, 2H). |
| 8-12 | 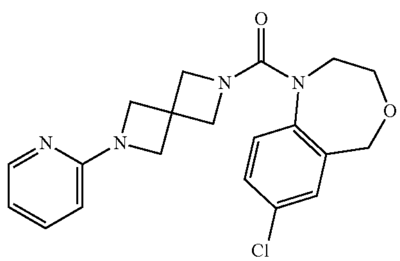 [SMILES: O=C(N1CC2(C1)CN(c1ccccn1)C2)N1CCOCc2cc(Cl)ccc21] | $^1$H NMR (400 MHz, DMSO, 383 K) δ 8.05-8.03 (m, 1H), 7.48-7.42 (m, 2H), 7.40-7.37 (m, 1H), 7.31 (d, J = 8.4 Hz, 1H), 6.59 (dd, J = 5.0, 6.8 Hz, 1H), 6.30 (d, J = 8.4 Hz, 1H), 4.63 (s, 2H), 3.95 (s, 4H), 3.81-3.75 (m, 2H), 3.73 (s, 4H), 3.71-3.64 (m, 2H). |
| 8-13 | 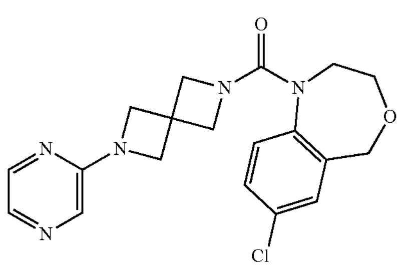 [SMILES: O=C(N1CC2(C1)CN(c1cnccn1)C2)N1CCOCc2cc(Cl)ccc21] | $^1$H NMR (400 MHz, DMSO, 383 K) δ 7.99-7.97 (m, 1H), 7.82-7.78 (m, 2H), 7.43 (d, J = 2.5 Hz, 1H), 7.40-7.37 (m, 1H), 7.31 (d, J = 8.5 Hz, 1H), 4.63 (s, 2H), 4.06 (s, 4H), 3.81-3.77 (m, 2H), 3.74 (s, 4H), 3.69-3.64 (m, 2H). |
| 8-14 | 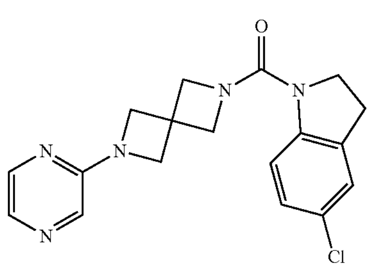 [SMILES: O=C(N1CC2(C1)CN(c1cnccn1)C2)N1CCc2cc(Cl)ccc21] | $^1$H NMR (400 MHz, CDCl$_3$) δ 8.05-8.03 (m, 1H), 7.90 (d, J = 2.8 Hz, 1H), 7.81 (d, J = 1.4 Hz, 1H), 7.61 (d, J = 8.5 Hz, 1H), 7.12-7.11 (m, 2H), 4.28 (s, 4H), 4.25 (s, 4H), 3.94 (t, J = 8.5 Hz, 2H), 3.13 (t, J = 8.5 Hz, 2H). |

TABLE 6-continued

| No. | Structure | Data |
|---|---|---|
| 8-15 | 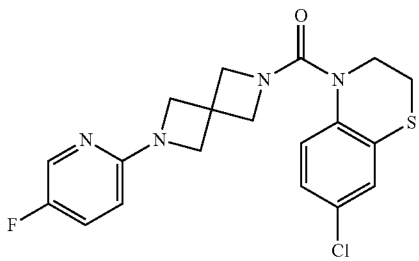 | ¹H NMR (400 MHz, DMSO) δ 8.03 (d, J = 3.0 Hz, 1H), 7.50-7.45 (m, 1H), 7.29 (d, J = 2.4 Hz, 1H), 7.22 (d, J = 8.8 Hz, 1H), 7.13 (dd, J = 2.4, 8.7 Hz, 1H), 6.38 (dd, J = 3.6, 9.1 Hz, 1H), 3.96 (s, 4H), 3.85 (s, 4H), 3.78 (t, J = 5.5 Hz, 2H), 3.21 (t, J = 5.5 Hz, 2H). |
| 8-16 | 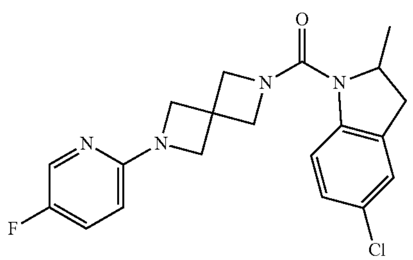 [SMILES: CC1Cc2cc(Cl)ccc2N1C(=O)N1CC2(C1)CN(c1ccc(F)cn1)C2] | ¹H NMR (400 MHz, DMSO, 383 K) δ 8.02 (d, J = 3.0 Hz, 1H), 7.54 (d, J = 8.5 Hz, 1H), 7.42 (dt, J = 3.1, 8.8 Hz, 1H), 7.20-7.20 (m, 1H), 7.14 (dd, J = 1.9, 8.6 Hz, 1H), 6.42 (dd, J = 3.6, 9.0 Hz, 1H), 4.45-4.38 (m, 1H), 4.26-4.15 (m, 4H), 4.10 (s, 4H), 3.33 (dd, J = 9.0, 16.1 Hz, 1H), 2.71-2.64 (m, 1H), 1.25 (d, J = 6.3 Hz, 3H). |
| 8-17 | 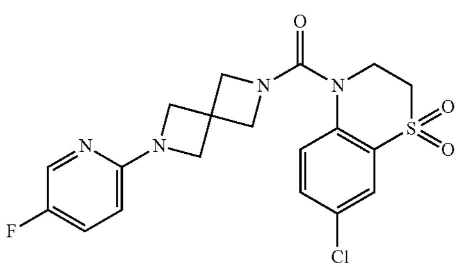 [SMILES: O=C(N1CC2(C1)CN(c1ccc(F)cn1)C2)N1CCS(=O)(=O)c2cc(Cl)ccc21] | ¹H NMR (400 MHz, DMSO) δ 8.05 (d, J = 2.9 Hz, 1H), 7.75 (d, J = 2.4 Hz, 1H), 7.64 (dd, J = 2.5, 9.0 Hz, 1H), 7.52-7.48 (m, 2H), 6.43 (dd, J = 3.6, 9.1 Hz, 1H), 4.17-4.12 (m, 2H), 4.05-4.01 (m, 8H), 3.85-3.80 (m, 2H), 3.60 (s, 2H), 3.47 (s, 1H). |

Example 9

Synthesis of (7-chloro-3-methyl-2,3-dihydro-4H-benzo[b][1,4]oxazin-4-yl)(6-(pyridazin-3-yl)-2,6-diazaspiro[3.3]heptan-2-yl)methanone (Compound No. 9-1)

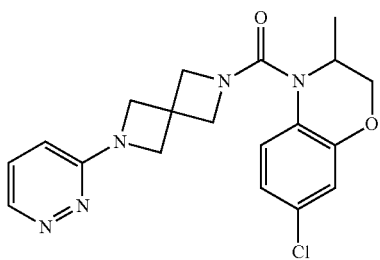

Step 1; tert-butyl 6-(pyridazin-3-yl)-2,6-diazaspiro[3.3]heptane-2-carboxylate

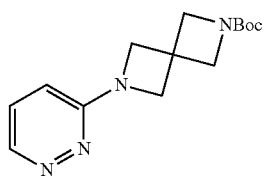 [SMILES: CC(C)(C)OC(=O)N1CC2(C1)CN(c1cccnn1)C2]

A mixture of tert-butyl 2,6-diazaspiro[3.3]heptane-2-carboxylate oxalate (1.0 g, 3.47 mmol, 1.0 eq.), 3-bromopyridazine (730 mg, 4.6 mmol, 1.3 eq.), 2-di-tert-butylphosphino-2',4',6'-triisopropylbiphenyl (150 mg, 0.35 mmol, 0.1 eq.) and sodium tert-butoxide (1.68 g, 17.5 mmol, 5 eq.) in tert-butanol (35 mL) was degassed using nitrogen for 30 minutes and [2-(di-tert-butylphosphino)-2',4',6'-triisopropyl-1,1'-biphenyl][2-(2-aminoethyl)phenyl)]palladium(II) chloride (240 mg, 0.35 mmol. 0.1 eq.) was added. The mixture was heated to 80° C. for 16 hours. The mixture was diluted with EtOAc and filtered through celite. The organic phase was separated, washed with aq. NaCl soln., dried (MgSO₄), filtered and concentrated in vacuo to give a brown oil. The crude material was purified by silica flash column chromatography 0-10% methanol in DCM to give the titled compound as a yellow solid (530 mg, 55% yield). ¹H NMR (400 MHz, CDCl₃) δ 8.61-8.60 (m, 1H), 7.21-7.17 (m, 1H), 6.55-6.52 (m, 1H), 4.25 (s, 4H), 4.13 (s, 4H), 1.45 (s, 9H).

Step 2; 2-(pyridazin-yl)-2,6-diazaspiro[3.3]heptane 2,2,2-trifluoroacetate

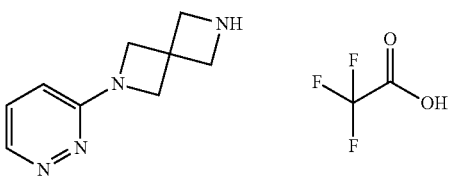 [SMILES: c1cnnc(N2CC3(CNC3)C2)c1 ; O=C(O)C(F)(F)F]

To a solution of tert-butyl 6-(pyridazin-3-yl)-2,6-diazaspiro[3.3]heptane-2-carboxylate (621 mg, 2.25 mmol, 1.0 eq.) in DCM (20 mL) was added TFA (3.0 mL) dropwise. The mixture was stirred at RT for 45 minutes, concentrated in vacuo and the residue was triturated with diethyl ether to afford the titled compound as a yellow solid. (280 mg, 43% yield). m/z 177 (M+H)⁺.

Step 3; (7-chloro-3-methyl-2,3-dihydro-4H-benzo[b][1,4]oxazin-4-yl)(6-(pyridazin-3-yl)-2,6-diazaspiro[3.3]heptan-2-yl)methanone (Compound No. 9-1)

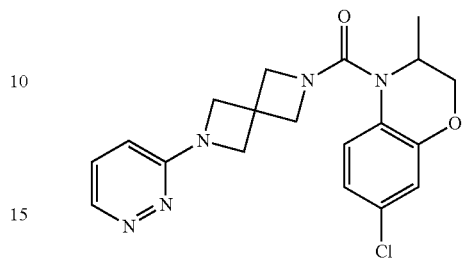

The titled compound was prepared in a similar manner to Example 1 Step 3. (91 mg, 24% yield). ¹H NMR (400 MHz, CDCl₃) δ 8.61-8.59 (m, 1H), 7.23-7.17 (m, 2H), 6.89-6.87 (m, 2H), 6.55-6.52 (m, 1H), 4.51-4.48 (m, 1H), 4.28-4.13 (m, 8H), 4.01 (d, J=9.2 Hz, 1H), 1.22 (d, J=6.8 Hz, 3H). m/z 386 (M+H)⁺.

Compound Nos. 9-2 through 9-9 listed in Table 7 below were prepared according to the methods described in Example 9 using the appropriately substituted or modified intermediates. Compound Nos. 9-10 through 9-32 are similarly prepared according to the methods described in Example 9 using appropriately substituted or modified intermediates.

TABLE 7

| No. | Structure | Data |
|---|---|---|
| 9-2 | 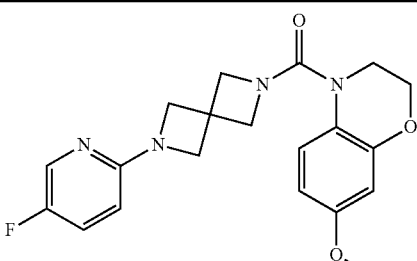 | ¹H NMR (400 MHz, DMSO) δ 8.04 (d, J = 3.0 Hz, 1H), 7.52-7.46 (m, 1H), 7.28 (d, J = 8.9 Hz, 1H), 6.48 (dd, J = 2.9, 9.0 Hz, 1H), 6.43-6.39 (m, 2H), 4.22 (t, J = 4.5 Hz, 2H), 4.03 (d, J = 11.3 Hz, 8H), 3.69 (s, 3H), 3.63 (t, J = 4.5 Hz, 2H). m/z 385 (M + H)⁺. |
| 9-3 | 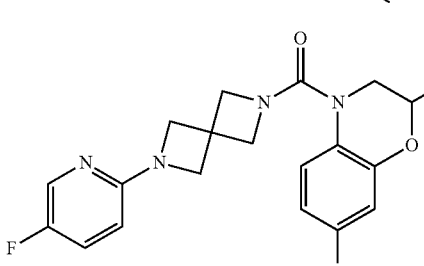 | ¹H NMR (400 MHz, DMSO) δ 8.05 (d, J = 3.0 Hz, 1H), 7.52-7.47 (m, 1H), 7.43-7.40 (m, 1H), 6.92-6.89 (m, 2H), 6.42 (dd, J = 3.5, 9.2 Hz, 1H), 4.32-4.27 (m, 1H), 4.15 (d, J = 9.3 Hz, 2H), 4.05 (d, J = 9.3 Hz, 6H), 3.91 (dd, J = 2.5, 13.2 Hz, 1H), 3.10 (dd, J = 8.0, 13.2 Hz, 1H), 1.30 (d, J = 6.3 Hz, 3H). m/z 403 (M + H)⁺. |
| 9-4 | 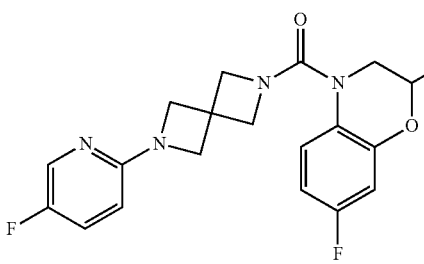 | ¹H NMR (400 MHz, DMSO) δ 8.05 (d, J = 3.0 Hz, 1H), 7.52-7.47 (m, 1H), 7.43-7.38 (m, 1H), 6.74-6.69 (m, 2H), 6.42 (dd, J = 3.5, 9.2 Hz, 1H), 4.32-4.27 (m, 1H), 4.14 (d, J = 9.2 Hz, 2H), 4.05-4.01 (m, 6H), 3.92 (dd, J = 2.5, 13.2 Hz, 1H), 3.09 (dd, J = 8.1, 13.2 Hz, 1H), 1.30 (d, J = 6.3 Hz, 3H). m/z 387 (M + H)⁺. |

TABLE 7-continued

| No. | Structure | Data |
|---|---|---|
| 9-5 | 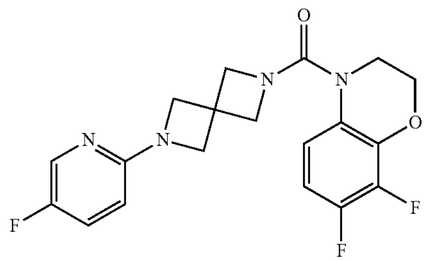 [SMILES: O=C(N1CC2(C1)CN(c1ccc(F)cn1)C2)N1CCOc2c1ccc(F)c2F] | $^1$H NMR (400 MHz, DMSO) δ 8.05 (d, J = 3.0 Hz, 1H), 7.53-7.47 (m, 1H), 7.23 (ddd, J = 2.4, 5.3, 9.5 Hz, 1H), 6.92 (dd, J = 9.8, 18.2 Hz, 1H), 6.43 (dd, J = 3.6, 9.1 Hz, 1H), 4.34 (t, J = 4.4 Hz, 2H), 4.10 (s, 4H), 4.03 (s, 4H), 3.69 (t, J = 4.5 Hz, 2H). m/z 391 (M + H)$^+$. |
| 9-6 | 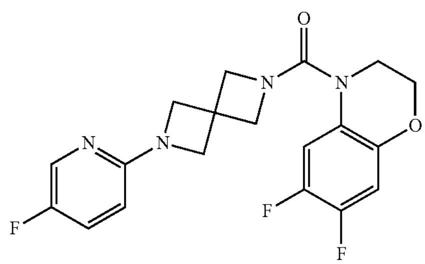 [SMILES: O=C(N1CC2(C1)CN(c1ccc(F)cn1)C2)N1CCOc2cc(F)c(F)cc21] | $^1$H NMR (400 MHz, DMSO) δ 8.05 (d, J = 3.0 Hz, 1H), 7.59-7.47 (m, 2H), 6.99 (dd, J = 7.9, 11.7 Hz, 1H), 6.44 (dd, J = 3.4, 9.2 Hz, 1H), 4.21 (t, J = 4.5 Hz, 2H), 4.15 (s, 4H), 4.05 (s, 4H), 3.64 (t, J = 4.5 Hz, 2H). m/z 391 (M + H)$^+$. |
| 9-7 | 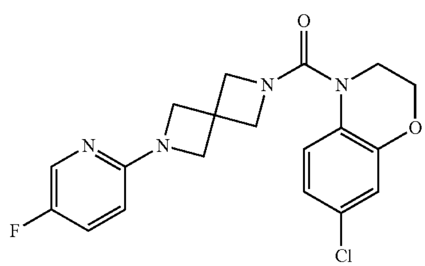 [SMILES: O=C(N1CC2(C1)CN(c1ccc(F)cn1)C2)N1CCOc2cc(Cl)ccc21] | $^1$H NMR (400 MHz, DMSO) δ 8.05 (d, J = 3.0 Hz, 1H), 7.53-7.47 (m, 1H), 7.43 (d, J = 8.7 Hz, 1H), 6.94-6.90 (m, 2H), 6.42 (dd, J = 3.6, 9.1 Hz, 1H), 4.27-4.23 (m, 2H), 4.10 (s, 4H), 4.04 (s, 4H), 3.65 (t, J = 4.5 Hz, 2H). m/z 389 (M + H)$^+$. |
| 9-8 | 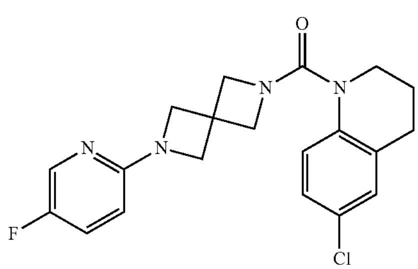 [SMILES: O=C(N1CC2(C1)CN(c1ccc(F)cn1)C2)N1CCCc2cc(Cl)ccc21] | $^1$H NMR (400 MHz, DMSO) δ 8.04 (d, J = 3.0 Hz, 1H), 7.52-7.45 (m, 1H), 7.30 (d, J = 8.5 Hz, 1H), 7.18-7.15 (m, 2H), 6.40 (dd, J = 3.6, 9.1 Hz, 1H), 3.99 (d, J = 13.1 Hz, 8H), 3.52 (dd, J = 6.1, 6.1 Hz, 2H), 2.71 (dd, J = 6.6, 6.6 Hz, 2H), 1.88-1.80 (m, 2H). m/z 387 (M + H)$^+$. |
| 9-9 | 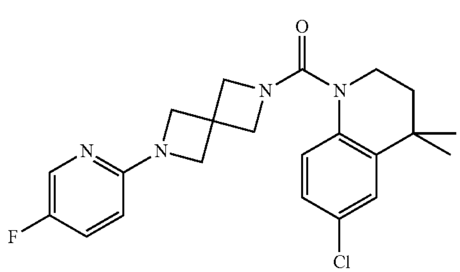 [SMILES: CC1(C)CCN(C(=O)N2CC3(C2)CN(c2ccc(F)cn2)C3)c2ccc(Cl)cc21] | $^1$H NMR (400 MHz, DMSO) δ 8.04 (d, J = 3.0 Hz, 1H), 7.52-7.46 (m, 1H), 7.35 (d, J = 2.4 Hz, 1H), 7.28 (d, J = 8.8 Hz, 1H), 7.16 (dd, J = 2.5, 8.8 Hz, 1H), 6.41 (dd, J = 3.5, 9.2 Hz, 1H), 4.00 (d, J = 8.2 Hz, 8H), 3.54 (dd, J = 6.0, 6.0 Hz, 2H), 1.70 (dd, J = 6.0, 6.0 Hz, 2H), 1.26 (s, 6H). m/z 415 (M + H)$^+$. |

Example 10

Synthesis of (7-chloro-2,3-dihydro-4H-benzo[b][1,4]oxazin-4-yl)(6-(methylsulfonyl)-2,6-diazaspiro[3.3]heptan-2-yl)methanone (Compound No. 10-1)

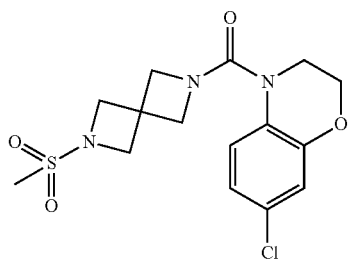 [SMILES: CS(=O)(=O)N1CC2(CN(C(=O)N3CCOc4cc(Cl)ccc43)C2)C1]

To a cooled solution of (7-chloro-2,3-dihydro-4H-benzo[b][1,4]oxazin-4-yl)(2,6-diazaspiro[3.3]heptan-2-yl)methanone 2,2,2-trifluoroacetate (100 mg, 0.25 mmol, 1.0 eq.) (from Step 2, Example 1) in DCM (3 mL) at 0° C. was added Et₃N (75.2 µL, 0.54 mmol, 2.20 eq.) and methanesulfonyl chloride (20.9 µL, 0.27 mmol, 1.10 eq.) and the mixture stirred at 0° C. for 30 minutes. The mixture was diluted with water, filtered, the solid residue was purified by preparative HPLC to afford the titled compound. (62 mg, 68%). ¹H NMR (400 MHz, CDCl₃) δ 7.23 (d, J=8.9 Hz, 1H), 6.89-6.84 (m, 2H), 4.30-4.26 (m, 2H), 4.02 (d, J=6.5 Hz, 8H), 3.77-3.74 (m, 2H), 2.83 (s, 3H). m/z 372 (M+H)⁺.

Compound Nos. 10-2 through 10-8 are similarly prepared according to the methods described in Example 10 using appropriately substituted or modified intermediates.

Example 11

Synthesis of (7-chloro-3-ethyl-2,3-dihydro-4H-benzo[b][1,4]oxazin-4-yl)(6-(pyridin-2-yl)-2,6-diazaspiro[3.3]heptan-2-yl)methanone (Compound No. 11-1)

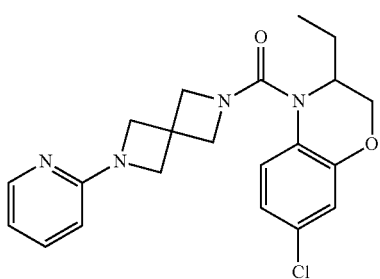 [SMILES: CCC1COc2cc(Cl)ccc2N1C(=O)N1CC2(C1)CN(c1ccccn1)C2]

Step 1; 7-chloro-3-ethyl-2H-benzo[b][1,4]oxazine

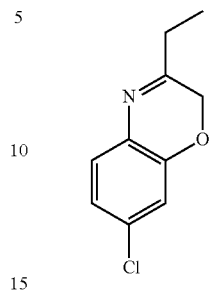

To an ice cooled mixture of 2-amino-5-chlorophenol (200 mg, 1.4 mmol, 1.0 eq.) and potassium carbonate (232 mg, 1.6 mmol, 1.2 eq.) in acetone was added 1-bromobutane-2-one (232 mg, 1.54 mmol, 1.10 eq.), the mixture was then stirred at RT for 3 hours. The mixture was filtered through celite and concentrated in vacuo to give the titled compound as a brown oil (373 mg, 98% yield). ¹H NMR (400 MHz, CDCl₃) δ 7.20 (d, J=8.3 Hz, 1H), 6.93 (dd, J=2.3, 8.3 Hz, 1H), 6.84 (d, J=2.3 Hz, 1H), 4.53 (s, 2H), 2.40 (q, J=7.5 Hz, 2H), 1.26-1.21 (m, 3H).

Step 2; 7-chloro-3-ethyl-3,4-dihydro-2H-benzo[b][1,4]oxazine

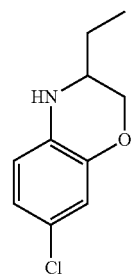

To a solution of 7-chloro-3-ethyl-2H-benzo[b][1,4]oxazine (272 mg, 1.39 mmol, 1.0 eq.) in ethanol (5 mL) was added NaBH₄ (63 mg, 1.67 mmol, 1.2 eq.) and the mixture was stirred at RT for 15 minutes. Water was added and the mixture was extracted with EtOAc (30 mL), the organic phase was dried (MgSO₄), filtered and concentrated in vacuo. The crude material was purified by silica flash column chromatography 20-100% EtOAc in isohexane to afford the titled compound as a clear oil (152 mg, 55% yield). ¹H NMR (400 MHz, CDCl₃) δ 6.77 (d, J=2.4 Hz, 1H), 6.71 (dd, J=2.3, 8.3 Hz, 1H), 6.49 (d, J=8.4 Hz, 1H), 4.21 (dd, J=2.8, 10.5 Hz, 1H), 3.84-3.80 (m, 1H), 3.74 (m, 1H), 3.27 (ddd, J=2.7, 6.9, 13.9 Hz, 1H), 1.56-1.46 (m, 2H), 1.01 (dd, J=7.5, 7.5 Hz, 3H).

Step 3; tert-butyl 6-(7-chloro-3-ethyl-3,4-dihydro-2H-benzo[b][1,4]oxazine-4-carbonyl)-2,6-diazaspiro[3.3]heptane-2-carboxylate

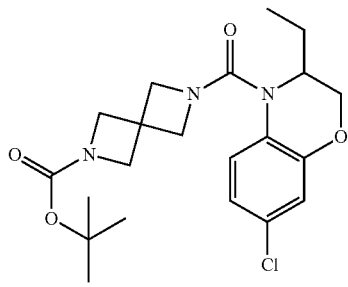 [SMILES: CCC1COc2cc(Cl)ccc2N1C(=O)N1CC2(CN(C(=O)OC(C)(C)C)C2)C1]

The titled compound was prepared in a similar manner to Example 1 Step 3. (389 mg, 91% yield). $^1$H NMR (400 MHz, CDCl$_3$) δ 7.18-7.15 (m, 1H), 6.88-6.85 (m, 2H), 4.33-4.26 (m, 2H), 4.15-4.09 (m, 3H), 4.03-3.95 (m, 4H), 3.80 (d, J=9.5 Hz, 2H), 1.57-1.45 (m, 2H), 1.41 (s, 9H), 0.95 (dd, J=7.5, 7.5 Hz, 3H).

Step 4; (7-chloro-3-ethyl-2,3-dihydro-4H-benzo[b][1,4]oxazin-4-yl)(6-(pyridin-2-yl)-2,6-diazaspiro[3.3]heptan-2-yl)methanone (Compound No. 11-1)

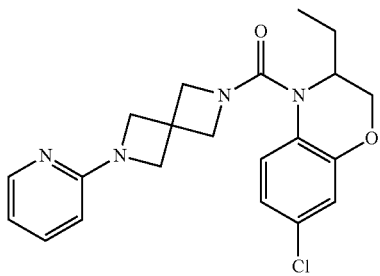 [SMILES: CCC1COc2cc(Cl)ccc2N1C(=O)N1CC2(C1)CN(c1ccccn1)C2]

To a solution of tert-butyl 6-(7-chloro-3-ethyl-3,4-dihydro-2H-benzo[b][1,4]oxazine-4-carbonyl)-2,6-diazaspiro[3.3]heptane-2-carboxylate (389 mg, 0.92 mmol, 0.9 eq.) in DCM (30 mL) was added TFA (3.0 mL) dropwise. The mixture was stirred at RT for 45 minutes, concentrated in vacuo and the residue was used without further purification. The titled compound was prepared in a similar manner to Example 1 Step 3. (59 mg, 47% yield). $^1$H NMR (400 MHz, CDCl$_3$) δ 8.14-8.12 (m, 1H), 7.47-7.41 (m, 1H), 7.21 (d, J=8.7 Hz, 1H), 6.89-6.85 (m, 2H), 6.62 (dd, J=5.3, 7.0 Hz, 1H), 6.26 (d, J=8.4 Hz, 1H), 4.34-4.30 (m, 2H), 4.22-4.19 (d, J=9.5, 2H) 4.14-4.05 (m, 5H), 3.89 (d, J=9.5 Hz, 2H), 1.56-1.47 (m, 2H), 0.96 (dd, J=7.4, 7.4 Hz, 3H). m/z 399 (M+H)$^+$.

Example 12

Synthesis of (7-fluoro-3-methyl-2,3-dihydro-4H-benzo[b][1,4]oxazin-4-yl)(6-(5-fluoropyridin-2-yl)-2,6-diazaspiro[3.3]heptan-2-yl)methanone (Compound No. 12-1)

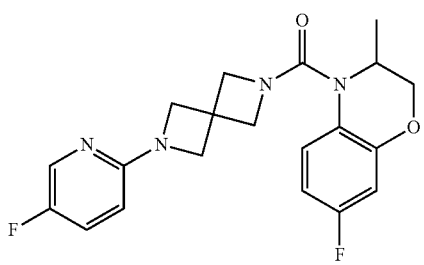

A mixture of 7-fluoro-3-methyl-3,4-dihydro-2H-benzo[b][1,4]oxazine (50 mg, 0.30 mmol, 1.0 eq.) and DIPEA (0.11 mL, 0.66 mmol, 2.2 eq.) in DCM (1.5 mL) was added dropwise to a cooled solution of triphosgene (98 mg, 0.33 mmol, 1.1 eq.) at 0° C. in DCM (1 mL). Mixture was stirred at RT for 3 hours and concentrated in vacuo. The residue, as a solution in DMF (3 mL), was added to a mixture of 2-(5-fluoropyridin-2-yl)-2,6-diazaspiro[3.3]heptane (110 mg, 0.58 mmol, 1.9 eq.) and DIPEA (0.12 mL, 0.632 mmol, 2.10 eq.) in DMF (3 mL) and the mixture was stirred at RT overnight. Water was added and the mixture was extracted with EtOAc (×3), the organic phases were combined, washed with brine, dried (MgSO$_4$), filtered and concentrated in vacuo. The residue was purified by purified by preparative HPLC to afford the titled compound. (62 mg, 28% yield). $^1$H NMR (400 MHz, DMSO) δ 8.05 (d, J=3.0 Hz, 1H), 7.52-7.46 (m, 1H), 7.30-7.25 (m, 1H), 6.76-6.72 (m, 2H), 6.42 (dd, J=3.5, 9.0 Hz, 1H), 4.32 (q, J=6.7 Hz, 1H), 4.18-3.97 (m, 10H), 1.09 (d, J=6.8 Hz, 3H). m/z 387 (M+H)$^+$.

Example 13

Synthesis of (6-chloro-4-hydroxy-3,4-dihydroquinolin-1(2H)-yl)(6-(5-fluoropyridin-2-yl)-2,6-diazaspiro[3.3]heptan-2-yl)methanone (Compound No. 13-1)

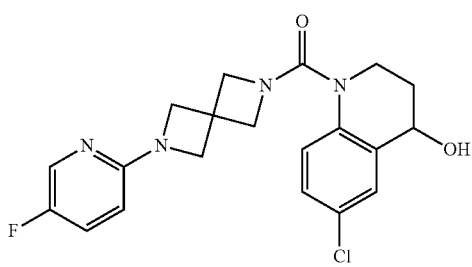 [SMILES: O=C(N1CC2(C1)CN(c1ccc(F)cn1)C2)N1CCC(O)c2cc(Cl)ccc21]

Step 1; 2-benzyl-6-(5-fluoropyridin-2-yl)-2,6-diazaspiro[3.3]heptane

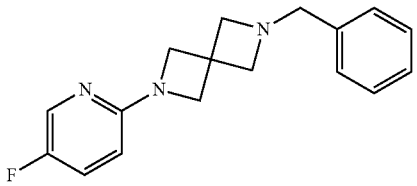 [SMILES: Fc1ccc(N2CC3(CN(Cc4ccccc4)C3)C2)nc1]

To a suspension of 2-benzyl-2,6-diazaspiro[3.3]heptane oxalate (1.0 g, 4.29 mmol, 1.0 eq.), 2-bromo-5-fluoropyridine (0.75 g, 4.29 mmol, 1.0 eq.), RuPhos (0.4 g, 0.857 mmol, 0.2 eq.) and cesium carbonate (4.2 g, 12.9 mmol, 3 eq.) in 1,4-dioxane was degassed using nitrogen for 5 minutes. Pd(OAc)$_2$ (0.096 g, 0.429 mmol, 0.1 eq.) was added and the mixture was heated to 80° C. overnight. Water (50 mL) was added and the mixture was extracted with EtOAc (×3), the combined organic layers were washed with brine, dried (MgSO$_4$), filtered and concentrated in vacuo. The residue was purified by flash column chromatography eluting with 0-5% MeOH in DCM to afford the titled compound as a yellow oil (731 mg, 60% yield). $^1$H NMR (400 MHz, CDCl$_3$) δ 8.00 (d, J=3.0 Hz, 1H), 7.34-7.29 (m, 2H), 7.29-7.25 (m, 3H), 7.25-7.19 (m, 1H), 6.23 (dd, J=3.5, 9.0 Hz, 1H), 4.05 (s, 4H), 3.60 (s, 2H), 3.41 (s, 4H).

Step 2; 2-(5-fluoropyridin-2-yl)-2,6-diazaspiro[3.3]heptane

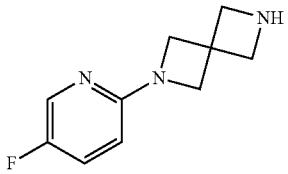 [SMILES: Fc1ccc(N2CC3(CNC3)C2)nc1]

To a solution of 2-benzyl-6-(5-fluoropyridin-2-yl)-2,6-diazaspiro[3.3]heptane (0.731 g, 2.58 mmol, 1.0 eq.) and 1-methyl-1,4-cyclohexadiene (1.45 mL, 12.9 mmol, 5.0 eq.) in ethanol (12 mL) was added 10% palladium on carbon (0.365 g, 50% water) and the mixture was heated to reflux for 3 hours. Additional 1-methyl-1,4-cyclohexadiene (1.45 mL, 12.9 mmol, 5.0 eq.) and 10% palladium on carbon (0.365 g, 50% water) were added and mixture was heated to reflux for 5 hours. The reaction mixture was filtered and concentrated in vacuo to afford the titled compound as a yellow residue. (0.434 g, 87% yield). $^1$H NMR (400 MHz, CDCl$_3$) δ 8.00 (d, J=2.9 Hz, 1H), 7.26-7.20 (m, 1H), 6.25 (dd, J=3.3, 8.9 Hz, 1H), 4.09 (s, 4H), 3.88 (s, 4H).

Step 3; 6-chloro-1-(6-(5-fluoropyridin-2-yl)-2,6-diazaspiro[3.3]heptane-2-carbonyl)-2,3-dihydroquinolin-4(1H)-one

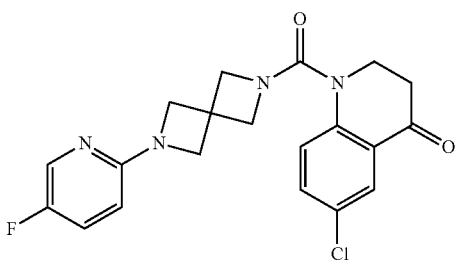

To a cooled mixture of 6-chloro-2,3-dihydroquinolin-4(1H)-one (0.10 g, 0.551 mmol, 1.0 eq.) and DIPEA (0.21 mL, 1.21 mmol, 2.2 eq.) in DCM at 0° C. was added triphosgene (0.18 g, 0.606 mmol, 1.1 eq.) and the mixture was stirred at RT for 3 hours. The reaction mixture was filtered and concentrated in vacuo to give a yellow residue. The residue was added as a solution in DMF (2.5 mL) to a solution of 2-(5-fluoropyridin-2-yl)-2,6-diazaspiro[3.3]heptane (0.21 g, 1.09 mmol, 2.0 eq.) and DIPEA (0.23 mL, 1.3 mmol, 2.4 eq.) in DMF (5 mL) and stirred at RT overnight. Water (50 mL) was added and the mixture was extracted with EtOAc (×3), the combined organic layers were washed with brine, dried (MgSO$_4$), filtered and concentrated in vacuo. The residue was purified by silica flash column chromatography eluting with 0-5% MeOH in DCM to afford the titled compound as a yellow oil (266 mg, 61% yield). $^1$H NMR (400 MHz, CDCl$_3$) δ 8.02-7.99 (m, 1H), 7.93 (d, J=2.6 Hz, 1H), 7.47 (dd, J=2.5, 8.7 Hz, 1H), 7.40 (d, J=8.6 Hz, 1H), 7.25-7.21 (m, 1H), 6.27-6.22 (m, 1H), 4.11-4.08 (m, 8H), 3.14-3.09 (m, 2H), 2.80-2.77 (m, 2H). m/z 401 (M+H)$^+$.

Step 4; 6-chloro-4-hydroxy-3,4-dihydroquinolin-1(2H)-yl)(6-(5-fluoropyridin-2-yl)-2,6-diazaspiro[3.3]heptan-2-yl)methanone (Compound No. 13-1)

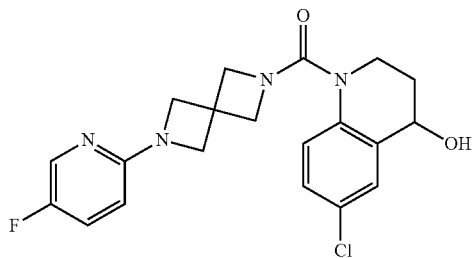 [SMILES: O=C(N1CC2(C1)CN(c1ccc(F)cn1)C2)N1CCC(O)c2cc(Cl)ccc21]

To a cooled solution of 6-chloro-1-(6-(5-fluoropyridin-2-yl)-2,6-diazaspiro[3.3]heptane-2-carbonyl)-2,3-dihydroquinolin-4(1H)-one (0.262 g, 0.664 mmol, 1.0 eq.) in MeOH was added sodium borohydride (0.025 g, 0.664 mmol, 1.0 eq.) and the mixture was stirred at RT for 5 minutes. Sat. NaHCO$_3$ soln. was added and the mixture was extracted EtOAc (×3). The organic phases were combined washed with brine, dried (MgSO$_4$), filtered and concentrated in vacuo. The residue was purified by preparative HPLC to afford the titled compound as a white solid (114 mg, 42% yield). $^1$H NMR (400 MHz, DMSO) δ 8.04 (d, J=3.0 Hz, 1H), 7.52-7.46 (m, 1H), 7.37-7.34 (m, 2H), 7.23 (dd, J=2.5, 8.8 Hz, 1H), 6.41 (dd, J=3.5, 9.0 Hz, 1H), 5.52 (d, J=5.4 Hz, 1H), 4.56 (q, J=5.5 Hz, 1H), 4.05-3.97 (m, 8H), 3.70-3.62 (m, 1H), 3.49-3.41 (m, 1H), 2.06-1.97 (m, 1H), 1.80-1.70 (m, 1H). m/z 403 (M+H)$^+$.

Compound Nos. 13-2 through 13-5 listed in Table 8 below were prepared according to the methods described in Example 13 using the appropriately substituted or modified intermediates. Compound Nos. 13-6 and 13-7 are similarly prepared according to the methods described in Example 13 using appropriately substituted or modified intermediates.

TABLE 8

| No. | Structure | Data |
|---|---|---|
| 13-2 | 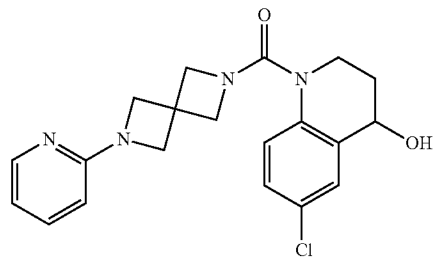 [SMILES: O=C(N1CC2(C1)CN(c1ccccn1)C2)N1CCC(O)c2cc(Cl)ccc21] | ¹H NMR (400 MHz, DMSO) δ 8.05 (dd, J = 1.4, 5.0 Hz, 1H), 7.53-7.47 (m, 1H), 7.37-7.34 (m, 2H), 7.23 (dd, J = 2.6, 8.8 Hz, 1H), 6.63 (dd, J = 5.3, 6.9 Hz, 1H), 6.36 (d, J = 8.4 Hz, 1H), 5.74-5.32 (m, 1H), 4.56 (dd, J = 5.6, 5.6 Hz, 1H), 4.05-3.97 (m, 8H), 3.70-3.61 (m, 1H), 3.50-3.41 (m, 1H), 2.06-1.98 (m, 1H), 1.80-1.70 (m, 1H). m/z 385 (M + H)⁺. |
| 13-3 | 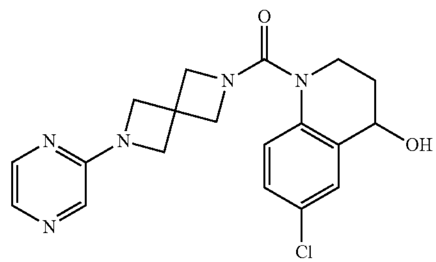 [SMILES: O=C(N1CC2(C1)CN(c1cnccn1)C2)N1CCC(O)c2cc(Cl)ccc21] | ¹H NMR (400 MHz, DMSO) δ 8.03 (dd, J = 1.4, 2.7 Hz, 1H), 7.86-7.83 (m, 2H), 7.37-7.34 (m, 2H), 7.23 (dd, J = 2.6, 8.8 Hz, 1H), 5.52 (d, J = 5.1 Hz, 1H), 4.56 (q, J = 5.1 Hz, 1H), 4.14 (s, 4H), 4.06 (d, J = 9.2 Hz, 2H), 3.98 (d, J = 9.3 Hz, 2H), 3.70-3.62 (m, 1H), 3.49-3.41 (m, 1H), 2.07-1.97 (m, 1H), 1.80-1.70 (m, 1H). m/z 386 (M + H)⁺. |
| 13-4 | 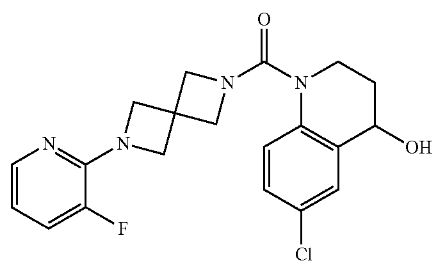 [SMILES: O=C(N1CC2(C1)CN(c1ncccc1F)C2)N1CCC(O)c2cc(Cl)ccc21] | ¹H NMR (400 MHz, DMSO) δ 7.90 (d, J = 4.9 Hz, 1H), 7.42-7.33 (m, 3H), 7.23 (dd, J = 2.6, 8.8 Hz, 1H), 6.72-6.67 (m, 1H), 5.52 (d, J = 5.4 Hz, 1H), 4.55 (q, J = 5.4 Hz, 1H), 4.16 (d, J = 1.8 Hz, 4H), 4.06 (d, J = 9.2 Hz, 2H), 3.97 (d, J = 9.2 Hz, 2H), 3.70-3.62 (m, 1H), 3.49-3.41 (m, 1H), 2.06-1.97 (m, 1H), 1.80-1.70 (m, 1H). m/z 403 (M + H)⁺. |
| 13-5 | 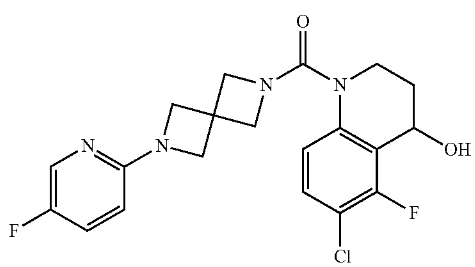 [SMILES: O=C(N1CC2(C1)CN(c1ccc(F)cn1)C2)N1CCC(O)c2c1ccc(Cl)c2F] | ¹H NMR (400 MHz, DMSO) δ 8.10 (d, J = 3.0 Hz, 1H), 7.58-7.51 (m, 1H), 7.42 (dd, J = 8.7, 8.7 Hz, 1H), 7.36-7.32 (m, 1H), 6.47 (dd, J = 3.5, 9.1 Hz, 1H), 5.48 (d, J = 5.3 Hz, 1H), 4.89-4.86 (m, 1H), 4.22 (d, J = 9.1 Hz, 2H), 4.07 (d, J = 11.4 Hz, 6H), 3.87-3.80 (m, 1H), 3.47-3.38 (m, 1H), 2.02-1.95 (m, 1H), 1.87-1.76 (m, 1H). m/z 421 (M + H)⁺. |

Example 14

Synthesis of (6-chloro-4-fluoro-3,4-dihydroquinolin-1(2H)-yl)(6-(5-fluoropyridin-2-yl)-2,6-diazaspiro[3.3]heptan-2-yl)methanone (Compound No. 14-1)

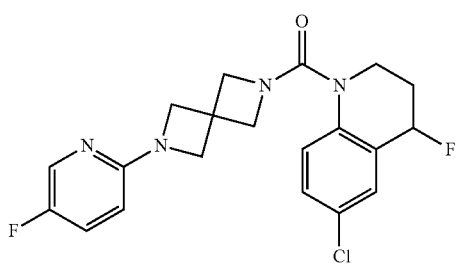

To a cooled solution of 6-chloro-4-hydroxy-3,4-dihydroquinolin-1(2H)-yl)(6-(5-fluoropyridin-2-yl)-2,6-diazaspiro[3.3]heptan-2-yl)methanone (120 mg, 0.3 mmol, 1.0 eq.), in DCM (20 mL) at 0° C. was added Deoxo-Fluor® (50% soln. in THF; 190 μL, 0.4 mmol, 1.33 eq.) over 2 minutes and the mixture was stirred at RT for 3 hours. The reaction mixture was treated with sat. NaHCO₃ soln., extracted with CHCl3 (×3) and the combined organics were concentrated in vacuo. The residue was purified by silica flash column chromatography eluting with 20-80% EtOAc in isohexane to afford the titled compound as a yellow oil. (29 mg, 24% yield). ¹H NMR (400 MHz, CDCl₃) δ 7.99 (d, J=3.0 Hz, 1H), 7.42-7.37 (m, 2H), 7.30-7.21 (m, 2H), 6.22 (dd, J=3.4, 9.0 Hz, 1H), 5.44 (td, J=3.7, 51.3 Hz. 1H), 4.17-3.95 (m, 9H), 3.52-3.45 (m, 1H), 2.40-2.29 (m, 1H), 2.17-1.99 (m, 1H). m/z 405 (M+H)⁺.

Example 15

Synthesis of (6-chloro-4-hydroxy-4-methyl-3,4-dihydroquinolin-1(2H)-yl)(6-(5-fluoropyridin-2-yl)-2,6-diazaspiro[3.3]heptan-2-yl)methanone (Compound No. 15-1)

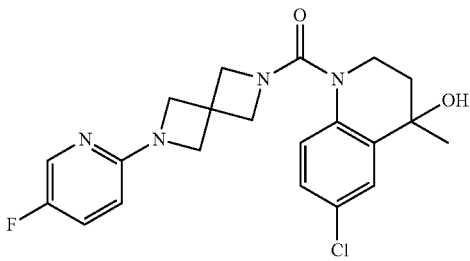 [SMILES: CC1(O)CCN(C(=O)N2CC3(C2)CN(c2ccc(F)cn2)C3)c2ccc(Cl)cc21]

To a cooled solution of 6-chloro-1-(6-(5-fluoropyridin-2-yl)-2,6-diazaspiro[3.3]heptane-2-carbonyl)-2,3-dihydroquinolin-4(1H)-one (120 mg, 0.3 mmol, 1.0 eq.), in THF (3 mL) at −78° C. was added methyl lithium (0.44 mL, 0.7 mmol, 2.3 eq.) and the mixture stirred at −78° C. for 1 hour. Mixture was allowed to warm to 0° C. and treated with sat. NH₄Cl soln., extracted with DCM and the organic phase concentrated in vacuo. The residue was purified by preparative HPLC to afford the titled compound as a white solid. (17.3 mg, 11% yield). $^1$H NMR (400 MHz, CDCl$_3$) δ 7.99 (d, J=2.8 Hz, 1H), 7.50 (d, J=2.5 Hz, 1H), 7.30 (d, J=9.4 Hz, 1H), 7.25-7.17 (m, 2H), 6.22 (dd, J=3.4, 9.0 Hz, 1H), 4.10-4.04 (m, 6H), 3.93 (d, J=9.6 Hz, 2H), 3.83-3.75 (m, 1H), 3.67-3.59 (m, 1H), 2.06-2.00 (m, 2H), 2.00-1.92 (m, 1H), 1.55 (s, 3H). m/z 417 (M+H)⁺.

Example 16

Synthesis of (6-chloro-4-methoxy-3,4-dihydroquinolin-1(2H)-yl)(6-(5-fluoropyridin-2-yl)-2,6-diazaspiro[3.3]heptan-2-yl)methanone (Compound No. 16-1)

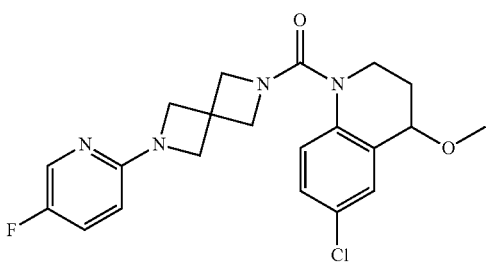 [SMILES: COC1CCN(C(=O)N2CC3(C2)CN(c2ccc(F)cn2)C3)c2ccc(Cl)cc21]

To a cooled solution of 6-chloro-4-hydroxy-3,4-dihydroquinolin-1(2H)-yl)(6-(5-fluoropyridin-2-yl)-2,6-diazaspiro[3.3]heptan-2-yl)methanone (120 mg, 0.3 mmol, 1.0 eq.), in DMF (3 mL) at −0° C. was added sodium hydride (13 mg, 0.33 mmol, 1.1 eq., 60% dispersion in mineral oil) and the mixture stirred at 0° C. for 30 minutes. To the mixture was added iodomethane (51 mg, 0.36 mmol, 1.2 eq.). The mixture was allowed to warm to RT and stirred for 2 hours. The mixture was treated with sat. NH₄Cl soln., extracted with EtOAc and the organic phase concentrated in vacuo. The residue was purified by preparative HPLC to afford the titled compound as an off white solid. (9 mg, 7% yield). $^1$H NMR (400 MHz, CDCl$_3$) δ 7.99 (d, J=3.0 Hz, 1H), 7.34-7.28 (m, 2H), 7.25-7.19 (m, 2H), 6.22 (dd, J=3.4, 9.0 Hz, 1H), 4.21 (dd, J=4.7, 4.7 Hz, 1H), 4.05-3.96 (m, 8H), 3.82-3.74 (m, 1H), 3.66-3.57 (m, 1H), 3.42 (s, 3H), 2.16-1.99 (m, 2H). m/z 417 (M+H)⁺.

Example 17

Synthesis of (6-chloro-4,4-difluoro-3,4-dihydroquinolin-1(2H)-yl)(6-(5-fluoropyridin-2-yl)-2,6-diazaspiro[3.3]heptan-2-yl)methanone (Compound No. 17-1)

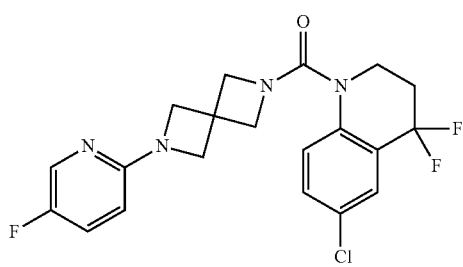 [SMILES: O=C(N1CC2(C1)CN(c1ccc(F)cn1)C2)N1CCC(F)(F)c2cc(Cl)ccc21]

To a cooled solution of 6-chloro-1-(6-(5-fluoropyridin-2-yl)-2,6-diazaspiro[3.3]heptane-2-carbonyl)-2,3-dihydroquinolin-4(1H)-one (120 mg, 0.3 mmol, 1.0 eq.), in DCM (20 mL) at 0° C. was added Deoxo-Fluor® (50% soln. in THF; 380 μL, 0.8 mmol, 2.66 eq.) over 2 minutes and the mixture was stirred at RT for 3 hours. The reaction mixture was treated with sat. NaHCO₃ soln., extracted with CHCl3 (×3) and the combined organics were concentrated in vacuo. The residue was purified by silica flash column chromatography eluting with 20-80% EtOAc in isohexane to afford the titled compound as a yellow oil. (7 mg, 5% yield). $^1$H NMR (400 MHz, CDCl$_3$) δ 8.00 (d, J=2.8 Hz, 1H), 7.61-7.59 (m, 1H), 7.41-7.35 (m, 2H), 7.24-7.20 (m, 1H), 6.23 (dd, J=3.4, 9.0 Hz, 1H), 4.07 (s, 8H), 3.89-3.84 (m, 2H), 2.49-2.37 (m, 2H). m/z 423 (M+H)⁺.

Example 18

Synthesis of (7-fluoro-3-methyl-2,3-dihydro-4H-benzo[b][1,4]oxazin-4-yl)(6-(pyrimidin-2-yl)-2,6-diazaspiro[3.3]heptan-2-yl)methanone (Compound No. 18-1)

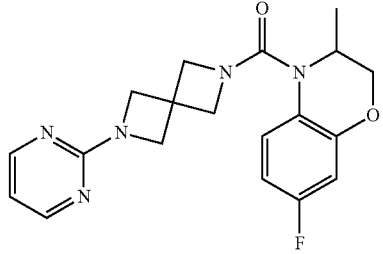 [SMILES: CC1COc2cc(F)ccc2N1C(=O)N1CC2(C1)CN(c1ncccn1)C2]

Step 1: Synthesis of tert-butyl 6-(pyrimidin-2-yl)-2,6-diazaspiro[3.3]heptane-2-carboxylate

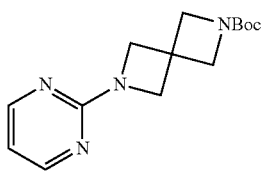 [SMILES: CC(C)(C)OC(=O)N1CC2(C1)CN(c1ncccn1)C2]

A mixture of tert-butyl 2,6-diazaspiro[3.3]heptane-2-carboxylate hemioxalate salt (10.0 g, 3.47 mmol, 1.0 eq.), 2-chloropyrimidine (5.9 g, 52 mmol, 1.5 eq.) in 1,4-dioxane (100 mL) and N,N-dimethylformamide (50 mL) was treated with N,N-diisopropylethylamine (24.2 mL, 138.7 mmol, 4.0 eq.) and the mixture was heated to 100° C. and stirred overnight. The mixture was concentrated in vacuo, the residue was dissolved in DCM (100 mL), washed with saturated aqueous sodium bicarbonate soln. and the aqueous layer was extracted with DCM (2×50 mL). The organics were passed through a phase separator cartridge and concentrated in vacuo. The residue was purified by flash column chromatography eluting with 20-100% EtOAc in isohexane to give the title compound an off-white solid (7.91 g, 55% yield). $^1$H NMR (400 MHz, CDCl$_3$) δ 8.32 (d, J=4.8 Hz, 2H), 6.57 (dd, J=4.8, 4.8 Hz, 1H), 4.24 (s, 4H), 4.12 (s, 4H), 1.45 (s, 9H).

Step 2: Synthesis of 2-(pyrimidin-2-yl)-2,6-diazaspiro[3.3]heptane bis(2,2,2-trifluoroacetate)

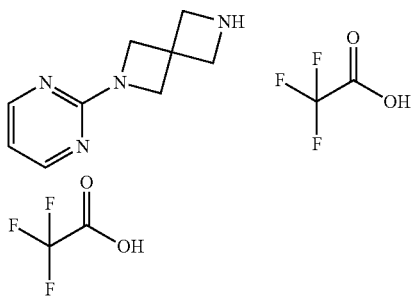

To a solution of tert-butyl 6-(pyrimidin-2-yl)-2,6-diazaspiro[3.3]heptane-2-carboxylate (7.65 g, 27.7 mmol, 1.0 eq.) in DCM (150 mL) was added TFA (63.6 mL, 830.5 mmol, 30 eq.) dropwise. The mixture was stirred at RT for 45 minutes, concentrated in vacuo and the residue was triturated with diethyl ether to afford the titled compound as a white solid. $^1$H NMR (400 MHz, DMSO-d$_6$) δ (9.31 g, 83% yield). 8.64-8.64 (m, 2H), 8.37 (d, J=4.8 Hz, 2H), 6.72 (dd, J=4.8, 4.8 Hz, 1H), 4.21-4.18 (m, 8H).

Step 3: Synthesis of (7-fluoro-3-methyl-2,3-dihydro-4H-benzo[b][1,4]oxazin-4-yl)(6-(pyrimidin-2-yl)-2,6-diazaspiro[3.3]heptan-2-yl)methanone (Compound No. 18-1)

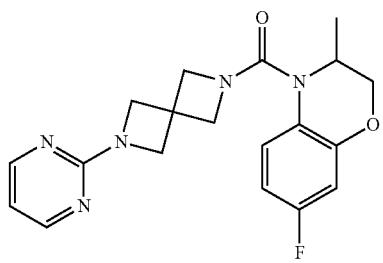

To a cooled solution of triphosgene (34 mg, 0.114 mmol, 0.33 eq.) at 0° C. in DCM (2 mL) was added a solution of 7-fluoro-3-methyl-3,4-dihydro-2H-benzo[b][1,4]oxazine (50 mg, 0.29 mmol, 1.0 eq.) and N,N-diisopropylethylamine (0.057 mL, 0.33 mmol, 1.1 eq.) in DCM (2 mL) dropwise. The reaction mixture was stirred at RT for 4 hours and concentrated in vacuo. To a solution of the residue in N,N-dimethylformamide (2 mL) was added 2-(pyrimidin-2-yl)-2,6-diazaspiro[3.3]heptane bis(2,2,2-trifluoroacetate) (0.12 g, 0.29 mmol, 1.0 eq.) and N,N-diisopropylethylamine (0.18 mL, 1.05 mmol, 3.5 eq.) in DMF (2 mL) and the mixture was stirred at RT overnight. The reaction was quenched with saturated aqueous sodium bicarbonate solution and was partitioned between DCM and water. The aqueous layer was extracted with DCM and the combined organics were dried and concentrated in vacuo. The residue was purified by preparative HPLC to give the title compound as a white solid (65 mg, 26% yield). $^1$H NMR (400 MHz, CDCl$_3$) δ 8.31 (d, J=4.8 Hz, 2H), 7.25-7.22 (m, 1H), 6.67-6.55 (m, 3H), 4.54-4.49 (m, 1H), 4.25-4.18 (m, 8H), 3.92 (d, J=9.4 Hz, 2H), 1.21 (d, J=6.9 Hz, 3H); m/z 370 (M+H)$^+$.

Compound Nos. 18-2 through 18-5 listed in Table 9 below were prepared according to the methods described in Example 18 using the appropriately substituted or modified intermediates.

TABLE 9

| Compound No. | Structure | Data |
|---|---|---|
| 18-2 | 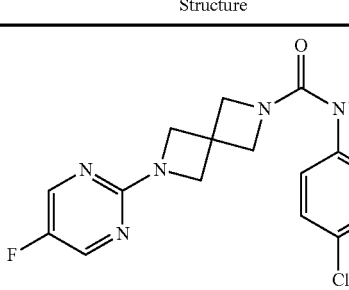 | $^1$H NMR (400 MHz, CDCl$_3$) δ 8.20 (s, 2H), 7.24-7.20 (m, 1H), 6.91-6.87 (m, 2H), 4.49 (q, J = 6.9 Hz, 1H), 4.26-4.15 (m, 8H), 3.92 (d, J = 9.4 Hz, 2H), 1.22 (d, J = 6.9 Hz, 3H). m/z 404 (M + H)$^+$. |

TABLE 9-continued

| Compound No. | Structure | Data |
|---|---|---|
| 18-3 | 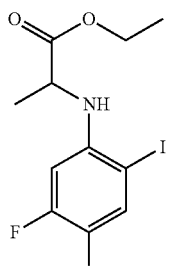 | $^1$H NMR (400 MHz, CDCl$_3$) δ 8.54 (dd, J = 1.1, 4.5 Hz, 1H), 7.71 (dd, J = 1.1, 8.5 Hz, 1H), 7.39 (dd, J = 4.5, 8.5 Hz, 1H), 7.23-7.20 (m, 1H), 6.90-6.86 (m, 2H), 4.51-4.46 (m, 4H), 4.28 (d, J = 9.5 Hz, 2H), 4.22-4.13 (m, 2H), 3.96 (d, J = 9.4 Hz, 2H), 2.01 (s, 1H), 1.22 (d, J = 6.9 Hz, 3H). m/z 426 (M + H)$^+$. |
| 18-4 | 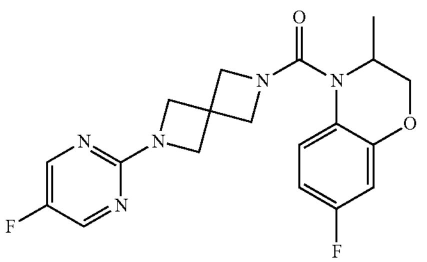 [SMILES: CC1COc2cc(F)ccc2N1C(=O)N1CC2(C1)CN(c1ncc(F)cn1)C2] | Not isolated as the racemate (see Table 13 for data corresponding to Compound Nos. 18-4A and 18-4B) |
| 18-5 | 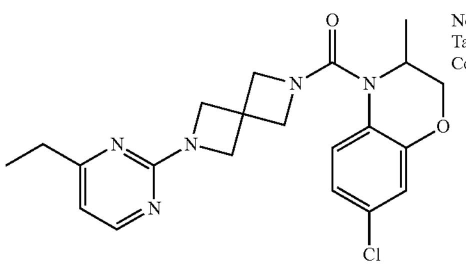 | Not isolated as the racemate (see Table 13 for data corresponding to Compound Nos. 18-5A and 18-5B) |

Example 19

Synthesis of (6,7-difluoro-3-methyl-2,3-dihydro-4H-benzo[b][1,4]oxazin-4-yl)(6-(pyrimidin-2-yl)-2,6-diazaspiro[3.3]heptan-2-yl)methanone (Compound No. 19-1)

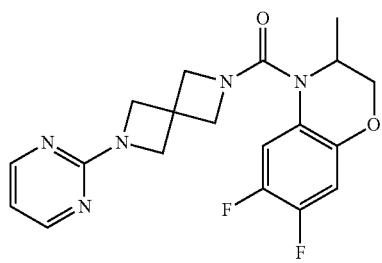 [SMILES: CC1COc2cc(F)c(F)cc2N1C(=O)N1CC2(C1)CN(c1ncccn1)C2]

Step 1: Synthesis of ethyl (4,5-difluoro-2-iodophenyl)alaninate

A solution of ethyl lactate (0.45 mL, 3.92 mmol, 1.0 eq.) and N,N-diisopropylethylamine (0.72 mL, 4.12 mmol, 1.05 eq.) in DCM (6 mL) was treated dropwise with trifluoromethanesulfonic anhydride (0.68 mL, 4.04 mmol, 1.03 eq.) at 0° C. and stirred for 10 minutes. The mixture was added dropwise to a solution of 4,5-difluoro-2-iodoaniline (1.0 g, 3.92 mmol, 1.0 eq.) and N,N-diisopropylethylamine (0.68 mL, 3.92 mmol, 1.0 eq.) in DCM (8 mL) at 0° C. The mixture was heated in a microwave at 120° C. for 30 minutes and was partitioned between water and DCM. The organic layer was dried and concentrated in vacuo. The residue was purified by flash column chromatography eluting with 5-10% EtOAc in isohexane to give the title compound as a yellow oil (0.92 g, 66% yield). $^1$H NMR (400 MHz, CDCl$_3$) 7.49 (dd, J=9.1, 9.1 Hz, 1H), 6.30 (dd, J=6.9, 12.8 Hz, 1H), 4.60 (d, J=6.8 Hz, 1H), 4.22 (q, J=7.2 Hz, 2H), 4.06-3.97 (m, 1H), 1.52 (d, J=6.8 Hz, 3H), 1.28 (t, J=7.2 Hz, 3H);

Step 2: Synthesis of 2-((4,5-difluoro-2-iodophenyl)amino)propan-1-ol

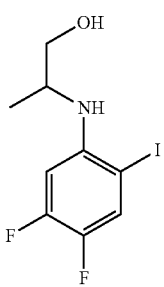

A solution of ethyl (4,5-difluoro-2-iodophenyl)alaninate (0.92 g, 2.60 mmol, 1.0 eq.) in ethanol (12 mL) at 0° C. was treated portion-wise with sodium borohydride (0.29 g, 7.79 mmol, 3.0 eq.) and stirred for 4 hours. The reaction was quenched with ethyl acetate and solid sodium bicarbonate and the mixture was concentrated to low volume. The mixture was partitioned between water and ethyl acetate and the aqueous layer was extracted with ethyl acetate (2×50 mL). The combined organics were dried and concentrated in vacuo to give the title compound as a yellow oil (0.72 g, 88% yield). $^1$H NMR (400 MHz, CDCl$_3$) 7.48 (dd, J=8.6, 9.4 Hz, 1H), 6.48 (dd, J=7.0, 13.1 Hz, 1H), 4.04 (d, J=5.0 Hz, 1H), 3.77-3.70 (m, 1H), 3.63-3.49 (m, 1H), 1.76 (dd, J=5.4, 5.5 Hz, 2H), 1.25 (d, J=6.4 Hz, 3H);

Step 3: Synthesis of 6,7-difluoro-3-methyl-3,4-dihydro-2H-benzo[b][1,4]oxazine

A mixture of 2-((4,5-difluoro-2-iodophenyl)amino)propan-1-ol (0.72 g, 2.30 mmol, 1.0 eq.) and 1,10-phenanthroline (83 mg, 0.46 mmol, 0.20 eq.) in dioxane (10 mL) was degassed by bubbling nitrogen through the solution. To this solution was added sodium tert-butoxide (0.44 g, 4.60 mmol, 2.0 eq.) and copper iodide (44 mg, 0.23 mmol, 0.1 eq.) and the mixture was heated at 100° C. for 50 minutes. The resulting mixture was filtered through celite, concentrated and partitioned between DCM and water. The aqueous layer was extracted with DCM (2×50 mL) and the combined organics were dried and concentrated in vacuo. The residue was purified by flash column chromatography eluting with 0-20% EtOAc in isohexane to give the title compound as a brown solid (0.31 g, 73% yield). (0.53 g, 64% yield). $^1$H NMR (400 MHz, CDCl$_3$) δ 6.61 (dd, J=7.6, 11.2 Hz, 1H), 6.37 (dd, J=7.7, 11.4 Hz, 1H), 4.15 (dd, J=2.8, 10.5 Hz, 1H), 3.71 (dd, J=8.0, 10.5 Hz, 1H), 3.53-3.44 (m, 1H), 1.17 (d, J=6.4 Hz, 3H).

Step 4: Synthesis of (6,7-difluoro-3-methyl-2,3-dihydro-4H-benzo[b][1,4]oxazin-4-yl)(6-(pyrimidin-2-yl)-2,6-diazaspiro[3.3]heptan-2-yl)methanone (Compound No. 19-1)

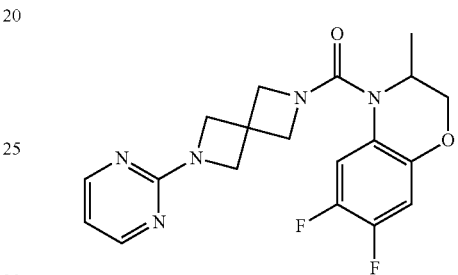

To a cooled solution of triphosgene (22 mg, 0.074 mmol, 0.33 eq.) at 0° C. in DCM (2 mL) was added a solution of 6,7-difluoro-3-methyl-3,4-dihydro-2H-benzo[b][1,4]oxazine (42 mg, 0.226 mmol, 1.0 eq.) and N,N-diisopropylethylamine (0.043 mL, 0.25 mmol, 1.1 eq.) in DCM (2 mL) dropwise. The reaction mixture was stirred at RT for 2 hours and concentrated in vacuo. To the residue in N,N-dimethylformamide (1 mL) was added 2-(pyrimidin-2-yl)-2,6-diazaspiro[3.3]heptane bis(2,2,2-trifluoroacetate) (0.10 g, 0.23 mmol, 1.0 eq.), N,N-diisopropylethylamine (0.137 mL, 0.248 mmol, 1.10 eq.) in DMF (2 mL) and the mixture was stirred at RT overnight. The reaction was quenched with saturated aqueous sodium bicarbonate solution and was partitioned between DCM and water. The aqueous layer was extracted with DCM and the combined organics were dried and concentrated in vacuo. The residue was purified by preparative HPLC to give the title compound as an off-white solid (25 mg, 26% yield). $^1$H NMR (400 MHz, CDCl$_3$) δ 8.31 (d, J=4.9 Hz, 2H), 7.19 (dd, J=8.2, 12.0 Hz, 1H), 6.69 (dd, J=7.5, 11.0 Hz, 1H), 6.57 (dd, J=4.8, 4.8 Hz, 1H), 4.42 (q, J=6.9 Hz, 1H), 4.31-4.21 (m, 6H), 4.18 (dd, J=1.5, 10.7 Hz, 1H), 4.11 (dd, J=2.7, 11.1 Hz, 1H), 3.97 (d, J=9.4 Hz, 2H), 1.22 (d, J=6.9 Hz, 3H); m/z 388 (M+H)$^+$.

Compound Nos. 19-2 through 19-6 listed in Table 10 below were prepared according to the methods described in Example 19 using the appropriately substituted or modified intermediates. Compound Nos. 19-7 through 19-18 are similarly prepared according to the methods described in Example 19 using appropriately substituted or modified intermediates.

TABLE 10

| No. | Structure | Data |
|---|---|---|
| 19-2 | 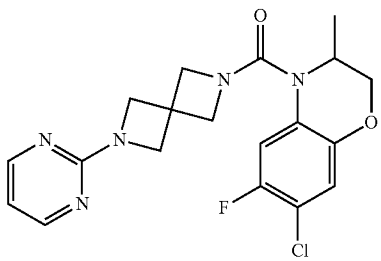 [SMILES: CC1COc2cc(Cl)c(F)cc2N1C(=O)N1CC2(C1)CN(c1ncccn1)C2] | $^1$H NMR (400 MHz, CDCl$_3$) δ 8.31 (d, J = 4.9 Hz, 2H), 7.17 (d, J = 10.7 Hz, 1H), 6.90 (d, J = 7.0 Hz, 1H), 6.58 (dd, J = 4.8, 4.8 Hz, 1H), 4.42 (q, J = 6.8 Hz, 1H), 4.32-4.13 (m, 8H), 3.98 (d, J = 9.4 Hz, 2H), 1.23 (d, J = 6.8 Hz, 3H). m/z 404 (M + H)$^+$. |
| 19-3 | 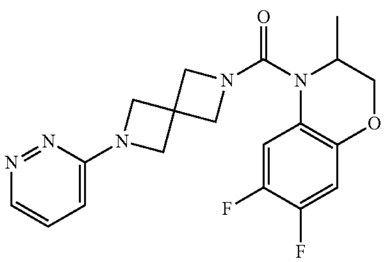 [SMILES: CC1COc2cc(F)c(F)cc2N1C(=O)N1CC2(C1)CN(c1cccnn1)C2] | $^1$H NMR (400 MHz, CDCl$_3$) δ 8.61 (dd, J = 1.3, 4.5 Hz, 1H), 7.22-7.15 (m, 2H), 6.70 (dd, J = 7.5, 11.0 Hz, 1H), 6.53 (dd, J = 1.4, 9.0 Hz, 1H), 4.43 (q, J = 6.9 Hz, 1H), 4.33-4.22 (m, 6H), 4.18 (dd, J = 1.4, 10.8 Hz, 1H), 4.12 (dd, J = 2.7, 11.0 Hz, 1H), 3.99 (d, J = 9.4 Hz, 2H), 1.22 (d, J = 6.9 Hz, 3H). m/z 388 (M + H)$^+$. |
| 19-4 | 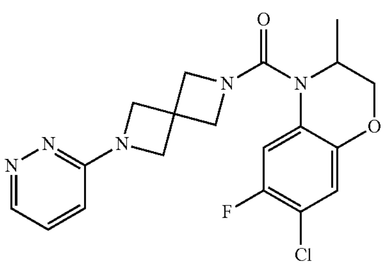 | $^1$H NMR (400 MHz, CDCl$_3$) δ 8.61 (dd, J = 1.3, 4.6 Hz, 1H), 7.20 (dd, J = 4.5, 9.0 Hz, 1H), 7.16 (d, J = 10.7 Hz, 1H), 6.91 (d, J = 7.0 Hz, 1H), 6.53 (dd, J = 1.4, 9.0 Hz, 1H), 4.42 (q, J = 6.9 Hz,1H), 4.32 (d, J = 9.5 Hz, 2H), 4.26 (dd, J = 8.9, 15.0 Hz, 4H), 4.19 (dd, J = 1.5, 10.8 Hz, 1H), 4.12 (dd, J = 2.4, 10.9 Hz, 1H), 3.99 (d, J = 9.5 Hz, 2H), 1.24 (d, J = 6.8 Hz, 3H). m/z 404 (M + H)$^+$. |
| 19-5 | 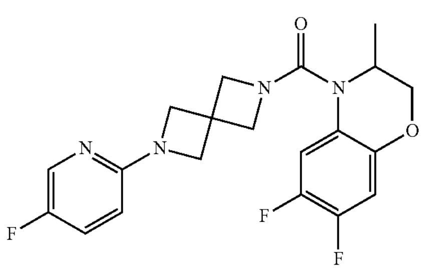 [SMILES: CC1COc2cc(F)c(F)cc2N1C(=O)N1CC2(C1)CN(c1ccc(F)cn1)C2] | $^1$H NMR (400 MHz, CDCl$_3$) δ 8.00 (d, J = 2.9 Hz, 1H), 7.24-7.15 (m, 2H), 6.69 (dd, J = 7.5, 11.0 Hz, 1H), 6.25 (dd, J = 3.3, 8.8 Hz, 1H), 4.45-4.40 (m, 1H), 4.27 (d, J = 9.4 Hz, 2H), 4.18 (dd, J = 1.5, 10.8 Hz, 1H), 4.13-4.06 (m, 5H), 3.95 (d, J = 9.5 Hz, 2H), 1.22 (d, J = 6.8 Hz, 3H). m/z 405 (M + H)$^+$. |
| 19-6 | 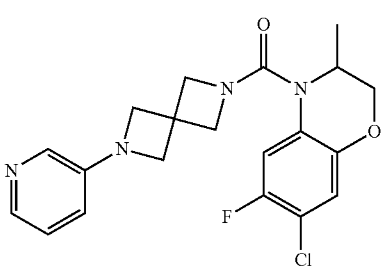 | $^1$H NMR (400 MHz, CDCl$_3$) δ 8.05-8.03 (m, 1H), 7.85 (d, J = 2.6 Hz, 1H), 7.15 (d, J = 10.6 Hz, 1H), 7.11 (ddd, J = 0.6, 4.7, 8.2 Hz, 1H), 6.91 (d, J = 7.2 Hz, 1H), 6.72 (ddd, J = 1.3, 2.8, 8.3 Hz, 1H), 4.43-4.39 (m, 1H), 4.30 (d, J = 9.4 Hz, 2H), 4.18 (dd, J = 1.4, 10.7 Hz, 1H), 4.11 (dd, J = 2.6, 10.9 Hz, 1H), 4.03 (dd, J = 7.7, 14.8 Hz, 4H), 3.97 (d, J = 9.7 Hz, 2H), 1.23 (d, J = 6.8 Hz, 3H). m/z 403 (M + H)$^+$. |

Example 20

Synthesis of (7-chloro-3-methyl-2,3-dihydro-4H-benzo[b][1,4]oxazin-4-yl)(6-(pyridin-3-yl)-2,6-diazaspiro[3.3]heptan-2-yl)methanone (Compound No. 20-1)

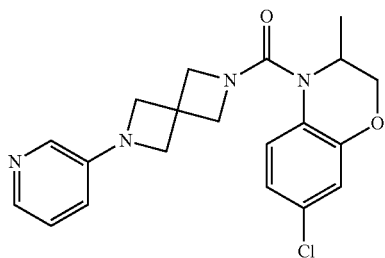

Step 1: Synthesis of tert-butyl 6-(pyridin-3-yl)-2,6-diazaspiro[3.3]heptane-2-carboxylate

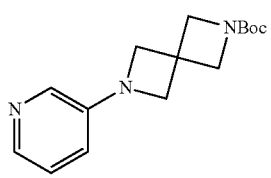

A mixture of tert-butyl 2,6-diazaspiro[3.3]heptane-2-carboxylate oxalate (1.0 g, 3.47 mmol, 1.0 eq.), 3-bromopyridine (0.66 g, 4.16 mmol, 1.2 eq.), RuPhos (0.32 g, 0.69 mmol, 0.2 eq.) and cesium carbonate (3.39 g, 10.41 mmol, 3.0 eq.) in 1,4-dioxane (18 mL) was degassed using nitrogen for 30 minutes. Palladium acetate (78 mg, 0.34 mmol, 0.1 eq.) was added and the mixture was heated to 80° C. overnight. The mixture partitioned between water and DCM and the organics were dried and concentrated in vacuo. The residue was purified by flash column chromatography eluting with 0-100% EtOAc in isohexane to give the title compound as an off-white solid (0.43 g, 46% yield). $^1$H NMR (400 MHz, CDCl$_3$) δ 8.04 (d, J=3.5 Hz, 1H), 7.87 (d, J=2.8 Hz, 1H), 7.11 (dd, J=4.7, 8.2 Hz, 1H), 6.74-6.72 (m, 1H), 4.11 (s, 4H), 4.02 (s, 4H), 1.45 (s, 9H).

Step 2: Synthesis of 2-(pyridin-3-yl)-2,6-diazaspiro[3.3]heptane 2,2,2-trifluoroacetate

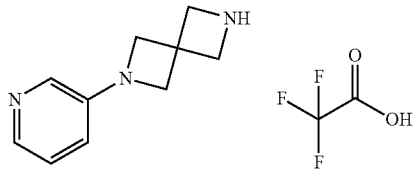 [SMILES: c1cncc(N2CC3(CNC3)C2)c1 ; O=C(O)C(F)(F)F]

To a solution of tert-butyl 6-(pyridin-3-yl)-2,6-diazaspiro[3.3]heptane-2-carboxylate (0.20 g, 0.73 mmol, 1.0 eq.) in DCM (4 mL) was added TFA (2.0 mL, 26.15 mmol, 36 eq.) dropwise. The mixture was stirred at RT for 30 minutes, concentrated in vacuo and the residue was triturated with diethyl ether to afford the titled compound as a white solid. (0.283 g, 97% yield). $^1$H NMR (400 MHz, DMSO-d$_6$) δ 8.73-8.73 (m, 2H), 8.14 (d, J=5.3 Hz, 1H), 8.09-8.06 (m, 1H), 7.72-7.67 (m, 1H), 7.47 (d, J=8.4 Hz, 1H), 4.18 (s, 8H).

Step 3: Synthesis of (7-chloro-3-methyl-2,3-dihydro-4H-benzo[b][1,4]oxazin-4-yl)(6-(pyridin-3-yl)-2,6-diazaspiro[3.3]heptan-2-yl)methanone (Compound No. 20-1)

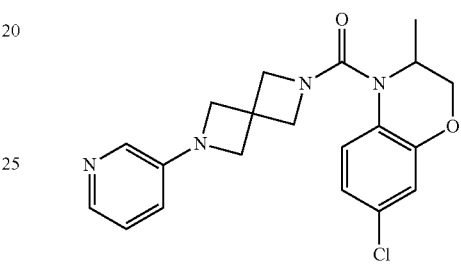

To a cooled solution of triphosgene (31 mg, 0.103 mmol, 0.38 eq.) at 0° C. in DCM (2 mL) was added a solution of 7-chloro-3-methyl-3,4-dihydro-2H-benzo[b][1,4]oxazine (50 mg, 0.27 mmol, 1.0 eq.) and N,N-diisopropylethylamine (0.052 mL, 0.3 mmol, 1.1 eq.) in DCM (2 mL) dropwise. The reaction mixture was stirred at RT for 2 hours and concentrated in vacuo. To the residue in N,N-dimethylformamide (2 mL) was added 2-(pyridin-3-yl)-2,6-diazaspiro[3.3]heptane 2,2,2-trifluoroacetate (110 mg, 0.27 mmol, 1.0 eq.), N,N-diisopropylethylamine (0.17 mL, 0.95 mmol, 3.5 eq.) in DMF (2 mL) and the mixture was stirred at RT overnight. The reaction was quenched with saturated aqueous sodium bicarbonate solution and was partitioned between DCM and water. The aqueous layer was extracted with DCM and the combined organics were dried and concentrated in vacuo. The residue was purified by preparative HPLC to give the title compound as a white solid (65 mg, 62% yield). $^1$H NMR (400 MHz, CDCl$_3$) δ 8.04 (d, J=3.8 Hz, 1H), 7.86 (d, J=2.6 Hz, 1H), 7.22-7.15 (m, 2H), 6.90-6.86 (m, 2H), 6.78 (dd, J=1.5, 8.3 Hz, 1H), 4.52-4.46 (m, 1H), 4.25 (d, J=9.5 Hz, 2H), 4.20 (dd, J=1.5, 10.8 Hz, 1H), 4.15 (dd, J=2.7, 10.9 Hz, 1H), 4.06-4.00 (m, 4H), 3.93 (d, J=9.5 Hz, 2H), 1.22 (d, J=6.9 Hz, 3H); m/z 385 (M+H)$^+$.

Compound Nos. 20-2 through 20-16 listed in Table 11 below were prepared according to the methods described in Example 20 using the appropriately substituted or modified intermediates.

TABLE 11

| No. | Structure | Data |
|---|---|---|
| 20-2 | 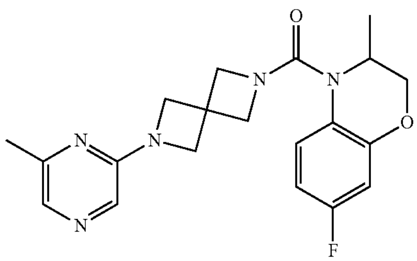 [SMILES: Cc1cncc(N2CC3(CN(C(=O)N4c5ccc(F)cc5OCC4C)C3)C2)n1] | ¹H NMR (400 MHz, CDCl₃) δ 7.76 (s, 1H), 7.56 (s, 1H), 7.23 (dd, J = 5.7, 9.1 Hz, 1H), 6.67-6.57 (m, 2H), 4.54-4.49 (m, 1H), 4.25-4.10 (m, 8H), 3.91 (d, J = 9.3 Hz, 2H), 2.36 (s, 3H), 1.21 (d, J = 6.8 Hz, 3H). m/z 384 (M + H)⁺. |
| 20-3 | 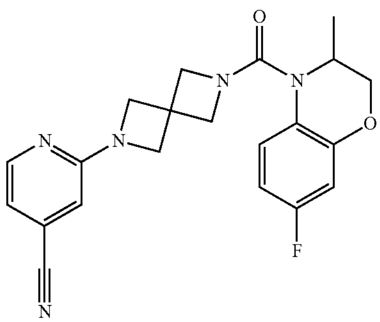 [SMILES: CC1COc2cc(F)ccc2N1C(=O)N1CC2(C1)CN(c1cc(C#N)ccn1)C2] | ¹H NMR (400 MHz, CDCl₃) δ 8.23 (d, J = 5.1 Hz, 1H), 7.25-7.22 (m, 1H), 6.77 (dd, J = 1.3, 5.1 Hz, 1H), 6.67-6.59 (m, 2H), 6.42 (s, 1H), 4.55-4.49 (m, 1H), 4.26-4.11 (m, 8H), 3.92 (d, J = 9.5 Hz, 2H), 1.21 (d, J = 6.8 Hz, 3H). m/z 394 (M + H)⁺. |
| 20-4 | 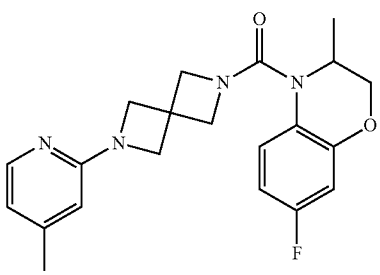 | ¹H NMR (400 MHz, CDCl₃) δ 7.99 (d, J = 5.3 Hz, 1H), 7.25-7.22 (m, 1H), 6.67-6.58 (m, 2H), 6.47 (d, J = 4.9 Hz, 1H), 6.08 (s, 1H), 4.54-4.48 (m, 1H), 4.24-4.16 (m, 4H), 4.12-4.04 (m, 4H), 3.90 (d, J = 9.4 Hz, 2H), 2.24 (s, 3H), 1.21 (d, J = 6.9 Hz, 3H). m/z 383 (M + H)⁺. |
| 20-5 | 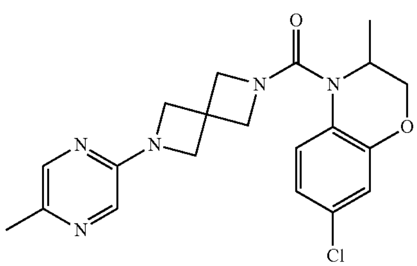 [SMILES: Cc1cnc(N2CC3(CN(C(=O)N4c5ccc(Cl)cc5OCC4C)C3)C2)cn1] | ¹H NMR (400 MHz, CDCl₃) δ 7.90 (s, 1H), 7.70 (d, J = 1.5 Hz, 1H), 7.23-7.20 (m, 1H), 6.90-6.86 (m, 2H), 4.49 (q, J = 6.9 Hz, 1H), 4.25 (d, J = 9.5 Hz, 2H), 4.20 (dd, J = 1.5, 10.8 Hz, 1H), 4.17-4.10 (m, 5H), 3.93 (d, J = 9.5 Hz, 2H), 2.40 (s, 3H), 1.22 (d, J = 6.9 Hz, 3H). m/z 400 (M + H)⁺. |
| 20-6 | 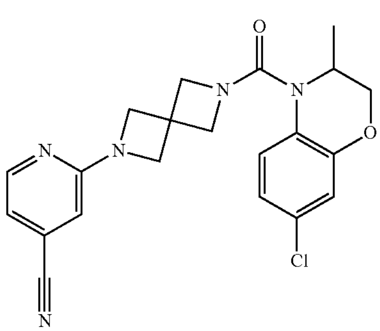 [SMILES: CC1COc2cc(Cl)ccc2N1C(=O)N1CC2(C1)CN(c1cc(C#N)ccn1)C2] | ¹H NMR (400 MHz, CDCl₃) δ 8.23 (d, J = 5.4 Hz, 1H), 7.22 (d, J = 9.3 Hz, 1H), 6.90-6.87 (m, 2H), 6.78 (dd, J = 1.2, 5.1 Hz, 1H), 6.42 (s, 1H), 4.53-4.47 (m, 1H), 4.26 (d, J = 9.4 Hz, 2H), 4.20 (dd, J = 1.4, 10.8 Hz, 1H), 4.18-4.11 (m, 5H), 3.93 (d, J = 9.7 Hz, 2H), 1.22 (d, J = 6.9 Hz, 3H). m/z 410 (M + H)⁺. |

TABLE 11-continued

| No. | Structure | Data |
|---|---|---|
| 20-7 | 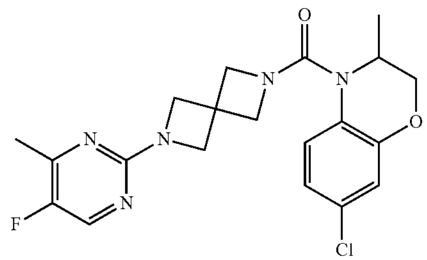 [SMILES: Cc1nc(N2CC3(CN(C(=O)N4c5ccc(Cl)cc5OCC4C)C3)C2)ncc1F] | $^1$H NMR (400 MHz, CDCl$_3$) δ 8.04 (d, J = 1.8 Hz, 1H), 7.23-7.20 (m, 1H), 6.89-6.86 (m, 2H), 4.51-4.46 (m, 1H), 4.24-4.13 (m, 8H), 3.90 (d, J = 9.4 Hz, 2H), 2.35 (d, J = 2.5 Hz, 3H), 1.21 (d, J = 6.8 Hz, 3H). m/z 418 (M + H)$^+$. |
| 20-8 | 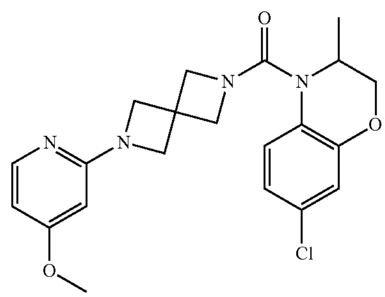 | $^1$H NMR (400 MHz, CDCl$_3$) δ 7.96 (d, J = 5.9 Hz, 1H), 7.23-7.20 (m, 1H), 6.89-6.86 (m, 2H), 6.25 (dd, J = 2.3, 5.9 Hz, 1H), 5.70 (d, J = 2.1 Hz, 1H), 4.51-4.45 (m, 1H), 4.23 (d, J = 9.3 Hz, 2H), 4.19 (dd, J = 1.9, 10.6 Hz, 1H), 4.15 (dd, J = 2.8, 10.9 Hz, 1H), 4.08 (q, J = 7.9 Hz, 4H), 3.91 (d, J = 9.5 Hz, 2H), 3.79 (s, 3H), 1.22 (d, J = 6.9 Hz, 3H. m/z 415 (M + H)$^+$. |
| 20-9 | 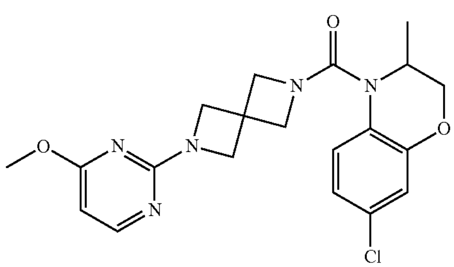 | $^1$H NMR (400 MHz, DMSO-d$_6$) δ 8.06 (d, J = 5.6 Hz, 1H), 7.28 (d, J = 8.5 Hz, 1H), 6.94 (d, J = 8.0 Hz, 2H), 6.12 (d, J = 5.6 Hz, 1H), 4.34-4.29 (m, 1H), 4.20-4.14 (m, 8H), 4.01 (d, J = 9.2 Hz, 2H), 3.83 (s, 3H), 1.11 (d, J = 6.9 Hz, 3H). m/z 416 (M + H)$^+$. |
| 20-10 | 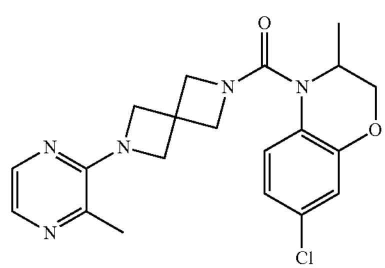 | $^1$H NMR (400 MHz, DMSO-d$_6$) δ 7.94 (d, J = 2.6 Hz, 1H), 7.79 (d, J = 2.8 Hz, 1H), 7.28 (d, J = 8.7 Hz, 1H), 6.94 (d, J = 8.3 Hz, 2H), 4.33 (q, J = 6.7 Hz, 1H), 4.25-4.15 (m, 8H), 4.00 (d, J = 9.0 Hz, 2H), 2.36 (s, 3H), 1.11 (d, J = 6.8 Hz, 3H). m/z 400 (M + H)$^+$. |
| 20-11 | 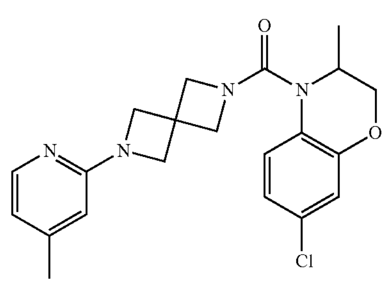 | $^1$H NMR (400 MHz, DMSO-d$_6$) δ 7.92 (d, J = 5.1 Hz, 1H), 7.29 (d, J = 8.8 Hz, 1H), 6.94 (d, J = 8.0 Hz, 2H), 6.49 (d, J = 4.9 Hz, 1H), 6.20 (s, 1H), 4.32 (q, J = 6.8 Hz, 1H), 4.23-4.16 (m, 3H), 4.11 (dd, J = 2.6, 11.0 Hz, 1H), 4.03-3.99 (m, 6H), 2.20 (s, 3H), 1.11 (d, J = 6.8 Hz, 3H). m/z 399 (M + H)$^+$. |

TABLE 11-continued

| No. | Structure | Data |
|---|---|---|
| 20-12 | 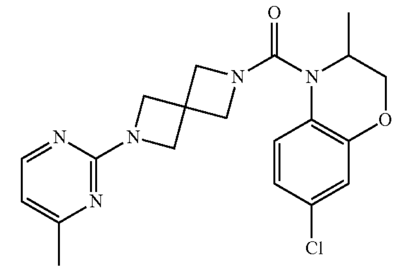 [SMILES: Cc1ccnc(N2CC3(CN(C(=O)N4c5ccc(Cl)cc5OCC4C)C3)C2)n1] | $^1$H NMR (400 MHz, DMSO-d$_6$) δ 8.23 (d, J = 5.1 Hz, 1H), 7.32 (d, J = 8.6 Hz, 1H), 6.98 (d, J = 8.1 Hz, 2H), 6.61 (d, J = 5.1 Hz, 1H), 4.39-4.32 (m, 1H), 4.25-4.16 (m, 8H), 4.05 (d, J = 9.1 Hz, 2H), 2.31 (s, 3H), 1.15 (d, J = 6.6 Hz, 3H). m/z 400 (M + H)$^+$. |
| 20-13 | 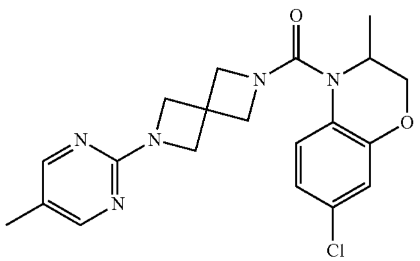 [SMILES: Cc1cnc(N2CC3(CN(C(=O)N4c5ccc(Cl)cc5OCC4C)C3)C2)nc1] | $^1$H NMR (400 MHz, DMSO-d$_6$) δ 8.25 (s, 2H), 7.32 (d, J = 9.1 Hz, 1H), 6.98 (d, J = 7.8 Hz, 2H), 4.36 (d, J = 6.8 Hz, 1H), 4.29-4.12 (m, 8H), 4.05 (d, J = 9.1 Hz, 2H), 2.13 (s, 3H), 1.15 (d, J = 6.6 Hz, 3H). m/z 400 (M + H)$^+$. |
| 20-14 | 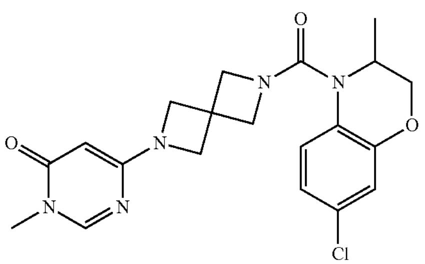 [SMILES: CC1COc2cc(Cl)ccc2N1C(=O)N1CC2(C1)CN(c1cc(=O)n(C)cn1)C2] | $^1$H NMR (400 MHz, DMSO-d$_6$) δ 8.20 (s, 1H), 7.31 (d, J = 8.3 Hz, 1H), 6.98 (d, J = 8.6 Hz, 2H), 4.96 (s, 1H), 4.35 (d, J = 7.1 Hz, 1H), 4.25-4.00 (m, 10H), 3.31 (s, 3H), 1.14 (d, J = 6.8 Hz, 3H). m/z 416 (M + H)$^+$. |
| 20-15 | 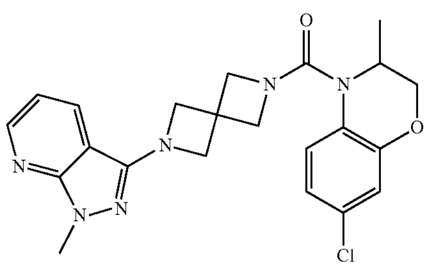 [SMILES: CC1COc2cc(Cl)ccc2N1C(=O)N1CC2(C1)CN(c1nn(C)c3ncccc13)C2] | Not isolated as the racemate (see Table 13 for data corresponding to Compound Nos. 20-15-A and 20-15B) |
| 20-16 | 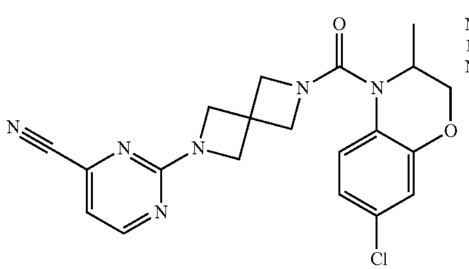 | Not isolated as the racemate (see Table 13 for data corresponding to Compound Nos. 20-16-A and 20-16-B) |

Example 21

Synthesis of (6-(benzo[d]isoxazol-3-yl)-2,6-diazaspiro[3.3]heptan-2-yl)(7-chloro-3-methyl-2,3-dihydro-4H-benzo[b][1,4]oxazin-4-yl)methanone (Compound No. 21-1)

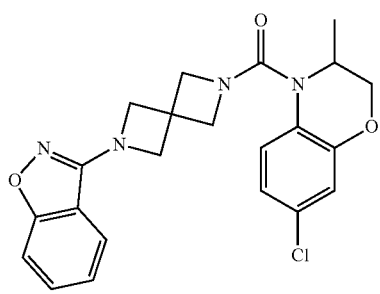

Step 1: Synthesis of ethyl (4-chloro-2-iodophenyl)alaninate

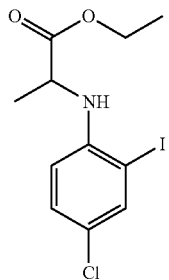 [SMILES: CCOC(=O)C(C)Nc1ccc(Cl)cc1I]

A mixture of ethyl-2-hydroxypropanoate (0.99 mL, 8.73 mmol, 1.0 eq.) and N,N-diisopropylethylamine (1.59 mL, 9.2 mmol, 1.05 eq.) in DCM (6 mL) was treated dropwise with trifluoromethanesulfonic anhydride (1.51 mL, 8.99 mmol, 1.03 eq.) at 0° C. and stirred for 10 minutes. This solution was added dropwise to a solution of 4-chloro-2-iodoaniline (2.21 g, 8.73 mmol, 1.0 eq.) and N,N-diisopropylethylamine (1.52 mL, 8.73 mmol, 1.0 eq.) in DCM (20 mL) at 0° C. and stirred overnight. The mixture partitioned between saturated aqueous sodium bicarbonate soln. and DCM and the organics were dried and concentrated in vacuo. The residue was purified by flash column chromatography eluting with 0-20% EtOAc in isohexane to give the title compound as a yellow oil (1.74 g, 56% yield). $^1$H NMR (400 MHz, CDCl$_3$) δ 7.65 (d, J=2.4 Hz, 1H), 7.15 (dd, J=2.4, 8.7 Hz, 1H), 6.39 (d, J=8.9 Hz, 1H), 4.69-4.69 (m, 1H), 4.21 (q, J=7.1 Hz, 2H), 4.09 (q, J=6.6 Hz, 1H), 1.52 (d, J=6.9 Hz, 3H), 1.27 (dd, J=7.1, 7.1 Hz, 3H).

Step 2: Synthesis of 2-((4-chloro-2-iodophenyl)amino)propan-1-ol

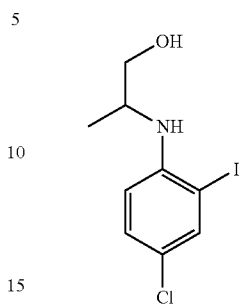

A solution of ethyl (4-chloro-2-iodophenyl)alaninate (1.74 g, 4.92 mmol, 1.0 eq.) in Ethanol (25 mL) at 0° C. was treated portion-wise with sodium borohydride (0.56 g, 14.76 mmol, 3.0 eq.) and stirred for 5 hours. The reaction was quenched with ethyl acetate and solid sodium bicarbonate and the mixture was concentrated to low volume. The mixture was partitioned between water and ethyl acetate and the aqueous layer was extracted with ethyl acetate (2×50 mL). The organics were dried, concentrated and the residue was purified by flash column chromatography eluting with 0-20% EtOAc in isohexane to give the title compound as a yellow oil (1.4 g, 56% yield). $^1$H NMR (400 MHz, CDCl$_3$) δ 7.64 (d, J=2.4 Hz, 1H), 7.17 (dd, J=2.4, 8.7 Hz, 1H), 6.57 (d, J=8.8 Hz, 1H), 4.15-4.06 (m, 1H), 3.75-3.56 (m, 3H), 1.82 (dd, J=4.7, 6.8 Hz, 1H), 1.28-1.23 (m, 3H).

Step 3: Synthesis of 7-chloro-3-methyl-3,4-dihydro-2H-benzo[b][1,4]oxazine

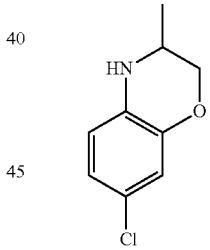

A mixture of 2-((4-chloro-2-iodophenyl)amino)propan-1-ol (1.4 g, 4.49 mmol, 1.0 eq.) and 1,10-phenanthroline (0.16 g, 0.89 mmol, 0.20 eq.) in dioxane (15 mL) was degassed by bubbling nitrogen through the solution. To this solution was added sodium tert-butoxide (0.86 g, 8.99 mmol, 2.0 eq.) and copper iodide (86 mg, 0.45 mmol, 0.1 eq.) and the mixture was heated at 100° C. for 20 minutes. The resulting mixture was filtered through celite, concentrated and partitioned between DCM and water. The aqueous layer was extracted with DCM (2×50 mL) and the combined organics were dried and concentrated in vacuo. The residue was purified by flash column chromatography eluting with 10-20% EtOAc in isohexane. The fractions were concentrated in vacuo and the residue was purified by chiral SFC to give the first eluting isomer of the title compound as a white solid (0.37 g, 39% yield). Chiral SFC purity 100% @ 2.6 mins, 100% ee (determined by SFC using a YMC Cellulose-C column— 55% CO$_2$/45% iPrOH (diethylamine 0.1%) 120 bar). $^1$H NMR (400 MHz, CDCl₃) δ 6.78 (d, J=2.3 Hz, 1H), 6.71 (dd, J=2.4, 8.4 Hz, 1H), 6.49 (d, J=8.4 Hz, 1H), 4.17 (dd, J=2.3, 10.4 Hz, 1H), 3.74 (dd, J=8.1, 10.5 Hz, 1H), 3.65 (s, 1H), 3.54-3.49 (m, 1H), 1.18 (d, J=6.4 Hz, 3H).

Step 4: Synthesis of (6-(benzo[d]isoxazol-3-yl)-2,6-diazaspiro[3.3]heptan-2-yl)(7-chloro-3-methyl-2,3-dihydro-4H-benzo[b][1,4]oxazin-4-yl)methanone (Compound No. 21-1)

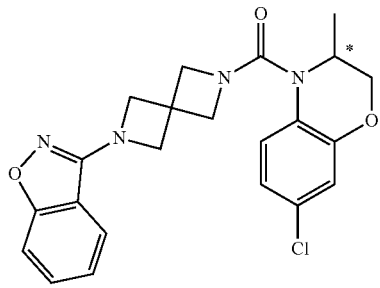

To a cooled solution of triphosgene (89 mg, 0.30 mmol, 1.1 eq.) at 0° C. in DCM (2 mL) was added a solution of 7-chloro-3-methyl-3,4-dihydro-2H-benzo[b][1,4]oxazine (50 mg, 0.27 mmol, 1.0 eq.) and N,N-diisopropylethylamine (0.052 mL, 0.098 mmol, 1.1 eq.) in DCM (2 mL) dropwise. The reaction mixture was stirred at RT for 2 hours and concentrated in vacuo. To the residue in N,N-dimethylformamide (1 mL) was added 3-(2,6-diazaspiro[3.3]heptan-2-yl)benzo[d]isoxazole 2,2,2-trifluoroacetate (90 mg, 0.27 mmol, 1.0 eq.), N,N-diisopropylethylamine (0.16 mL, 0.95 mmol, 3.5 eq.) in DMF (2 mL) and the mixture was stirred at RT overnight. The reaction was quenched with saturated aqueous sodium bicarbonate solution and was partitioned between DCM and water. The aqueous layer was extracted with DCM and the combined organics were dried and concentrated in vacuo. The residue was purified by preparative HPLC to give the title compound as a white solid (83 mg, 71% yield). ¹H NMR (400 MHz, CDCl₃) δ 7.51-7.45 (m, 2H), 7.42 (d, J=8.4 Hz, 1H), 7.22 (d, J=9.3 Hz, 2H), 6.91-6.87 (m, 2H), 4.49 (q, J=6.9 Hz, 1H), 4.37 (q, J=7.6 Hz, 4H), 4.29 (d, J=9.6 Hz, 2H), 4.22-4.13 (m, 2H), 3.96 (d, J=9.5 Hz, 2H), 1.22 (d, J=6.9 Hz, 3H); m/z 425 (M+H)⁺.

Compounds 21-2 through 21-11 Table 12 below were prepared according to the methods described in Example 21 using the appropriately substituted or modified intermediates.

TABLE 12

| No. | Structure | Data |
|---|---|---|
| 21-2 | 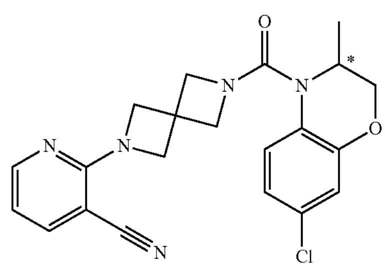 [SMILES: CC1COc2cc(Cl)ccc2N1C(=O)N1CC2(C1)CN(c1ncccc1C#N)C2] | ¹H NMR (400 MHz, CDCl₃) δ 8.26 (dd, J = 1.8, 4.8 Hz, 1H), 7.66 (dd, J = 1.9, 7.7 Hz, 1H), 7.21 (d, J = 9.0 Hz, 1H), 6.89 (d, J = 7.7 Hz, 2H), 6.65 (dd, J = 4.8, 7.7 Hz, 1H), 4.54-4.46 (m, 1H), 4.41 (dd, J = 9.8, 14.7 Hz, 4H), 4.25 (d, J = 9.4 Hz, 2H), 4.20 (dd, J = 1.5, 10.9 Hz, 1H), 4.16 (dd, J = 2.8, 10.8 Hz, 1H), 3.93 (d, J = 9.5 Hz, 2H), 1.22 (d, J = 6.8 Hz, 3H). m/z 410 (M + H)⁺. |
| 21-3 | 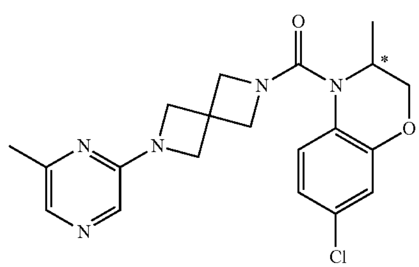 [SMILES: Cc1cncc(N2CC3(CN(C(=O)N4c5ccc(Cl)cc5OCC4C)C3)C2)n1] | ¹H NMR (400 MHz, CDCl₃) δ 7.77 (s, 1H), 7.57 (s, 1H), 7.23-7.19 (m, 1H), 6.90-6.87 (m, 2H), 4.52-4.48 (m, 1H), 4.25 (d, J = 9.2 Hz, 2H), 4.22-4.11 (m, 6H), 3.92 (d, J = 9.3 Hz, 2H), 2.36 (s, 3H), 1.22 (d, J = 6.8 Hz, 3H). m/z 400 (M + H)⁺. |
| 21-4 | 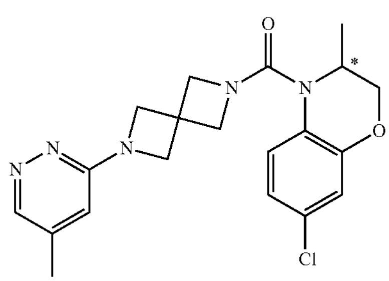 | ¹H NMR (400 MHz, DMSO-d₆) δ 8.47 (s, 1H), 7.33 (d, J = 9.1 Hz, 1H), 7.00-6.95 (m, 2H), 6.65 (s, 1H), 4.40-4.35 (m, 1H), 4.28-4.14 (m, 8H), 4.07 (d, J = 8.8 Hz, 2H), 2.25 (s, 3H), 1.15 (d, J = 6.8 Hz, 3H). m/z 400 (M + H)⁺. |

TABLE 12-continued

| No. | Structure | Data |
|---|---|---|
| 21-5 | 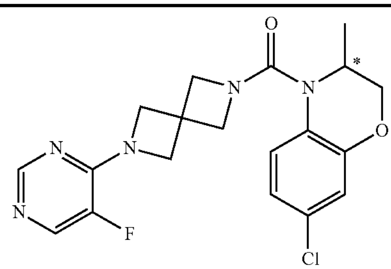 | $^1$H NMR (400 MHz, DMSO-d$_6$) δ 8.34 (d, J = 3.3 Hz, 1H), 8.22 (d, J = 4.5 Hz, 1H), 7.31 (d, J = 9.1 Hz, 1H), 6.98 (d, J = 8.3 Hz, 2H), 4.43-4.35 (m, 5H), 4.28-4.15 (m, 4H), 4.05 (d, J = 9.1 Hz, 2H), 1.14 (d, J = 6.8 Hz, 3H). m/z 404 (M + H)$^+$. |
| 21-6 | 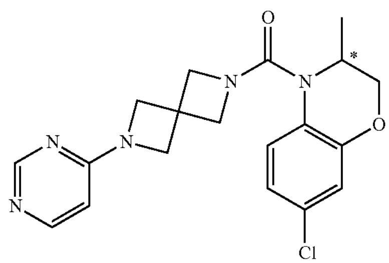 [SMILES: CC1COc2cc(Cl)ccc2N1C(=O)N1CC2(C1)CN(c1ccncn1)C2] | $^1$H NMR (400 MHz, DMSO-d$_6$) δ 8.50 (s, 1H), 8.20 (d, J = 5.8 Hz, 1H), 7.32 (d, J = 8.6 Hz, 1H), 6.98 (d, J = 8.3 Hz, 2H), 6.42 (d, J = 5.3 Hz, 1H), 4.36 (d, J = 6.8 Hz, 1H), 4.25-4.18 (m, 8H), 4.05 (d, J = 9.1 Hz, 2H), 1.14 (d, J = 6.6 Hz, 3H). m/z 386 (M + H)$^+$. |
| 21-7 | 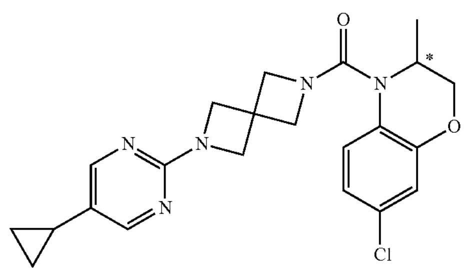 [SMILES: CC1COc2cc(Cl)ccc2N1C(=O)N1CC2(C1)CN(c1ncc(C3CC3)cn1)C2] | $^1$H NMR (400 MHz, CDCl$_3$) 8.11 (s, 2H), 7.22 (d, J = 9.3 Hz, 1H), 6.90-6.86 (m, 2H), 4.49 (d, J = 6.1 Hz, 1H), 4.26-4.14 (m, 8H), 3.91 (d, J = 9.3 Hz, 2H), 1.75-1.67 (m, 1H), 1.22 (d, J = 6.8 Hz, 3H), 0.94-0.88 (m, 2H), 0.61-0.55 (m, 2H). m/z 426 (M + H)$^+$. |
| 21-8 | 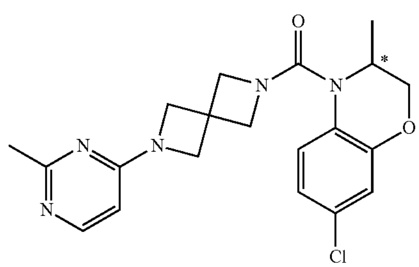 [SMILES: Cc1nccc(N2CC3(CN(C(=O)N4c5ccc(Cl)cc5OCC4C)C3)C2)n1] | $^1$H NMR (400 MHz, CDCl$_3$) δ 8.15 (d, J = 6.1 Hz, 1H), 7.22-7.19 (m, 1H), 6.89-6.87 (m, 2H), 6.02 (d, J = 6.1 Hz, 1H), 4.50 (q, J = 6.8 Hz, 1H), 4.27-4.15 (m, 8H), 3.93 (d, J = 9.5 Hz, 2H), 2.52 (s, 3H), 1.21 (d, J = 6.9 Hz, 3H). m/z 400 (M + H)$^+$. |
| 21-9 | 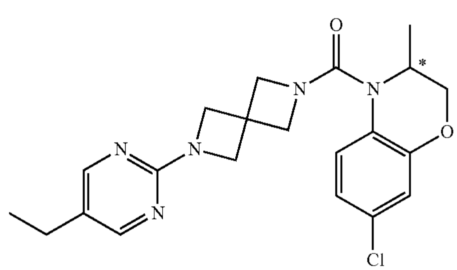 [SMILES: CCc1cnc(N2CC3(CN(C(=O)N4c5ccc(Cl)cc5OCC4C)C3)C2)nc1] | $^1$H NMR (400 MHz, CDCl$_3$) δ 8.17 (s, 2H), 7.24-7.21 (m, 1H), 6.90-6.87 (m, 2H), 4.51-4.46 (m, 1H), 4.26-4.16 (m, 8H), 3.92 (d, J = 9.4 Hz, 2H), 2.47 (q, J = 7.6 Hz, 2H), 1.22 (d, J = 6.7 Hz, 3H), 1.18 (t, J = 7.6 Hz, 3H) m/z 414 (M + H)$^+$. |
| 21-10 | 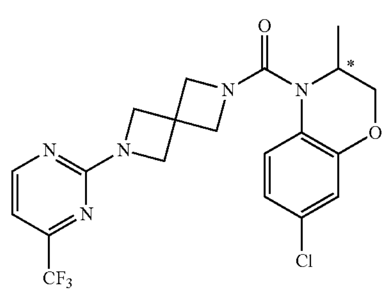 [SMILES: CC1COc2cc(Cl)ccc2N1C(=O)N1CC2(C1)CN(c1nccc(C(F)(F)F)n1)C2] | $^1$H NMR (400 MHz, CDCl$_3$) δ 8.49 (d, J = 4.9 Hz, 1H), 7.22 (d, J = 9.3 Hz, 1H), 6.90-6.86 (m, 2H), 6.83 (d, J = 4.9 Hz, 1H), 4.52-4.48 (m, 1H), 4.31-4.23 (m, 6H), 4.20 (dd, J = 1.5, 10.9 Hz, 1H), 4.16 (dd, J = 2.6, 10.8 Hz, 1H), 3.93 (d, J = 9.5 Hz, 2H), 1.22 (d, J = 6.8 Hz, 3H) m/z 454 (M + H)$^+$. |

TABLE 12-continued

| No. | Structure | Data |
| --- | --- | --- |
| 21-11 | 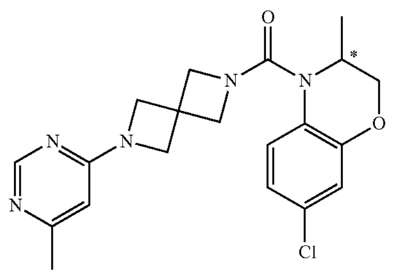 | $^1$H NMR (400 MHz, CDCl$_3$) δ 8.49 (s, 1H), 7.21 (d, J = 9.3 Hz, 1H), 6.90-6.86 (m, 2H), 6.02 (s, 1H), 4.52-4.47 (m, 1H), 4.25 (d, J = 9.7 Hz, 2H), 4.20 (dd, J = 1.5, 10.6 Hz, 1H), 4.17-4.12 (m, 5H), 3.92 (d, J = 9.7 Hz, 2H), 2.35 (s, 3H), 1.22 (d, J = 6.8 Hz, 3H) m/z 400 (M + H)$^+$. |

Example 22

Synthesis of (7-chloro-3-methyl-2,3-dihydro-4H-benzo[b][1,4]oxazin-4-yl)(6-(pyrimidin-2-yl)-2,6-diazaspiro[3.3]heptan-2-yl)methanone (Compound No. 1-83-B)

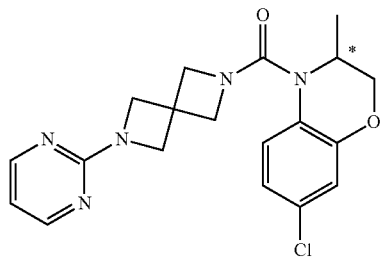

To a cooled solution of triphosgene (89 mg, 0.30 mmol, 1.1 eq.) at 0° C. in DCM (2 mL) was added a solution of 7-chloro-3-methyl-3,4-dihydro-2H-benzo[b][1,4]oxazine (50 mg, 0.27 mmol, 1.0 eq.) and N,N-diisopropylethylamine (0.052 mL, 0.098 mmol, 1.1 eq.) in DCM (2 mL) dropwise. The reaction mixture was stirred at RT for 2 hours and concentrated in vacuo. To the residue in N,N-dimethylformamide (1 mL) was added 2-(pyrimidin-2-yl)-2,6-diazaspiro[3,3]heptane bis-(2,2,2-trifluoro)acetate (110 mg, 0.27 mmol, 1.0 eq.), N,N-diisopropylethylamine (0.16 mL, 0.95 mmol, 3.5 eq.) in DMF (2 mL) and the mixture was stirred at RT overnight. The reaction was quenched with saturated aqueous sodium bicarbonate solution and was partitioned between DCM and water. The aqueous layer was extracted with DCM and the combined organics were dried and concentrated in vacuo. The residue was purified by preparative HPLC to give the title compound as a white solid (93 mg, 89% yield). $^1$H NMR (400 MHz, CDCl$_3$) δ 8.30 (d, J=4.8 Hz, 2H), 7.25-7.21 (m, 1H), 6.89-6.86 (m, 2H), 6.56 (t, J=4.4 Hz, 1H), 4.50-4.47 (m, 1H), 4.26-4.13 (m, 8H), 3.92 (d, J=9.6 Hz, 2H), 1.22 (d, J=6.7 Hz, 3H).

Example 23

Isomer Separation

Racemates were resolved by chiral HPLC to give isomer A and isomer B with the first eluting peak identified as A and the second eluting peak identified as B. Either a Waters Thar Prep100 preparative SFC system (P200 CO$_2$ pump, 2545 modifier pump, 2998 UV/VIS detector, 2767 liquid handler with Stacked Injection Module) or Waters Thar Investigator semi preparative system (Waters Fluid Delivery Module, 2998 UV/VIS detector, Waters Fraction Collection Module) were used. Where the Waters 2767 liquid handler was used it acted as both auto-sampler and fraction collector. The compounds were purified using the appropriate preparative column selected from the following: YMC Amylose-C, YMC Cellulose-C, YMC Cellulose-SC, Phenomenex LUX Cellulose-3 or Phenomenex LUX Cellulose-4. Appropriate isocratic methods were selected using the following solvents: methanol, ethanol, 2-propanol, heptane and CO$_2$ (Table 13A). The modifier diethyl amine (0.1% V/V) was also used for all methods with a flow rate of 100 ml/min (or as appropriate), 120 Bar back pressure and 40° C. column temperature. As summarized in Table 13, the retention time was obtained for each compound using the appropriate analytical column. The purification was controlled either by Waters Fractionlynx or Waters Chromscope software through monitoring at 210-400 nm and triggered a threshold collection value at an appropriate wavelength. Collected fractions were analysed by SFC (Waters/Thar SFC systems with Waters SQD or Waters UPCC with Waters QDa). The fractions that contained the desired product were concentrated by vacuum centrifugation.

TABLE 13

Chiral Separation Conditions

| Stationary Phase | Mobile Phase (solvent 1) | Mobile Phase (solvent 2) | Method |
| --- | --- | --- | --- |
| LUX Cellulose-4 | 20% 2-Propanol | 80% CO$_2$ | 1 |
| LUX Cellulose-4 | 20% Methanol | 80% CO$_2$ | 2 |
| LUX Cellulose-4 | 30% 2-Propanol | 70% CO$_2$ | 3 |
| LUX Cellulose-4 | 40% 2-Propanol | 60% CO$_2$ | 4 |
| LUX Cellulose-4 | 40% Methanol | 60% CO$_2$ | 5 |
| LUX Cellulose-4 | 50% 2-Propanol | 50% Heptane | 6 |
| YMC Amylose-C | 30% Ethanol | 70% CO$_2$ | 7 |
| YMC Amylose-C | 30% Methanol | 70% CO$_2$ | 8 |
| YMC Amylose-C | 50% 2-Propanol | 50% CO$_2$ | 9 |
| YMC Amylose-C | 55% Methanol | 45% CO$_2$ | 10 |
| YMC Cellulose-C | 20% 2-Propanol | 80% CO$_2$ | 11 |
| YMC Cellulose-C | 20% Methanol | 80% CO$_2$ | 12 |
| YMC Cellulose-C | 30% 2-Propanol | 70% CO$_2$ | 13 |
| YMC Cellulose-C | 30% Methanol | 70% CO$_2$ | 14 |
| YMC Cellulose-C | 35% Methanol | 65% CO$_2$ | 15 |
| YMC Cellulose-C | 40% Methanol | 60% CO$_2$ | 16 |
| YMC Cellulose-C | 45% 2-Propanol | 55% CO$_2$ | 17 |
| YMC Cellulose-C | 50% 2-Propanol | 50% CO$_2$ | 18 |
| YMC Cellulose-C | 50% Methanol | 50% CO$_2$ | 19 |
| YMC Cellulose-C | 55% 2-Propanol | 45% CO$_2$ | 20 |
| YMC Cellulose-C | 55% Methanol | 45% CO$_2$ | 21 |
| YMC Cellulose-SC | 40% 2-Propanol | 60% CO$_2$ | 22 |

TABLE 13-continued

Chiral Separation Conditions

| Stationary Phase | Mobile Phase (solvent 1) | Mobile Phase (solvent 2) | Method |
|---|---|---|---|
| YMC Cellulose-SC | 40% Methanol | 60% $CO_2$ | 23 |
| YMC Cellulose-SC | 55% Methanol | 45% $CO_2$ | 24 |

The compounds listed in Table 14 below were purified using SFC chiral separation as described in Example 23. The first column lists the compound by Compound Number ("No."), which designates the racemic mixture of the compound identified by the structure shown in the third column (the asterick designating the chiral atom). Such compounds have one of two isomeric forms; namely, "Isomer A" or "Isomer B". While the exact conformation has not been designated (e.g., R or S), Isomer A always has a shorter retention time than Isomer B, as indicated in the sixth column (i.e., Isomer A is always first eluting) when utilizing the SFC methodology listed in the fifth column (and specified in Table 13), in order to specifically identify the isomeric form utilized to generate the activity data presented in Table 15 below.

TABLE 14

| No. | Isomer | Structure | Data | SFC Method | Ret. Time (min) |
|---|---|---|---|---|---|
| 1-55 | Isomer A | | $^1$H NMR (400 MHz, CDCl$_3$) δ 7.99 (d, J = 2.9 Hz, 1H), 7.25-7.19 (m, 2H), 6.89-6.85 (m, 2H), 6.22 (dd, J = 3.1, 9.0 Hz, 1H), 4.32 (d, J = 10.5 Hz, 2H), 4.20 (d, J = 9.5 Hz, 2H), 4.13 (dd, J = 3.0, 10.8 Hz, 1H), 4.05 (q, J = 8.3 Hz, 4H), 3.88 (d, J = 9.5 Hz, 2H), 1.55-1.40 (m, 2H), 0.96 (dd, J = 7.4, 7.4 Hz, 3H). m/z 417 (M + H)$^+$. | 16 | 1.2 |
| 1-55 | Isomer B | | $^1$H NMR (400 MHz, CDCl$_3$) δ 7.99 (d, J = 2.9 Hz, 1H), 7.25-7.19 (m, 2H), 6.89-6.85 (m, 2H), 6.22 (dd, J = 3.5, 9.0 Hz, 1H), 4.32 (d, J = 10.5 Hz, 2H), 4.22-4.01 (m, 7H), 3.88 (d, J = 9.5 Hz, 2H), 1.55-1.46 (m, 2H), 0.96 (dd, J = 7.4, 7.4 Hz, 3H). m/z 417 (M + H)$^+$. | 16 | 2.3 |
| 1-57 | Isomer A | | $^1$H NMR (400 MHz, CDCl$_3$) δ 7.91 (d, J = 5.0 Hz, 1H), 7.22 (d, J = 9.3 Hz, 1H), 7.14 (ddd, J = 1.4, 7.9, 11.9 Hz, 1H), 6.90-6.86 (m, 2H), 6.63-6.59 (m, 1H), 4.51-4.46 (m, 1H), 4.26-4.15 (m, 8H), 3.92 (d, J = 9.5 Hz, 2H), 1.22 (d, J = 6.8 Hz, 3H). m/z 403/405 (M + H)$^+$. | 8 | 2.0 |
| 1-57 | Isomer B | | $^1$H NMR (400 MHz, CDCl$_3$) δ δ 7.91 (d, J = 5.0 Hz, 1H), 7.22-7.20 (m, 1H), 7.14 (ddd, J = 1.4, 7.9, 11.9 Hz, 1H), 6.90-6.87 (m, 2H), 6.63-6.59 (m, 1H), 4.52-4.46 (m, 1H), 4.26-4.15 (m, 8H), 3.92 (d, J = 9.5 Hz, 2H), 1.22 (d, J = 6.8 Hz, 3H). m/z 403/405 (M + H)$^+$. | 8 | 2.8 |

TABLE 14-continued

| No. | Isomer | Structure | Data | SFC Method | Ret. Time (min) |
|---|---|---|---|---|---|
| 1-58 | Isomer A | | ¹H NMR (400 MHz, CDCl₃) δ 8.02 (dd, J = 1.5, 2.6 Hz, 1H), 7.88 (d, J = 2.6 Hz, 1H), 7.77 (d, J = 1.5 Hz, 1H), 7.22 (d, J = 9.4 Hz, 1H), 6.90-6.86 (m, 2H), 4.53-4.47 (m, 1H), 4.26 (d, J = 9.6 Hz, 2H), 4.22-4.13 (m, 6H), 3.94 (d, J = 9.5 Hz, 2H), 1.22 (d, J = 6.9 Hz, 3H). m/z 386 (M + H)⁺. | 21 | 1.5 |
| 1-58 | Isomer B | | ¹H NMR (400 MHz, CDCl₃) δ 8.02 (dd, J = 1.5, 2.8 Hz, 1H), 7.88 (d, J = 2.8 Hz, 1H), 7.77 (d, J = 1.5 Hz, 1H), 7.22 (d, J = 9.2 Hz, 1H), 6.90-6.87 (m, 2H), 4.52-4.47 (m, 1H), 4.26 (d, J = 9.6 Hz, 2H), 4.22-4.13 (m, 6H), 3.94 (d, J = 9.7 Hz, 2H), 1.22 (d, J = 6.8 Hz, 3H). m/z 386 (M + H)⁺. | 21 | 2.2 |
| 1-59 | Isomer A | | ¹H NMR (400 MHz, CDCl₃) δ 7.99 (d, J = 3.0 Hz, 1H), 7.23 (dd, J = 3.0, 8.7 Hz, 1H), 7.19 (d, J = 8.9 Hz, 1H), 6.50 (dd, J = 2.9, 8.9 Hz, 1H), 6.42 (d, J = 2.9 Hz, 1H), 6.22 (dd, J = 3.1, 9.0 Hz, 1H), 4.55-4.49 (m, 1H), 4.23-4.16 (m, 4H), 4.05 (q, J = 8.3 Hz, 4H), 3.88 (d, J = 9.4 Hz, 2H), 3.76 (s, 3H), 1.20 (d, J = 6.9 Hz, 3H). m/z 399 (M + H)⁺. | 15 | 1.5 |
| 1-59 | Isomer B | | ¹H NMR (400 MHz, CDCl₃) δ 7.99 (d, J = 2.9 Hz, 1H), 7.23 (dd, J = 3.0, 8.7 Hz, 1H), 7.19 (d, J = 9.0 Hz, 1H), 6.50 (dd, J = 2.8, 9.0 Hz, 1H), 6.42 (d, J = 2.8 Hz, 1H), 6.22 (dd, J = 3.1, 9.0 Hz, 1H), 4.55-4.49 (m, 1H), 4.23-4.16 (m, 4H), 4.05 (q, J = 8.3 Hz, 4H), 3.88 (d, J = 9.4 Hz, 2H), 3.76 (s, 3H), 1.20 (d, J = 6.9 Hz, 3H). m/z 399 (M + H)⁺. | 15 | 2.1 |
| 1-60 | Isomer A | 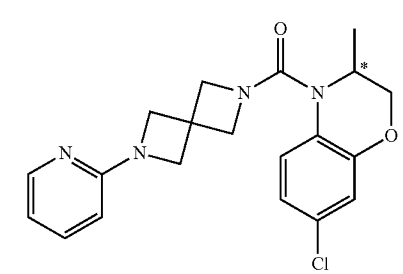 | ¹H NMR (400 MHz, DMSO-d₆) δ 8.06 (dd, J = 1.5, 5.0 Hz, 1H), 7.53-7.48 (m, 1H), 7.29 (d, J = 9.0 Hz, 1H), 6.94 (d, J = 7.9 Hz, 2H), 6.64 (dd, J = 5.0, 6.8 Hz, 1H), 6.37 (d, J = 8.3 Hz, 1H), 4.32 (q, J = 6.8 Hz, 1H), 4.24-4.16 (m, 3H), 4.11 (dd, J = 3.0, 10.9 Hz, 1H), 4.08-4.04 (m, 4H), 4.01 (d, J = 9.2 Hz, 2H), 1.11 (d, J = 6.8 Hz, 3H). m/z 385 (M + H)⁺. | 22 | 3.1 |

TABLE 14-continued

| No. | Isomer | Structure | Data | SFC Method | Ret. Time (min) |
|---|---|---|---|---|---|
| 1-60 | Isomer B | 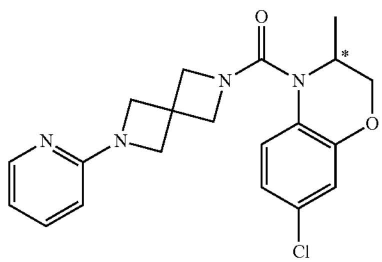 | $^1$H NMR (400 MHz, DMSO-d$_6$) δ 8.06 (dd, J = 1.5, 5.0 Hz, 1H), 7.53-7.48 (m, 1H), 7.29 (d, J = 9.0 Hz, 1H), 6.94 (d, J = 7.9 Hz, 2H), 6.64 (dd, J = 5.0, 6.8 Hz, 1H), 6.37 (d, J = 8.3 Hz, 1H), 4.32 (q, J = 6.7 Hz, 1H), 4.23-4.16 (m, 3H), 4.11 (dd, J = 2.6, 10.8 Hz, 1H), 4.08-4.04 (m, 4H), 4.01 (d, J = 9.3 Hz, 2H), 1.11 (d, J = 6.8 Hz, 3H). m/z 385 (M + H)$^+$. | 22 | 3.7 |
| 1-62 | Isomer A | | $^1$H NMR (400 MHz, CDCl$_3$) δ 8.60 (dd, J = 1.3, 4.6 Hz, 1H), 7.25-7.17 (m, 2H), 6.67-6.59 (m, 2H), 6.51 (dd, J = 1.4, 8.9 Hz, 1H), 4.55-4.49 (m, 1H), 4.27-4.14 (m, 8H), 3.94 (d, J = 9.5 Hz, 2H), 1.21 (d, J = 6.9 Hz, 3H). m/z 370/371 (M + H)$^+$. | 14 | 2.6 |
| 1-62 | Isomer B | | $^1$H NMR (400 MHz, CDCl$_3$) δ 8.60 (dd, J = 1.3, 4.5 Hz, 1H), 7.25-7.17 (m, 2H), 6.67-6.59 (m, 2H), 6.51 (dd, J = 1.3, 9.0 Hz, 1H), 4.52 (q, J = 6.9 Hz, 1H), 4.28-4.16 (m, 8H), 3.94 (d, J = 9.5 Hz, 2H), 1.21 (d, J = 6.9 Hz, 3H). m/z 370 / 371 (M + H)$^+$. | 14 | 3.2 |
| 1-65 | Isomer A | | $^1$H NMR (400 MHz, DMSO) δ 8.04 (dd, J = 1.5, 2.8 Hz, 1H), 7.87-7.84 (m, 2H), 7.30-7.25 (m, 1H), 6.77-6.72 (m, 2H), 4.32 (q, J = 6.8 Hz, 1H), 4.22-4.08 (m, 8H) 4.00 (d, J = 9.2 Hz, 2H), 1.09 (d, J = 6.8 Hz, 3H). m/z 370 (M + H)$^+$. | 14 | 2.1 |
| 1-65 | Isomer B | | $^1$H NMR (400 MHz, DMSO) δ 8.04 (dd, J = 1.5, 2.6 Hz, 1H), 7.87-7.84 (m, 2H), 7.30-7.25 (m, 1H), 6.77-6.72 (m, 2H), 4.33 (q, J = 6.6 Hz, 1H), 4.22-4.08 (m, 8H), 4.00 (d, J = 9.0 Hz, 2H), 1.09 (d, J = 6.8 Hz, 3H). m/z 370 (M + H)$^+$. | 14 | 3.0 |

TABLE 14-continued

| No. | Isomer | Structure | Data | SFC Method | Ret. Time (min) |
|---|---|---|---|---|---|
| 1-66 | Isomer A | | $^1$H NMR (400 MHz, DMSO) δ 8.06-8.05 (m, 1H), 7.53-7.48 (m, 1H), 7.30-7.25 (m, 1H), 6.77-6.72 (m, 2H), 6.63 (dd, J = 5.0, 6.8 Hz, 1H), 6.37 (d, J = 8.4 Hz, 1H), 4.34-4.31 (m, 1H), 4.22-4.08 (m, 4H), 4.05-3.98 (m, 6H), 1.10 (d, J = 6.9 Hz, 3H). m/z 369 (M + H)$^+$. | 14 | 1.9 |
| 1-66 | Isomer B | | $^1$H NMR (400 MHz, DMSO) δ 8.06-8.05 (m, 1H), 7.53-7.48 (m, 1H), 7.30-7.25 (m, 1H), 6.77-6.72 (m, 2H), 6.63 (dd, J = 5.0, 6.8 Hz, 1H), 6.37 (d, J = 8.4 Hz, 1H), 4.35-4.31 (m, 1H), 4.22-4.08 (m, 4H), 4.05-3.98 (m, 6H), 1.10 (d, J = 6.8 Hz, 3H). m/z 369 (M + H)$^+$. | 14 | 2.8 |
| 1-67 | Isomer A | | $^1$H NMR (400 MHz, DMSO) δ 7.90 (d, J = 4.9 Hz, 1H), 7.41 (ddd, J = 1.3, 7.9, 12.6 Hz, 1H), 7.30-7.25 (m, 1H), 6.76-6.68 (m, 3H), 4.33 (q, J = 6.6 Hz, 1H), 4.19-4.15 (m, 8H), 3.99 (d, J = 9.0 Hz, 2H), 1.10 (d, J = 6.8 Hz, 3H). m/z 387 (M + H)$^+$. | 13 | 1.5 |
| 1-67 | Isomer B | | $^1$H NMR (400 MHz, DMSO) δ 7.90 (d, J = 5.0 Hz, 1H), 7.41 (ddd, J = 1.3, 7.9, 12.5 Hz, 1H), 7.29-7.25 (m, 1H), 6.76-6.68 (m, 3H), 4.35-4.29 (m, 1H), 4.19-4.15 (m, 8H), 3.99 (d, J = 9.0 Hz, 2H), 1.10 (d, J = 6.9 Hz, 3H). m/z 387 (M + H)$^+$. | 13 | 2.2 |
| 1-73 | Isomer A | 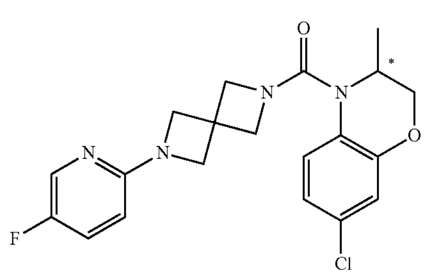 | $^1$H NMR (400 MHz, DMSO) δ 8.05 (d, J = 3.0 Hz, 1H), 7.52-7.46 (m, 1H), 7.28 (d, J = 8.5 Hz, 1H), 6.93 (d, J = 8.2 Hz, 2H), 6.42 (dd, J = 3.5, 9.0 Hz, 1H), 4.31 (q, J = 6.6 Hz, 1H), 4.23-4.09 (m, 4H), 4.04-3.98 (m, 6H), 1.10 (d, J = 6.9 Hz, 3H). m/z 403 (M + H)$^+$. | 10 | 1.5 |

TABLE 14-continued

| No. | Isomer | Structure | Data | SFC Method | Ret. Time (min) |
|---|---|---|---|---|---|
| 1-73 | Isomer B | 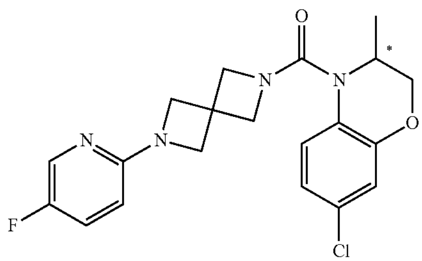 | ¹H NMR (400 MHz, DMSO) δ 8.05 (d, J = 3.0 Hz, 1H), 7.52-7.46 (m, 1H), 7.28 (d, J = 8.5 Hz, 1H), 6.93 (d, J = 8.3 Hz, 2H), 6.42 (dd, J = 3.6, 9.1 Hz, 1H), 4.31 (q, J = 6.7 Hz, 1H), 4.23-4.09 (m, 4H), 4.04-3.98 (m, 6H), 1.10 (d, J = 6.9 Hz, 3H). m/z 403 (M + H)⁺. | 10 | 2.3 |
| 1-83 | Isomer A | | ¹H NMR (400 MHz, CDCl₃) δ 8.31 (d, J = 4.9 Hz, 2H), 7.24-7.21 (m, 1H), 6.90-6.87 (m, 2H), 6.57 (t, J = 4.8 Hz, 1H), 4.52-4.47 (m, 1H), 4.27-4.16 (m, 8H), 3.93 (d, J = 9.5 Hz, 2H), 1.22 (d, J = 6.9 Hz, 3H). m/z 386 (M + H)⁺. | 17 | 1.6 |
| 1-83 | Isomer B | | ¹H NMR (400 MHz, CDCl₃) δ 8.31 (d, J = 4.8 Hz, 2H), 7.24-7.21 (m, 1H), 6.90-6.87 (m, 2H), 6.57 (t, J = 4.8 Hz, 1H), 4.52-4.46 (m, 1H), 4.27-4.16 (m, 8H), 3.93 (d, J = 9.5 Hz, 2H), 1.22 (d, J = 6.9 Hz, 3H). m/z 386 (M + H)⁺. | 17 | 2.5 |
| 4-3 | Isomer A | | ¹H NMR (400 MHz, CDCl₃) δ 7.51-7.45 (m, 2H), 7.42 (d, J = 8.3 Hz, 1H), 7.26-7.19 (m, 2H), 6.68-6.59 (m, 2H), 4.54-4.49 (m, 1H), 4.38 (d, J = 8.3 Hz, 2H), 4.35 (d, J = 8.5 Hz, 2H), 4.27 (d, J = 9.7 Hz, 2H), 4.20 (dd, J = 1.5, 10.8 Hz, 1H), 4.16 (dd, J = 2.7, 10.9 Hz, 1H), 3.95 (d, J = 9.7 Hz, 2H), 1.21 (d, J = 6.9 Hz, 3H). m/z 409 (M + H)⁺. | 19 | 1.9 |
| 4-3 | Isomer B | | ¹H NMR (400 MHz, CDCl₃) δ 7.51-7.45 (m, 2H), 7.42 (d, J = 8.4 Hz, 1H), 7.26-7.19 (m, 2H), 6.68-6.59 (m, 2H), 4.54-4.49 (m, 1H), 4.38 (d, J = 8.3 Hz, 2H), 4.35 (d, J = 8.7 Hz, 2H), 4.27 (d, J = 9.7 Hz, 2H), 4.20 (dd, J = 1.5, 10.8 Hz, 1H), 4.16 (dd, J = 2.7, 10.7 Hz, 1H), 3.95 (d, J = 9.5 Hz, 2H), 1.21 (d, J = 6.8 Hz, 3H). m/z 409 (M + H)⁺. | 19 | 2.5 |

TABLE 14-continued

| No. | Isomer | Structure | Data | SFC Method | Ret. Time (min) |
|---|---|---|---|---|---|
| 9-1 | Isomer A | | ¹H NMR (400 MHz, CDCl₃) δ 8.60 (dd, J = 1.3, 4.6 Hz, 1H), 7.23-7.17 (m, 2H), 6.90-6.87 (m, 2H), 6.51 (dd, J = 1.3, 9.0 Hz, 1H), 4.50 (q, J = 6.9 Hz, 1H), 4.29-4.16 (m, 8H), 3.95 (d, J = 9.5 Hz, 2H), 1.22 (d, J = 6.8 Hz, 3H). m/z 386/388 (M + H)⁺. | 19 | 1.7 |
| 9-1 | Isomer B | | ¹H NMR (400 MHz, CDCl₃) δ 8.60 (dd, J = 1.3, 4.6 Hz, 1H), 7.23-7.17 (m, 2H), 6.90-6.87 (m, 2H), 6.51 (dd, J = 1.4, 9.0 Hz, 1H), 4.52-4.47 (m, 1H), 4.29-4.16 (m, 8H), 3.95 (d, J = 9.5Hz, 2H), 1.22 (d, J = 6.9 Hz, 3H). m/z 386/388 (M + H)⁺. | 19 | 2.4 |
| 9-3 | Isomer A | | ¹H NMR (400 MHz, DMSO) δ 8.05 (d, J = 3.0 Hz, 1H), 7.53-7.47 (m, 1H), 7.43-7.40 (m, 1H), 6.92-6.89 (m, 2H), 6.42 (dd, J = 3.5, 9.0 Hz, 1H), 4.33-4.27 (m, 1H), 4.15 (d, J = 9.3 Hz, 2H), 4.05 (d, J = 9.2 Hz, 6H), 3.91 (dd, J = 2.5, 13.2 Hz, 1H), 3.10 (dd, J = 8.1, 13.2 Hz, 1H), 1.30 (d, J = 6.3 Hz, 3H). m/z 403 (M + H)⁺. | 1 | 5.7 |
| 9-3 | Isomer B | | ¹H NMR (400 MHz, DMSO) δ 8.05 (d, J = 3.0 Hz, 1H), 7.53-7.47 (m, 1H), 7.43-7.40 (m, 1H), 6.92-6.89 (m, 2H), 6.42 (dd, J = 3.5, 9.0 Hz, 1H), 4.33-4.27 (m, 1H), 4.15 (d, J = 9.3 Hz, 2H), 4.05 (d, J = 9.2 Hz, 6H), 3.91 (dd, J = 2.4, 13.1 Hz, 1H), 3.10 (dd, J = 8.0, 13.2 Hz, 1H), 1.29 (d, J = 6.3 Hz, 3H). m/z 403 (M + H)⁺. | 1 | 6.6 |
| 9-4 | Isomer A | 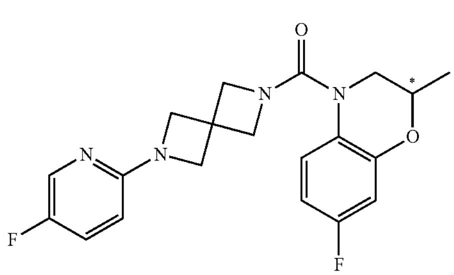 [SMILES: CC1CN(C(=O)N2CC3(C2)CN(c2ccc(F)cn2)C3)c2ccc(F)cc2O1] | ¹H NMR (400 MHz, DMSO) δ 8.05 (d, J = 3.0 Hz, 1H), 7.52-7.47 (m, 1H), 7.43-7.38 (m, 1H), 6.74-6.69 (m, 2H), 6.42 (dd, J = 3.5, 9.0 Hz, 1H), 4.32-4.26 (m, 1H), 4.14(d, J = 9.3 Hz, 2H), 4.05-4.01 (m, 6H), 3.92 (dd, J = 2.5, 13.2 Hz, 1H), 3.09 (dd, J = 8.1, 13.2 Hz, 1H), 1.30 (d, J = 6.3 Hz, 3H). m/z 387 (M + H)⁺. | 7 | 2.5 |

TABLE 14-continued

| No. | Isomer | Structure | Data | SFC Method | Ret. Time (min) |
|---|---|---|---|---|---|
| 9-4 | Isomer B | 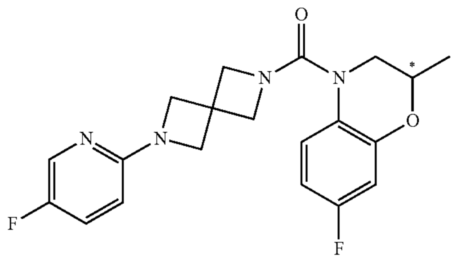 [SMILES: CC1CN(C(=O)N2CC3(C2)CN(c2ccc(F)cn2)C3)c2ccc(F)cc2O1] | ¹H NMR (400 MHz, DMSO) δ 8.05 (d, J = 3.0 Hz, 1H), 7.52-7.47 (m, 1H), 7.43-7.38 (m, 1H), 6.74-6.69 (m, 2H), 6.42 (dd, J = 3.6, 9.1 Hz, 1H), 4.33-4.27 (m, 1H), 4.14 (d, J = 9.2 Hz, 2H), 4.05-4.01 (m, 6H), 3.92 (dd, J = 2.6, 13.2 Hz, 1H), 3.09 (dd, J = 8.1, 13.2 Hz, 1H), 1.30 (d, J = 6.3 Hz, 3H). m/z 387 (M + H)⁺. | 7 | 3.3 |
| 12-1 | Isomer A | | ¹H NMR (400 MHz, DMSO) δ 8.05 (d, J = 3.0 Hz, 1H), 7.52-7.46 (m, 1H), 7.30-7.25 (m, 1H), 6.76-6.72 (m, 2H), 6.42 (dd, J = 3.5, 9.0 Hz, 1H), 4.33 (q, J = 6.6 Hz, 1H), 4.21-4.08 (m, 4H), 4.04-3.97 (m, 6H), 1.09 (d, J = 6.9 Hz, 3H). m/z 387 (M + H)⁺. | 8 | 1.6 |
| 12-1 | Isomer B | | ¹H NMR (400 MHz, DMSO) δ 7.97 (d, J = 3.0 Hz, 1H), 7.44-7.39 (m, 1H), 7.22-7.17 (m, 1H), 6.69-6.64 (m, 2H), 6.34 (dd, J = 3.5, 9.0 Hz, 1H), 4.25 (q, J = 6.7 Hz, 1H), 4.10-3.89 (m, 10H), 1.02 (d, J = 6.8 Hz, 3H). m/z 387 (M + H)⁺. | 8 | 2.4 |
| 13-1 | Isomer A | | ¹H NMR (400 MHz, DMSO) δ 8.04 (1H, d, J = 3.0 Hz), 7.52-7.46 (1H, m), 7.35 (2H, d, J = 8.7 Hz), 7.23 (1H, dd, J = 2.6, 8.8 Hz), 6.41 (1H, dd, J = 3.5, 9.0 Hz), 5.52 (1H, d, J = 5.4 Hz), 4.56 (1H, q, J = 5.5 Hz), 4.05-3.97 (8H, m), 3.70-3.62 (1H, m), 3.49-3.41 (1H, m), 2.06-1.97 (1H, m), 1.80-1.70 (1H, m); m/z 403 (M + H)⁺. | 10 | 2.0 |
| 13-1 | Isomer B | | ¹H NMR (400 MHz, DMSO) δ 7.96 (d, J = 3.0 Hz, 1H), 7.44-7.38 (m, 1H), 7.29-7.26 (m, 2H), 7.15 (dd, J = 2.5, 8.8 Hz, 1H), 6.33 (dd, J = 3.5, 9.1 Hz, 1H), 5.44 (d, J = 5.3 Hz, 1H), 4.47 (q, J = 5.5 Hz, 1H), 3.97-3.88 (m, 8H), 3.62-3.54 (m, 1H), 3.40-3.34 (m, 1H), 1.99-1.89 (m, 1H), 1.72-1.62 (m, 1H). m/z 403 (M + H)⁺. | 9 | 2.7 |

TABLE 14-continued

| No. | Isomer | Structure | Data | SFC Method | Ret. Time (min) |
|---|---|---|---|---|---|
| 13-2 | Isomer A | | $^1$H NMR (400 MHz, DMSO) δ 8.05 (dd, J = 1.5, 5.0 Hz, 1H), 7.53-7.47 (m, 1H), 7.37-7.34 (m, 2H), 7.23 (dd, J = 2.6, 8.8 Hz, 1H), 6.63 (dd, J = 5.4, 7.0 Hz, 1H), 6.36 (d, J = 8.4 Hz, 1H), 5.52 (d, J = 5.4 Hz, 1H), 4.56 (q, J = 5.6 Hz, 1H), 4.06-3.98 (m, 8H), 3.70-3.62 (m, 1H), 3.49-3.37 (m, 1H), 2.06-1.97 (m, 1H), 1.80-1.71 (m, 1H). m/z 385 (M + H)$^+$. | 4 | 3.8 |
| 13-2 | Isomer B | | $^1$H NMR (400 MHz, DMSO) δ 8.05 (dd, J = 1.4, 5.0 Hz, 1H), 7.53-7.47 (m, 1H), 7.37-7.34 (m, 2H), 7.23 (dd, J = 2.6, 8.8 Hz, 1H), 6.63 (dd, J = 5.1, 6.7 Hz, 1H), 6.36 (d, J = 8.4 Hz, 1H), 5.51 (d, J = 5.5 Hz, 1H), 4.55 (q, J = 5.5 Hz, 1H), 4.06-3.97 (m, 8H), 3.70-3.62 (m, 1H), 3.49-3.37 (m, 1H), 2.06-1.97 (m, 1H), 1.80-1.71 (m, 1H). m/z 385 (M + H)$^+$. | 4 | 4.9 |
| 13-3 | Isomer A | | $^1$H NMR (400 MHz, DMSO) δ 8.03 (dd, J = 1.5, 2.8 Hz, 1H), 7.86-7.83 (m, 2H), 7.37-7.34 (m, 2H), 7.23 (dd, J = 2.6, 8.8 Hz, 1H), 5.52 (d, J = 5.3 Hz, 1H), 4.56 (q, J = 5.5 Hz, 1H), 4.14 (s, 4H), 4.06 (d, J = 9.3 Hz, 2H), 3.98 (d, J = 9.2 Hz, 2H), 3.70-3.62 (m, 1H), 3.49-3.41 (m, 1H), 2.07-1.97 (m, 1H), 1.80-1.70 (m, 1H). m/z 386 (M + H)$^+$. | 4 | 4.7 |
| 13-3 | Isomer B | | $^1$H NMR (400 MHz, DMSO) δ 8.03 (dd, J = 1.5, 2.8 Hz, 1H), 7.86-7.83 (m, 2H), 7.37-7.34 (m, 2H), 7.23 (dd, J = 2.6, 8.8 Hz, 1H), 5.52 (d, J = 5.3 Hz, 1H), 4.56 (q, J = 5.5 Hz, 1H), 4.14 (s, 4H), 4.06 (d, J = 9.2 Hz, 2H), 3.98 (d, J = 9.2 Hz, 2H), 3.70-3.62 (m, 1H), 2.08 (s, 1H), 2.07-1.98 (m, 1H), 1.80-1.70 (m, 1H). m/z 386 (M + H)$^+$. | 4 | 5.9 |
| 13-4 | Isomer A | 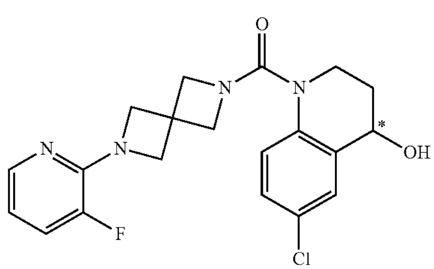 [SMILES: O=C(N1CC2(C1)CN(c1ncccc1F)C2)N1CCC(O)c2cc(Cl)ccc21] | $^1$H NMR (400 MHz, DMSO) δ 7.90 (d, J = 4.9 Hz, 1H), 7.42-7.33 (m, 3H), 7.23 (dd, J = 2.6, 8.8 Hz, 1H), 6.72-6.67 (m, 1H), 5.51 (d, J = 5.1 Hz, 1H), 4.55 (q, J = 5.2 Hz, 1H), 4.16 (d, J = 1.8 Hz, 4H), 4.06 (d, J = 9.2 Hz, 2H), 3.97 (d, J = 9.2 Hz, 2H), 3.70-3.62 (m, 1H), 3.49-3.41 (m, 1H), 2.06-1.97 (m, 1H), 1.80-1.70 (m, 1H). m/z 403 (M + H)$^+$. | 3 | 5.1 |

TABLE 14-continued

| No. | Isomer | Structure | Data | SFC Method | Ret. Time (min) |
|---|---|---|---|---|---|
| 13-4 | Isomer B | 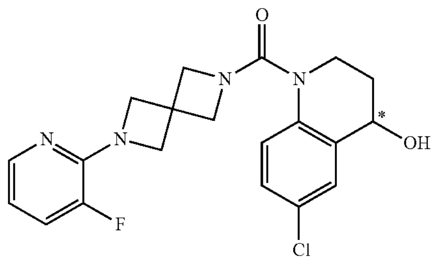 [SMILES: O=C(N1CC2(C1)CN(c1ncccc1F)C2)N1CCC(O)c2cc(Cl)ccc21] | $^1$H NMR (400 MHz, DMSO) δ 7.90 (d, J = 4.9 Hz, 1H), 7.42-7.33 (m, 3H), 7.23 (dd, J = 2.6, 8.8 Hz, 1H), 6.72-6.67 (m, 1H), 5.52 (s, 1H), 4.55 (dd, J = 5.5, 5.5 Hz, 1H), 4.16 (d, J = 1.9 Hz, 4H), 4.06 (d, J = 9.2 Hz, 2H), 3.97 (d, J = 9.2 Hz, 2H), 3.70-3.62 (m, 1H), 3.49-3.41 (m, 1H), 2.06-1.97 (m, 1H), 1.80-1.70 (m, 1H). m/z 403 (M + H)$^+$. | 3 | 6.3 |
| 13-5 | Isomer A | | $^1$H NMR (400 MHz, CDCl$_3$) δ 8.00 (d, J = 2.8 Hz, 1H), 7.27-7.21 (m, 3H), 6.24 (dd, J = 3.4, 9.0 Hz, 1H), 5.08 (d, J = 2.0 Hz, 1H), 4.20 (d, J = 9.3 Hz, 2H), 4.09-4.06 (m, 4H), 3.99 (d, J = 9.1 Hz, 2H), 3.96-3.91 (m, 1H), 3.56-3.48 (m, 1H), 2.30 (m, 1H), 2.15 (ddd, J = 2.7, 6.6, 14.2 Hz, 1H), 1.95-1.86 (m, 1H). m/z 421 (M + H)$^+$. | 12 | 4.3 |
| 13-5 | Isomer B | | $^1$H NMR (400 MHz, CDCl$_3$) δ 8.00 (d, J = 2.8 Hz, 1H), 7.27-7.23 (m, 3H), 6.24 (dd, J = 3.4, 9.0 Hz, 1H), 5.08 (d, J = 2.0 Hz, 1H), 4.20 (d, J = 9.3 Hz, 2H), 4.10-4.06 (m, 4H), 4.00 (d, J = 9.1 Hz, 2H), 3.96-3.91 (m, 1H), 3.56-3.48 (m, 1H), 2.30 (m, 1H), 2.15 (ddd, J = 2.7, 6.6, 14.2 Hz, 1H), 1.95-1.86 (m, 1H). m/z 421 (M + H)$^+$. | 12 | 5.5 |
| 18-2 | Isomer A | | $^1$H NMR (400 MHz, CDCl$_3$) δ 8.20 (s, 2H), 7.24-7.21 (m, 1H), 6.90-6.87 (m, 2H), 4.49 (q, J = 6.9 Hz, 1H), 4.26-4.15 (m, 8H), 3.92 (d, J = 9.5 Hz, 2H), 1.22 (d, J = 6.9 Hz, 3H). m/z 404 (M + H)$^+$. | 13 | 1.6 |
| 18-2 | Isomer B | | $^1$H NMR (400 MHz, CDCl$_3$) δ 8.20 (s, 2H), 7.24-7.21 (m, 1H), 6.90-6.87 (m, 2H), 4.52-4.46 (m, 1H), 4.26-4.15 (m, 8H), 3.92 (d, J = 9.5 Hz, 2H), 1.22 (d, J = 6.9 Hz, 3H). m/z 404 (M + H)$^+$. | 13 | 2.6 |

TABLE 14-continued

| No. | Isomer | Structure | Data | SFC Method | Ret. Time (min) |
|---|---|---|---|---|---|
| 18-3 | Isomer A | | ¹H NMR (400 MHz, CDCl₃) δ 8.54 (dd, J = 1.1, 4.5 Hz, 1H), 7.71 (dd, J = 1.1, 8.7 Hz, 1H), 7.39 (dd, J = 4.5, 8.5 Hz, 1H), 7.23-7.20 (m, 1H), 6.90-6.86 (m, 2H), 4.51-4.44 (m, 5H), 4.28 (d, J = 9.5 Hz, 2H), 4.20 (dd, J = 1.4, 10.8 Hz, 1H), 4.15 (dd, J = 2.9, 10.9 Hz, 1H), 3.96 (d, J = 9.5 Hz, 2H), 1.22 (d, J = 6.8 Hz, 3H). m/z 426 (M + H)⁺. | 24 | 2.3 |
| 18-3 | Isomer B | | ¹H NMR (400 MHz, CDCl₃) δ 8.54 (dd, J = 1.1, 4.5Hz, 1H), 7.71 (dd, J = 1.1, 8.5 Hz, 1H), 7.39 (dd, J = 4.5, 8.5 Hz, 1H), 7.23-7.20 (m, 1H), 6.90-6.86 (m, 2H), 4.51-4.44 (m, 5H), 4.28 (d, J = 9.5 Hz, 2H), 4.20 (dd, J = 1.5, 10.8 Hz, 1H), 4.16 (dd, J = 2.7, 10.7 Hz, 1H), 3.96 (d, J = 9.5 Hz, 2H), 1.22 (d, J = 6.8 Hz, 3H). m/z 426 (M + H)⁺. | 24 | 3.3 |
| 18-4 | Isomer A | | ¹H NMR (400 MHz, CDCl₃) δ 8.19 (s, 2H), 7.25-7.21 (m, 1H), 6.68-6.57 (m, 2H), 4.51 (q, J = 6.6 Hz, 1H), 4.25-4.14 (m, 8H), 3.91 (d, J = 9.3 Hz, 2H), 1.20 (d, J = 6.8 Hz, 3H). m/z 388 (M + H)⁺. | 11 | 1.4 |
| 18-4 | Isomer B | | ¹H NMR (400 MHz, CDCl₃) δ 8.20 (s, 2H), 7.25-7.21 (m, 1H), 6.68-6.57 (m, 2H), 4.51 (d, J = 6.8 Hz, 1H), 4.25-4.14 (m, 8H), 3.91 (d, J = 9.3 Hz, 2H), 1.21 (d, J = 6.8 Hz, 3H). m/z 388 (M + H)⁺. | 11 | 2.2 |
| 18-5 | Isomer A | 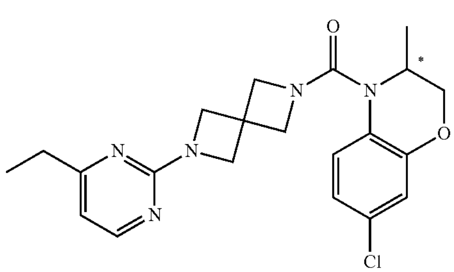 | ¹H NMR (400 MHz, CDCl₃) δ 8.18 (d, J = 5.1 Hz, 1H), 7.22 (d, J = 9.3 Hz, 1H), 6.90-6.87 (m, 2H), 6.45 (d, J = 5.0 Hz, 1H), 4.51-4.46 (m, 1H), 4.25-4.15 (m, 8H), 3.91 (d, J = 9.4 Hz, 2H), 2.60 (q, J = 7.6 Hz, 2H), 1.23 (m, 6H). m/z 414 (M + H)⁺. | 24 | 1.3 |

TABLE 14-continued

| No. | Isomer | Structure | Data | SFC Method | Ret. Time (min) |
|---|---|---|---|---|---|
| 18-5 | Isomer B | 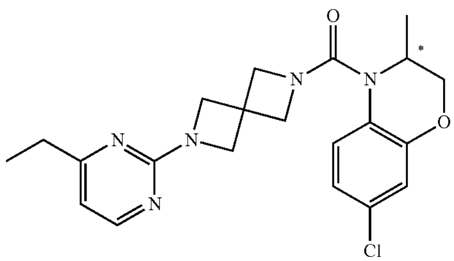 | $^1$H NMR (400 MHz, CDCl$_3$) δ 8.18 (d, J = 5.0 Hz, 1H), 7.22 (d, J = 9.3 Hz, 1H), 6.90-6.87 (m, 2H), 6.46 (d, J = 5.0 Hz, 1H), 4.49 (q, J = 6.9 Hz, 1H), 4.26-4.15 (m, 8H), 3.92 (d, J = 9.4 Hz, 2H), 2.60 (q, J = 7.6 Hz, 2H), 1.23 (t, J = 7.6 Hz, 6H). m/z 414 (M + H)$^+$. | 24 | 2.5 |
| 19-1 | Isomer A | | $^1$H NMR (400 MHz, CDCl$_3$) δ 8.32 (dd, J = 2.1, 4.8 Hz, 2H), 7.20 (dd, J = 8.2, 11.9 Hz, 1H), 6.70 (dd, J = 7.6, 11.0 Hz, 1H), 6.60-6.55 (m, 1H), 4.43 (q, J = 6.7 Hz, 1H), 4.32-4.11 (m, 8H), 3.97 (d, J = 9.3 Hz, 2H), 1.22 (d, J = 6.9 Hz, 3H). m/z 388 (M + H)$^+$. | 2 | 3.0 |
| 19-1 | Isomer B | | $^1$H NMR (400 MHz, CDCl$_3$) δ 8.31 (d, J = 4.8 Hz, 2H). 7.19 (dd, J = 8.2, 12.0 Hz, 1H), 6.69 (dd, J = 7.6, 11.1 Hz, 1H), 6.57 (t, J = 4.8 Hz, 1H), 4.43 (q, J = 6.7 Hz, 1H), 4.31-4.11 (m, 8H), 3.97 (d, J = 9.3 Hz, 2H), 1.22 (d, J = 6.8 Hz, 3H). m/z 388 (M + H)$^+$. | 2 | 3.6 |
| 19-2 | Isomer A | | $^1$H NMR (400 MHz, CDCl$_3$) δ 8.31 (d, J = 4.8 Hz, 2H), 7.17 (d, J = 10.5 Hz, 1H), 6.90 (d, J = 7.0 Hz, 1H), 6.58 (t, J = 4.8 Hz, 1H), 4.45-4.41 (m, 1H), 4.32-4.21 (m, 6H), 4.18 (dd, J = 1.5, 10.7 Hz, 1H), 4.11 (dd, J = 2.5, 10.9 Hz, 1H), 3.98 (d, J = 9.5 Hz, 2H), 1.23 (d, J = 6.8 Hz, 3H). m/z 404 (M + H)$^+$. | 23 | 1.8 |
| 19-2 | Isomer B | | $^1$H NMR (400 MHz, CDCl$_3$) δ 8.31 (d, J = 4.8 Hz, 2H), 7.17 (d, J = 10.7 Hz, 1H), 6.90 (d, J = 7.0 Hz, 1H), 6.58 (t, J = 4.8 Hz, 1H), 4.42 (q, J = 6.9 Hz, 1H), 4.32-4.21 (m, 6H), 4.18 (dd, J = 1.5, 10.8 Hz, 1H), 4.11 (dd, J = 2.6, 10.8 Hz, 1H), 3.98 (d, J = 9.4 Hz, 2H), 1.2.3 (d, J = 6.8 Hz, 3H). m/z 404 (M + H)$^+$. | 23 | 2.0 |

TABLE 14-continued

| No. | Isomer | Structure | Data | SFC Method | Ret. Time (min) |
|---|---|---|---|---|---|
| 19-3 | Isomer B | 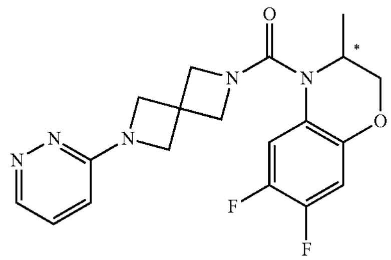 | $^1$H NMR (400 MHz, CDCl$_3$) δ 8.61 (dd, J = 1.3, 4.5 Hz, 1H), 7.22-7.16 (m, 2H), 6.70 (dd, J = 7.5, 11.0 Hz, 1H), 6.53 (dd, J = 1.3, 9.0 Hz, 1H), 4.43 (q, J = 6.9 Hz, 1H), 4.31 (d, J = 9.4 Hz, 2H), 4.29-4.22 (m, 4H), 4.18 (dd, J = 1.5, 10.8 Hz, 1H), 4.12 (dd, J = 2.6, 10.8 Hz, 1H), 3.99 (d, J = 9.5 Hz, 2H), 1.22 (d, J = 6.9 Hz, 3H). m/z 388 (M + H)$^+$. | 14 | 2.0 |
| 19-4 | Isomer A | | $^1$H NMR (400 MHz, CDCl3) 8.61 (dd, J = 1.3, 4.5 Hz, 1H), 7.20 (dd, J = 4.6, 9.0 Hz, 1H), 7.16 (d, J = 10.7 Hz, 1H), 6.91 (d, J = 7.0 Hz, 1H), 6.53 (dd, J = 1.4, 9.0 Hz, 1H), 4.42 (q, J = 6.8 Hz, 1H), 4.32 (d, J = 9.7 Hz, 2H), 4.26 (dd, J = 9.1, 14.9 Hz, 4H), 4.19 (dd, J = 1.6, 10.7 Hz, 1H), 4.12 (dd, J = 2.6, 10.6 Hz, 1H), 3.99 (d, J = 9.5 Hz, 2H), 1.24 (d, J = 6.8 Hz, 3H). m/z 404 (M + H)$^+$. | 5 | 2.8 |
| 19-4 | Isomer B | | $^1$H NMR (400 MHz, CDCl3) 8.62-8.60 (m, 1H), 7.20 (dd, J = 4.6, 8.9 Hz, 1H), 7.16 (d, J = 10.6 Hz, 1H), 6.91 (d, J = 7.0 Hz, 1H), 6.53 (dd, J = 1.3, 8.9 Hz, 1H), 4.43 (q, J = 6.9 Hz, 1H), 4.32 (d, J = 9.5 Hz, 2H), 4.26 (dd, J = 9.0, 14.9 Hz, 4H), 4.19 (dd, J = 1.4, 10.9 Hz, 1H), 4.12 (dd, J = 2.6, 11.0 Hz, 1H), 3.99 (d, J = 9.5 Hz, 2H), 1.24 (d, J = 6.9 Hz, 3H). m/z 404 (M + H)$^+$. | 5 | 3.5 |
| 19-5 | Isomer A | | $^1$H NMR (400 MHz, CDCl$_3$) δ 8.00 (d, J = 2.9 Hz, 1H), 7.25-7.21 (m, 1H), 7.18 (dd, J = 8.1, 12.0 Hz, 1H), 6.69 (dd, J = 7.5, 11.0 Hz, 1H), 6.25 (dd, J = 3.4, 9.0 Hz, 1H), 4.42 (q, J = 6.9 Hz, 1H), 4.27 (d, J = 9.4 Hz, 2H), 4.18 (dd, J = 1.5, 10.7 Hz, 1H), 4.13-4.06 (m, 5H), 3.95 (d, J = 9.4 Hz, 2H), 1.22 (d, J = 6.8 Hz, 3H). m/z 405 (M + H)$^+$. | 14 | 0.6 |
| 19-5 | Isomer B | | $^1$H NMR (400 MHz, CDCl$_3$) δ 8.00 (d, J = 3.0 Hz, 1H), 7.25-7.21 (m, 1H), 7.18 (dd, J = 8.2, 11.9 Hz, 1H), 6.69 (dd, J = 7.7, 11.0 Hz, 1H), 6.25 (dd, J = 3.3, 9.0 Hz, 1H), 4.42 (q, J = 6.9 Hz, 1H), 4.27 (d, J = 9.4 Hz, 2H), 4.18 (dd, J = 1.4, 10.8 Hz, 1H), 4.13-4.07 (m, 5H), 3.95 (d, J = 9.4 Hz, 2H), 1.22 (d, J = 6.8 Hz, 3H). m/z 405 (M + H)$^+$. | 14 | 0.9 |

TABLE 14-continued

| No. | Isomer | Structure | Data | SFC Method | Ret. Time (min) |
|---|---|---|---|---|---|
| 20-1 | Isomer A | | $^1$H NMR (400 MHz, CDCl$_3$) δ 8.04 (d, J = 4.5 Hz, 1H), 7.84 (d, J = 2.5 Hz, 1H), 7.23-7.19(11), 1H), 7.10 (dd, J = 4.7, 8.2 Hz, 1H), 6.88 (dd, J = 2.3, 4.3 Hz, 2H), 6.73-6.69 (m, 1H), 4.52-4.48 (m, 1H), 4.25 (d, J = 9.5 Hz, 2H), 4.19 (d, J = 10.0 Hz, 1H), 4.15 (dd, J = 2.7, 11.1 Hz, 1H), 4.00 (q, J = 7.3 Hz, 4H), 3.92 (d, J = 9.6 Hz, 2H), 1.22 (d, J = 6.8 Hz, 3H). m/z 385 (M + H)$^+$. | 18 | 1.6 |
| 20-1 | Isomer B | | $^1$H NMR (400 MHz, CDCl$_3$) δ 8.04 (dd, J = 1.4, 4.6 Hz, 1H), 7.84 (d, J = 2.5 Hz, 1H), 7.22-7.19 (m, 1H), 7.10 (dd, J = 4.8, 8.1 Hz, 1H), 6.90-6.86 (m, 2H), 6.70 (ddd, J = 1.3, 2.9, 8.3 Hz, 1H), 4.52-4.46 (m, 1H), 4.25 (d, J = 9.4 Hz, 2H), 4.20 (dd, J = 1.5, 10.9 Hz, 1H), 4.15 (dd, J = 2.9, 11.0 Hz, 1H), 4.02 (d, J = 7.8 Hz, 2H), 3.99 (d, J = 7.6 Hz, 2H), 3.92 (d, J = 9.5 Hz, 2H), 1.22 (d, J = 6.8 Hz, 3H). m/z 385 (M + H)$^+$. | 18 | 2.5 |
| 20-2 | Isomer A | | $^1$H NMR (400 MHz, CDCl$_3$) δ 7.76 (s, 1H), 7.57 (s, 1H), 7.25-7.21 (m, 1H), 6.67-6.58 (m, 2H), 4.55-4.48 (m, 1H), 4.23 (d, J = 9.3 Hz, 2H), 4.20-4.11 (m, 6H), 3.91 (d, J = 9.6 Hz, 2H), 2.36 (s, 3H), 1.21 (d, J = 7.1 Hz, 3H). m/z 384 (M + H)$^+$. | 16 | 1.5 |
| 20-2 | Isomer B | | $^1$H NMR (400 MHz, CDCl$_3$) δ 7.76 (s, 1H), 7.56 (s, 1H), 7.23 (dd, J = 6.0, 9.0 Hz, 1H), 6.67-6.57 (m, 2H), 4.55-4.49 (m, 1H), 4.25-4.11 (m, 8H), 3.91 (d, J = 9.3 Hz, 2H), 2.36 (s, 3H), 1.21 (d, J = 6.8 Hz, 3H). m/z 384 (M + H)$^+$. | 16 | 2.2 |
| 20-3 | Isomer A | 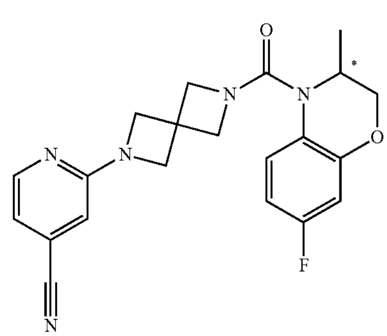 | $^1$H NMR (400 MHz, CDCl$_3$) δ 8.23 (d, J = 5.1 Hz, 1H), 7.24 (dd, J = 5.8, 9.1 Hz, 1H), 6.78 (dd, J = 1.3, 5.1 Hz, 1H), 6.67-6.59 (m, 2H), 6.42 (s, 1H), 4.55-4.49 (m, 1H), 4.26-4.11 (m, 8H), 3.92 (d, J = 9.5 Hz, 2H), 1.21 (d, J = 6.9 Hz, 3H). m/z 394 (M + H)$^+$. | 10 | 1.0 |

TABLE 14-continued

| No. | Isomer | Structure | Data | SFC Method | Ret. Time (min) |
|---|---|---|---|---|---|
| 20-3 | Isomer B | 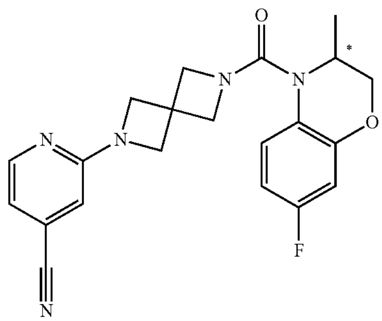 | $^1$H NMR (400 MHz, CDCl$_3$) δ 8.23 (d, J = 5.1 Hz, 1H), 7.24 (dd, J = 5.8, 9.0 Hz, 1H), 6.78 (dd, J = 1.3, 5.1 Hz, 1H), 6.67-6.59 (m, 2H), 6.42 (s, 1H), 4.55-4.49 (m, 1H), 4.26-4.11(m, 8H), 3.92 (d, J = 9.5 Hz, 2H), 1.21 (d, J = 6.9 Hz, 3H). m/z 394 (M + H)$^+$. | 10 | 2.3 |
| 20-4 | Isomer A | | $^1$H NMR (400 MHz, CDCl$_3$) δ 7.99 (d, J = 5.1 Hz, 1H), 7.25-7.22 (m, 1H), 6.67-6.58 (m, 2H), 6.47 (d, J = 4.9 Hz, 1H), 6.08 (s, 1H), 4.53-4.48 (m, 1H), 4.22 (d, J = 9.5 Hz, 2H), 4.19-4.16 (m, 2H), 4.11-4.04 (m, 4H), 3.90 (d, J = 9.5 Hz, 2H), 2.24 (s, 3H), 1.21 (d, J = 6.9 Hz, 3H). m/z 383 (M + H)$^+$. | 7 | 1.2 |
| 20-4 | Isomer B | | $^1$H NMR (400 MHz, CDCl$_3$) δ 7.99 (d, J = 5.1 Hz, 1H), 7.25-7.22 (m, 1H), 6.67-6.58 (m, 2H), 6.47 (d, J = 5.1 Hz, 1H), 6.08 (s, 1H), 4.53-4.48 (m, 1H), 4.22 (d, J = 9.6 Hz, 2H), 4.19-4.16(m, 2H), 4.11-4.04 (m, 4H), 3.90 (d, J = 9.4 Hz, 2H), 2.24 (s, 3H), 1.21 (d, J = 6.9 Hz, 3H). m/z 383 (M + H)$^+$. | 8 | 1.8 |
| 20-5 | Isomer A | | $^1$H NMR (400 MHz, CDCl$_3$) δ 7.90 (s, 1H), 7.70 (d, J = 1.4 Hz, 1H), 7.21 (d, J = 9.3 Hz, 1H), 6.90-6.86 (m, 2H), 4.52-4.46 (m, 1H), 4.25 (d, J = 9.5 Hz, 2H), 4.20 (dd, J = 1.6, 10.7 Hz, 1H), 4.17-4.10 (m, 5H), 3.93 (d, J = 9.5 Hz, 2H), 2.40 (s, 3H), 1.22 (d, J = 6.8 Hz, 3H). m/z 400 (M + H)$^+$. | 5 | 4.3 |
| 20-5 | Isomer B | | $^1$H NMR (400 MHz, CDCl$_3$) δ 7.90 (s, 1H), 7.70 (d, J = 1.5 Hz, 1H), 7.23-7.20 (m, 1H), 6.90-6.86 (m, 2H), 4.52-4.47 (m, 1H), 4.25 (d, J = 9.4 Hz, 2H), 4.20 (dd, J = 1.5, 10.8 Hz, 1H), 4.17-4.10 (m, 5H), 3.93 (d, J = 9.5 Hz, 2H), 2.40 (s, 3H), 1.22 (d, J = 6.9 Hz, 3H). m/z 400 (M + H)$^+$. | 5 | 5.2 |

TABLE 14-continued

| No. | Isomer | Structure | Data | SFC Method | Ret. Time (min) |
|---|---|---|---|---|---|
| 20-6 | Isomer A | | $^1$H NMR (400 MHz, CDCl$_3$) δ 8.24 (d, J = 4.8 Hz, 1H), 7.22 (d, J = 9.2 Hz, 1H), 6.90-6.87 (m, 2H), 6.78 (dd, J = 1.3, 5.1 Hz, 1H), 6.42 (s, 1H), 4.53-4.47 (m, 1H), 4.26 (d, J = 9.4 Hz, 2H), 4.20 (dd, J = 1.5, 10.7 Hz, 1H), 4.18-4.11 (m, 5H), 3.93 (d, J = 9.5 Hz, 2H), 1.22 (d, J = 6.8 Hz, 3H). m/z 410 (M + H)$^+$. | 18 | 1.1 |
| 20-6 | Isomer B | | $^1$H NMR (400 MHz, CDCl$_3$) δ 8.24 (d, J = 4.8 Hz, 1H), 7.22 (d, J = 9.3 Hz, 1H), 6.90-6.87 (m, 2H), 6.78 (dd, J = 1.3, 5.1 Hz, 1H), 6.42 (s, 1H), 4.50 (q, J = 6.9 Hz, 1H), 4.26 (d, J = 9.7 Hz, 2H), 4.20 (dd, J = 1.5, 10.8 Hz, 1H), 4.17-4.11 (m, 5H), 3.93 (d, J = 9.5 Hz, 2H), 1.22 (d, J = 6.9 Hz, 3H). m/z 410 (M + H)$^+$. | 18 | 2.3 |
| 20-7 | Isomer A | | $^1$H NMR (400 MHz, CDCl$_3$) δ 8.04 (d, J = 1.9 Hz, 1H), 7.23-7.20 (m, 1H), 6.89-6.86 (m, 2H), 4.51-4.46 (m, 1H), 4.24-4.13 (m, 8H), 3.90 (d, J = 9.4 Hz, 2H), 2.35 (d, J = 2.5 Hz, 3H), 1.22 (d, J = 6.8 Hz, 3H). m/z 418 (M + H)$^+$. | 23 | 1.5 |
| 20-7 | Isomer B | | $^1$H NMR (400 MHz, CDCl$_3$) δ 8.04 (d, J = 1.8 Hz, 1H), 7.23-7.20 (m, 1H), 6.90-6.86 (m, 2H), 4.49 (q, J = 6.8 Hz, 1H), 4.25-4.13 (m, 8H), 3.90 (d, J = 9.5 Hz, 2H), 2.35 (d, J = 2.5 Hz, 3H), 1.22 (d, J = 6.8 Hz, 3H). m/z 418 (M + H)$^+$. | 23 | 2.0 |
| 20-8 | Isomer A | 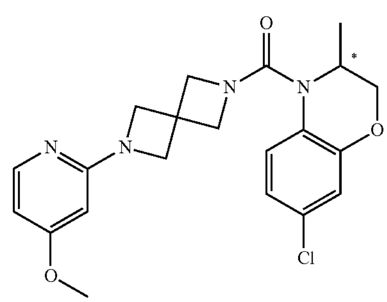 [SMILES: COc1ccnc(N2CC3(CN(C(=O)N4c5ccc(Cl)cc5OCC4C)C3)C2)c1] | $^1$H NMR (400 MHz, CDCl$_3$) δ 7.97 (d, J = 6.1 Hz, 1H), 7.24-7.20 (m, 1H), 6.88 (dd, J = 2.3, 4.5 Hz, 2H), 6.25 (dd, J = 2.0, 5.8 Hz, 1H), 5.70 (d, J = 1.8 Hz, 1H), 4.52-4.46 (m, 1H), 4.26-4.12 (m, 4H), 4.08 (dd, J = 8.5, 15.0 Hz, 4H), 3.91 (d, J = 9.3 Hz, 2H), 3.79 (s, 3H), 1.22 (d, J = 6.8 Hz, 3H). m/z 415 (M + H)$^+$. | 10 | 1.1 |

TABLE 14-continued

| No. | Isomer | Structure | Data | SFC Method | Ret. Time (min) |
|---|---|---|---|---|---|
| 20-8 | Isomer B | 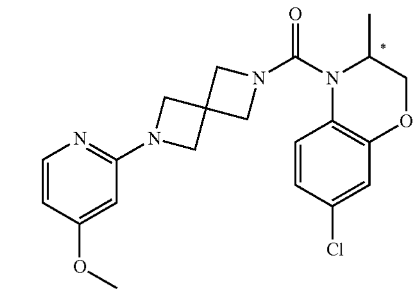 [SMILES: COc1ccnc(N2CC3(CN(C(=O)N4c5ccc(Cl)cc5OCC4C)C3)C2)c1] | $^1$H NMR (400 MHz, CDCl$_3$) δ 7.97 (d, J = 5.8 Hz, 1H), 7.24-7.20 (m, 1H), 6.88 (dd, J = 2.3, 4.5 Hz, 2H), 6.25 (dd, J = 2.0, 5.8 Hz, 1H), 5.70 (d, J = 2.0 Hz, 1H), 4.48 (q, J = 6.3 Hz, 1H), 4.26-4.12 (m, 4H), 4.08 (dd, J = 8.5, 15.1Hz, 4H), 3.91 (d, J = 9.3 Hz, 2H), 3.79 (s, 3H), 1.24-1.20 (m, 3H). m/z 415 (M + H)$^+$. | 10 | 1.8 |
| 20-9 | Isomer A | | $^1$H NMR (400 MHz, DMSO-d$_6$) δ 8.10 (d, J = 5.8 Hz, 1H), 7.32 (d, J = 8.8 Hz, 1H), 6.98 (d, J = 8.1 Hz, 2H), 6.16 (d, J = 5.6 Hz, 1H), 4.39-4.35 (m, 1H), 4.25-4.17 (m, 8H), 4.05 (d, J = 9.3 Hz, 2H), 3.87 (s, 3H), 1.15 (d, J = 6.8 Hz, 3H). m/z 416 (M + H)$^+$. | 24 | 1.4 |
| 20-9 | Isomer B | | $^1$H NMR (400 MHz, DMSO-d$_6$) δ 8.10 (d, J = 5.6 Hz, 1H), 7.32 (d, J = 9.1 Hz, 1H), 6.98 (d, J = 7.8 Hz, 2H), 6.16 (d, J = 5.6 Hz, 1H), 4.39-4.32 (m, 1H), 4.25-4.18 (m, 8H), 4.05 (d, J = 9.1 Hz, 2H), 3.87 (s, 3H), 1.15 (d, J = 6.8 Hz, 3H). m/z 416 (M + H)$^+$. | 24 | 2.3 |
| 20-10 | Isomer A | | $^1$H NMR (400 MHz, DMSO-d$_6$) δ 7.97 (d, J = 2.5 Hz, 1H), 7.83 (d, J = 2.8 Hz, 1H), 7.32 (d, J = 8.3 Hz, 1H), 6.99 (d, J = 8.1 Hz, 2H), 4.37 (d, J = 7.1 Hz, 1H), 4.29-4.19 (m, 8H), 4.04 (d, J = 9.1 Hz, 2H), 2.40 (s, 3H), 1.15 (d, J = 6.8 Hz, 3H). m/z 400 (M + H)$^+$. | 8 | 1.3 |
| 20-10 | Isomer B | | $^1$H NMR (400 MHz, DMSO-d$_6$) δ 7.97 (d, J = 2.5 Hz, 1H), 7.83 (d, J = 2.8 Hz, 1H), 7.32 (d, J = 8.6 Hz, 1H), 6.99 (d, J = 8.1 Hz, 2H), 4.39-4.35 (m, 1H), 4.29-4.19 (m, 8H), 4.04 (d, J = 9.1 Hz, 2H), 2.40 (s, 3H), 1.15 (d, J = 6.8 Hz, 3H). m/z 400 (M + H)$^+$. | 8 | 1.8 |

| No. | Isomer | Structure | Data | SFC Method | Ret. Time (min) |
|---|---|---|---|---|---|
| 20-11 | Isomer A | | ¹H NMR (400 MHz, DMSO-d₆) δ 7.96 (d, J = 5.1 Hz, 1H), 7.33 (d, J = 8.8 Hz, 1H), 6.98 (d, J = 7.8 Hz, 2H), 6.53 (d, J = 4.8 Hz, 1H), 6.24 (s, 1H), 4.38-4.32 (m, 1H), 4.28-4.12 (m, 4H), 4.05 (d, J = 12.6 Hz, 6H), 2.24 (s, 3H), 1.15 (d, J = 6.6 Hz, 3H). m/z 399 (M + H)⁺. | 10 | 1.0 |
| 20-11 | Isomer B | | ¹H NMR (400 MHz, DMSO-d₆) δ 7.96 (d, J = 5.1 Hz, 1H), 7.33 (d, J = 8.8 Hz, 1H), 6.98 (d, J = 7.8 Hz, 2H), 6.53 (d, J = 5.1 Hz, 1H), 6.24 (s, 1H), 4.38-4.32 (m, 1H), 4.27-4.12 (m, 4H), 4.05 (d, J = 12.6 Hz, 6H), 2.24 (s, 3H), 1.15 (d, J = 6.6 Hz, 3H). m/z 399 (M + H)⁺. | 10 | 1.4 |
| 20-12 | Isomer A | | ¹H NMR (400 MHz, DMSO-d₆) δ 8.10 (d, J = 5.0 Hz, 1H), 7.20 (d, J = 8.7 Hz, 1H), 6.85 (d, J = 8.2 Hz, 2H), 6.48 (d, J = 5.0 Hz, 1H), 4.23 (q, J = 6.7 Hz, 1H), 4.15-3.99 (m, 8H), 3.92 (d, J = 9.2 Hz, 2H), 2.18 (s, 3H), 1.02 (d, J = 6.8 Hz, 3H). m/z 400 (M + H)⁺. | 6 | 6.9 |
| 20-12 | Isomer B | | ¹H NMR (400 MHz, DMSO-d₆) δ 8.10 (d, J = 4.9 Hz, 1H), 7.20 (d, J = 8.7 Hz, 1H), 6.85 (d, J = 8.0 Hz, 2H), 6.48 (d, J = 5.0 Hz, 1H), 4.23 (q, J = 6.6 Hz, 1H), 4.15-3.99 (m, 8H), 3.92 (d, J = 9.2 Hz, 2H), 2.18 (s, 3H), 1.02 (d, J = 6.8 Hz, 3H). m/z 400 (M + H)⁺. | 6 | 13.4 |
| 20-13 | Isomer A | 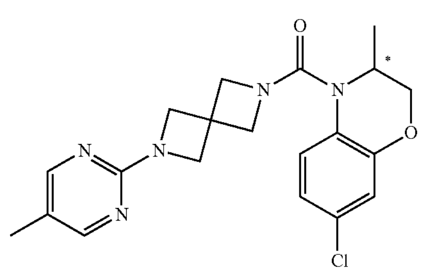 [SMILES: Cc1cnc(N2CC3(CN(C(=O)N4c5ccc(Cl)cc5OCC4C)C3)C2)nc1] | ¹H NMR (400 MHz, DMSO-d₆) δ 8.21 (s, 2H), 7.28 (d, J = 9.0 Hz, 1H), 6.94 (d, J = 7.9 Hz, 2H), 4.34-4.29 (m, 1H), 4.23-4.08 (m, 8H), 4.01 (d, J = 9.2 Hz, 2H), 2.09 (s, 3H), 1.11 (d, J = 6.8 Hz, 3H). m/z 400 (M + H)⁺. | 6 | 6.9 |

TABLE 14-continued

| No. | Isomer | Structure | Data | SFC Method | Ret. Time (min) |
|---|---|---|---|---|---|
| 20-13 | Isomer B | 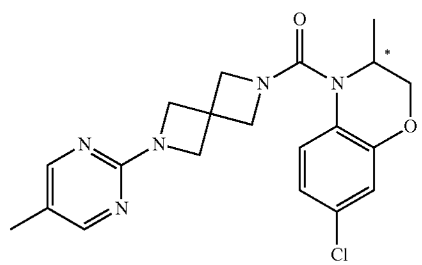 [SMILES: Cc1cnc(N2CC3(CN(C(=O)N4c5ccc(Cl)cc5OCC4C)C3)C2)nc1] | ¹H NMR (400 MHz, DMSO-d₆) δ 8.25 (s, 2H), 7.32 (d, J = 9.1 Hz, 1H), 6.98 (d, J = 8.1 Hz, 2H), 4.39-4.34 (m, 1H), 4.25-4.15 (m, 8H), 4.05 (d, J = 9.1Hz, 2H), 2.13 (s, 3H), 1.15 (d, J = 6.8 Hz, 3H). m/z 400 (M + H)⁺. | 6 | 13.5 |
| 20-14 | Isomer A | | ¹H NMR (400 MHz, DMSO-d₆) δ 8.07 (s, 1H), 7.18 (d, J = 8.3 Hz, 1H), 6.87-6.82 (m, 2H), 4.84 (s, 1H), 4.22 (d, J = 6.3 Hz, 1H), 4.13-3.93 (m, 8H), 3.91 (d, J = 9.2 Hz, 2H), 3.18 (s, 3H), 1.01 (d, J = 6.6 Hz, 3H). m/z 416 (M + H)⁺. | 20 | 1.2 |
| 20-14 | Isomer B | | ¹H NMR (400 MHz, DMSO-d₆) δ 8.07 (s, 1H), 7.18 (d, J = 8.3 Hz, 1H), 6.87-6.82 (m, 2H), 4.84 (s, 1H), 4.24-4.19 (m, 1H), 4.12-3.88 (m, 10H), 3.18 (s, 3H), 1.01 (d, J = 6.8 Hz, 3H). m/z 416 (M + H)⁺. | 20 | 1.6 |
| 20-15 | Isomer A | | ¹H NMR (400 MHz, DMSO-d₆) δ 8.49 (dd, J = 1.3, 4.5 Hz, 1H), 8.06 (dd, J = 1.4, 8.0 Hz, 1H), 7.33 (d, J = 9.1 Hz, 1H), 7.07 (dd, J = 4.5, 7.8 Hz, 1H), 6.99 (d, J = 8.1 Hz, 2H), 4.37 (d, J = 7.6 Hz, 1H), 4.28-4.21 (m, 7H), 4.18-4.14 (m, 1H), 4.07 (d, J = 9.1 Hz, 2H), 3.88 (s, 3H), 1.15 (d, J = 6.8 Hz, 3H). m/z 439 (M + H)⁺. | 21 | 1.8 |
| 20-15 | Isomer B | | ¹H NMR (400 MHz, DMSO-d₆) δ 8.49 (d, J = 3.0 Hz, 1H), 8.06 (dd, J = 1.1, 8.0 Hz, 1H), 7.33 (d, J = 8.8 Hz, 1H), 7.07 (dd, J = 4.7, 8.0 Hz, 1H), 6.99 (d, J = 8.1 Hz, 2H), 4.37 (d, J = 6.8 Hz, 2H), 4.28-4.21 (m, 7H), 4.15 (d, J = 9.6 Hz, 1H), 4.07 (d, J = 9.1 Hz, 2H), 3.88 (s, 3H), 1.15 (d, J = 6.8 Hz, 3H). m/z 439 (M + H)⁺. | 21 | 4.2 |

TABLE 14-continued

| No. | Isomer | Structure | Data | SFC Method | Ret. Time (min) |
|---|---|---|---|---|---|
| 20-16 | Isomer A | | $^1$H NMR (400 MHz, CDCl$_3$) δ 8.44 (d, J = 4.8 Hz, 1H), 7.22 (d, J = 9.3 Hz, 1H), 6.90-6.88 (m, 2H), 6.82 (d, J = 4.8 Hz, 1H), 4.50 (q, J = 6.9 Hz, 1H), 4.29-4.18 (m, 7H), 4.16 (dd, J = 2.4, 10.7 Hz, 1H), 3.93 (d, J = 9.5 Hz, 2H), 1.22 (d, J = 6.8 Hz, 3H). m/z 411 (M + H)$^+$. | 3 | 2.2 |
| 20-16 | Isomer B | | $^1$H NMR (400 MHz, CDCl$_3$) δ 8.44 (d, J = 4.8 Hz, 1H), 7.23-7.20 (m, 1H), 6.90-6.88 (m, 2H), 6.82 (d, J = 4.6 Hz, 1H), 4.50 (q, J = 6.9 Hz, 1H), 4.29-4.18 (m, 7H), 4.16 (dd, J = 2.7, 10.7 Hz, 1H), 3.93 (d, J = 9.5 Hz, 2H), 1.22 (d, J = 6.9 Hz, 3H). m/z 411 (M + H)$^+$. | 3 | 3.7 |

Example 24

Vasopressin V1a Receptor Antagonist Assay

The purpose of this assay was to determine the inhibitory effect of synthesized compounds on the Vasopressin V1a receptor. The assay was performed in Chinese Hamster Ovary (CHO) cells expressing the human Arginine Vasopressin Receptor 1a (AVPR1a). Arginine Vasopressin (AVP) evokes an increase in intracellular calcium in CHO-AVPR1a cells which is measured in a fluorescence assay on the FLIPR$^{TETRA}$ using calcium sensitive dyes. Test compounds were assessed for their ability to affect the magnitude of the response to AVP, with antagonists showing a concentration-dependent reduction in the AVP-mediated fluorescence. Compounds were tested in duplicate in a 10-point, 1:3 dilution series starting at a nominal concentration of 3 μM in the assay.

CHO-AVPR1a cells were maintained in routine culture in T175 Flasks at 37° C., 5% CO$_2$. The growth medium consists of Ham's F12 media supplemented with 10% v/v fetal bovine serum, 1× non-essential amino acids, and 0.4 mg/ml Geneticin G418.

On day one, cells were harvested from T175 flasks when they are 80-90% confluent by first washing the cell monolayer with PBS and then dissociated using trypsin 0.05%/EDTA (3 mL for a T175 Flask). The flasks were incubated at room temperature until the cells detached. To the cell suspension, 10 ml of growth media was added and the cell density determined using the Vi-Cell automated cell counter. The cells were spun at 1000 rpm for 3 minutes, then the supernatant was carefully removed and discarded. The cell pellet was re-suspended at 6.0e$^5$ cells/ml in growth media. 25 μL of cells in growth media was dispensed into each well (15,000 cells per well) of a poly-D-lysine coated black, clear bottomed, 384-well plate. The plates were incubated at 37° C., 5% CO$_2$ overnight.

At the start of each assay day, the potency of AVP was assessed and an EC$_{80}$ concentration determined for subsequent compound profiling. Assays were performed using a two-step addition protocol on the FLIPR$^{TETRA}$; first addition of 5 μl of control or test compound at 10× final in assay buffer with 15 min incubation at 37° C., 5% CO$_2$ followed by 10 μl of AVP at 6× final concentration in assay buffer. Changes in fluorescence were monitored for 3 min after both additions on the FLIPR$^{TETRA}$ using 470-495 nm excitation and 515-575 nm emission wavelengths. The assay buffer consisted of HBSS (+Ca/+Mg) supplemented with 20 mM HEPES, and for the preparation of the AVP agonist only, 0.1% w/v bovine serum albumin. The assay was initiated by the removal of growth media from the cells and replacement with 45 μl of Calcium-6 dye (Molecular Devices) prepared at 1× in assay buffer. Cells were loaded with dye for 60-90 min at 37° C., 5% CO$_2$ before initiation of the FLIPR$^{TETRA}$ protocol. For the AVP potency determination, the first addition consisted of assay buffer containing 3% v/v DMSO and the second addition, a 10-point dilution series of AVP (1:3 dilutions from 1 μM) in assay buffer supplemented with 0.1% BSA. For compound profiling, test compounds were first serially diluted in DMSO (10-point curve, 1:3 dilutions) then diluted 33.3-fold in assay buffer prior to addition to the dye loaded cells on the FLIPR$^{TETRA}$. At the end of the incubation period, 10 μl of AVP in assay buffer containing 0.1% BSA was added at the previously determined EC$_{80}$ concentration.

In-plate controls for the assay included balovaptan and PF-184563 concentration-response curves as reference V1a antagonists, and an AVP concentration-response curve to confirm the reproducibility of the EC$_{80}$ used for the compound challenge.

MAX-MIN raw data was normalised to in-plate assay controls comprising DMSO matched solutions of 300 nM SR49059 (100% inhibition) and AVP $EC_{80}$ (0% inhibition).

Selectivity profiling of certain example compounds was determined against Vasopressin V1b and V2 receptors.

Example 25

Vasopressin V1b Receptor Antagonist Assay

The purpose of the assay was to determine the inhibitory effect of synthesized compounds on the Vasopressin V1b receptor. The assay was performed in Chinese Hamster Ovary (CHO) cells expressing the human Arginine Vasopressin Receptor 1b (AVPR1b). Arginine Vasopressin (AVP) evokes an increase in intracellular calcium in CHO-AVPR1b cells which is measured in a fluorescence assay on the FLIPR$^{TETRA}$ using calcium sensitive dyes. Test compounds were assessed for their ability to affect the magnitude of the response to AVP, with antagonists showing a concentration-dependent reduction in the AVP-mediated fluorescence.

CHO-AVPR1b cells were maintained in routine culture in T175 Flasks at 37° C., 5% CO2. The growth medium consisted of Ham's F12 media supplemented with 10% v/v fetal bovine serum, 1× non-essential amino acids, and 0.4 mg/ml Geneticin G418.

Cells were harvested from T175 flasks when they were 80-90% confluent by first washing the cell monolayer with PBS and then dissociated using trypsin 0.05%/EDTA (3 mL for a T175 Flask). The flasks were incubated at room temperature until the cells detached. To the cell suspension, 10 ml of growth media was added and the cell density determined using the Vi-Cell automated cell counter. The cells were spun at 1000 rpm for 3 minutes, then the supernatant was carefully removed and discarded. The cell pellet was re-suspended at $6.0e^5$ cells/ml in growth media. 25 µL of cells in growth media was dispensed into each well (15,000 cells per well) of a poly-D-lysine coated black, clear bottomed, 384-well plate. The plates were incubated at 37° C., 5% $CO_2$ overnight.

At the start of each assay day, the potency of AVP was assessed and an $EC_{80}$ concentration determined for subsequent compound profiling. Assays were performed using a two-step addition protocol on the FLIPR$^{TETRA}$; first addition of 5 µl of control or test compound at 10× final in assay buffer with 15 min incubation at 37° C., 5% $CO_2$ followed by 10 µl of AVP at 6× final concentration in assay buffer. Changes in fluorescence were monitored for 3 min after both additions on the FLIPR$^{TETRA}$ using 470-495 nm excitation and 515-575 nm emission wavelengths. The assay buffer consisted of HBSS (+Ca/+Mg) supplemented with 20 mM HEPES, and for the preparation of the AVP agonist only, 0.1% w/v bovine serum albumin. The assay was initiated by the removal of growth media from the cells and replacement with 45 µl of Calcium-6 dye (Molecular Devices) prepared at 1× in assay buffer. Cells were loaded with dye for 60-90 min at 37° C., 5% $CO_2$ before initiation of the FLIPR$^{TETRA}$ protocol. For the AVP potency determination, the first addition consisted of assay buffer containing 3% v/v DMSO and the second addition a 10-point dilution series of AVP (1:3 dilutions from 1 µM) in assay buffer supplemented with 0.1% BSA. For compound profiling, test compounds were first serially diluted in DMSO (10-point curve, 1:3 dilutions) then diluted 33.3-fold in assay buffer prior to addition to the dye loaded cells on the FLIPR$^{TETRA}$. At the end of the incubation period 10 µl of AVP in assay buffer containing 0.1% BSA was added at the previously determined $EC_{80}$ concentration.

In-plate controls for the assay included a Nelivaptan concentration-response curve as the reference V1b antagonist and an AVP concentration-response curve to confirm the reproducibility of the $EC_{80}$ used for the compound challenge.

MAX-MIN raw data was normalised to in-plate assay controls comprising DMSO matched solutions of 3 µM nelivaptan (100% inhibition) and AVP $EC_{80}$ (0% inhibition).

Example 26

Vasopressin V2 Receptor Antagonist Assay

The purpose of the assay was to determine the inhibitory effect of synthesized compounds on the Vasopressin receptor 2. The assay was performed in commercially available 1321N1 cells expressing the human Arginine Vasopressin Receptor V2 (AVPR2) (Perkin Elmer #ES-363-CF). Arginine Vasopressin (AVP) evokes an increase in intracellular cAMP in these cells which is measured in a TR-FRET assay using a Europium cAMP tracer and ULight labelled antibody reagents contained in a LANCE Ultra cAMP kit (Perkin Elmer #TRF0263). Increases in cAMP in the assay result in a reduction in TR-FRET as the cAMP produced by the stimulated cells competes with the Eu-cAMP tracer for binding sites on the ULight labelled antibody. Test compounds were assessed for their ability to affect the magnitude of the response to AVP, with antagonists showing a concentration-dependent decrease in the AVP-mediated reduction in TR-FRET signal.

cAMPZen V2 assay ready cells were thawed at 37° C. and resuspended directly from frozen in 9 ml growth medium consisting of DMEM supplemented with 10% v/v fetal bovine serum, 1× non-essential amino acids, and 1 mM sodium pyruvate. Cells were spun at 1000 rpm for 3 minutes and the supernatant was carefully removed and discarded. The pellet was resuspended in 5 ml stimulation buffer and the cell density determined using the Vi-Cell automated cell counter. The cell suspension was diluted to a $0.2\times10^6$/ml suspension ready for plating. To all wells of a white 384-well Optiplate (Perkin Elmer #6007299) 5 µL of cells in stimulation buffer were dispensed (1,000 cells per well). Stimulation buffer consisted of HBSS (+Ca/+Mg) supplemented with 5 mM HEPES, 0.1% BSA stabiliser and 0.5 mM IBMX.

At the start of each assay day the potency of AVP was assessed and an $EC_{80}$ concentration determined for subsequent compound profiling. Assays were performed by first an addition of 2.5 µl of control or test compound at 4× final concentration in stimulation buffer followed by 2.5 µl of AVP at 4× final concentration in stimulation buffer. After a 1 hour reaction, detection reagents were added by first an addition of 5 µl EU-cAMP tracer, followed by 5 µl ULight-anti-cAMP both diluted as per the manufacturer's instructions. After a one hour incubation, plates were ready to be read (signals then remained stable for up to 24 hours). Changes in time resolved fluorescence were monitored with excitation via a laser (337 nm) measuring both 615 nm and 665 nm emission wavelengths. For the AVP potency determination the first addition consisted of stimulation buffer containing 3% v/v DMSO and the second addition a 10-point dilution series of AVP (1:3 dilutions from 0.1 nM) in stimulation buffer. For compound profiling, test compounds were dispensed by the Labcyte Echo (10-point curve, 1:3 dilutions) in a target 0.1 µl volume then diluted 750-fold in stimulation buffer containing 3% DMSO prior to addition to the cells. At the end of the incubation period, 2.5 µl of AVP in stimulation buffer was added at the previously determined $EC_{80}$ concentration.

In-plate controls for the assay included a Tolvaptan concentration-response curve as the reference V2 antagonist and an AVP concentration-response curve to confirm the reproducibility of the $EC_{80}$ used for the compound challenge.

Data for fluorescence at 665 nm is normalised to in-plate assay controls comprising DMSO matched solutions of assay buffer without agonist (100% inhibition) and AVP $EC_{80}$ (0% inhibition).

Example 27

Oxytocin Receptor (OTR) Antagonist Assay

This assay was performed in CHEM-1 cells expressing the human Oxytocin Receptor (hOTR) to determine the inhibitory effect of the compounds of the invention on the human Oxytocin receptor. Oxytocin evokes an increase in intracellular calcium in CHEM-1-hOTR cells which is measured in a fluorescence assay on the FLIPR$^{TETRA}$ using calcium sensitive dyes. Test compounds were assessed for their ability to affect the magnitude of the response to oxytocin, with antagonists showing a concentration-dependent reduction in the oxytocin-mediated fluorescence. Compounds displaying potency at the vasopressin V1a receptor of <100 nM were progressed to selectivity testing against hOTR and were tested in triplicate in a 10-point, 1:3 dilution series starting at a nominal concentration of 3 µM in the assay.

CHEM-1-hOTR ready was used to assay frozen cells (Eurofins #HTS090RTA) which are supplied with a proprietary Media Component.

Day 1 of the Assay:

Cells were thawed in a 37° C. water bath and diluted with the supplied Media Component to a final volume of 10 ml. The cell suspension was centrifuged at 1000 rpm for 3 min at room temperature and the supernatant was discarded. The cell pellet was resuspended in Media Component (10.5 ml) and the cells (25 µL) were dispensed into a poly-D-lysine coated black, clear bottomed, 384-well plate. The plates were incubated overnight at 37° C., 5% $CO_2$.

Day 2:

At the start of each assay day the potency of oxytocin was assessed and an $EC_{80}$ concentration was determined for subsequent compound profiling. Assays were performed using a two-step addition protocol on the FLIPR$^{TETRA}$; first addition of 5 µl of control or test compound at 10× final in assay buffer with 15 min incubation at 37° C., 5% $CO_2$ followed by 10 µl of oxytocin at 6× final concentration in assay buffer. Changes in fluorescence were monitored for 3 min after both additions on the FLIPR$^{TETRA}$ using 470-495 nm excitation and 515-575 nm emission wavelengths. The assay buffer consisted of HBSS (+Ca/+Mg) supplemented with 20 mM HEPES, and for the preparation of the oxytocin agonist only, 0.1% w/v bovine serum albumin. The assay was initiated by the removal of growth media from the cells and replaced with 45 µl of Calcium-6 dye (Molecular Devices) prepared at 1× in assay buffer. Cells were loaded with dye for 60-90 min at 37° C., 5% $CO_2$ before initiation of the FLIPR$^{TETRA}$ protocol. For the oxytocin potency determination the first addition consisted of assay buffer containing 3% v/v DMSO and the second addition involved a 10-point dilution series of oxytocin (1:3 dilutions from 1 µM) in assay buffer supplemented with 0.1% BSA. For compound profiling, test compounds were first serially diluted in DMSO (10-point curve, 1:3 dilutions) then diluted 33.3-fold in assay buffer prior to addition to the dye loaded cells on the FLIPR$^{TETRA}$. At the end of the incubation period 10 µl of oxytocin in assay buffer containing 0.1% BSA was added at the previously determined $EC_{80}$ concentration.

In-plate controls for the assay included a L-368,899 concentration-response curve as the reference OTR antagonist and an oxytocin concentration-response curve to confirm the reproducibility of the $EC_{80}$ used for the compound challenge.

MAX-MIN raw data is normalised to in-plate assay controls comprising DMSO matched solutions of assay buffer without agonist (100% inhibition) and oxytocin $EC_{80}$ (0% inhibition).

Activity expressed as $IC_{50}$ of representative compounds against the V1a (Example 24), V1b (Example 25), V2 (Example 26) and OTR (Example 27) receptors is provided in Table 15 below. With respect to V1a, V1b, V2 and OTR activity: "++++" denotes an $IC_{50}$ of less than 100 nM; "+++" denotes an $IC_{50}$ of from 100 nM to less than 500 nM; "++" denotes an $IC_{50}$ of from 500 nM to less than 1000 nM; and "+" denotes an $IC_{50}$ of 1000 nM or more.

TABLE 15

Activity of Representative Compounds

| No. | V1a $IC_{50}$ (nM) | V1b $IC_{50}$ (nM) | V2 $IC_{50}$ (nM) | OTR $IC_{50}$ (nM) |
| --- | --- | --- | --- | --- |
| 1-1 | ++++ | + | — | — |
| 1-2 | ++++ | — | — | — |
| 1-3 | ++++ | + | +++ | ++ |
| 1-4 | ++++ | + | + | — |
| 1-5 | ++++ | + | + | — |
| 1-6 | ++++ | — | — | — |
| 1-7 | +++ | — | — | — |
| 1-8 | +++ | — | — | — |
| 1-9 | ++ | — | — | — |
| 1-10 | +++ | — | — | — |
| 1-11 | + | — | — | — |
| 1-12 | + | — | — | — |
| 1-13 | ++++ | — | — | — |
| 1-14 | ++++ | + | + | — |
| 1-15 | ++++ | + | + | — |
| 1-16 | +++ | — | — | — |
| 1-17 | +++ | — | — | — |
| 1-18 | ++++ | + | + | — |
| 1-19 | ++++ | — | — | — |
| 1-20 | ++++ | + | + | — |
| 1-21 | ++++ | — | — | — |
| 1-22 | ++++ | + | + | + |
| 1-23 | ++++ | — | — | — |
| 1-24 | ++ | — | — | — |
| 1-25 | + | — | — | — |
| 1-26 | +++ | — | — | — |
| 1-27 | +++ | — | — | — |
| 1-28 | + | — | — | — |
| 1-29 | ++++ | — | — | — |
| 1-30 | ++++ | + | ++ | ++ |
| 1-31 | +++ | — | — | — |
| 1-32 | +++ | — | — | — |
| 1-33 | ++++ | — | — | — |
| 1-34 | + | — | — | — |
| 1-35 | + | — | — | — |
| 1-36 | + | — | — | — |
| 1-37 | +++ | — | — | — |
| 1-38 | ++++ | — | — | — |
| 1-39 | ++++ | + | + | +++ |
| 1-40 | +++ | — | — | — |
| 1-41 | +++ | — | — | — |
| 1-42 | +++ | — | — | — |
| 1-43 | ++++ | + | + | — |

TABLE 15-continued

Activity of Representative Compounds

| No. | V1a IC$_{50}$ (nM) | V1b IC$_{50}$ (nM) | V2 IC$_{50}$ (nM) | OTR IC$_{50}$ (nM) |
|---|---|---|---|---|
| 1-44 | ++++ | — | — | — |
| 1-45 | ++++ | + | + | — |
| 1-46 | ++++ | — | — | — |
| 1-47 | ++++ | — | — | — |
| 1-48 | +++ | — | — | — |
| 1-49 | ++++ | + | + | — |
| 1-50 | ++++ | — | — | — |
| 1-51 | ++++ | + | + | + |
| 1-52 | ++++ | — | — | — |
| 1-53 | ++++ | + | + | — |
| 1-54 | +++ | — | — | — |
| 1-55 | ++++ | — | — | — |
| 1-55-A | ++ | — | — | — |
| 1-55-B | ++++ | + | ++++ | ++++ |
| 1-56 | ++++ | — | — | — |
| 1-57 | ++++ | — | — | — |
| 1-57-A | ++++ | + | ++++ | — |
| 1-57-B | + | — | — | ++++ |
| 1-58 | ++++ | — | — | — |
| 1-58-A | + | — | — | — |
| 1-58-B | ++++ | + | ++++ | ++++ |
| 1-59 | ++++ | — | — | — |
| 1-59-A | + | — | — | — |
| 1-59-B | ++++ | + | +++ | +++ |
| 1-60 | ++++ | + | +++ | ++++ |
| 1-60-A | ++ | — | — | — |
| 1-60-B | ++++ | + | ++++ | ++++ |
| 1-61 | ++ | — | — | — |
| 1-62 | ++++ | — | — | — |
| 1-62-A | + | — | — | — |
| 1-62-B | ++++ | — | — | — |
| 1-63 | +++ | — | — | — |
| 1-64 | ++++ | + | + | — |
| 1-65 | ++++ | — | — | — |
| 1-65-A | + | — | — | — |
| 1-65-B | ++++ | + | + | +++ |
| 1-66 | ++++ | — | — | — |
| 1-66-A | + | — | — | — |
| 1-66-B | ++++ | + | ++ | +++ |
| 1-67 | ++++ | + | + | +++ |
| 1-67-A | ++++ | + | +++ | +++ |
| 1-67-B | + | — | — | — |
| 1-68 | ++++ | + | + | — |
| 1-69 | ++++ | + | + | + |
| 1-70 | ++++ | + | + | + |
| 1-71 | ++++ | + | + | — |
| 1-72 | ++++ | + | — | — |
| 1-73 | ++++ | — | — | — |
| 1-73-A | ++++ | + | + | — |
| 1-73-B | ++++ | + | ++++ | ++++ |
| 1-74 | + | — | — | — |
| 1-75 | + | — | — | — |
| 1-76 | ++++ | + | + | — |
| 1-77 | ++++ | + | + | — |
| 1-78 | ++++ | + | + | + |
| 1-79 | ++++ | + | + | — |
| 1-80 | ++++ | — | — | — |
| 1-81 | ++++ | + | + | — |
| 1-82 | ++++ | — | — | — |
| 1-83-A | +++ | — | — | — |
| 1-83-B | ++++ | + | + | +++ |
| 2-1 | + | — | — | — |
| 2-2 | + | — | — | — |
| 2-3 | + | — | — | — |
| 2-4 | + | — | — | — |
| 2-5 | + | — | — | — |
| 2-6 | + | — | — | — |
| 3-1 | ++++ | — | — | — |
| 4-1 | ++++ | + | + | — |
| 4-2 | ++++ | + | + | — |
| 4-3 | ++++ | + | + | — |
| 4-3-A | +++ | — | — | — |
| 4-3-B | ++++ | + | ++ | + |
| 5-1 | +++ | — | — | — |
| 6-1 | ++++ | + | + | — |
| 7-1 | +++ | — | — | — |
| 8-1 | +++ | — | — | — |
| 8-2 | ++++ | + | + | — |
| 8-3 | ++++ | + | + | — |
| 8-4 | ++++ | + | — | + |
| 8-5 | + | — | — | — |
| 8-6 | + | — | — | — |
| 8-7 | + | — | — | — |
| 8-8 | ++++ | — | — | — |
| 8-9 | ++++ | — | — | — |
| 8-10 | ++++ | — | — | — |
| 8-11 | ++++ | + | + | — |
| 8-12 | ++++ | + | + | ++ |
| 8-13 | ++++ | + | + | + |
| 8-14 | ++++ | + | + | — |
| 8-15 | ++++ | — | — | — |
| 8-16 | ++++ | + | ++++ | ++++ |
| 8-17 | +++ | — | — | — |
| 9-1 | ++++ | + | + | +++ |
| 9-1-A | + | + | + | — |
| 9-1-B | ++++ | + | + | +++ |
| 9-2 | ++++ | + | + | — |
| 9-3 | ++++ | + | + | ++ |
| 9-3-A | ++++ | + | + | ++ |
| 9-3-B | ++++ | — | — | — |
| 9-4 | ++++ | — | — | — |
| 9-4-A | +++ | — | — | — |
| 9-4-B | ++++ | + | + | + |
| 9-5 | ++++ | — | — | — |
| 9-6 | ++++ | + | + | — |
| 9-7 | ++++ | + | + | + |
| 9-8 | ++++ | — | — | — |
| 9-9 | ++++ | — | — | — |
| 10-1 | + | — | — | — |
| 11-1 | ++++ | + | ++++ | ++++ |
| 12-1 | ++++ | + | +++ | ++ |
| 12-1-A | + | — | — | — |
| 12-1-B | ++++ | + | +++ | +++ |
| 13-1 | ++++ | + | — | + |
| 13-1-A | ++++ | + | + | + |
| 13-1-B | ++++ | + | + | + |
| 13-2 | ++++ | — | — | — |
| 13-2-A | ++++ | + | + | ++ |
| 13-2-B | ++++ | + | + | ++ |
| 13-3 | ++++ | + | + | + |
| 13-3-A | ++++ | + | + | + |
| 13-3-B | ++++ | + | + | + |
| 13-4 | ++++ | — | — | — |
| 13-4-A | ++++ | — | — | — |
| 13-4-B | ++++ | — | — | — |
| 13-5 | ++++ | — | — | — |
| 13-5-A | ++++ | — | — | — |
| 13-5-B | ++++ | — | — | — |
| 14-1 | ++++ | + | + | + |
| 15-1 | ++++ | — | — | — |
| 16-1 | ++++ | — | — | — |
| 17-1 | ++++ | + | + | — |
| 18-1 | ++++ | + | + | — |
| 18-2 | ++++ | — | — | — |
| 18-2-A | ++++ | — | — | — |
| 18-2-B | ++++ | + | +++ | +++ |
| 18-3 | ++++ | + | +++ | + |
| 18-3-A | + | — | — | — |
| 18-3-B | ++++ | + | +++ | + |
| 18-4-A | + | — | — | — |
| 18-4-B | ++++ | + | + | — |
| 18-5-A | + | — | — | — |
| 18-5-B | ++++ | — | — | — |
| 19-1 | ++++ | + | + | — |
| 19-1-A | + | — | — | — |
| 19-1-B | ++++ | + | + | + |
| 19-2 | ++++ | + | + | ++ |
| 19-2-A | +++ | — | — | — |

TABLE 15-continued

Activity of Representative Compounds

| No. | V1a IC$_{50}$ (nM) | V1b IC$_{50}$ (nM) | V2 IC$_{50}$ (nM) | OTR IC$_{50}$ (nM) |
|---|---|---|---|---|
| 19-2-B | ++++ | + | +++ | ++ |
| 19-3 | ++++ | + | + | — |
| 19-3-B | ++++ | + | + | — |
| 19-4 | ++++ | + | + | +++ |
| 19-4-A | ++++ | + | + | +++ |
| 19-4-B | ++++ | — | — | — |
| 19-5 | ++++ | + | ++++ | +++ |
| 19-5-A | +++ | — | — | — |
| 19-5-B | ++++ | + | ++++ | — |
| 19-6 | ++++ | + | + | +++ |
| 20-1 | ++++ | + | + | +++ |
| 20-1-A | + | — | — | — |
| 20-1-B | ++++ | + | + | — |
| 20-2 | ++++ | + | ++++ | +++ |
| 20-2-A | ++ | + | + | — |
| 20-2-B | ++++ | + | ++++ | +++ |
| 20-3 | ++++ | — | — | — |
| 20-3-A | + | — | — | — |
| 20-3-B | ++++ | + | +++ | +++ |
| 20-4 | ++++ | — | — | — |
| 20-4-A | + | — | — | — |
| 20-4-B | ++++ | + | ++++ | ++ |
| 20-5 | ++++ | — | — | — |
| 20-5-A | ++++ | — | — | — |
| 20-5-B | ++++ | + | ++++ | +++ |
| 20-6 | ++++ | + | ++++ | ++++ |
| 20-6-A | + | — | — | — |
| 20-6-B | ++++ | + | ++++ | ++++ |
| 20-7 | ++++ | + | +++ | +++ |
| 20-7-A | + | — | — | — |
| 20-7-B | ++++ | + | ++++ | +++ |
| 20-8 | ++++ | + | +++ | +++ |
| 20-8-A | +++ | — | — | — |
| 20-8-B | ++++ | + | ++++ | +++ |
| 20-9 | ++++ | + | +++ | +++ |
| 20-9-A | + | — | — | — |
| 20-9-B | ++++ | + | +++ | ++ |
| 20-10 | ++++ | + | ++ | +++ |
| 20-10-A | ++++ | + | +++ | +++ |
| 20-10-B | + | — | — | — |
| 20-11 | ++++ | + | ++++ | +++ |
| 20-11-A | ++ | — | — | — |
| 20-11-B | ++++ | — | — | — |
| 20-12 | ++++ | + | ++++ | +++ |
| 20-12-A | + | — | — | — |
| 20-12-B | ++++ | + | ++++ | ++++ |
| 20-13 | ++++ | + | +++ | — |
| 20-13-B | ++++ | + | ++++ | — |
| 20-13-A | + | — | — | + |
| 20-14 | +++ | — | — | — |
| 20-14-A | + | — | — | — |
| 20-14-B | ++++ | + | ++ | — |
| 20-15-A | +++ | — | — | — |
| 20-15-B | ++++ | + | ++++ | ++ |
| 20-16-A | + | — | — | — |
| 20-16-B | ++++ | — | — | — |
| 21-1 | ++++ | + | + | ++ |
| 21-2 | ++++ | + | + | +++ |
| 21-3 | ++++ | + | ++++ | ++++ |
| 21-4 | ++++ | + | +++ | ++ |
| 21-5 | ++++ | + | +++ | +++ |
| 21-6 | ++++ | + | + | +++ |
| 21-7 | +++ | — | — | — |
| 21-8 | ++++ | + | +++ | +++ |
| 21-9 | ++++ | + | +++ | + |
| 21-10 | ++++ | + | +++ | ++ |
| 21-11 | ++++ | + | ++ | — |

Example 28

MDCK-MDR1 Effective Efflux Ratio

The MDR1-MDCK effective efflux assay was performed as described in the BioFocus Standard Operating Procedure, ADME-SOP-56. Both wild-type (WT) and MDR1-MDCK cells (Solvo Biotechnology) were seeded onto 24-well Transwell plates at 2.35×105 cells per well and used in confluent monolayers after a 3 day culture at 37° C. under 5% CO2. For both cell types, test and control compounds (propranolol, vinblastine) were added (10 μM, 0.1% DMSO final, n=2) to donor compartments of the Transwell plate assembly in assay buffer (Hanks balanced salt solution supplemented with 25 mM HEPES, adjusted to pH 7.4) for both apical to basolateral (A>B) and basolateral to apical (B>A) measurements. Incubations were performed at 37° C., with samples removed from both donor and acceptor chambers at T=0 and 1 hour and compound analysed by mass spectrometry (LC-MS/MS) including an analytical internal standard.

Apparent permeability (Papp) values were determined from the relationship:

$$\text{Papp} = [\text{CompoundAcceptor } T=\text{end}] \times V\text{ Acceptor}/([\text{Compound Donor } T=0] \times V\text{ Donor})/\text{incubation time} \times V\text{ Donor}/\text{Area} \times 60 \times 10^{-6} \text{ cm/s}$$

In this equation, V is the volume of each Transwell compartment (apical 125 μL, basolateral 600 μL), and concentrations are the relative MS responses for compound (normalized to internal standard) in the donor chamber before incubation and acceptor chamber at the end of the incubation, and Area is the area of cells exposed for drug transfer (0.33 cm$^2$).

Efflux ratios (Papp B>A/Papp A>B) were calculated for each compound from the mean Papp values in each direction for both wild-type and MDR1-MDCK cells. The MDR1-MDCK cell line has been engineered to over-express the efflux transporter, MDR1 (P-glycoprotein), and a finding of good permeability B>A, but poor permeability A>B, indicates that a compound is a substrate for this transporter.

In order to confirm the involvement of MDR1 in any efflux seen, an "effective efflux ratio" (EER) was calculated by comparing compound efflux ratios (ER) in the two cell types by the following equation:

$$\text{EER} = \text{ER}(\text{MDR1-MDCK})/\text{ER}(\text{wild-type MDCK})$$

This ratio illustrates the effect of the over-expressed MDR1 normalised for the background movement of compound through the wild-type cells.

Lucifer Yellow (LY) was added to the apical buffer in all wells to assess viability of the cell layer. As LY cannot freely permeate lipophilic barriers, a high degree of LY transport indicates poor integrity of the cell layer and wells with a LY Papp>10×10$^{-6}$ cm/s were rejected. (Note that an integrity failure in one well does not affect the validity of other wells on the plate.) Compound recovery from the wells was determined from MS responses (normalized to internal standard) in donor and acceptor chambers at the end of incubation compared to response in the donor chamber pre-incubation. Recoveries <50% indicates compound solubility, stability or binding issues, thereby reducing the reliability of a result.

The inherent ability of a potential drug molecule to penetrate the blood brain barrier and avoid efflux by transporters expressed in the brain, can be roughly correlated with the Papp(A-B) and the efflux ratio (as defined above), respectively. A potential drug molecule with an apparent permeability <7 (10^−6 cm/sec) has low permeability (+), >7 (10^−6 cm/sec) but <10 (10^−6 cm/sec) has moderate permeability (++), >10 (10^−6 cm/sec) but <20 (10^−6 cm/sec) has good permeability (+++), and >20 (10^−6 cm/sec) is highly permeable (++++). High permeability in the WT and MDCK II cell permeability assay increases the probability of blood brain barrier penetration and access to the CNS. A potential drug molecule in the above assay system with an efflux ratio or effective efflux ratio of <1 has low probability of being an efflux substrate (++++), >1 but <2 has moderate probability of being an efflux substrate (+++), >2 but <3 has has an increased probability of being an efflux substrate (++), and >3 has a high probability of being an efflux substrate (+). If a potential drug molecule is an efflux substrate, the molecule will have a low probability of reaching exposures in the brain (site of action) that will result in efficacious levels of receptor occupancy.

TABLE 16

| | Papp ($10^{-6}$ cm/sec) A -> B, Efflux Ratio (ER), and Effective Efflux Ratio (EER) | | | | |
|---|---|---|---|---|---|
| No. | Papp AB WT | ER WT | Papp AB MDR1 | ER MDR1 | EER |
| 1-18 | ++++ | ++++ | ++++ | ++++ | ++++ |
| 1-22 | ++++ | ++++ | ++++ | +++ | +++ |
| 1-58B | ++++ | +++ | ++++ | +++ | +++ |
| 1-59B | ++++ | ++++ | ++++ | +++ | +++ |
| 1-60 | ++++ | ++++ | ++++ | ++++ | ++++ |
| 1-60B | ++++ | ++++ | ++++ | ++++ | +++ |
| 1-64 | ++++ | ++++ | ++++ | +++ | +++ |
| 1-65B | ++++ | +++ | ++++ | +++ | ++++ |
| 1-70 | ++++ | +++ | ++++ | +++ | ++++ |
| 1-71 | ++++ | ++++ | ++++ | +++ | + |
| 1-72 | ++++ | ++++ | ++++ | ++++ | +++ |
| 1-83B | ++++ | ++++ | ++++ | +++ | +++ |
| 4-3 | ++++ | ++++ | ++++ | ++++ | ++++ |
| 4-3B | ++++ | ++++ | ++++ | ++++ | ++++ |
| 8-2 | ++++ | ++++ | ++++ | ++++ | +++ |
| 8-3 | ++++ | ++++ | ++++ | +++ | +++ |
| 8-4 | ++++ | +++ | ++++ | +++ | +++ |
| 8-11 | ++++ | ++++ | ++++ | ++++ | ++++ |
| 8-12 | ++++ | ++++ | ++++ | ++ | ++ |
| 8-14 | ++++ | +++ | ++++ | +++ | ++++ |
| 9-1B | ++++ | +++ | ++++ | + | ++ |
| 9-7 | ++++ | ++++ | ++++ | ++++ | +++ |
| 12-1A | ++++ | ++++ | ++++ | ++++ | +++ |
| 12-1B | ++++ | ++++ | ++++ | ++++ | +++ |
| 13-1 | ++++ | ++++ | ++++ | + | + |
| 13-1A | ++++ | ++++ | ++++ | + | + |
| 13-1B | ++++ | ++++ | ++++ | + | + |
| 13-2B | ++++ | +++ | ++++ | + | + |
| 13-3B | ++++ | +++ | ++++ | + | + |
| 17-1 | ++++ | ++++ | ++++ | ++++ | +++ |
| 18-2B | ++++ | ++++ | ++++ | ++++ | ++++ |
| 18-3 | ++++ | ++++ | ++++ | ++++ | ++++ |
| 18-3B | ++++ | ++++ | ++++ | ++++ | ++++ |
| 19-1B | ++++ | +++ | ++++ | +++ | ++++ |
| 19-2B | ++++ | +++ | ++++ | +++ | ++++ |
| 19-4 | ++++ | ++++ | ++++ | ++++ | ++++ |
| 19-4A | ++++ | +++ | ++++ | ++ | ++ |
| 19-5 | ++++ | ++++ | ++++ | +++ | +++ |
| 20-2 | ++++ | +++ | ++++ | +++ | +++ |
| 20-2A | ++++ | ++++ | ++++ | +++ | +++ |
| 20-2B | ++++ | ++++ | ++++ | +++ | +++ |
| 20-3 | ++++ | +++ | ++++ | +++ | ++++ |
| 20-3B | ++++ | ++++ | ++++ | +++ | +++ |
| 20-4B | ++++ | ++++ | ++++ | +++ | +++ |
| 20-6A | ++++ | ++++ | ++++ | ++++ | +++ |
| 20-6B | ++++ | ++++ | ++++ | ++++ | ++++ |
| 20-7A | ++++ | ++++ | ++++ | ++++ | ++++ |
| 20-7B | ++++ | ++++ | ++++ | ++++ | +++ |
| 20-8 | ++++ | ++++ | ++++ | ++++ | ++++ |
| 20-8B | ++++ | ++++ | ++++ | ++++ | ++++ |
| 20-9 | ++++ | ++++ | ++++ | ++++ | ++++ |
| 20-9B | ++++ | ++++ | ++++ | +++ | +++ |
| 20-10 | ++++ | ++++ | ++++ | ++++ | ++++ |
| 20-10A | ++++ | ++++ | ++++ | +++ | +++ |
| 20-11 | ++++ | ++++ | ++++ | ++++ | ++++ |
| 20-12B | ++++ | ++++ | ++++ | +++ | +++ |
| 20-13B | ++++ | ++++ | ++++ | +++ | +++ |
| 20-15B | ++++ | ++++ | ++++ | ++++ | +++ |
| 2-16B | ++++ | ++++ | ++++ | +++ | +++ |
| 21-1 | +++ | ++++ | ++ | +++ | ++ |
| 21-2 | ++++ | ++++ | ++++ | +++ | +++ |
| 21-3 | ++++ | ++++ | ++++ | +++ | +++ |
| 21-4 | ++++ | +++ | ++++ | + | + |
| 21-5 | ++++ | +++ | ++++ | +++ | ++++ |
| 21-6 | ++++ | ++++ | ++++ | ++++ | ++ |
| 21-8 | ++++ | ++++ | ++++ | +++ | ++ |
| 21-10 | +++ | +++ | +++ | +++ | +++ |

Example 29

Evaluation of Behavioral, Biochemical and/or Neurophysiological Characteristics in the Valproate Model Valproate (VPA) is an anticonvulsant drug commonly prescribed for patients with epilepsy. During pregnancy, administration of VPA elevates the risk of neurodevelopmental disorders in the offspring and this effect has been modeled similarly in rodents to better understand the mechanisms underlying the VPA-induced neurodevelopmental changes. V1a antagonists are assessed for preventative and/or restorative effects in rodents following the administration of a single injection of valproate acid (600 mg/kg) or vehicle (sham) to pregnant females dams on gestational day 13 (embryonic day 13). Pregnant dams are monitored on a daily basis for changes in weight and health, or in their feeding patterns. After birth, pups are monitored for any signs of physical abnormalities (e.g., weights, food and water intake, postnatal day of eye opening).

Selective studies are conducted to evaluate behavioral, biochemical and/or neurophysiological characteristics of the valproate treated animals as compared to control animals. More specifically, the effects of V1 antagonists administered to VPA treated animals are assessed using standard methodology for behavioral changes such as anxiety (e.g., ultrasonic vocalizations, elevated plus maze), learning and memory (e.g., Morris water maze, novel object recognition), social interactions, sensorimotor gating and locomotor activity. Biochemical changes are measured by assessing synaptic proteins and mRNA (e.g., gamma-aminobutyric acid [GABA] synthesis, glutamic acid decarboxylase [GAD], brain derived neurotrophic factor [BDNF]). Neurophysiological characteristics are assessed by whole cell recordings of the electrophysiological properties of neurons from VPA- and sham-treated animals to identify differences in neuronal function with and without V1 antagonists.

Activity and/or Telemetry Studies in Rodents and Non-Human Primates to Assess Sleep/Wake Cycles and Circadian Rhythms:

The vasopressin system is important in regulating biological circadian rhythms and re-entrainment following environmental alterations. In these studies, animals are housed on a 12 hour light/dark cycle and activity is monitored using an infrared beam break system or by wheel running (rodents) or by activity monitors attached to the collar of the animal (non-human primates). Activity data is collected for up to 30 days to establish circadian rhythms and changes induced by phase shifting the light/dark cycle by e.g., 4, 8 or 12 hours is recorded and analyzed. V1a antagonist is administered to improve re-entrainment as measured by re-establishment of the regular activity patterns. Additional endpoints may include cognitive assessment (e.g., spatial working memory).

Implantation of a telemetry device with electrodes to record electroencephalography/electromyography/electroculography (EEG/EMG/EOG) for staging sleep/wake cycles is used. In this case, EEG/EMG electrodes and transmitters are implanted in fully anesthetized animals by trained surgeons. The transmitter module is implanted subcutaneously below the scapular region or into the abdomen. Biopotential leads are guided subcutaneously from the back to the head via a midline incision. Using a stereotaxic approach, stainless steel screws are implanted into the skull over areas of interest until the tips are on the surface of the dura mater. The biopotential leads are wrapped around the screws and referenced. The EMG or EOG leads are sutured into the temporalis muscle or intra-ocular muscle, respectively. Animals receive postoperative analgesia and antibiotics and recover for a minimum of 21-days before testing. Receiver boards are placed in close proximity to the animal to facilitate real-time EEG/EMG/EOG recordings during testing.

Physiological Measures

Vasopressin is an important regulator of water conservation and blood pressure in the body and its release into the peripheral blood supply can be induced by an increase in plasma osmolality. In healthy adults, a rise in plasma osmolality of 1-2% above basal level produces thirst that promotes water intake and normalization of osmolality. Intravenous administration of a hyperosmolic solution to rodents or humans increases the plasma vasopressin concentration and other measures (e.g., thirst, urine output and vasoconstriction). V1a antagonist is evaluated for its ability to alter plasma vasopressin concentrations, vasoconstriction, urine output and/or qEEG parameters following administration of a normal saline (0.9% sodium chloride solution) or hyperosmolic solution (>0.9% sodium chloride solution).

Example 30

Arginine-Vasopressin (AVP) Induced Phospho-ERK Measurement in Native Tissue

When V1a receptors are coupled to phospholipase C (PLC), they increase intracellular Ca2+ concentrations and protein kinase C (PKC) activity, and transactivate the mitogen-activated protein kinases/extracellular signal-regulated kinase (MAPK/Erk) and PI3 kinase/Akt pathways upon activation (Chen et al., J Neuroendocrinol. 2010). Rat choroid plexus (RCP) cell lines express functional V1a receptors measured by increased calcium concentrations in response to V1a receptor agonists (Battle et al., Biochem. Biophys. Res. Comm. 2000). In these studies, RCP were stimulated with AVP and V1a receptor antagonists reference compounds relcovaptan and balovaptan and Compound No. 1-83B were evaluated.

RCP P9(18) cells were seeded 30K/well, in 100 µl growth medium containing 10% FBS in polystyrene 96-well plates and incubated at 37° C., 5% $CO_2$ and incubated overnight. The following day, the growth medium was replaced with 50 µl pre-warmed HBSS containing 20 mM HEPES and the cells were incubated at 37° C., 5% $CO_2$ for 1.5 hrs. 1 mM AVP (Sigma V9879) was freshly prepared in distilled water in a glass vial and diluted to 3× concentrations in HBSS containing 20 mM HEPES and 0.1% BSA in glass vials and kept on ice. Cells were treated with 25 µl 3× vehicle, 3× eBioscience Cell Stimulation Cocktail (Thermo Fisher Scientific 00-4970-93) or 3×AVP and incubated at 37° C., 5% CO2 for 5, 10 or 20 min. Final concentrations of AVP: 10, 100 or 1000 nM. Final concentrations of components in Cell Stimulation Cocktail: 81 nM PMA, 1.34 µM ionomycin, 0.2% ethanol. Cells were lysed with 25 µl 4×CST lysis buffer containing protease and phosphatase inhibitors, PMSF and SDS and then stored at −80° C., for 48 h. The lysates were thawed, centrifuged at 2000 g for 30 min at 4° C. and 40 µl supernatants assayed for pERK1/2 (Thr202/Tyr204; Thr185/Tyr187) and total ERK1/2 using MSD kit K15107D. The MSD ECL data for the lysates were corrected for no cell blanks, then phospho-protein levels expressed as a ratio to the total ERK1/2 level. The ratios were expressed as fold-change from the vehicle-treated control at each timepoint.

In a first study 1, the $IC_{50}$ values for relcovaptan, Compound No. 1-83B and balovaptan were 0.03 nM, 16.0 nM and 10.9 nM, respectively. In a second study, the $IC_{50}$ values for relcovaptan, Compound No. 1-83B and balovaptan were 0.08 nM, 20.0 nM and 13.6 nM, respectively. In these studies, relcovaptan and balovaptan were purchased commercially.

Example 31

Arginine-Vasopressin (AVP) Induced Behavior in Mouse

Administration of Arginine-Vasopressin (AVP) intracerebroventricularly (i.c.v.) elicits characteristic scratching, digging and grooming behavior in mice that can be measured readily and is sensitive to blockade with vasopressin antagonists (Meisenberg, Ann N Y Acad Sci. 525:257-69, 1988; Bleickardt et. al., Psychopharmacology (Berl). 202(4):711-8, 2009).

Male CD-1 mice (Charles River Germany) weighing 22-25 g upon the study in-life were used for this study. Animals were housed in groups of 4-5 per cage in standard temperature (22±1° C.) and light-controlled environment (lights on from 7 am to 8 pm), with ad libitum access to food and water. Prior to commencing any procedures to the mice, they were allowed to habituate in the vivarium for a minimum of 7 days. Anesthesia was induced in a plexiglass chamber for 2-3 min with 5% isoflurane and maintained through a snout mask with 1-2% isoflurane thereafter. A homeothermic blanket system with a rectal probe was used to monitor and maintain the animal's body temperature at 37.0° C.±1.5° C. during the operation. Anesthetized mice were placed in a stereotaxic apparatus and skin between the ears shaved and disinfected with povidone-iodine solution (Betadine). A 10-µl Hamilton syringe with 28-gauge needle was used for the i.c.v. injections. All animals receive identical AVP injections (3.689 µM) or sterile saline (0.9% sodium chloride solution) into the right lateral ventricle at the following coordinates: AP=+0.5 mm; ML=+1.0 mm; DV=−2.5 mm (approximately from bregma). The actual coordinates were calculated by the distance from the point in midline between the eyes and no skin incision was made. After the needle was placed in the ventricle and the AVP was delivered, the needle was left in place for 3 minutes before withdrawal. Finally, the mouse was detached from the anesthesia mask and immediately placed in a clean cage to commence the observation.

Mice were observed and video-recorded for 15 minutes following AVP/saline administration and behaviors were measured (in seconds) and a cumulative time was calculated. The following behaviors were considered as AVP-related: scratching of limbs or torso, digging, licking and face washing (swiping of face). Using this assay, balovaptan (100 and 300 mg/kg, po), JNJ-17308616 (30, 100 mg/kg, po) and Compound No. 1-83B (100, 300, 500 mg/kg, po) were evaluated for antagonist activity to AVP-induced scratching behaviors. Balovaptan was effective at 100 mg/kg, JNJ-17308616 showed weak effects at 100 mg/kg, and 1-83B was effective at 300 and 500 mg/kg.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A compound having the structure of Formula (I) or a pharmaceutically acceptable isomer, racemate, hydrate, solvate, isotope, or salt thereof:

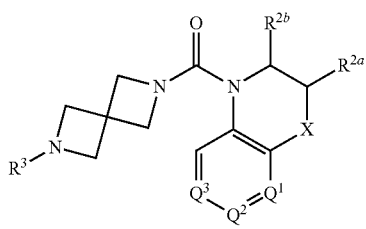

wherein:
X is —$(CR^xR^y)_nO(CR^xR^y)_q$—, —$(CR^xR^y)_nS(o)_t(CR^xR^y)_q$—, —$(CR^xR^y)_nN(R^x)(CR^xR^y)_q$—, or —$(CR^xR^y)_n$—, $R^x$ is, at each occurrence, independently H, lower alkyl, lower haloalkyl, halo, or $R^6$;

$R^y$ is, at each occurrence, independently H, —OH, lower alkyl, lower alkoxy, or halo;

$Q^1$ is N or $CR^{1a}$, $Q^2$ is N or $CR^{1b}$, and $Q^3$ is N or $CR^{1c}$, wherein at least one $Q^1$, $Q^2$, or $Q^3$ is not N;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^3$ is —$(CHR^z)_m$-Q-$(R^4)_p$, —$S(=O)_2R^5$, or —$C(=O)R^5$;

$R^z$ is H or $CH_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

$R^5$ is H, cycloalkyl, lower alkyl, lower haloalkyl, lower alkoxy, aryl, heteroaryl, cycloalkylalkyl, heterocyclyl, or —O-heterocyclyl;

$R^6$ is cycloalkyl, heterocyclyl, or —$C(=O)R^7$;

$R^7$ is H, lower alkyl, or lower haloalkyl;

n is 0, 1, or 2;

q is 0, 1, or 2;

t is 0, 1, or 2;

m is 0, 1, 2, 3, 4, 5, or 6; and p is 0, 1, or 2.

2. The compound of claim 1 having the structure of Formula (II):

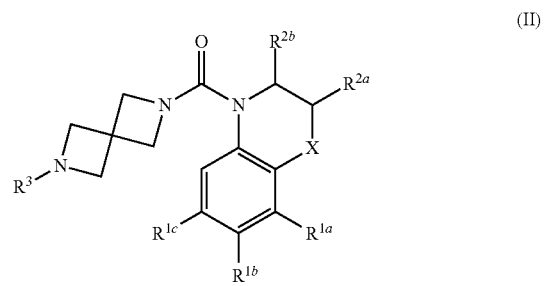

wherein:
X is —$(CR^xR^y)_nO(CR^xR^y)_q$—, —$(CR^xR^y)_nS(O)_t(CR^xR^y)_q$—, —$(CR^xR^y)_nN(R^x)(CR^xR^y)_q$—, or —$(CR^xR^y)_n$—, $R^x$ is, at each occurrence, independently H, lower alkyl, lower haloalkyl, halo, or $R^6$;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^3$ is —$(CHR^z)_m$-Q-$(R^4)_p$, —$S(=O)_2R^5$, or —$C(=O)R^5$;

$R^z$ is H or $CH_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

$R^5$ is H, cycloalkyl, lower alkyl, lower haloalkyl, lower alkoxy, aryl, heteroaryl, cycloalkylalkyl, heterocyclyl, or —O-heterocyclyl;

$R^6$ is cycloalkyl, heterocyclyl, or —$C(=O)R^7$;

$R^7$ is H, lower alkyl, or lower haloalkyl;

n is 0, 1, or 2;

q is 0, 1, or 2;

t is 0, 1, or 2;

m is 0, 1, 2, 3, 4, 5, or 6; and p is 0, 1, or 2.

3. The compound of claim 2 having the structure of Formula (II-a):

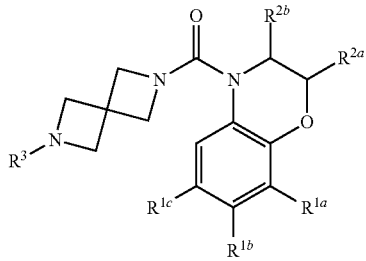

wherein:
R$^{1a}$, R$^{1b}$, and R$^{1c}$ are each, independently, H, lower alkyl, lower haloalkyl, lower alkoxy, cyano, or halo;
R$^{2a}$ and R$^{2b}$ are each, independently, H, lower alkyl, lower haloalkyl, or lower alkoxy;
R$^3$ is —(CHR$^z$)$_m$-Q-(R$^4$)$_p$, —S(=O)$_2$R$^5$, or —C(=O)R$^5$;
R$^z$ is H or CH$_3$
Q is aryl or heteroaryl;
R$^4$ is, at each occurrence, independently H, —OH, =O, cycloalkyl, lower alkyl, lower haloalkyl, lower alkoxy, lower haloalkoxy, halo, or cyano;
R$^5$ is H, cycloalkyl, lower alkyl, lower haloalkyl, lower alkoxy, cycloalkylalkyl, heterocyclyl, or —O-heterocyclyl;
m is 0, 1, 2, 3, 4, 5, or 6; and
p is 0, 1, or 2.

4. The compound of claim 3, wherein R$^3$ is —(CHR$^z$)$_m$-Q-(R$^4$)$_p$, m and p are both 0, and Q is heteroaryl.

5. The compound of claim 2 having the structure of Formula (II-b):

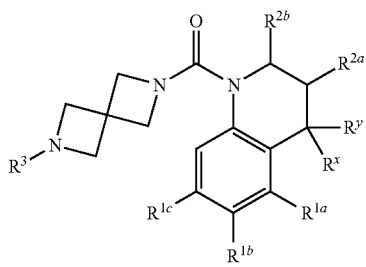

wherein:
R$^x$ is, at each occurrence, independently H, lower alkyl, lower haloalkyl, or halo;
R$^y$ is, at each occurrence, independently H, —OH, lower alkyl, lower alkoxy, or halo;
R$^{1a}$, R$^{1b}$, and R$^{1c}$ are each, independently, H, lower alkyl, lower haloalkyl, lower alkoxy, cyano, or halo;
R$^{2a}$ and R$^{2b}$ are each, independently, H, lower alkyl, lower haloalkyl, or lower alkoxy;
R$^3$ is —(CHR$^z$)$_m$-Q-(R$^4$)$_p$, —S(=O)$_2$R$^5$, or —C(=O)R$^5$;
R$^z$ is H or CH$_3$
Q is aryl or heteroaryl;
R$^4$ is, at each occurrence, independently H, —OH, =O, cycloalkyl, lower alkyl, lower haloalkyl, lower alkoxy, lower haloalkoxy, halo, or cyano;
R$^5$ is H, cycloalkyl, lower alkyl, lower haloalkyl, lower alkoxy, aryl, heteroaryl, cycloalkylalkyl, heterocyclyl, or —O-heterocyclyl;
m is 0, 1, 2, 3, 4, 5, or 6; and
p is 0, 1, or 2.

6. The compound of claim 2 having the structure of Formula (II-c):

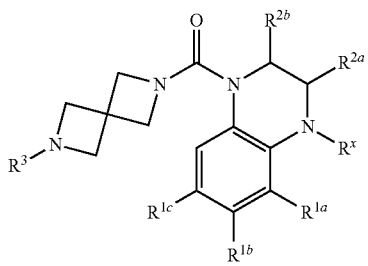

wherein:
R$^x$ is, at each occurrence, independently H, lower alkyl, lower haloalkyl, or halo;
R$^{1a}$, R$^{1b}$, and R$^{1c}$ are each, independently, H, lower alkyl, lower haloalkyl, lower alkoxy, cyano, or halo;
R$^{2a}$ and R$^{2b}$ are each, independently, H, lower alkyl, lower haloalkyl, or lower alkoxy;
R$^3$ is —(CHR$^z$)$_m$-Q-(R$^4$)$_p$, —S(=O)$_2$R$^5$, or —C(=O)R$^5$;
R$^z$ is H or CH$_3$
Q is aryl or heteroaryl;
R$^4$ is, at each occurrence, independently H, —OH, =O, cycloalkyl, lower alkyl, lower haloalkyl, lower alkoxy, lower haloalkoxy, halo, or cyano;
R$^5$ is H, cycloalkyl, lower alkyl, lower haloalkyl, lower alkoxy, aryl, heteroaryl, cycloalkylalkyl, heterocyclyl, or —O-heterocyclyl;
m is 0, 1, 2, 3, 4, 5, or 6; and
p is 0, 1, or 2.

7. The compound of claim 2 having the structure of Formula (II-d):

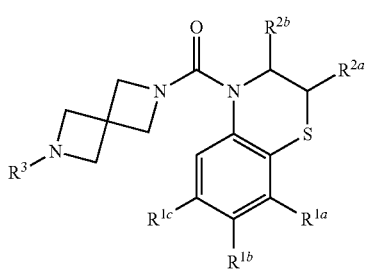

wherein:
R$^{1a}$, R$^{1b}$, and R$^{1c}$ are each, independently, H, lower alkyl, lower haloalkyl, lower alkoxy, cyano, or halo;
R$^{2a}$ and R$^{2b}$ are each, independently, H, lower alkyl, lower haloalkyl, or lower alkoxy;
R$^3$ is —(CHR$^z$)$_m$-Q-(R$^4$)$_p$, —S(=O)$_2$R$^5$, or —C(=O)R$^5$;
R$^z$ is H or CH$_3$
Q is aryl or heteroaryl;
R4 is, at each occurrence, independently H, —OH, =O, cycloalkyl, lower alkyl, lower haloalkyl, lower alkoxy, lower haloalkoxy, halo, or cyano;
R$^5$ is H, cycloalkyl, lower alkyl, lower haloalkyl, lower alkoxy, aryl, heteroaryl, cycloalkylalkyl, heterocyclyl, or —O-heterocyclyl;
m is 0, 1, 2, 3, 4, 5, or 6; and
p is 0, 1, or 2.

8. The compound of claim 2 having the structure of Formula (II-e):

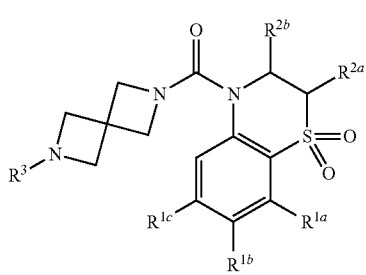

(II-e)

wherein:
- $R^{1a}$, $R^{1b}$, and $R^{1c}$ are each, independently, H, lower alkyl, lower haloalkyl, lower alkoxy, cyano, or halo;
- $R^{2a}$ and $R^{2b}$ are each, independently, H, lower alkyl, lower haloalkyl, or lower alkoxy;
- $R^3$ is —$(CHR^z)_m$-Q-$(R^4)_p$, —$S(=O)_2R^5$, or —$C(=O)R^5$;
- $R^z$ is H or $CH_3$
- Q is aryl or heteroaryl;
- $R^4$ is, at each occurrence, independently H, —OH, =O, cycloalkyl, lower alkyl, lower haloalkyl, lower alkoxy, lower haloalkoxy, halo, or cyano;
- $R^5$ is H, cycloalkyl, lower alkyl, lower haloalkyl, lower alkoxy, aryl, heteroaryl, cycloalkylalkyl, heterocyclyl, or —O-heterocyclyl;
- m is 0, 1, 2, 3, 4, 5, or 6; and
- p is 0, 1, or 2.

9. The compound of claim 2 having the structure of Formula (II-f):

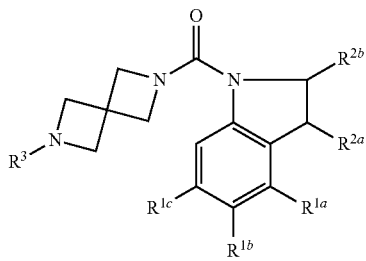

(II-f)

wherein:
- $R^{1a}$, $R^{1b}$, and $R^{1c}$ are each, independently, H, lower alkyl, lower haloalkyl, lower alkoxy, cyano, or halo;
- $R^{2a}$ and $R^{2b}$ are each, independently, H, lower alkyl, lower haloalkyl, or lower alkoxy;
- $R^3$ is —$(CHR^z)_m$-Q-$(R^4)_p$, —$S(=O)_2R^5$, or —$C(=O)R^5$;
- $R^z$ is H or $CH_3$
- Q is aryl or heteroaryl;
- R4 is, at each occurrence, independently H, —OH, =O, cycloalkyl, lower alkyl, lower haloalkyl, lower alkoxy, lower haloalkoxy, halo, or cyano;
- $R^5$ is H, cycloalkyl, lower alkyl, lower haloalkyl, lower alkoxy, aryl, heteroaryl, cycloalkylalkyl, heterocyclyl, or —O-heterocyclyl;
- m is 0, 1, 2, 3, 4, 5, or 6; and
- p is 0, 1, or 2.

10. The compound of claim 2 having the structure of Formula (II-g):

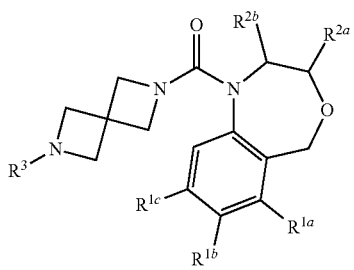

(II-g)

wherein:
- $R^{1a}$, $R^{1b}$, and $R^{1c}$ are each, independently, H, lower alkyl, lower haloalkyl, lower alkoxy, cyano, or halo;
- $R^{2a}$ and $R^{2b}$ are each, independently, H, lower alkyl, lower haloalkyl, or lower alkoxy;
- $R^3$ is —$(CHR^z)_m$-Q-$(R^4)_p$, —$S(=O)_2R^5$, or —$C(=O)R^5$;
- $R^z$ is H or $CH_3$
- Q is aryl or heteroaryl;
- $R^4$ is, at each occurrence, independently H, —OH, =O, cycloalkyl, lower alkyl, lower haloalkyl, lower alkoxy, lower haloalkoxy, halo, or cyano;
- $R^5$ is H, cycloalkyl, lower alkyl, lower haloalkyl, lower alkoxy, aryl, heteroaryl, cycloalkylalkyl, heterocyclyl, or —O-heterocyclyl;
- m is 0, 1, 2, 3, 4, 5, or 6; and
- p is 0, 1, or 2.

11. The compound of claim 2 having the structure of Formula (II-h):

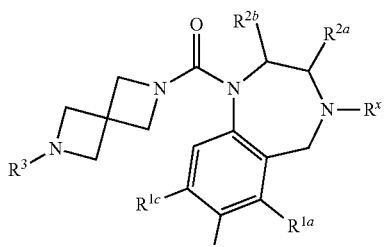

(II-h)

wherein:
- $R^x$ is, at each occurrence, independently H, lower alkyl, lower haloalkyl, or halo;
- $R^{1a}$, $R^{1b}$, and $R^{1c}$ are each, independently, H, lower alkyl, lower haloalkyl, lower alkoxy, cyano, or halo;
- $R^{2a}$ and $R^{2b}$ are each, independently, H, lower alkyl, lower haloalkyl, or lower alkoxy;
- $R^3$ is —$(CHR^z)_m$-Q-$(R^4)_p$, —$S(=O)_2R^5$, or —$C(=O)R^5$;
- $R^z$ is H or $CH_3$
- Q is aryl or heteroaryl;
- $R^4$ is, at each occurrence, independently H, —OH, =O, cycloalkyl, lower alkyl, lower haloalkyl, lower alkoxy, lower haloalkoxy, halo, or cyano;
- $R^5$ is H, cycloalkyl, lower alkyl, lower haloalkyl, lower alkoxy, aryl, heteroaryl, cycloalkylalkyl, heterocyclyl, or —O-heterocyclyl;
- m is 0, 1, 2, 3, 4, 5, or 6; and
- p is 0, 1, or 2.

12. The compound of claim 2 having the structure of Formula (II-i):

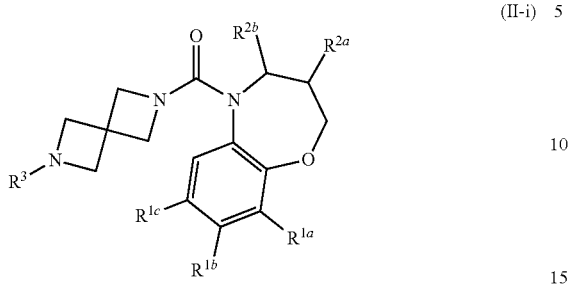

(II-i)

wherein:
- $R^{1a}$, $R^{1b}$, and $R^{1c}$ are each, independently, H, lower alkyl, lower haloalkyl, lower alkoxy, cyano, or halo;
- $R^{2a}$ and $R^{2b}$ are each, independently, H, lower alkyl, lower haloalkyl, or lower alkoxy;
- $R^3$ is —$(CHR^z)_m$-Q-$(R^4)_p$, —S(=O)$_2$R$^5$, or —C(=O)R$^5$;
- $R^z$ is H or CH$_3$
- Q is aryl or heteroaryl;
- $R^4$ is, at each occurrence, independently H, —OH, =O, cycloalkyl, lower alkyl, lower haloalkyl, lower alkoxy, lower haloalkoxy, halo, or cyano;
- $R^5$ is H, cycloalkyl, lower alkyl, lower haloalkyl, lower alkoxy, aryl, heteroaryl, cycloalkylalkyl, heterocyclyl, or —O-heterocyclyl;
- m is 0, 1, 2, 3, 4, 5, or 6; and
- p is 0, 1, or 2.

13. The compound of claim 2 having the structure of Formula (II-j):

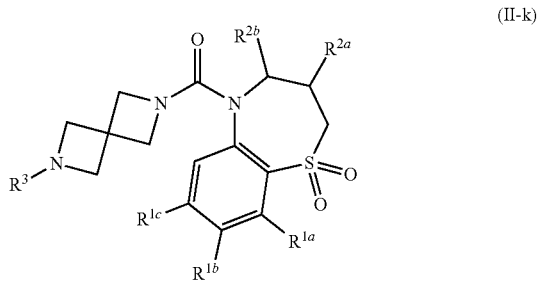

(II-j)

wherein:
- $R^x$ is, at each occurrence, independently H, lower alkyl, lower haloalkyl, or halo;
- $R^{1a}$, $R^{1b}$, and $R^{1c}$ are each, independently, H, lower alkyl, lower haloalkyl, lower alkoxy, cyano, or halo;
- $R^{2a}$ and $R^{2b}$ are each, independently, H, lower alkyl, lower haloalkyl, or lower alkoxy;
- $R^3$ is —$(CHR^z)_m$-Q-$(R^4)_p$, —S(=O)$_2$R$^5$, or —C(=O)R$^5$;
- $R^z$ is H or CH$_3$
- Q is aryl or heteroaryl;
- $R^4$ is, at each occurrence, independently H, —OH, =O, cycloalkyl, lower alkyl, lower haloalkyl, lower alkoxy, lower haloalkoxy, halo, or cyano;
- $R^5$ is H, cycloalkyl, lower alkyl, lower haloalkyl, lower alkoxy, aryl, heteroaryl, cycloalkylalkyl, heterocyclyl, or —O-heterocyclyl;
- m is 0, 1, 2, 3, 4, 5, or 6; and
- p is 0, 1, or 2.

14. The compound of claim 2 having the structure of Formula (II-k):

(II-k)

wherein:
- $R^{1a}$, $R^{1b}$, and $R^{1c}$ are each, independently, H, lower alkyl, lower haloalkyl, lower alkoxy, cyano, or halo;
- $R^{2a}$ and $R^{2b}$ are each, independently, H, lower alkyl, lower haloalkyl, or lower alkoxy;
- $R^3$ is —$(CHR^z)_m$-Q-$(R^4)_p$, —S(=O)$_2$R$^5$, or —C(=O)R$^5$;
- $R^z$ is H or CH$_3$
- Q is aryl or heteroaryl;
- $R^4$ is, at each occurrence, independently H, —OH, =O, cycloalkyl, lower alkyl, lower haloalkyl, lower alkoxy, lower haloalkoxy, halo, or cyano;
- $R^5$ is H, cycloalkyl, lower alkyl, lower haloalkyl, lower alkoxy, aryl, heteroaryl, cycloalkylalkyl, heterocyclyl, or —O-heterocyclyl;
- m is 0, 1, 2, 3, 4, 5, or 6; and
- p is 0, 1, or 2.

15. The compound of claim 2 wherein $R^3$ is —$(CHR^z)_m$-Q-$(R^4)_p$ and having the structure of Formula (III):

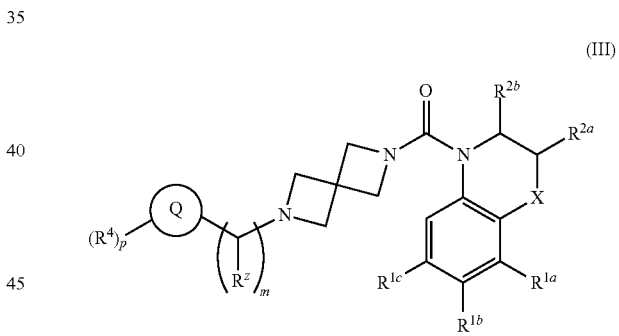

(III)

wherein:
- X is —$(CR^xR^y)_nO(CR^xR^y)_q$—, —$(CR^xR^y)_nS(O)_t(CR^xR^y)_q$—, —$(CR^xR^y)_nN(R^x)(CR^xR^y)_q$—, or —$(CR^xR^y)_n$—,
- $R^x$ is, at each occurrence, independently H, lower alkyl, lower haloalkyl, or halo;
- $R^y$ is, at each occurrence, independently H, —OH, lower alkyl, lower alkoxy, or halo;
- $R^{1a}$, $R^{1b}$, and $R^{1c}$ are each, independently, H, lower alkyl, lower haloalkyl, lower alkoxy, cyano, or halo;
- $R^{2a}$ and $R^{2b}$ are each, independently, H, lower alkyl, lower haloalkyl, or lower alkoxy;
- $R^z$ is H or CH$_3$
- Q is aryl or heteroaryl;
- $R^4$ is, at each occurrence, independently H, —OH, =O, cycloalkyl, lower alkyl, lower haloalkyl, lower alkoxy, lower haloalkoxy, halo, or cyano;
- n is 0, 1, or 2;
- q is 0, 1, or 2;

t is 0, 1, or 2;

m is 0, 1, 2, 3, 4, 5, or 6; and p is 0, 1, or 2.

16. The compound of claim 15 wherein m is 1, Q is aryl or heteroaryl of structure , and having the structure of Formula (IV):

(IV)

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—,

R$^x$ is, at each occurrence, independently H, lower alkyl, lower haloalkyl, or halo;

R$^y$ is, at each occurrence, independently H, —OH, lower alkyl, lower alkoxy, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^z$ is H or CH$_3$

J$^1$, J$^2$, J$^3$, and J$^4$ are each, independently, N, CH, or CR$^4$;

R$^4$ is, at each occurrence, independently H, —OH, ═O, cycloalkyl, lower alkyl, lower haloalkyl, lower alkoxy, lower haloalkoxy, halo, or cyano;

n is 0, 1, or 2;

q is 0, 1, or 2;

t is 0, 1, or 2;

p is 0, 1, or 2.

17. The compound of claim 15 wherein m is 0, Q is aryl or heteroaryl of structure , and having the structure of Formula (V):

(V)

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—,

R$^x$ is, at each occurrence, independently H, lower alkyl, lower haloalkyl, or halo;

R$^y$ is, at each occurrence, independently H, —OH, lower alkyl, lower alkoxy, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

J$^1$, J$^2$, J$^3$, and J$^4$ are each, independently, N, O—CH, or CR$^4$;

R$^4$ is, at each occurrence, independently H, —OH, ═O, cycloalkyl, lower alkyl, lower haloalkyl, lower alkoxy, lower haloalkoxy, halo, or cyano;

n is 0, 1, or 2;

q is 0, 1, or 2;

t is 0, 1, or 2;

p is 0, 1, or 2.

18. The compound of claim 15 wherein m is 0, Q is heteroaryl of structure , and having the structure of Formula (VI):

(VI)

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—,

R$^x$ is, at each occurrence, independently H, lower alkyl, lower haloalkyl, or halo;

R$^y$ is, at each occurrence, independently H, —OH, lower alkyl, lower alkoxy, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano;

n is 0, 1, or 2;
q is 0, 1, or 2;
t is 0, 1, or 2;
p is 0, 1, or 2.

19. The compound of claim 15 wherein m is 0, Q is heteroaryl of structure

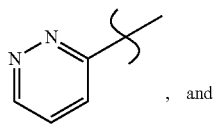

, and having the structure of Formula (VII):

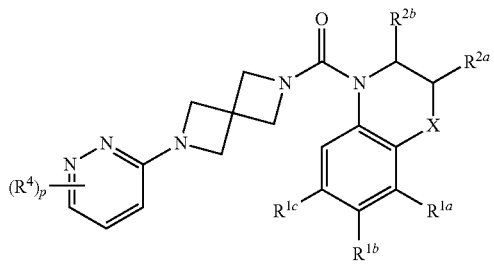

(VII)

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—;

R$^x$ is, at each occurrence, independently H, lower alkyl, lower haloalkyl, or halo;

R$^y$ is, at each occurrence, independently H, —OH, lower alkyl, lower alkoxy, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano;

n is 0, 1, or 2;
q is 0, 1, or 2;
t is 0, 1, or 2;
p is 0, 1, or 2.

20. The compound of claim 15 wherein m is 0, Q is heteroaryl of structure

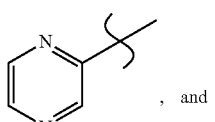

, and having the structure of Formula (VIII):

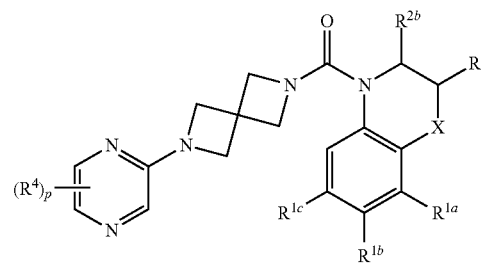

(VIII)

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—;

R$^x$ is, at each occurrence, independently H, lower alkyl, lower haloalkyl, or halo;

R$^y$ is, at each occurrence, independently H, —OH, lower alkyl, lower alkoxy, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^4$ is, at each occurrence, independently H, —OH, =O, cycloalkyl, lower alkyl, lower haloalkyl, lower alkoxy, lower haloalkoxy, halo, or cyano;

n is 0, 1, or 2;
q is 0, 1, or 2;
t is 0, 1, or 2;
p is 0, 1, or 2.

21. The compound of claim 15 wherein m is 0, Q is heteroaryl of structure

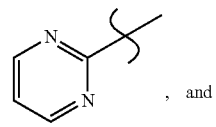

, and having the structure of Formula (IX):

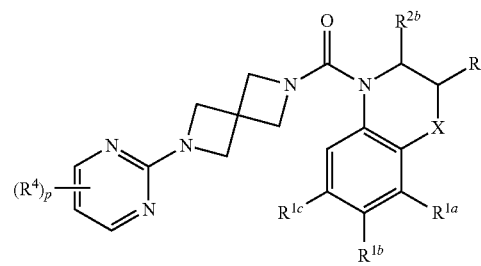

(IX)

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—;

R$^x$ is, at each occurrence, independently H, lower alkyl, lower haloalkyl, or halo;

R$^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano;

n is 0, 1, or 2;
q is 0, 1, or 2;
t is 0, 1, or 2;
p is 0, 1, or 2.

22. The compound of claim 15 wherein m is 0, Q is aryl or heteroaryl of structure

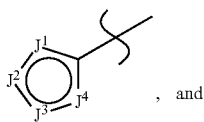
, and having the structure of Formula (X):

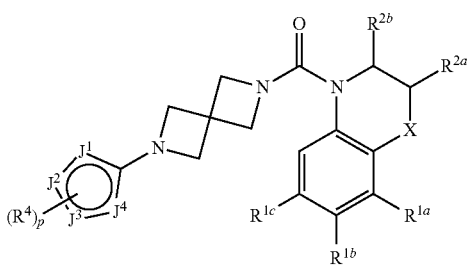

wherein:
X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—, $R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$J^1$, $J^2$, $J^3$, and $J^4$ are each, independently, N, O, CH, or CR$^4$;

$R^4$ is, at each occurrence, independently H, —OH, =O, cycloalkyl, lower alkyl, lower haloalkyl, lower alkoxy, lower haloalkoxy, halo, or cyano;

n is 0, 1, or 2;
q is 0, 1, or 2;
t is 0, 1, or 2;
p is 0, 1, or 2.

23. The compound of claim 22 wherein Q is heteroaryl of structure

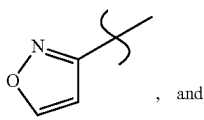
, and having the structure of Formula (XI):

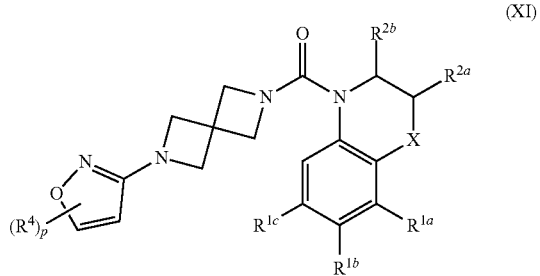

wherein:
X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—, $R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano;

n is 0, 1, or 2;
q is 0, 1, or 2;
t is 0, 1, or 2; and
p is 0, 1, or 2.

24. The compound of claim 22 wherein Q is heteroaryl of structure

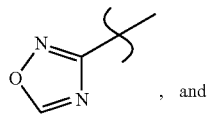
, and having the structure of Formula (XII):

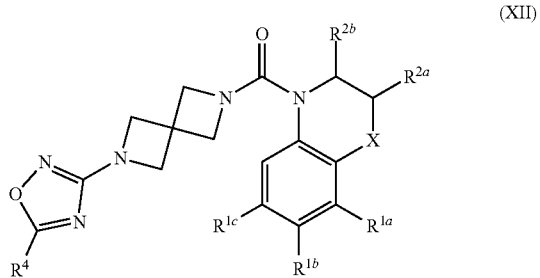

wherein:
X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—, $R^x$ is, at each occurrence, independently H, lower alkyl, lower haloalkyl, or halo;

$R^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano;

n is 0, 1, or 2;
q is 0, 1, or 2;
t is 0, 1, or 2; and
p is 0, 1, or 2.

25. The compound of claim 22 wherein Q is heteroaryl of structure

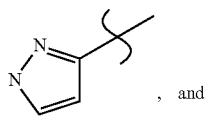, and having the structure of Formula (XIII):

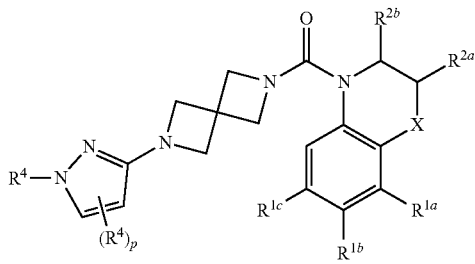

(XIII)

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—,

R$^x$ is, at each occurrence, independently H, lower alkyl, lower haloalkyl, or halo;

R$^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano;

n is 0, 1, or 2;
q is 0, 1, or 2;
t is 0, 1, or 2; and
p is 0, 1, or 2.

26. The compound of claim 22 wherein Q is heteroaryl of structure

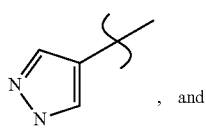, and having the structure of Formula (XIV):

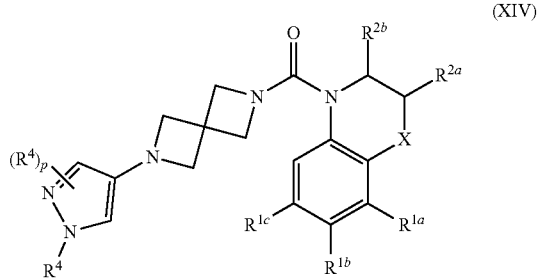

(XIV)

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—,

R$^x$ is, at each occurrence, independently H, lower alkyl, lower haloalkyl, or halo;

R$^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^4$ is, at each occurrence, independently H, —OH, =O, cycloalkyl, lower alkyl, lower haloalkyl, lower alkoxy, lower haloalkoxy, halo, or cyano;

n is 0, 1, or 2;
q is 0, 1, or 2;
t is 0, 1, or 2; and
p is 0, 1, or 2.

27. The compound of claim 1 having the structure of Formula (XV):

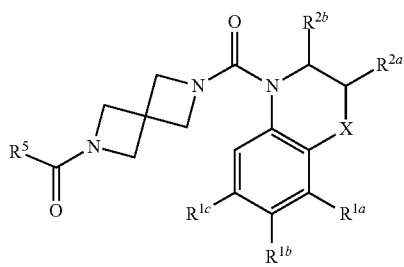

(XV)

wherein:

X is —(CR$^x$R$^y$)$_n$O(CR$^x$R$^y$)$_q$—, —(CR$^x$R$^y$)$_n$S(O)$_t$(CR$^x$R$^y$)$_q$—, —(CR$^x$R$^y$)$_n$N(R$^x$)(CR$^x$R$^y$)$_q$—, or —(CR$^x$R$^y$)$_n$—,

R$^x$ is, at each occurrence, independently H, lower alkyl, lower haloalkyl, or halo;

R$^y$ is, at each occurrence, independently H, —OH, lower alkyl, lower alkoxy, or halo;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^5$ is H, cycloalkyl, lower alkyl, lower haloalkyl, lower alkoxy, aryl, heteroaryl, cycloalkylalkyl, heterocyclyl, or —O-heterocyclyl;

n is 0, 1, or 2;
q is 0, 1, or 2; and
t is 0, 1, or 2.

28. The compound of claim 1 having the structure of Formula (XVI):

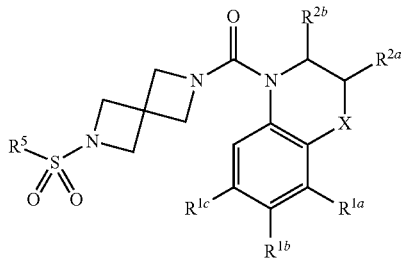

(XVI)

wherein:
X is —(C$R^x$R$^y$)$_n$O(C$R^x$R$^y$)$_q$—, —(C$R^x$R$^y$)$_n$S(O)$_t$(C$R^x$R$^y$)$_q$—, —(C$R^x$R$^y$)$_n$N(R$^x$)(C$R^x$R$^y$)$_q$—, or —(C$R^x$R$^y$)$_n$—, R$^x$ is, at each occurrence, independently H, lower alkyl, lower haloalkyl, or halo;

R$^y$ is, at each occurrence, independently H, —OH, lower alkyl, lower alkoxy, or halo;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^5$ is H, cycloalkyl, lower alkyl, lower haloalkyl, lower alkoxy, aryl, heteroaryl, cycloalkylalkyl, heterocyclyl, or —O-heterocyclyl;

n is 0, 1, or 2;
q is 0, 1, or 2; and
t is 0, 1, or 2.

29. A substantially enantiomerically pure compound having the structure of Formula (XVII-S), or a pharmaceutically acceptable hydrate, solvate, isotope, or salt thereof:

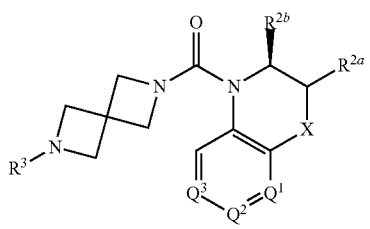

(XVII-S)

wherein:
X is —(C$R^x$R$^y$)$_n$O(C$R^x$R$^y$)$_q$—, —(C$R^x$R$^y$)$_n$S(o)$_t$(C$R^x$R$^y$)$_q$—, —(C$R^x$R$^y$)$_n$N(R$^x$)(C$R^x$R$^y$)$_q$—, or —(C$R^x$R$^y$)$_n$—, R$^x$ is, at each occurrence, independently H, lower alkyl, lower haloalkyl, halo, or R$^6$;

R$^y$ is, at each occurrence, independently H, —OH, lower alkyl, lower alkoxy, or halo;

Q$^1$ is N or CR$^{1a}$, Q$^2$ is N or CR$^{1b}$, and Q$^3$ is N or CR$^{1c}$, wherein at least one Q$^1$, Q$^2$, or Q$^3$ is not N;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^3$ is —(CHR$^z$)$_m$-Q-(R$^4$)$_p$, —S(=O)$_2$R$^5$, or —C(=O)R$^5$;
R$^z$ is H or CH$_3$
Q is aryl or heteroaryl;

R$^4$ is, at each occurrence, independently H, —OH, =O, cycloalkyl, lower alkyl, lower haloalkyl, lower alkoxy, lower haloalkoxy, halo, or cyano;

R$^5$ is H, cycloalkyl, lower alkyl, lower haloalkyl, lower alkoxy, aryl, heteroaryl, cycloalkylalkyl, heterocyclyl, or —O-heterocyclyl;

R$^6$ is cycloalkyl, heterocyclyl, or —C(=O)R$^7$;
R$^7$ is H, lower alkyl, or lower haloalkyl;
n is 0, 1, or 2;
q is 0, 1, or 2;
t is 0, 1, or 2;
m is 0, 1, 2, 3, 4, 5, or 6; and
p is 0, 1, or 2.

30. A substantially enantiomerically pure compound having the structure of Formula (XVII-R), or a pharmaceutically acceptable hydrate, solvate, isotope, or salt thereof:

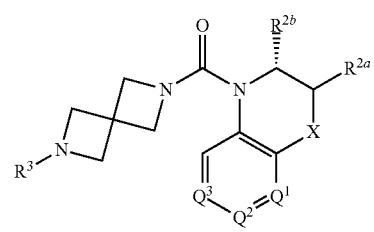

(XVII-R)

wherein:
X is —(C$R^x$R$^y$)$_n$O(C$R^x$R$^y$)$_q$—, —(C$R^x$R$^y$)$_n$S(O)$_t$(C$R^x$R$^y$)$_q$—, —(C$R^x$R$^y$)$_n$N(R$^x$)(C$R^x$R$^y$)$_q$—, or —(C$R^x$R$^y$)$_n$—, R$^x$ is, at each occurrence, independently H, lower alkyl, lower haloalkyl, halo, or R$^6$;

R$^y$ is, at each occurrence, independently H, —OH, lower alkyl, lower alkoxy, or halo;

Q$^1$ is N or CR$^{1a}$, Q$^2$ is N or CR$^{1b}$, and Q$^3$ is N or CR$^1$c, wherein at least one Q$^1$, Q$^2$, or Q$^3$ is not N;

R$^{1a}$, R$^{1b}$, and R$^{1c}$ are each, independently, H, lower alkyl, lower haloalkyl, lower alkoxy, cyano, or halo;

R$^{2a}$ and R$^{2b}$ are each, independently, H, lower alkyl, lower haloalkyl, or lower alkoxy;

R$^3$ is —(CHR$^z$)$_m$-Q-(R$^4$)$_p$, —S(=O)$_2$R$^5$, or —C(=O)R$^5$;
R$^z$ is H or CH$_3$
Q is aryl or heteroaryl;

R$^4$ is, at each occurrence, independently H, —OH, =O, cycloalkyl, lower alkyl, lower haloalkyl, lower alkoxy, lower haloalkoxy, halo, or cyano;

R$^5$ is H, cycloalkyl, lower alkyl, lower haloalkyl, lower alkoxy, aryl, heteroaryl, cycloalkylalkyl, heterocyclyl, or —O-heterocyclyl;

R$^6$ is cycloalkyl, heterocyclyl, or —C(=O)R$^7$;
R$^7$ is H, lower alkyl, or lower haloalkyl;
n is 0, 1, or 2;
q is 0, 1, or 2;
t is 0, 1, or 2;
m is 0, 1, 2, 3, 4, 5, or 6; and
p is 0, 1, or 2.

31. A substantially enantiomerically pure compound having the structure of Formula (XVIII-S), or a pharmaceutically acceptable hydrate, solvate, isotope, or salt thereof:

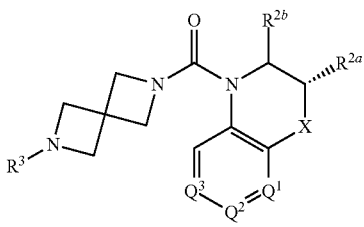

(XVIII-S)

wherein:
X is —(C$R^xR^y$)$_n$O(C$R^xR^y$)$_q$—, —(C$R^xR^y$)$_n$S(O)$_t$(C$R^xR^y$)$_q$—, —(C$R^xR^y$)$_n$N($R^x$)(C$R^xR^y$)$_q$—, or —(C$R^xR^y$)$_n$—, $R^x$ is, at each occurrence, independently H, lower alkyl, lower haloalkyl, halo, or $R^6$;

$R^y$ is, at each occurrence, independently H, —OH, lower alkyl, lower alkoxy, or halo;

$Q^1$ is N or C$R^{1a}$, $Q^2$ is N or C$R^{1b}$, and $Q^3$ is N or C$R^{1c}$, wherein at least one $Q^1$, $Q^2$, or $Q^3$ is not N;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^3$ is —(CH$R^z$)$_m$-Q-($R^4$)$_p$, —S(=O)$_2R^5$, or —C(=O)$R^5$;

$R^z$ is H or CH$_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

$R^5$ is H, cycloalkyl, lower alkyl, lower haloalkyl, lower alkoxy, aryl, heteroaryl, cycloalkylalkyl, heterocyclyl, or —O-heterocyclyl;

$R^6$ is cycloalkyl, heterocyclyl, or —C(=O)$R^7$;

$R^7$ is H, lower alkyl, or lower haloalkyl;

n is 0, 1, or 2;

q is 0, 1, or 2;

t is 0, 1, or 2;

m is 0, 1, 2, 3, 4, 5, or 6; and p is 0, 1, or 2.

32. A substantially enantiomerically pure compound having the structure of Formula (XVIII-R), or a pharmaceutically acceptable hydrate, solvate, isotope, or salt thereof:

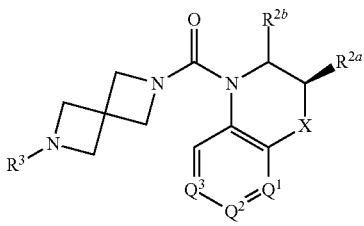

(XVIII-R)

wherein:
X is —(C$R^xR^y$)$_n$O(C$R^xR^y$)$_q$—, —(C$R^xR^y$)$_n$S(O)$_t$(C$R^xR^y$)$_q$—, —(C$R^xR^y$)$_n$N($R^x$)(C$R^xR^y$)$_q$—, or —(C$R^xR^y$)$_n$—, $R^x$ is, at each occurrence, independently H, lower alkyl, lower haloalkyl, halo, or $R^6$;

$R^y$ is, at each occurrence, independently H, —OH, lower alkyl, lower alkoxy, or halo;

$Q^1$ is N or C$R^{1a}$, $Q^2$ is N or C$R^{1b}$, and $Q^3$ is N or C$R^{1c}$, wherein at least one $Q^1$, $Q^2$, Or $Q^3$ is not N;

$R^{1a}$, $R^{1b}$, and $R^{1c}$ are each, independently, H, lower alkyl, lower haloalkyl, lower alkoxy, cyano, or halo;

$R^{2a}$ and $R^{2b}$ are each, independently, H, lower alkyl, lower haloalkyl, or lower alkoxy;

$R^3$ is —(CH$R^z$)$_m$-Q-($R^4$)$_p$, —S(=O)$_2R^5$, or —C(=O)$R^5$;

$R^z$ is H or CH$_3$

Q is aryl or heteroaryl;

$R^4$ is, at each occurrence, independently H, —OH, =O, cycloalkyl, lower alkyl, lower haloalkyl, lower alkoxy, lower haloalkoxy, halo, or cyano;

$R^5$ is H, cycloalkyl, lower alkyl, lower haloalkyl, lower alkoxy, aryl, heteroaryl, cycloalkylalkyl, heterocyclyl, or —O-heterocyclyl;

$R^6$ is cycloalkyl, heterocyclyl, or —C(=O)$R^7$;

$R^7$ is H, lower alkyl, or lower haloalkyl;

n is 0, 1, or 2;

q is 0, 1, or 2;

t is 0, 1, or 2;

m is 0, 1, 2, 3, 4, 5, or 6; and p is 0, 1, or 2.

33. The compound of claim 1, wherein $R^{1b}$ is halogen.

34. The compound of claim 33, wherein $R^{1b}$ is Cl.

35. The compound of claim 1, wherein $R^{1b}$ is lower alkyl.

36. The compound of claim 35, wherein $R^{1b}$ is methyl, ethyl, or isopropyl.

37. The compound of claim 1, wherein $R^{1b}$ is lower haloalkyl.

38. The compound of claim 37, wherein $R^{1b}$ is —CF$_3$.

39. The compound of claim 1, wherein $R^{1b}$ is lower alkoxy.

40. The compound of claim 39, wherein $R^{1b}$ is methoxy, ethoxy, isopropoxy, or t-butoxy.

41. The compound of claim 1, wherein $R^{1b}$ is cyano.

42. The compound of claim 1, wherein at least one $R^x$ is hydrogen.

43. The compound of claim 1, wherein at least one $R^x$ is lower alkyl.

44. The compound of claim 43, wherein at least one $R^x$ is methyl, ethyl, or isopropyl.

45. The compound of claim 1, wherein at least one $R^y$ is lower alkoxy.

46. The compound of claim 45, wherein at least one $R^y$ is methoxy, ethoxy, isopropoxy, or t-butoxy.

47. The compound of claim 1, wherein at least one $R^x$ is cycloalkyl.

48. The compound of claim 47, wherein at least one $R^x$ is cyclopropyl or cyclobutyl.

49. The compound of claim 1, wherein $R^4$ is halogen.

50. The compound of claim 49, wherein $R^4$ is F or Cl.

51. The compound of claim 1, wherein $R^4$ is lower alkyl.

52. The compound of claim 51, wherein $R^4$ is methyl or ethyl.

53. The compound of claim 1, wherein $R^4$ is lower alkoxy.

54. The compound of claim 53, wherein $R^4$ is methoxy or ethoxy.

55. The compound of claim 1, wherein $R^4$ is cyano.

56. The compound of claim 1, wherein $R^4$ is hydroxy.

57. The compound of claim 1, wherein $R^5$ is lower alkyl.

58. The compound of claim 57, wherein $R^5$ is methyl, ethyl, or isopropyl.

59. The compound of claim 1, wherein $R^5$ is lower alkoxy.

60. The compound of claim 59, wherein $R^5$ is t-butoxy.

61. A compound having a structure listed in Table 1, or a pharmaceutically acceptable isomer, racemate, hydrate, solvate, isotope, or salt thereof.

62. A substantially enantiomerically pure form of a compound having a structure listed in Table 2, or pharmaceutically acceptable hydrate, solvate, isotope, or salt thereof.

63. A composition comprising a compound of claim 1, or a pharmaceutically acceptable isomer, racemate, hydrate, solvate, isotope, or salt thereof, and a pharmaceutically acceptable carrier, diluent, or excipient.

64. The compound of claim 61, wherein the compound is Compound No. 1-3 of Table 1, or a pharmaceutically acceptable isomer, racemate, hydrate, solvate, isotope, or salt thereof.

65. The compound of claim 61, wherein the compound is Compound No. 1-22 of Table 1, or a pharmaceutically acceptable isomer, racemate, hydrate, solvate, isotope, or salt thereof.

66. The compound of claim 61, wherein the compound is Compound No. 1-30 of Table 1, or a pharmaceutically acceptable isomer, racemate, hydrate, solvate, isotope, or salt thereof.

67. The compound of claim 61, wherein the compound is Compound No. 1-39 of Table 1, or a pharmaceutically acceptable isomer, racemate, hydrate, solvate, isotope, or salt thereof.

68. The compound of claim 61, wherein the compound is Compound No. 1-51 of Table 1, or a pharmaceutically acceptable isomer, racemate, hydrate, solvate, isotope, or salt thereof.

69. The compound of claim 61, wherein the compound is Compound No. 1-59 of Table 1, or a pharmaceutically acceptable isomer, racemate, hydrate, solvate, isotope, or salt thereof.

70. The compound of claim 61, wherein the compound is Compound No. 1-65 of Table 1, or a pharmaceutically acceptable isomer, racemate, hydrate, solvate, isotope, or salt thereof.

71. The compound of claim 61, wherein the compound is Compound No. 1-66 of Table 1, or a pharmaceutically acceptable isomer, racemate, hydrate, solvate, isotope, or salt thereof.

72. The compound of claim 61, wherein the compound is Compound No. 1-67 of Table 1, or a pharmaceutically acceptable isomer, racemate, hydrate, solvate, isotope, or salt thereof.

73. The compound of claim 61, wherein the compound is Compound No. 1-69 of Table 1, or a pharmaceutically acceptable isomer, racemate, hydrate, solvate, isotope, or salt thereof.

74. The compound of claim 61, wherein the compound is Compound No. 1-70 of Table 1, or a pharmaceutically acceptable isomer, racemate, hydrate, solvate, isotope, or salt thereof.

75. The compound of claim 61, wherein the compound is Compound No. 1-78 of Table 1, or a pharmaceutically acceptable isomer, racemate, hydrate, solvate, isotope, or salt thereof.

76. The compound of claim 61, wherein the compound is Compound No. 1-83 of Table 1, or a pharmaceutically acceptable isomer, racemate, hydrate, solvate, isotope, or salt thereof.

77. The compound of claim 61, wherein the compound is Compound No. 4-3 of Table 1, or a pharmaceutically acceptable isomer, racemate, hydrate, solvate, isotope, or salt thereof.

78. The compound of claim 61, wherein the compound is Compound No. 8-12 of Table 1, or a pharmaceutically acceptable isomer, racemate, hydrate, solvate, isotope, or salt thereof.

79. The compound of claim 61, wherein the compound is Compound No. 8-13 of Table 1, or a pharmaceutically acceptable isomer, racemate, hydrate, solvate, isotope, or salt thereof.

80. The compound of claim 61, wherein the compound is Compound No. 9-1 of Table 1, or a pharmaceutically acceptable isomer, racemate, hydrate, solvate, isotope, or salt thereof.

81. The compound of claim 61, wherein the compound is Compound No. 9-3 of Table 1, or a pharmaceutically acceptable isomer, racemate, hydrate, solvate, isotope, or salt thereof.

82. The compound of claim 61, wherein the compound is Compound No. 9-4 of Table 1, or a pharmaceutically acceptable isomer, racemate, hydrate, solvate, isotope, or salt thereof.

83. The compound of claim 61, wherein the compound is Compound No. 9-7 of Table 1, or a pharmaceutically acceptable isomer, racemate, hydrate, solvate, isotope, or salt thereof.

84. The compound of claim 61, wherein the compound is Compound No. 12-1 of Table 1, or a pharmaceutically acceptable isomer, racemate, hydrate, solvate, isotope, or salt thereof.

85. The compound of claim 61, wherein the compound is Compound No. 13-1 of Table 1, or a pharmaceutically acceptable isomer, racemate, hydrate, solvate, isotope, or salt thereof.

86. The compound of claim 61, wherein the compound is Compound No. 13-2 of Table 1, or a pharmaceutically acceptable isomer, racemate, hydrate, solvate, isotope, or salt thereof.

87. The compound of claim 61, wherein the compound is Compound No. 13-3 of Table 1, or a pharmaceutically acceptable isomer, racemate, hydrate, solvate, isotope, or salt thereof.

88. The compound of claim 61, wherein the compound is Compound No. 14-1 of Table 1, or a pharmaceutically acceptable isomer, racemate, hydrate, solvate, isotope, or salt thereof.

89. The compound of claim 61, wherein the compound is Compound No. 18-2 of Table 1, or a pharmaceutically acceptable isomer, racemate, hydrate, solvate, isotope, or salt thereof.

90. The compound of claim 61, wherein the compound is Compound No. 18-3 of Table 1, or a pharmaceutically acceptable isomer, racemate, hydrate, solvate, isotope, or salt thereof.

91. The compound of claim 61, wherein the compound is Compound No. 19-1 of Table 1, or a pharmaceutically acceptable isomer, racemate, hydrate, solvate, isotope, or salt thereof.

92. The compound of claim 61, wherein the compound is Compound No. 19-2 of Table 1, or a pharmaceutically acceptable isomer, racemate, hydrate, solvate, isotope, or salt thereof.

93. The compound of claim 61, wherein the compound is Compound No. 19-4 of Table 1, or a pharmaceutically acceptable isomer, racemate, hydrate, solvate, isotope, or salt thereof.

94. The compound of claim 61, wherein the compound is Compound No. 20-3 of Table 1, or a pharmaceutically acceptable isomer, racemate, hydrate, solvate, isotope, or salt thereof.

95. The compound of claim 61, wherein the compound is Compound No. 20-9 of Table 1, or a pharmaceutically acceptable isomer, racemate, hydrate, solvate, isotope, or salt thereof.

96. The compound of claim 61, wherein the compound is Compound No. 20-10 of Table 1, or a pharmaceutically acceptable isomer, racemate, hydrate, solvate, isotope, or salt thereof.

97. The compound of claim 61, wherein the compound is Compound No. 21-1 of Table 1, or a pharmaceutically acceptable isomer, racemate, hydrate, solvate, isotope, or salt thereof.

98. The compound of claim 61, wherein the compound is Compound No. 21-2 of Table 1, or a pharmaceutically acceptable isomer, racemate, hydrate, solvate, isotope, or salt thereof.

99. The compound of claim 61, wherein the compound is Compound No. 21-4 of Table 1, or a pharmaceutically acceptable isomer, racemate, hydrate, solvate, isotope, or salt thereof.

100. The compound of claim 61, wherein the compound is Compound No. 21-5 of Table 1, or a pharmaceutically acceptable isomer, racemate, hydrate, solvate, isotope, or salt thereof.

101. The compound of claim 61, wherein the compound is Compound No. 21-6 of Table 1, or a pharmaceutically acceptable isomer, racemate, hydrate, solvate, isotope, or salt thereof.

102. The compound of claim 61, wherein the compound is Compound No. 21-8 of Table 1, or a pharmaceutically acceptable isomer, racemate, hydrate, solvate, isotope, or salt thereof.

103. The compound of claim 61, wherein the compound is Compound No. 21-9 of Table 1, or a pharmaceutically acceptable isomer, racemate, hydrate, solvate, isotope, or salt thereof.

104. The compound of claim 61, wherein the compound is Compound No. 21-10 of Table 1, or a pharmaceutically acceptable isomer, racemate, hydrate, solvate, isotope, or salt thereof.

\* \* \* \* \*